(12) United States Patent
Gerling et al.

(10) Patent No.: US 12,270,030 B2
(45) Date of Patent: Apr. 8, 2025

(54) METHOD FOR STABILIZING NUCLEIC ACID NANOSTRUCTURES

(71) Applicant: Technische Universitat Munchen, Munich (DE)

(72) Inventors: Thomas Gerling, Munich (DE); Hendrik Dietz, Haar (DE)

(73) Assignee: Technische Universität München, Munich (DE)

( * ) Notice: Subject to any disclaimer, the term of this patent is extended or adjusted under 35 U.S.C. 154(b) by 1101 days.

(21) Appl. No.: 15/734,938

(22) PCT Filed: Jun. 5, 2019

(86) PCT No.: PCT/EP2019/064707
§ 371 (c)(1),
(2) Date: Dec. 3, 2020

(87) PCT Pub. No.: WO2019/234122
PCT Pub. Date: Dec. 12, 2019

(65) Prior Publication Data
US 2021/0230587 A1    Jul. 29, 2021

(30) Foreign Application Priority Data
Jun. 5, 2018 (DE) .......... 102018004454.9

(51) Int. Cl.
| | | |
|---|---|---|
| *C12Q 1/68* | (2018.01) | |
| *C07H 21/04* | (2006.01) | |
| *C12N 15/113* | (2010.01) | |
| *B82Y 40/00* | (2011.01) | |

(52) U.S. Cl.
CPC ........... *C12N 15/113* (2013.01); *C07H 21/04* (2013.01); *B82Y 40/00* (2013.01); *C12N 2320/52* (2013.01)

(58) Field of Classification Search
None
See application file for complete search history.

(56) References Cited

U.S. PATENT DOCUMENTS

2016/0215317 A1* 7/2016 He ................ C12Q 1/6816

FOREIGN PATENT DOCUMENTS

| | | |
|---|---|---|
| CN | 101851619 A | 10/2010 |
| CN | 107698640 A | 2/2018 |
| CN | 106715453 B | 4/2021 |
| WO | 2021165528 A1 | 8/2021 |
| WO | 2023209161 A1 | 11/2023 |

OTHER PUBLICATIONS

Tagawa et al; Soft Matter, 2011, vol. 7, pp. 10931-10934 (Year: 2011).*
Wang et la; Phys. Chem. 2019, 19: pp. 28907-28916 (Year: 2019).*
Abdallah, et al. "Stabilisation of self-assembled DNA crystals by triplex-directed photo-cross-linking" Chem. Commun., 2016, vol. 52, No. 51, p. 8014-8017, doi: 10.1039/c6cc03695c.
Nakamura, et al. "Creation of DNA array structure equipped with heat resistance by ultrafast photocrosslinking" J. Chem. Technol. Biotechnol., 2014, vol. 89, p. 1086-1090, DOI 10.1002/jctb.4205.
Rajendran, et al. "Photo-Cross-Linking-Assisted Thermal Stability of DNA Origami Structures and Its Application for Higher-Temperature Self-Assembly" JACS, 2011, vol. 133, p. 14488-14491, dx.doi.org/10.1021/ja204546h.
International Report on Patentability dated Dec. 8, 2020 for PCT/EP2019/064707.
Abdallah , et al., "Stabilisation of Self-Assembled DNA Crystals by Triplex-Directed Photo-Cross-Linking", Chemical Communications, vol. 52, No. 51.
Gerling , et al., "Sequence-Programmable Covalent Bonding of Designed DNA Assemblies", Science Advances, vol. 4 No. 8, Aug. 17, 2018, eaau 1157.
Hong , et al., "DNA Oragami Scaffold for Creating Higher Order Structures", Chemical Reviews, vol. 117 No. 20, Oct. 25, 2017, 12584-12640.
Ke , "Three-Dimensional Structures Self-Assembled from DNA Bricks", Science, vol. 338 No. 6111, Nov. 30, 2012, 1177-1183.
Nakumura , et al., "Creation of DNA Array Structure Equipped with Heat Resistance by Ultrafast Photocrosslinking", Journal of Chemical Technology and Biotechnology, vol. 89 No. 7, Oct. 10, 2013, 1086-1090.
Ranjendran , et al., "Photo-Cross-Linking-Assisted Thermal Stability of DNA Origami Structures and Its Application for Higher-Temperature Self-Assembly", J.Am.Chem.Soc., vol. 133, Aug. 22, 2011.
Wei , et al., "Complex Shapes Self-Assembled from Single-Stranded DNA Tiles", Nature, vol. 485 No. 7400, May 30, 2012, 623-626.
Monferrer et al, "DNA origami traps for large viruses", Cell Reports Physical Science 4, 101237, Jan. 18, 2023.
Sigl et al, "Programmable icosahedral shell system for virus trapping", Nat Mater, Sep. 1, 2021, 20(9): 1281-1289.

* cited by examiner

*Primary Examiner* — Jehanne S Sitton
(74) *Attorney, Agent, or Firm* — Dorsey & Whitney LLP

(57) ABSTRACT

The present invention relates to a novel method for stabilizing nucleic acid nanostructures by curing with ultraviolet light, particularly by crosslinking pyrimidine nucleotides.

22 Claims, 35 Drawing Sheets
Specification includes a Sequence Listing.

E

F

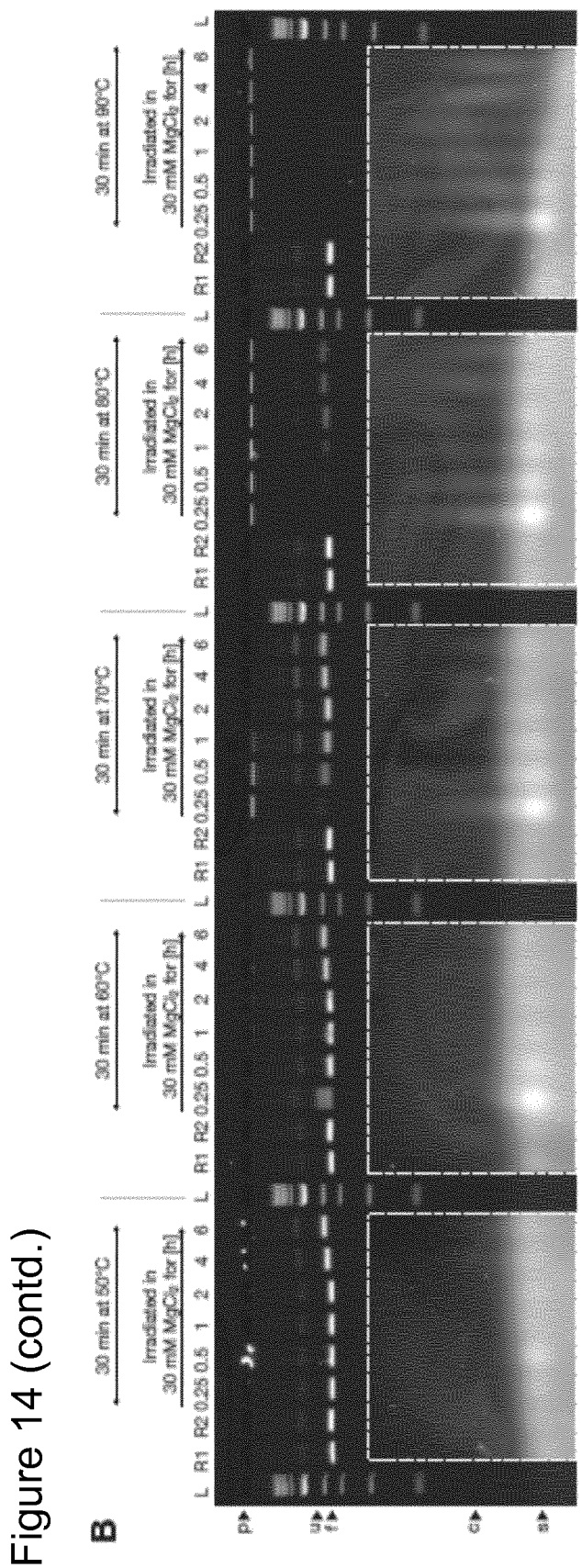
Figure 14 (contd.)

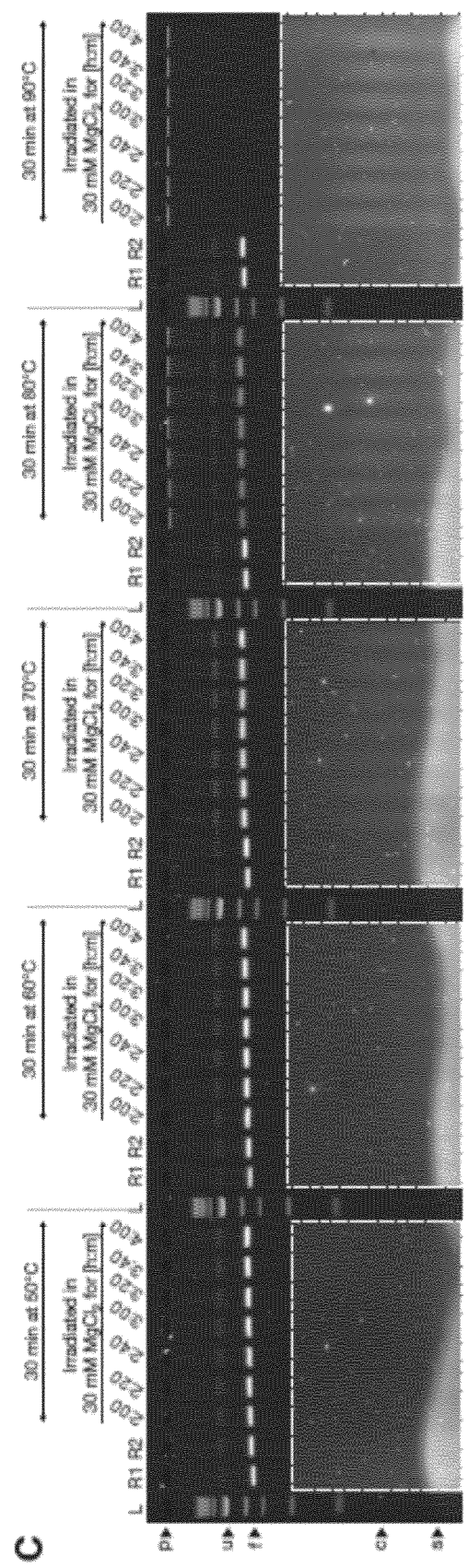
Figure 14 (contd.)

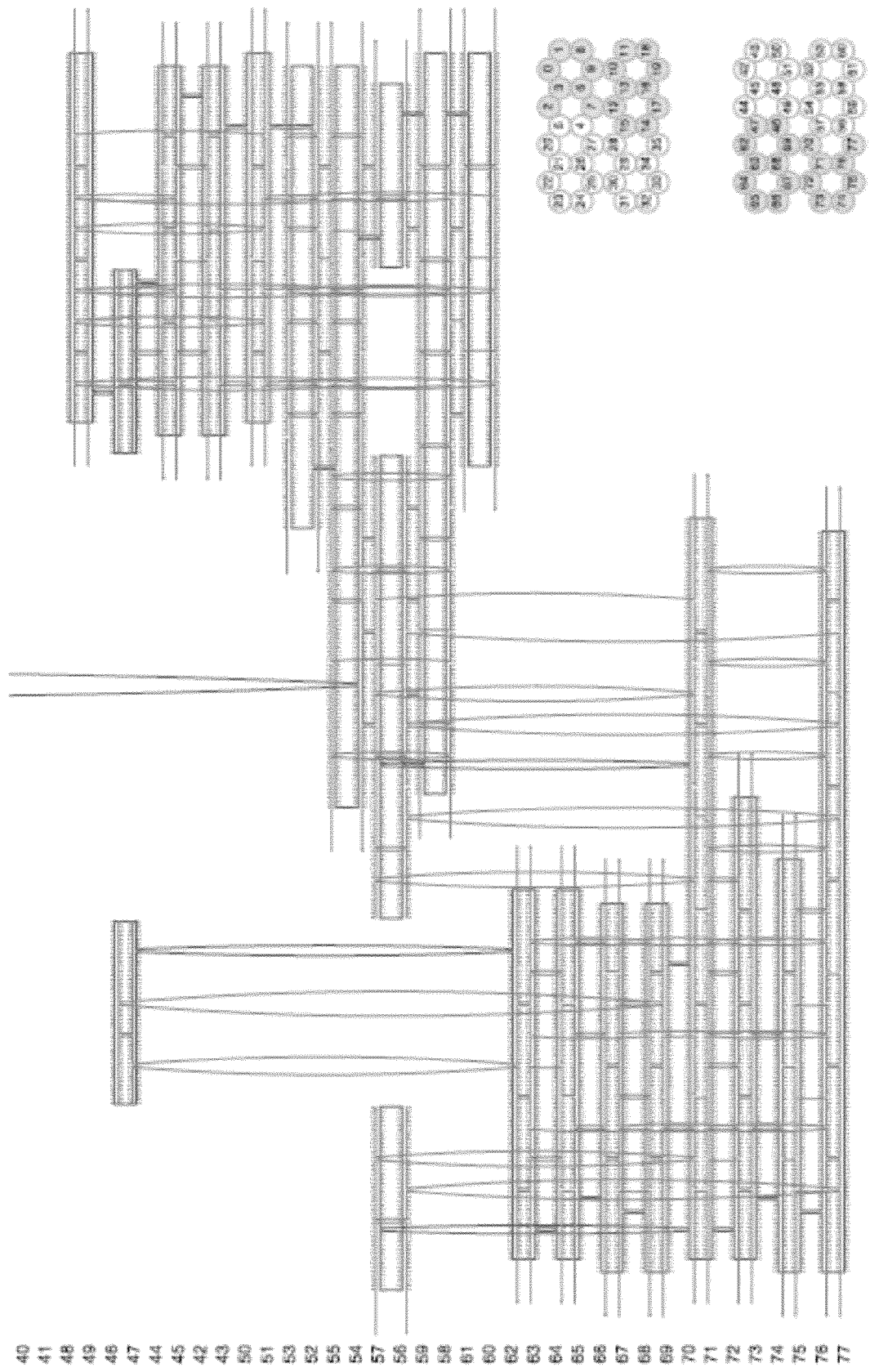
Figure 27 (contd.)

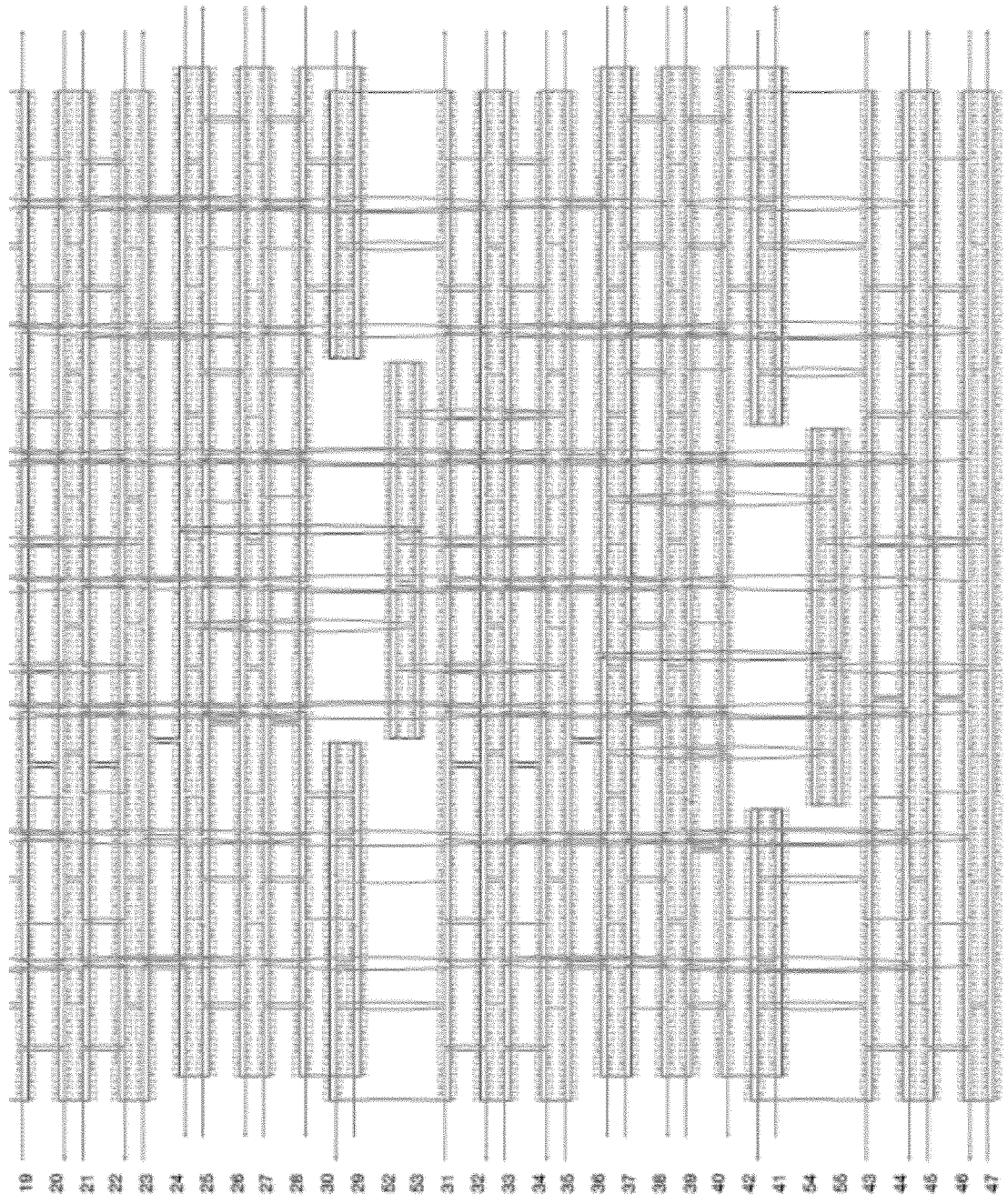
Figure 28 (contd.)

SEQUENCE LISTING

<160> NUMBER OF SEQ ID NOS: 965

<210> SEQ ID NO 1
<211> LENGTH: 61
<212> TYPE: DNA
<213> ORGANISM: Artificial sequence
<220> FEATURE:
<223> OTHER INFORMATION: artificial primer sequence

<400> SEQUENCE: 1

```
tttttagtt atgatattta taaatattac gtagatttta ccagcgccaa attaacgaac      60
t                                                                     61

<210> SEQ ID NO 2
<211> LENGTH: 40
<212> TYPE: DNA
<213> ORGANISM: Artificial sequence
<220> FEATURE:
<223> OTHER INFORMATION: artificial primer sequence

<400> SEQUENCE: 2
tttttgcggt taacaaacgg cggattgatt aagcaaatat                            40

<210> SEQ ID NO 3
<211> LENGTH: 42
<212> TYPE: DNA
<213> ORGANISM: Artificial sequence
<220> FEATURE:
<223> OTHER INFORMATION: artificial primer sequence

<400> SEQUENCE: 3
tttttcatcg ttgatgaata tacagtaaca ttatcaatat at                         42

<210> SEQ ID NO 4
<211> LENGTH: 40
<212> TYPE: DNA
<213> ORGANISM: Artificial sequence
<220> FEATURE:
<223> OTHER INFORMATION: artificial primer sequence

<400> SEQUENCE: 4
tttttaatgt ttctttagga gcactaactt acgaatatat                            40

<210> SEQ ID NO 5
<211> LENGTH: 40
<212> TYPE: DNA
<213> ORGANISM: Artificial sequence
<220> FEATURE:
<223> OTHER INFORMATION: artificial primer sequence

<400> SEQUENCE: 5
tttttaactt tgtatcaccg tactcaggtt ccgtaatcat                            40

<210> SEQ ID NO 6
<211> LENGTH: 52
<212> TYPE: DNA
<213> ORGANISM: Artificial sequence
<220> FEATURE:
<223> OTHER INFORMATION: artificial primer sequence

<400> SEQUENCE: 6
ttttgccatt acgacgattc actatcataa cccttcacat tcttttgccc tt              52

<210> SEQ ID NO 7
<211> LENGTH: 46
<212> TYPE: DNA
<213> ORGANISM: Artificial sequence
<220> FEATURE:
<223> OTHER INFORMATION: artificial primer sequence

<400> SEQUENCE: 7
ttttcagcgg agtgagttaa tctccttaag acagttttag actcct                     46

<210> SEQ ID NO 8
<211> LENGTH: 31
```

```
<212> TYPE: DNA
<213> ORGANISM: Artificial sequence
<220> FEATURE:
<223> OTHER INFORMATION: artificial primer sequence

<400> SEQUENCE: 8
ttttaacgtc attatggctt agagcttaat t                              31

<210> SEQ ID NO 9
<211> LENGTH: 40
<212> TYPE: DNA
<213> ORGANISM: Artificial sequence
<220> FEATURE:
<223> OTHER INFORMATION: artificial primer sequence

<400> SEQUENCE: 9
ttttaaattt tacggaggat ccccgggttt accacagact                     40

<210> SEQ ID NO 10
<211> LENGTH: 37
<212> TYPE: DNA
<213> ORGANISM: Artificial sequence
<220> FEATURE:
<223> OTHER INFORMATION: artificial primer sequence

<400> SEQUENCE: 10
tttgtatcat taaagccaga atggaattac aaataat                        37

<210> SEQ ID NO 11
<211> LENGTH: 40
<212> TYPE: DNA
<213> ORGANISM: Artificial sequence
<220> FEATURE:
<223> OTHER INFORMATION: artificial primer sequence

<400> SEQUENCE: 11
tttcataatt tgacgagaaa caccagaatt gaagcccgat                     40

<210> SEQ ID NO 12
<211> LENGTH: 61
<212> TYPE: DNA
<213> ORGANISM: Artificial sequence
<220> FEATURE:
<223> OTHER INFORMATION: artificial primer sequence

<400> SEQUENCE: 12
tttaggcatt atatttattt aagaaattaa taacgttcgg aaattattca tttccatttg     60
t                                                               61

<210> SEQ ID NO 13
<211> LENGTH: 40
<212> TYPE: DNA
<213> ORGANISM: Artificial sequence
<220> FEATURE:
<223> OTHER INFORMATION: artificial primer sequence

<400> SEQUENCE: 13
tttaccctga ttaatccccc tcaaatgctt tggagacagt                     40

<210> SEQ ID NO 14
<211> LENGTH: 42
<212> TYPE: DNA
<213> ORGANISM: Artificial sequence
<220> FEATURE:
<223> OTHER INFORMATION: artificial primer sequence
```

<400> SEQUENCE: 14
tttacaggta ttatagaaaa ttcatatggt ttaaatacat at                          42

<210> SEQ ID NO 15
<211> LENGTH: 39
<212> TYPE: DNA
<213> ORGANISM: Artificial sequence
<220> FEATURE:
<223> OTHER INFORMATION: artificial primer sequence

<400> SEQUENCE: 15
tttaatgccc cctgcctatt tcggaatttt gctcagtat                              39

<210> SEQ ID NO 16
<211> LENGTH: 52
<212> TYPE: DNA
<213> ORGANISM: Artificial sequence
<220> FEATURE:
<223> OTHER INFORMATION: artificial primer sequence

<400> SEQUENCE: 16
tttaatcatt gcgcgtttta accgccttct ccatgttact tattgcgatt at               52

<210> SEQ ID NO 17
<211> LENGTH: 54
<212> TYPE: DNA
<213> ORGANISM: Artificial sequence
<220> FEATURE:
<223> OTHER INFORMATION: artificial primer sequence

<400> SEQUENCE: 17
tttaagagtt cgagtagttt catcagttag gagccttaaa caactttcaa cagt             54

<210> SEQ ID NO 18
<211> LENGTH: 42
<212> TYPE: DNA
<213> ORGANISM: Artificial sequence
<220> FEATURE:
<223> OTHER INFORMATION: artificial primer sequence

<400> SEQUENCE: 18
tttaaaggcc ttgtatcggt ttatcagctt ttacaacatt at                          42

<210> SEQ ID NO 19
<211> LENGTH: 31
<212> TYPE: DNA
<213> ORGANISM: Artificial sequence
<220> FEATURE:
<223> OTHER INFORMATION: artificial primer sequence

<400> SEQUENCE: 19
ttgtgagtga ttttgaaagg aattgaggaa t                                      31

<210> SEQ ID NO 20
<211> LENGTH: 38
<212> TYPE: DNA
<213> ORGANISM: Artificial sequence
<220> FEATURE:
<223> OTHER INFORMATION: artificial primer sequence

<400> SEQUENCE: 20
ttgctgaatt ttttcatttg gggcgcgtta gcatgtat                               38

<210> SEQ ID NO 21
<211> LENGTH: 40

```
<212> TYPE: DNA
<213> ORGANISM: Artificial sequence
<220> FEATURE:
<223> OTHER INFORMATION: artificial primer sequence

<400> SEQUENCE: 21
ttgatgaaat tgaagtatta gactttactt ctggagtgat                    40

<210> SEQ ID NO 22
<211> LENGTH: 52
<212> TYPE: DNA
<213> ORGANISM: Artificial sequence
<220> FEATURE:
<223> OTHER INFORMATION: artificial primer sequence

<400> SEQUENCE: 22
ttgaggcggt cagtattgcc agcattaacc tcatttggca aattctgatt at      52

<210> SEQ ID NO 23
<211> LENGTH: 54
<212> TYPE: DNA
<213> ORGANISM: Artificial sequence
<220> FEATURE:
<223> OTHER INFORMATION: artificial primer sequence

<400> SEQUENCE: 23
ttgagaagtg ttttattttt gcccttttac tcgtcttcag ggctttaaat tttt    54

<210> SEQ ID NO 24
<211> LENGTH: 52
<212> TYPE: DNA
<213> ORGANISM: Artificial sequence
<220> FEATURE:
<223> OTHER INFORMATION: artificial primer sequence

<400> SEQUENCE: 24
ttgaatggct attagtttta cctcttagtg cggttcattt gattttgcc ct       52

<210> SEQ ID NO 25
<211> LENGTH: 38
<212> TYPE: DNA
<213> ORGANISM: Artificial sequence
<220> FEATURE:
<223> OTHER INFORMATION: artificial primer sequence

<400> SEQUENCE: 25
ttctgtatgg gattttgctt ttttaatttt gcttttgt                      38

<210> SEQ ID NO 26
<211> LENGTH: 36
<212> TYPE: DNA
<213> ORGANISM: Artificial sequence
<220> FEATURE:
<223> OTHER INFORMATION: artificial primer sequence

<400> SEQUENCE: 26
ttctggagca aacaagattg gtcattgcct gagagt                        36

<210> SEQ ID NO 27
<211> LENGTH: 45
<212> TYPE: DNA
<213> ORGANISM: Artificial sequence
<220> FEATURE:
<223> OTHER INFORMATION: artificial primer sequence

<400> SEQUENCE: 27
```

```
ttcgtctttc cagacgttta ggtgaattcg gtcgcttccg tcgat          45
```

<210> SEQ ID NO 28
<211> LENGTH: 61
<212> TYPE: DNA
<213> ORGANISM: Artificial sequence
<220> FEATURE:
<223> OTHER INFORMATION: artificial primer sequence

<400> SEQUENCE: 28

```
ttcgaatttt caggaagttg tcaatctttg aacggtaatc gtttagagat ctttatgacc  60
t                                                                  61
```

<210> SEQ ID NO 29
<211> LENGTH: 40
<212> TYPE: DNA
<213> ORGANISM: Artificial sequence
<220> FEATURE:
<223> OTHER INFORMATION: artificial primer sequence

<400> SEQUENCE: 29

```
ttccagacga ttgtaggtaa aacatgtaat ttatagcttt                        40
```

<210> SEQ ID NO 30
<211> LENGTH: 30
<212> TYPE: DNA
<213> ORGANISM: Artificial sequence
<220> FEATURE:
<223> OTHER INFORMATION: artificial primer sequence

<400> SEQUENCE: 30

```
ttcatatgcg ttatacaaat tttgggttat                                   30
```

<210> SEQ ID NO 31
<211> LENGTH: 42
<212> TYPE: DNA
<213> ORGANISM: Artificial sequence
<220> FEATURE:
<223> OTHER INFORMATION: artificial primer sequence

<400> SEQUENCE: 31

```
ttcaggctgc ttgccagggt tttcccagtc ttgaacgtta tt                     42
```

<210> SEQ ID NO 32
<211> LENGTH: 28
<212> TYPE: DNA
<213> ORGANISM: Artificial sequence
<220> FEATURE:
<223> OTHER INFORMATION: artificial primer sequence

<400> SEQUENCE: 32

```
ttcactgccc gctttccatt ctgaaagt                                     28
```

<210> SEQ ID NO 33
<211> LENGTH: 28
<212> TYPE: DNA
<213> ORGANISM: Artificial sequence
<220> FEATURE:
<223> OTHER INFORMATION: artificial primer sequence

<400> SEQUENCE: 33

```
ttcaagagaa ggattatttg ccatctttt                                     28
```

<210> SEQ ID NO 34
<211> LENGTH: 40

```
<212> TYPE: DNA
<213> ORGANISM: Artificial sequence
<220> FEATURE:
<223> OTHER INFORMATION: artificial primer sequence

<400> SEQUENCE: 34
ttcaaatcac ttatcataat tactagaaat tcaaatccat                           40

<210> SEQ ID NO 35
<211> LENGTH: 53
<212> TYPE: DNA
<213> ORGANISM: Artificial sequence
<220> FEATURE:
<223> OTHER INFORMATION: artificial primer sequence

<400> SEQUENCE: 35
ttcaaaaatt cgattttttg ggaagattta ccgatttcga tctaaagttt tgt           53

<210> SEQ ID NO 36
<211> LENGTH: 40
<212> TYPE: DNA
<213> ORGANISM: Artificial sequence
<220> FEATURE:
<223> OTHER INFORMATION: artificial primer sequence

<400> SEQUENCE: 36
ttcaaaaaag acgctgagat taaaaatcta aaatcatttt                           40

<210> SEQ ID NO 37
<211> LENGTH: 40
<212> TYPE: DNA
<213> ORGANISM: Artificial sequence
<220> FEATURE:
<223> OTHER INFORMATION: artificial primer sequence

<400> SEQUENCE: 37 ttattttttgt taattaatgg tttgaaattt tcttctgact                          40

<210> SEQ ID NO 38
<211> LENGTH: 28
<212> TYPE: DNA
<213> ORGANISM: Artificial sequence
<220> FEATURE:
<223> OTHER INFORMATION: artificial primer sequence

<400> SEQUENCE: 38
ttataactat atgtaaattt aacgccat                                        28

<210> SEQ ID NO 39
<211> LENGTH: 42
<212> TYPE: DNA
<213> ORGANISM: Artificial sequence
<220> FEATURE:
<223> OTHER INFORMATION: artificial primer sequence

<400> SEQUENCE: 39
ttagataata ttccctgcca tctgtaagca ttcaccgcct gt                        42

<210> SEQ ID NO 40
<211> LENGTH: 42
<212> TYPE: DNA
<213> ORGANISM: Artificial sequence
<220> FEATURE:
<223> OTHER INFORMATION: artificial primer sequence

<400> SEQUENCE: 40
```
ttaattttaa ttacgagcac gtataacgtg ttccagaatc ct            42

<210> SEQ ID NO 41
<211> LENGTH: 37
<212> TYPE: DNA
<213> ORGANISM: Artificial sequence
<220> FEATURE:
<223> OTHER INFORMATION: artificial primer sequence

<400> SEQUENCE: 41
ttaattgctt cccagcattt caggccgatt aaagggt                  37

<210> SEQ ID NO 42
<211> LENGTH: 40
<212> TYPE: DNA
<213> ORGANISM: Artificial sequence
<220> FEATURE:
<223> OTHER INFORMATION: artificial primer sequence

<400> SEQUENCE: 42
ttaatgcagt tatatatttt aaatgcaatt ctgtagccat               40

<210> SEQ ID NO 43
<211> LENGTH: 36
<212> TYPE: DNA
<213> ORGANISM: Artificial sequence
<220> FEATURE:
<223> OTHER INFORMATION: artificial primer sequence

<400> SEQUENCE: 43
ttaagtttat tgaaacgcaa agacacgttt accagt                   36

<210> SEQ ID NO 44
<211> LENGTH: 52
<212> TYPE: DNA
<213> ORGANISM: Artificial sequence
<220> FEATURE:
<223> OTHER INFORMATION: artificial primer sequence

<400> SEQUENCE: 44
ttaagaatta gcaaattcca acagttgcgt tttttataag gcttaactaa tt   52

<210> SEQ ID NO 45
<211> LENGTH: 46
<212> TYPE: DNA
<213> ORGANISM: Artificial sequence
<220> FEATURE:
<223> OTHER INFORMATION: artificial primer sequence

<400> SEQUENCE: 45
ttaaacagtt taccaagcgc gaaacaaagt acaatttcga aatcct         46

<210> SEQ ID NO 46
<211> LENGTH: 31
<212> TYPE: DNA
<213> ORGANISM: Artificial sequence
<220> FEATURE:
<223> OTHER INFORMATION: artificial primer sequence

<400> SEQUENCE: 46
ttaaacagga attactatta aagaacgtgg t                        31

<210> SEQ ID NO 47
<211> LENGTH: 46
<212> TYPE: DNA
<213> ORGANISM: Artificial sequence

```
<220> FEATURE:
<223> OTHER INFORMATION: artificial primer sequence

<400> SEQUENCE: 47
tgtttttttt ccatcattcc gcgctttcgg ggaaagccgg cgaact            46

<210> SEQ ID NO 48
<211> LENGTH: 55
<212> TYPE: DNA
<213> ORGANISM: Artificial sequence
<220> FEATURE:
<223> OTHER INFORMATION: artificial primer sequence

<400> SEQUENCE: 48
tgtttgcctt tagcccgttt cgcccacgca taaccgatat attttttct taaat    55

<210> SEQ ID NO 49
<211> LENGTH: 47
<212> TYPE: DNA
<213> ORGANISM: Artificial sequence
<220> FEATURE:
<223> OTHER INFORMATION: artificial primer sequence

<400> SEQUENCE: 49
tgttaaataa ttaaactttt tcaaatatat tttagttttt taatatt            47

<210> SEQ ID NO 50
<211> LENGTH: 61
<212> TYPE: DNA
<213> ORGANISM: Artificial sequence
<220> FEATURE:
<223> OTHER INFORMATION: artificial primer sequence

<400> SEQUENCE: 50
tgtggcgaga aaggattacg ctgcttcata ttctttcaac agttataacc tttcatagcg  60
t                                                                61

<210> SEQ ID NO 51
<211> LENGTH: 51
<212> TYPE: DNA
<213> ORGANISM: Artificial sequence
<220> FEATURE:
<223> OTHER INFORMATION: artificial primer sequence

<400> SEQUENCE: 51
tgtagcgaca ttggctcatt aaaatcacca tttagctatc ttacgaatga t         51

<210> SEQ ID NO 52
<211> LENGTH: 41
<212> TYPE: DNA
<213> ORGANISM: Artificial sequence
<220> FEATURE:
<223> OTHER INFORMATION: artificial primer sequence

<400> SEQUENCE: 52
tggtttaatt tagcaaagcg gattgcatct tcaatactgc t                   41

<210> SEQ ID NO 53
<211> LENGTH: 40
<212> TYPE: DNA
<213> ORGANISM: Artificial sequence
<220> FEATURE:
<223> OTHER INFORMATION: artificial primer sequence

<400> SEQUENCE: 53
```
tggtgtaatt ttcgccatta aaaatacctt cacacgacct                40

<210> SEQ ID NO 54
<211> LENGTH: 42
<212> TYPE: DNA
<213> ORGANISM: Artificial sequence
<220> FEATURE:
<223> OTHER INFORMATION: artificial primer sequence

<400> SEQUENCE: 54
tggtcaataa ttctttcctt atcattccaa tttttgaata ct             42

<210> SEQ ID NO 55
<211> LENGTH: 38
<212> TYPE: DNA
<213> ORGANISM: Artificial sequence
<220> FEATURE:
<223> OTHER INFORMATION: artificial primer sequence

<400> SEQUENCE: 55
tggggccttt tccagtgaga cgggcaactt ccaacgct                  38

<210> SEQ ID NO 56
<211> LENGTH: 55
<212> TYPE: DNA
<213> ORGANISM: Artificial sequence
<220> FEATURE:
<223> OTHER INFORMATION: artificial primer sequence

<400> SEQUENCE: 56
tgggcgcgta ttgaggccac cgagtaaaag agtctgttct tttcattgaa tcggt    55

<210> SEQ ID NO 57
<211> LENGTH: 36
<212> TYPE: DNA
<213> ORGANISM: Artificial sequence
<220> FEATURE:
<223> OTHER INFORMATION: artificial primer sequence

<400> SEQUENCE: 57
tgggcgcaga acaatattac cgccagttcg tctgat                    36

<210> SEQ ID NO 58
<211> LENGTH: 61
<212> TYPE: DNA
<213> ORGANISM: Artificial sequence
<220> FEATURE:
<223> OTHER INFORMATION: artificial primer sequence

<400> SEQUENCE: 58
tggccttctt tgcctgatta aaggcctttt aaacatttaa gactttcaac cgattgaggg    60
t                                                         61

<210> SEQ ID NO 59
<211> LENGTH: 38
<212> TYPE: DNA
<213> ORGANISM: Artificial sequence
<220> FEATURE:
<223> OTHER INFORMATION: artificial primer sequence

<400> SEQUENCE: 59
tggcaaaatt ggaaccgaac tgaccaatta tcaccggt                  38

<210> SEQ ID NO 60
<211> LENGTH: 45

```
<212> TYPE: DNA
<213> ORGANISM: Artificial sequence
<220> FEATURE:
<223> OTHER INFORMATION: artificial primer sequence

<400> SEQUENCE: 60 tggattctttt caagaaatta aatcgcttaa gcgccattcg ccatt            45

<210> SEQ ID NO 61
<211> LENGTH: 46
<212> TYPE: DNA
<213> ORGANISM: Artificial sequence
<220> FEATURE:
<223> OTHER INFORMATION: artificial primer sequence

<400> SEQUENCE: 61
tggattagtt cgggatcgtc accctcagca gcgattaaaa aaaagt           46

<210> SEQ ID NO 62
<211> LENGTH: 42
<212> TYPE: DNA
<213> ORGANISM: Artificial sequence
<220> FEATURE:
<223> OTHER INFORMATION: artificial primer sequence

<400> SEQUENCE: 62
tggataaaaa ttagcgagta acaacccgtc tttttgttaa at              42

<210> SEQ ID NO 63
<211> LENGTH: 52
<212> TYPE: DNA
<213> ORGANISM: Artificial sequence
<220> FEATURE:
<223> OTHER INFORMATION: artificial primer sequence

<400> SEQUENCE: 63
tggacgtttt aagaactttg aatcaattgc cgccattcct gataaattgt gt    52

<210> SEQ ID NO 64
<211> LENGTH: 42
<212> TYPE: DNA
<213> ORGANISM: Artificial sequence
<220> FEATURE:
<223> OTHER INFORMATION: artificial primer sequence

<400> SEQUENCE: 64
tggaatcgtc tttcaaccgt tctagctgat ttaaataagg ct              42

<210> SEQ ID NO 65
<211> LENGTH: 40
<212> TYPE: DNA
<213> ORGANISM: Artificial sequence
<220> FEATURE:
<223> OTHER INFORMATION: artificial primer sequence

<400> SEQUENCE: 65
tgctttcatt ttcagctcat tttttaactt ctcctggttt                 40

<210> SEQ ID NO 66
<211> LENGTH: 61
<212> TYPE: DNA
<213> ORGANISM: Artificial sequence
<220> FEATURE:
<223> OTHER INFORMATION: artificial primer sequence

<400> SEQUENCE: 66
```
tgctggcgaa agggttctc ttcgttttac atcttcgaga acttaaacaa cttaacaaag    60
t                                                                  61

<210> SEQ ID NO 67
<211> LENGTH: 40
<212> TYPE: DNA
<213> ORGANISM: Artificial sequence
<220> FEATURE:
<223> OTHER INFORMATION: artificial primer sequence

<400> SEQUENCE: 67
tgctccaaat tttgagattt aggaatactt tccacggaat                        40

<210> SEQ ID NO 68
<211> LENGTH: 28
<212> TYPE: DNA
<213> ORGANISM: Artificial sequence
<220> FEATURE:
<223> OTHER INFORMATION: artificial primer sequence

<400> SEQUENCE: 68
tgcggggaga ggcggttttt caccagtt                                     28

<210> SEQ ID NO 69
<211> LENGTH: 40
<212> TYPE: DNA
<213> ORGANISM: Artificial sequence
<220> FEATURE:
<223> OTHER INFORMATION: artificial primer sequence

<400> SEQUENCE: 69
tgcgacctgt taccctcaga gccaccactt ttccagagct                        40

<210> SEQ ID NO 70
<211> LENGTH: 45
<212> TYPE: DNA
<213> ORGANISM: Artificial sequence
<220> FEATURE:
<223> OTHER INFORMATION: artificial primer sequence

<400> SEQUENCE: 70
tgcgacattt tccttattac gcagtatgtt agcaattttc attgt                  45

<210> SEQ ID NO 71
<211> LENGTH: 38
<212> TYPE: DNA
<213> ORGANISM: Artificial sequence
<220> FEATURE:
<223> OTHER INFORMATION: artificial primer sequence

<400> SEQUENCE: 71
tgccctgaga ttaacctgtc gtgccagctg cattaatt                          38

<210> SEQ ID NO 72
<211> LENGTH: 38
<212> TYPE: DNA
<213> ORGANISM: Artificial sequence
<220> FEATURE:
<223> OTHER INFORMATION: artificial primer sequence

<400> SEQUENCE: 72
tgcccgtatt gagggttgat ataagtattt ttagcgtt                          38

<210> SEQ ID NO 73
<211> LENGTH: 49

```
<212> TYPE: DNA
<213> ORGANISM: Artificial sequence
<220> FEATURE:
<223> OTHER INFORMATION: artificial primer sequence

<400> SEQUENCE: 73
tgcccaattt gagccagcat accagtcatt agggaaggta aatattgat          49

<210> SEQ ID NO 74
<211> LENGTH: 40
<212> TYPE: DNA
<213> ORGANISM: Artificial sequence
<220> FEATURE:
<223> OTHER INFORMATION: artificial primer sequence

<400> SEQUENCE: 74
tgcagccttt taatatccca tcctaattttt ctgtaatact                   40

<210> SEQ ID NO 75
<211> LENGTH: 40
<212> TYPE: DNA
<213> ORGANISM: Artificial sequence
<220> FEATURE:
<223> OTHER INFORMATION: artificial primer sequence

<400> SEQUENCE: 75
tgcactcatt tgggagaaac aataacggtt aattaccttt                    40

<210> SEQ ID NO 76
<211> LENGTH: 40
<212> TYPE: DNA
<213> ORGANISM: Artificial sequence
<220> FEATURE:
<223> OTHER INFORMATION: artificial primer sequence

<400> SEQUENCE: 76
tgcaaggcga ttttatcatt ttgcggaact tccgctacat                    40

<210> SEQ ID NO 77
<211> LENGTH: 36
<212> TYPE: DNA
<213> ORGANISM: Artificial sequence
<220> FEATURE:
<223> OTHER INFORMATION: artificial primer sequence

<400> SEQUENCE: 77 tgaggggtt aaatatcttg tcaaaaatga aaatat                         36

<210> SEQ ID NO 78
<211> LENGTH: 42
<212> TYPE: DNA
<213> ORGANISM: Artificial sequence
<220> FEATURE:
<223> OTHER INFORMATION: artificial primer sequence

<400> SEQUENCE: 78
tgagccgcca ttaacagcca tattatttat ttcataaaaa ct                 42

<210> SEQ ID NO 79
<211> LENGTH: 41
<212> TYPE: DNA
<213> ORGANISM: Artificial sequence
<220> FEATURE:
<223> OTHER INFORMATION: artificial primer sequence

<400> SEQUENCE: 79
```

```
tgaccccat tgccggaacg aggcgcagat tcctccctca t          41
```

\<210\> SEQ ID NO 80
\<211\> LENGTH: 36
\<212\> TYPE: DNA
\<213\> ORGANISM: Artificial sequence
\<220\> FEATURE:
\<223\> OTHER INFORMATION: artificial primer sequence

\<400\> SEQUENCE: 80

```
tgaatacca aaagaactgg catgatttgt tcagat               36
```

\<210\> SEQ ID NO 81
\<211\> LENGTH: 32
\<212\> TYPE: DNA
\<213\> ORGANISM: Artificial sequence
\<220\> FEATURE:
\<223\> OTHER INFORMATION: artificial primer sequence

\<400\> SEQUENCE: 81

```
tgaatacatt ttctgaaaca tgaaagtatt at                  32
```

\<210\> SEQ ID NO 82
\<211\> LENGTH: 52
\<212\> TYPE: DNA
\<213\> ORGANISM: Artificial sequence
\<220\> FEATURE:
\<223\> OTHER INFORMATION: artificial primer sequence

\<400\> SEQUENCE: 82

```
tgaacgaacc accagttctc cgaattctga cgcttggtta tcttccacca gt    52
```

\<210\> SEQ ID NO 83
\<211\> LENGTH: 52
\<212\> TYPE: DNA
\<213\> ORGANISM: Artificial sequence
\<220\> FEATURE:
\<223\> OTHER INFORMATION: artificial primer sequence

\<400\> SEQUENCE: 83

```
tgaaagattt taaattgttc ccttatttgg aaccgttcgg tcaatcataa gt    52
```

\<210\> SEQ ID NO 84
\<211\> LENGTH: 27
\<212\> TYPE: DNA
\<213\> ORGANISM: Artificial sequence
\<220\> FEATURE:
\<223\> OTHER INFORMATION: artificial primer sequence

\<400\> SEQUENCE: 84

```
tgaaaccaat ttcgaattat tcatttt                        27
```

\<210\> SEQ ID NO 85
\<211\> LENGTH: 34
\<212\> TYPE: DNA
\<213\> ORGANISM: Artificial sequence
\<220\> FEATURE:
\<223\> OTHER INFORMATION: artificial primer sequence

\<400\> SEQUENCE: 85

```
tctttgaaag aggacttaag gcactttgag gaat                34
```

\<210\> SEQ ID NO 86
\<211\> LENGTH: 52
\<212\> TYPE: DNA
\<213\> ORGANISM: Artificial sequence

```
<220> FEATURE:
<223> OTHER INFORMATION: artificial primer sequence

<400> SEQUENCE: 86
tcttgctgtt gcaaatgtta gagtcattgc ttaggttttc ttaccagtat at      52

<210> SEQ ID NO 87
<211> LENGTH: 42
<212> TYPE: DNA
<213> ORGANISM: Artificial sequence
<220> FEATURE:
<223> OTHER INFORMATION: artificial primer sequence

<400> SEQUENCE: 87
tcttaccaac ttgtaattga gcgctaatat ttgtaattct gt                 42

<210> SEQ ID NO 88
<211> LENGTH: 61
<212> TYPE: DNA
<213> ORGANISM: Artificial sequence
<220> FEATURE:
<223> OTHER INFORMATION: artificial primer sequence

<400> SEQUENCE: 88
tctctgactt caataggttg ctgatgttaa gcctgtttag tattgggtga gttgtaatgt   60
t                                                                   61

<210> SEQ ID NO 89
<211> LENGTH: 38
<212> TYPE: DNA
<213> ORGANISM: Artificial sequence
<220> FEATURE:
<223> OTHER INFORMATION: artificial primer sequence

<400> SEQUENCE: 89
tctctatgat tggtccacgc tggtttgctt gttgcgct                      38

<210> SEQ ID NO 90
<211> LENGTH: 52
<212> TYPE: DNA
<213> ORGANISM: Artificial sequence
<220> FEATURE:
<223> OTHER INFORMATION: artificial primer sequence

<400> SEQUENCE: 90
tctcacattt ggaagcattc acaattccac acattaccga gcttgctcgc ct      52

<210> SEQ ID NO 91
<211> LENGTH: 45
<212> TYPE: DNA
<213> ORGANISM: Artificial sequence
<220> FEATURE:
<223> OTHER INFORMATION: artificial primer sequence

<400> SEQUENCE: 91
tctattattt cgggagattc cagttattaa gtacggtgtc tggat              45

<210> SEQ ID NO 92
<211> LENGTH: 36
<212> TYPE: DNA
<213> ORGANISM: Artificial sequence
<220> FEATURE:
<223> OTHER INFORMATION: artificial primer sequence

<400> SEQUENCE: 92
```

-continued tctattacgc agggttagaa cctaccttac ttctgt         36

<210> SEQ ID NO 93
<211> LENGTH: 40
<212> TYPE: DNA
<213> ORGANISM: Artificial sequence
<220> FEATURE:
<223> OTHER INFORMATION: artificial primer sequence

<400> SEQUENCE: 93
tctaatttgt tattaactga cacccctgtt atgttcagct         40

<210> SEQ ID NO 94
<211> LENGTH: 53
<212> TYPE: DNA
<213> ORGANISM: Artificial sequence
<220> FEATURE:
<223> OTHER INFORMATION: artificial primer sequence

<400> SEQUENCE: 94
tctaaataac tagcatttat tgtatttccg taatttttg agcaaaagaa gat         53

<210> SEQ ID NO 95
<211> LENGTH: 38
<212> TYPE: DNA
<213> ORGANISM: Artificial sequence
<220> FEATURE:
<223> OTHER INFORMATION: artificial primer sequence

<400> SEQUENCE: 95
tcggtacgtt ctttcctttg ggcgaaaaac cgtctatt         38

<210> SEQ ID NO 96
<211> LENGTH: 37
<212> TYPE: DNA
<213> ORGANISM: Artificial sequence
<220> FEATURE:
<223> OTHER INFORMATION: artificial primer sequence

<400> SEQUENCE: 96
tcggggtttt cctattattc taaaacactc atctttt         37

<210> SEQ ID NO 97
<211> LENGTH: 28
<212> TYPE: DNA
<213> ORGANISM: Artificial sequence
<220> FEATURE:
<223> OTHER INFORMATION: artificial primer sequence

<400> SEQUENCE: 97
tcggagattt gtgccttgag taacagtt         28

<210> SEQ ID NO 98
<211> LENGTH: 43
<212> TYPE: DNA
<213> ORGANISM: Artificial sequence
<220> FEATURE:
<223> OTHER INFORMATION: artificial primer sequence

<400> SEQUENCE: 98
tcgcgagatt gaataaacac cggattcatc aatttaaccc tct         43

<210> SEQ ID NO 99
<211> LENGTH: 56
<212> TYPE: DNA
<213> ORGANISM: Artificial sequence
<220> FEATURE:
<223> OTHER INFORMATION: artificial primer sequence

<400> SEQUENCE: 99
tcgcgaactg ttccaacaga gatagaaccc ttctgacttg tcgggattga gttgct    56

<210> SEQ ID NO 100
<211> LENGTH: 61
<212> TYPE: DNA
<213> ORGANISM: Artificial sequence
<220> FEATURE:
<223> OTHER INFORMATION: artificial primer sequence

<400> SEQUENCE: 100
tcgacaattt aagcaagttc ccaattctgc gaatttccat atttagcgtc tttcctcaga    60
t    61

<210> SEQ ID NO 101
<211> LENGTH: 30
<212> TYPE: DNA
<213> ORGANISM: Artificial sequence
<220> FEATURE:
<223> OTHER INFORMATION: artificial primer sequence

<400> SEQUENCE: 101
tccttcattt agagtacctt taattgctct    30

<210> SEQ ID NO 102
<211> LENGTH: 52
<212> TYPE: DNA
<213> ORGANISM: Artificial sequence
<220> FEATURE:
<223> OTHER INFORMATION: artificial primer sequence

<400> SEQUENCE: 102
tcctgtttag ctatatttat aatgttcaaa taattcacca cctttagcgt tt    52

<210> SEQ ID NO 103
<211> LENGTH: 61
<212> TYPE: DNA
<213> ORGANISM: Artificial sequence
<220> FEATURE:
<223> OTHER INFORMATION: artificial primer sequence

<400> SEQUENCE: 103
tccgtgggtt gagaagcttt gccggattga ctggatttat aaaattttt gtcacaatca    60 t    61

<210> SEQ ID NO 104
<211> LENGTH: 38
<212> TYPE: DNA
<213> ORGANISM: Artificial sequence
<220> FEATURE:
<223> OTHER INFORMATION: artificial primer sequence

<400> SEQUENCE: 104
tccggaaatt cgacggccag tgccaagtta attcgact    38

<210> SEQ ID NO 105
<211> LENGTH: 45
<212> TYPE: DNA
<213> ORGANISM: Artificial sequence
<220> FEATURE:
<223> OTHER INFORMATION: artificial primer sequence

```
<400> SEQUENCE: 105
tccctcagtt ttcatcgtta taagtgtttg aggcttgcag ggagt            45

<210> SEQ ID NO 106
<211> LENGTH: 47
<212> TYPE: DNA
<213> ORGANISM: Artificial sequence
<220> FEATURE:
<223> OTHER INFORMATION: artificial primer sequence

<400> SEQUENCE: 106
tcccaatctt ctgtagctca acatgtttta aatatttttc gcaaatt          47

<210> SEQ ID NO 107
<211> LENGTH: 47
<212> TYPE: DNA
<213> ORGANISM: Artificial sequence
<220> FEATURE:
<223> OTHER INFORMATION: artificial primer sequence

<400> SEQUENCE: 107
tccataaatt tcagaggttg ctaacgttaa cagttgattt tagcgat          47

<210> SEQ ID NO 108
<211> LENGTH: 42
<212> TYPE: DNA
<213> ORGANISM: Artificial sequence
<220> FEATURE:
<223> OTHER INFORMATION: artificial primer sequence

<400> SEQUENCE: 108
tccaggcggt tgcattttcg gtcatagcct tggcttgaga tt               42

<210> SEQ ID NO 109
<211> LENGTH: 47
<212> TYPE: DNA
<213> ORGANISM: Artificial sequence
<220> FEATURE:
<223> OTHER INFORMATION: artificial primer sequence

<400> SEQUENCE: 109
tccacacccg ttcgcaaatt aaccgttgta gcaatacttg gccttgt          47

<210> SEQ ID NO 110
<211> LENGTH: 61
<212> TYPE: DNA
<213> ORGANISM: Artificial sequence
<220> FEATURE:
<223> OTHER INFORMATION: artificial primer sequence

<400> SEQUENCE: 110
tcattagatt agtcagattt tcaactttta acggattgct ttcgtttagt aaatgaattt   60
t                                                                   61

<210> SEQ ID NO 111
<211> LENGTH: 43
<212> TYPE: DNA
<213> ORGANISM: Artificial sequence
<220> FEATURE:
<223> OTHER INFORMATION: artificial primer sequence

<400> SEQUENCE: 111
tcattacctt catcgatttc agcatttttct tgatattcac aat             43
```

```
<210> SEQ ID NO 112
<211> LENGTH: 34
<212> TYPE: DNA
<213> ORGANISM: Artificial sequence
<220> FEATURE:
<223> OTHER INFORMATION: artificial primer sequence

<400> SEQUENCE: 112
tcatgacaag aaccgttaga cttttcatc ggat                          34

<210> SEQ ID NO 113
<211> LENGTH: 45
<212> TYPE: DNA
<213> ORGANISM: Artificial sequence
<220> FEATURE:
<223> OTHER INFORMATION: artificial primer sequence

<400> SEQUENCE: 113
tcataaaggt ggcaacattt agcgtcttaa aaagattaga ataat             45

<210> SEQ ID NO 114
<211> LENGTH: 40
<212> TYPE: DNA
<213> ORGANISM: Artificial sequence
<220> FEATURE:
<223> OTHER INFORMATION: artificial primer sequence

<400> SEQUENCE: 114
tcagcttgat taaaatctac gttaataatt gacaaaaggt                   40

<210> SEQ ID NO 115
<211> LENGTH: 40
<212> TYPE: DNA
<213> ORGANISM: Artificial sequence
<220> FEATURE:
<223> OTHER INFORMATION: artificial primer sequence

<400> SEQUENCE: 115
tcagactgta ttttgtgaat taccttatgt ttcaggtctt                   40

<210> SEQ ID NO 116
<211> LENGTH: 30
<212> TYPE: DNA
<213> ORGANISM: Artificial sequence
<220> FEATURE:
<223> OTHER INFORMATION: artificial primer sequence

<400> SEQUENCE: 116
tcagaagata aaacagaggt taatggattt                              30

<210> SEQ ID NO 117
<211> LENGTH: 51
<212> TYPE: DNA
<213> ORGANISM: Artificial sequence
<220> FEATURE:
<223> OTHER INFORMATION: artificial primer sequence

<400> SEQUENCE: 117
tcaatttttt ccgccgctta gcagcattag gtttattcac cctcattttc t      51

<210> SEQ ID NO 118
<211> LENGTH: 31
<212> TYPE: DNA
<213> ORGANISM: Artificial sequence
<220> FEATURE:
<223> OTHER INFORMATION: artificial primer sequence
```

-continued

<400> SEQUENCE: 118
tcaattacct gttcggcacc gcttctggtg t							31

<210> SEQ ID NO 119
<211> LENGTH: 42
<212> TYPE: DNA
<213> ORGANISM: Artificial sequence
<220> FEATURE:
<223> OTHER INFORMATION: artificial primer sequence

<400> SEQUENCE: 119
tcaagttaca ttacaaaatt aattacattt ttagccgtca at						42

<210> SEQ ID NO 120
<211> LENGTH: 61
<212> TYPE: DNA
<213> ORGANISM: Artificial sequence
<220> FEATURE:
<223> OTHER INFORMATION: artificial primer sequence

<400> SEQUENCE: 120
tcaactaaat cggaatttgc tttgttaagt ttgttagatt agttaacaat tttaaatgtg		60 t												61

<210> SEQ ID NO 121
<211> LENGTH: 61
<212> TYPE: DNA
<213> ORGANISM: Artificial sequence
<220> FEATURE:
<223> OTHER INFORMATION: artificial primer sequence

<400> SEQUENCE: 121
tattttagac aggaattagc aagctttacc gacttgataa agttgtaaac gttaatttca		60 t												61

<210> SEQ ID NO 122
<211> LENGTH: 41
<212> TYPE: DNA
<213> ORGANISM: Artificial sequence
<220> FEATURE:
<223> OTHER INFORMATION: artificial primer sequence

<400> SEQUENCE: 122
tatttcacat aagcatcact tctggtaata tcccagggtg t					41

<210> SEQ ID NO 123
<211> LENGTH: 51
<212> TYPE: DNA
<213> ORGANISM: Artificial sequence
<220> FEATURE:
<223> OTHER INFORMATION: artificial primer sequence

<400> SEQUENCE: 123
tatttagagc ttgatttaat gcgttaaaga aatttaaaat attgaaacag t				51

<210> SEQ ID NO 124
<211> LENGTH: 28
<212> TYPE: DNA
<213> ORGANISM: Artificial sequence
<220> FEATURE:
<223> OTHER INFORMATION: artificial primer sequence

<400> SEQUENCE: 124
tatttacatt ggcagatttt gcgtattt							28

<210> SEQ ID NO 125
<211> LENGTH: 61
<212> TYPE: DNA
<213> ORGANISM: Artificial sequence
<220> FEATURE:
<223> OTHER INFORMATION: artificial primer sequence

<400> SEQUENCE: 125
tattgtttgg attatttata tcaattaacg tcatttagga atttaggtaa attcagagag    60
t                                                                   61

<210> SEQ ID NO 126
<211> LENGTH: 52
<212> TYPE: DNA
<213> ORGANISM: Artificial sequence
<220> FEATURE:
<223> OTHER INFORMATION: artificial primer sequence

<400> SEQUENCE: 126
tattctggtt atagccctaa aacattgagt aaattggtgg gcttaactaa tt            52

<210> SEQ ID NO 127
<211> LENGTH: 45
<212> TYPE: DNA
<213> ORGANISM: Artificial sequence
<220> FEATURE:
<223> OTHER INFORMATION: artificial primer sequence

<400> SEQUENCE: 127
tattcgcctt tgggaaggg cgatcggtgc gggcttgatg tgctt                     45

<210> SEQ ID NO 128
<211> LENGTH: 42
<212> TYPE: DNA
<213> ORGANISM: Artificial sequence
<220> FEATURE:
<223> OTHER INFORMATION: artificial primer sequence

<400> SEQUENCE: 128
tattcgcatt tttaagctac gtggtgcttg tttctttaat gt                       42

<210> SEQ ID NO 129
<211> LENGTH: 45
<212> TYPE: DNA
<213> ORGANISM: Artificial sequence
<220> FEATURE:
<223> OTHER INFORMATION: artificial primer sequence

<400> SEQUENCE: 129
tatcgcaaga caaagaattt gttaaattca acatttttca tttgt                    45

<210> SEQ ID NO 130
<211> LENGTH: 43
<212> TYPE: DNA
<213> ORGANISM: Artificial sequence
<220> FEATURE:
<223> OTHER INFORMATION: artificial primer sequence

<400> SEQUENCE: 130
tatcctcatc gttccagaac caccaccaga gttatcctga att                      43

<210> SEQ ID NO 131
<211> LENGTH: 59
<212> TYPE: DNA

<213> ORGANISM: Artificial sequence
<220> FEATURE:
<223> OTHER INFORMATION: artificial primer sequence

<400> SEQUENCE: 131
tatagcaatt gtagcacttg gaattattag gaaccttcat tccacagaca gccctcatt    59

<210> SEQ ID NO 132
<211> LENGTH: 40
<212> TYPE: DNA
<213> ORGANISM: Artificial sequence
<220> FEATURE:
<223> OTHER INFORMATION: artificial primer sequence

<400> SEQUENCE: 132
tagtttcatt tcgagtagat ttagtttgtt ccaagtacct    40

<210> SEQ ID NO 133
<211> LENGTH: 33
<212> TYPE: DNA
<213> ORGANISM: Artificial sequence
<220> FEATURE:
<223> OTHER INFORMATION: artificial primer sequence

<400> SEQUENCE: 133
tagttagcgt aattagttgc gccgacaagc aat    33

<210> SEQ ID NO 134
<211> LENGTH: 35
<212> TYPE: DNA
<213> ORGANISM: Artificial sequence
<220> FEATURE:
<223> OTHER INFORMATION: artificial primer sequence

<400> SEQUENCE: 134
tagtaataaa agggacttga atcggttagc tgatt    35

<210> SEQ ID NO 135
<211> LENGTH: 61
<212> TYPE: DNA
<213> ORGANISM: Artificial sequence
<220> FEATURE:
<223> OTHER INFORMATION: artificial primer sequence

<400> SEQUENCE: 135
tagtaacatt ttaagttggg taacttgcaa ctgtttgatt gcttgaacgg gttctgttta    60
t    61

<210> SEQ ID NO 136
<211> LENGTH: 39
<212> TYPE: DNA
<213> ORGANISM: Artificial sequence
<220> FEATURE:
<223> OTHER INFORMATION: artificial primer sequence

<400> SEQUENCE: 136
tagggatatg acaacaacca ttgaataggt tggggtcat    39

<210> SEQ ID NO 137
<211> LENGTH: 42
<212> TYPE: DNA
<213> ORGANISM: Artificial sequence
<220> FEATURE:
<223> OTHER INFORMATION: artificial primer sequence

<400> SEQUENCE: 137
tagggaagcg tttcaacaat agataagtcc tttcaacgca at        42

<210> SEQ ID NO 138
<211> LENGTH: 43
<212> TYPE: DNA
<213> ORGANISM: Artificial sequence
<220> FEATURE:
<223> OTHER INFORMATION: artificial primer sequence

<400> SEQUENCE: 138
taggagaatt agctttctta ggggacttca ggcaaggcaa cgt       43

<210> SEQ ID NO 139
<211> LENGTH: 50
<212> TYPE: DNA
<213> ORGANISM: Artificial sequence
<220> FEATURE:
<223> OTHER INFORMATION: artificial primer sequence

<400> SEQUENCE: 139
tagctgaaaa ggtggttttt gcggttggat tagttcaaga gtaatctaat    50

<210> SEQ ID NO 140
<211> LENGTH: 29
<212> TYPE: DNA
<213> ORGANISM: Artificial sequence
<220> FEATURE:
<223> OTHER INFORMATION: artificial primer sequence

<400> SEQUENCE: 140
tagcgcagtt gagtgtactg gtaataagt                      29

<210> SEQ ID NO 141
<211> LENGTH: 38
<212> TYPE: DNA
<213> ORGANISM: Artificial sequence
<220> FEATURE:
<223> OTHER INFORMATION: artificial primer sequence

<400> SEQUENCE: 141
tagattataa ttcgcgtctt ttacataatt gtaccttt            38

<210> SEQ ID NO 142
<211> LENGTH: 43
<212> TYPE: DNA
<213> ORGANISM: Artificial sequence
<220> FEATURE:
<223> OTHER INFORMATION: artificial primer sequence

<400> SEQUENCE: 142
tagagtcctt aagaatattc ttaagtgtcc tacttctttc tct       43

<210> SEQ ID NO 143
<211> LENGTH: 31
<212> TYPE: DNA
<213> ORGANISM: Artificial sequence
<220> FEATURE:
<223> OTHER INFORMATION: artificial primer sequence

<400> SEQUENCE: 143
tagaggctgc attcaaccta aaacgaaaga t                   31

<210> SEQ ID NO 144
<211> LENGTH: 61
<212> TYPE: DNA

<213> ORGANISM: Artificial sequence
<220> FEATURE:
<223> OTHER INFORMATION: artificial primer sequence

<400> SEQUENCE: 144
tacgacgttg taaaattcca ggcattgcag aggttcaata atttgaaaaa ttttacagag    60
t                                                                    61

<210> SEQ ID NO 145
<211> LENGTH: 40
<212> TYPE: DNA
<213> ORGANISM: Artificial sequence
<220> FEATURE:
<223> OTHER INFORMATION: artificial primer sequence

<400> SEQUENCE: 145
tacctccctt ctaagaacgc gaggcgtttt ccgttttat                            40

<210> SEQ ID NO 146
<211> LENGTH: 52
<212> TYPE: DNA
<213> ORGANISM: Artificial sequence
<220> FEATURE:
<223> OTHER INFORMATION: artificial primer sequence

<400> SEQUENCE: 146
taccgaccgt gtgatttaaa ttaattcttt atttttgaac aattcggctg tt             52

<210> SEQ ID NO 147
<211> LENGTH: 61
<212> TYPE: DNA
<213> ORGANISM: Artificial sequence
<220> FEATURE:
<223> OTHER INFORMATION: artificial primer sequence

<400> SEQUENCE: 147
taatcgcctt gaggcatttc gacaaattca ttaccttgct tatccggtat tttgacttgc    60
t                                                                    61

<210> SEQ ID NO 148
<211> LENGTH: 52
<212> TYPE: DNA
<213> ORGANISM: Artificial sequence
<220> FEATURE:
<223> OTHER INFORMATION: artificial primer sequence

<400> SEQUENCE: 148
tactccaacg tcaaattcgt tagatttaaa tccttggatt tattcaaaca tt             52

<210> SEQ ID NO 149
<211> LENGTH: 38
<212> TYPE: DNA
<213> ORGANISM: Artificial sequence
<220> FEATURE:
<223> OTHER INFORMATION: artificial primer sequence

<400> SEQUENCE: 149
taatcagttt ctatggtttc cctaaaggga gcccccgt                             38

<210> SEQ ID NO 150
<211> LENGTH: 36
<212> TYPE: DNA
<213> ORGANISM: Artificial sequence
<220> FEATURE:
<223> OTHER INFORMATION: artificial primer sequence

<400> SEQUENCE: 150
taatattttt tcgtaagaat acgtggatac gagcct                36

<210> SEQ ID NO 151
<211> LENGTH: 52
<212> TYPE: DNA
<213> ORGANISM: Artificial sequence
<220> FEATURE:
<223> OTHER INFORMATION: artificial primer sequence

<400> SEQUENCE: 151
taatagtgct gaattttctg ccagttggga tagttaaaac attttacaaa gt       52

<210> SEQ ID NO 152
<211> LENGTH: 44
<212> TYPE: DNA
<213> ORGANISM: Artificial sequence
<220> FEATURE:
<223> OTHER INFORMATION: artificial primer sequence

<400> SEQUENCE: 152
taataatgga cattaaggag cggaattatc atttgcgtaa ccat         44

<210> SEQ ID NO 153
<211> LENGTH: 40
<212> TYPE: DNA
<213> ORGANISM: Artificial sequence
<220> FEATURE:
<223> OTHER INFORMATION: artificial primer sequence

<400> SEQUENCE: 153
taagacttct ttaatagtaa aatgtttatt gagggtagct            40

<210> SEQ ID NO 154
<211> LENGTH: 27
<212> TYPE: DNA
<213> ORGANISM: Artificial sequence
<220> FEATURE:
<223> OTHER INFORMATION: artificial primer sequence

<400> SEQUENCE: 154
taactcgtat ttatcagagc gggagct                  27

<210> SEQ ID NO 155
<211> LENGTH: 52
<212> TYPE: DNA
<213> ORGANISM: Artificial sequence
<220> FEATURE:
<223> OTHER INFORMATION: artificial primer sequence

<400> SEQUENCE: 155
taacgcgctt tattaaatta ccattagata catttgcaac tattcaaaat at       52

<210> SEQ ID NO 156
<211> LENGTH: 27
<212> TYPE: DNA
<213> ORGANISM: Artificial sequence
<220> FEATURE:
<223> OTHER INFORMATION: artificial primer sequence

<400> SEQUENCE: 156
taaccagagc ttgaaacgat tttttgt                  27

<210> SEQ ID NO 157

```
<211> LENGTH: 40
<212> TYPE: DNA
<213> ORGANISM: Artificial sequence
<220> FEATURE:
<223> OTHER INFORMATION: artificial primer sequence

<400> SEQUENCE: 157
taaacgacga agcccttttt tacaacgcca gattcaaaat                              40

<210> SEQ ID NO 158
<211> LENGTH: 55
<212> TYPE: DNA
<213> ORGANISM: Artificial sequence
<220> FEATURE:
<223> OTHER INFORMATION: artificial primer sequence

<400> SEQUENCE: 158
tttctttgtt agcggtctta gggaagaaag cgaaaggagc gggcgttttt ttttt            55

<210> SEQ ID NO 159
<211> LENGTH: 39
<212> TYPE: DNA
<213> ORGANISM: Artificial sequence
<220> FEATURE:
<223> OTHER INFORMATION: artificial primer sequence

<400> SEQUENCE: 159
ttgtaccatt gtcacgttgg tgtagatggt ttttttttt                              39

<210> SEQ ID NO 160
<211> LENGTH: 55
<212> TYPE: DNA
<213> ORGANISM: Artificial sequence
<220> FEATURE:
<223> OTHER INFORMATION: artificial primer sequence

<400> SEQUENCE: 160
ttgcttcttt caggttttta attatttgca cgtaaaacag aaatattttt ttttt            55

<210> SEQ ID NO 161
<211> LENGTH: 39
<212> TYPE: DNA
<213> ORGANISM: Artificial sequence
<220> FEATURE:
<223> OTHER INFORMATION: artificial primer sequence

<400> SEQUENCE: 161
ttctaatctt atcctgtttg atggtggttt ttttttttt                              39

<210> SEQ ID NO 162
<211> LENGTH: 39
<212> TYPE: DNA
<213> ORGANISM: Artificial sequence
<220> FEATURE:
<223> OTHER INFORMATION: artificial primer sequence

<400> SEQUENCE: 162
ttcagtgatt aattcgagct tcaaagcgat ttttttttt                              39

<210> SEQ ID NO 163
<211> LENGTH: 30
<212> TYPE: DNA
<213> ORGANISM: Artificial sequence
<220> FEATURE:
<223> OTHER INFORMATION: artificial primer sequence

<400> SEQUENCE: 163
```
tgtttccatt aaacgggtaa tttttttttt                                          30

<210> SEQ ID NO 164
<211> LENGTH: 55
<212> TYPE: DNA
<213> ORGANISM: Artificial sequence
<220> FEATURE:
<223> OTHER INFORMATION: artificial primer sequence

<400> SEQUENCE: 164
tgtaccgctt gatacagttt ctctgaattt accgttccag taagcttttt ttttt            55

<210> SEQ ID NO 165
<211> LENGTH: 39
<212> TYPE: DNA
<213> ORGANISM: Artificial sequence
<220> FEATURE:
<223> OTHER INFORMATION: artificial primer sequence

<400> SEQUENCE: 165
tgaatcgatt atatgtaccc cggttgatat ttttttttt                                39

<210> SEQ ID NO 166
<211> LENGTH: 46
<212> TYPE: DNA
<213> ORGANISM: Artificial sequence
<220> FEATURE:
<223> OTHER INFORMATION: artificial primer sequence

<400> SEQUENCE: 166
tcgttgaatt aatagaaagg aacaactaaa ggaattttt tttttt                          46

<210> SEQ ID NO 167
<211> LENGTH: 39
<212> TYPE: DNA
<213> ORGANISM: Artificial sequence
<220> FEATURE:
<223> OTHER INFORMATION: artificial primer sequence

<400> SEQUENCE: 167
tcgcacgatt gcccgagata gggttgagtt ttttttttt                                39

<210> SEQ ID NO 168
<211> LENGTH: 39
<212> TYPE: DNA
<213> ORGANISM: Artificial sequence
<220> FEATURE:
<223> OTHER INFORMATION: artificial primer sequence

<400> SEQUENCE: 168
tatccgcttt taaagtgtaa agcctggggt ttttttttt                                39

<210> SEQ ID NO 169
<211> LENGTH: 55
<212> TYPE: DNA
<213> ORGANISM: Artificial sequence
<220> FEATURE:
<223> OTHER INFORMATION: artificial primer sequence

<400> SEQUENCE: 169 tataacccctt ccagctattg ggaggttttg aagccttaaa tcagtttttt ttttt            55

<210> SEQ ID NO 170
<211> LENGTH: 39
<212> TYPE: DNA

<213> ORGANISM: Artificial sequence
<220> FEATURE:
<223> OTHER INFORMATION: artificial primer sequence

<400> SEQUENCE: 170
tagagcaatt taaaaaccaa aatagcgagt ttttttttt                                    39

<210> SEQ ID NO 171
<211> LENGTH: 30
<212> TYPE: DNA
<213> ORGANISM: Artificial sequence
<220> FEATURE:
<223> OTHER INFORMATION: artificial primer sequence

<400> SEQUENCE: 171
tacgagggta gcaacggcta ttttttttttt                                             30

<210> SEQ ID NO 172
<211> LENGTH: 39
<212> TYPE: DNA
<213> ORGANISM: Artificial sequence
<220> FEATURE:
<223> OTHER INFORMATION: artificial primer sequence

<400> SEQUENCE: 172
taatcatatt gacgacagta tcggcctcat ttttttttt                                    39

<210> SEQ ID NO 173
<211> LENGTH: 54
<212> TYPE: DNA
<213> ORGANISM: Artificial sequence
<220> FEATURE:
<223> OTHER INFORMATION: artificial primer sequence

<400> SEQUENCE: 173
tttttttttt tggttgtgaa ttcatgtttg gatgttcttc aagtttttt tttt                    54

<210> SEQ ID NO 174
<211> LENGTH: 30
<212> TYPE: DNA
<213> ORGANISM: Artificial sequence
<220> FEATURE:
<223> OTHER INFORMATION: artificial primer sequence

<400> SEQUENCE: 174
tttttttttt tgcctaatga gtgagctaat                                              30

<210> SEQ ID NO 175
<211> LENGTH: 54
<212> TYPE: DNA
<213> ORGANISM: Artificial sequence
<220> FEATURE:
<223> OTHER INFORMATION: artificial primer sequence

<400> SEQUENCE: 175
tttttttttt tcaatatctg gtcagtttaa tatcaaaccc tcaattttt tttt                    54

<210> SEQ ID NO 176
<211> LENGTH: 60
<212> TYPE: DNA
<213> ORGANISM: Artificial sequence
<220> FEATURE:
<223> OTHER INFORMATION: artificial primer sequence

<400> SEQUENCE: 176
tttttttttt taattttccc ttagaatcct tatttatcaa aatcataggt tttttttttt             60

<210> SEQ ID NO 177
<211> LENGTH: 54
<212> TYPE: DNA
<213> ORGANISM: Artificial sequence
<220> FEATURE:
<223> OTHER INFORMATION: artificial primer sequence

<400> SEQUENCE: 177
tttttttttt taacaaagct gctcatttat tacccaaatc aacgtttttt tttt            54

<210> SEQ ID NO 178
<211> LENGTH: 30
<212> TYPE: DNA
<213> ORGANISM: Artificial sequence
<220> FEATURE:
<223> OTHER INFORMATION: artificial primer sequence

<400> SEQUENCE: 178
tttttttttt gttgttccag tttggaacat                                       30

<210> SEQ ID NO 179
<211> LENGTH: 60
<212> TYPE: DNA
<213> ORGANISM: Artificial sequence
<220> FEATURE:
<223> OTHER INFORMATION: artificial primer sequence

<400> SEQUENCE: 179
tttttttttt gtcatacatg gcttttgatt tcaccctcag aaccgccacc tttttttttt      60

<210> SEQ ID NO 180
<211> LENGTH: 54
<212> TYPE: DNA
<213> ORGANISM: Artificial sequence
<220> FEATURE:
<223> OTHER INFORMATION: artificial primer sequence

<400> SEQUENCE: 180
tttttttttt gtagggctta attgagttaa gccaacgctc aacattttt tttt             54

<210> SEQ ID NO 181
<211> LENGTH: 39
<212> TYPE: DNA
<213> ORGANISM: Artificial sequence
<220> FEATURE:
<223> OTHER INFORMATION: artificial primer sequence

<400> SEQUENCE: 181
tttttttttt ggaagatcgc actccagcct tgccagggt                             39

<210> SEQ ID NO 182
<211> LENGTH: 39
<212> TYPE: DNA
<213> ORGANISM: Artificial sequence
<220> FEATURE:
<223> OTHER INFORMATION: artificial primer sequence

<400> SEQUENCE: 182
tttttttttt gcgcatcgta accgtgcatt tgtcaacct                             39

<210> SEQ ID NO 183
<211> LENGTH: 39
<212> TYPE: DNA
<213> ORGANISM: Artificial sequence
<220> FEATURE:

<223> OTHER INFORMATION: artificial primer sequence

<400> SEQUENCE: 183
tttttttttt gcgaataata attttttcat tgcagatat                              39

<210> SEQ ID NO 184
<211> LENGTH: 60
<212> TYPE: DNA
<213> ORGANISM: Artificial sequence
<220> FEATURE:
<223> OTHER INFORMATION: artificial primer sequence

<400> SEQUENCE: 184
tttttttttt gcctgagtag aagaactcat taacaggaaa aacgctcatg tttttttttt       60

<210> SEQ ID NO 185
<211> LENGTH: 54
<212> TYPE: DNA
<213> ORGANISM: Artificial sequence
<220> FEATURE:
<223> OTHER INFORMATION: artificial primer sequence

<400> SEQUENCE: 185
tttttttttt gcattaacat ccaatatttc tactaatagt agtattttttt tttt            54

<210> SEQ ID NO 186
<211> LENGTH: 55
<212> TYPE: DNA
<213> ORGANISM: Artificial sequence
<220> FEATURE:
<223> OTHER INFORMATION: artificial primer sequence

<400> SEQUENCE: 186
tttttttttt gaaataccta cattttgacg ctcaatttcc attgcttaac tatct            55

<210> SEQ ID NO 187
<211> LENGTH: 39
<212> TYPE: DNA
<213> ORGANISM: Artificial sequence
<220> FEATURE:
<223> OTHER INFORMATION: artificial primer sequence

<400> SEQUENCE: 187
tttttttttt cttttgataa gaggtcattt tcatcaatt                              39

<210> SEQ ID NO 188
<211> LENGTH: 55
<212> TYPE: DNA
<213> ORGANISM: Artificial sequence
<220> FEATURE:
<223> OTHER INFORMATION: artificial primer sequence

<400> SEQUENCE: 188
tttttttttt ctgagagact acctttttaa cctccgttat agtgattttg aaaat            55

<210> SEQ ID NO 189
<211> LENGTH: 60
<212> TYPE: DNA
<213> ORGANISM: Artificial sequence
<220> FEATURE:
<223> OTHER INFORMATION: artificial primer sequence

<400> SEQUENCE: 189
tttttttttt ctcagaaccg ccaccctcat tcgtaacact gagtttcgtc tttttttttt       60

```
<210> SEQ ID NO 190
<211> LENGTH: 60
<212> TYPE: DNA
<213> ORGANISM: Artificial sequence
<220> FEATURE:
<223> OTHER INFORMATION: artificial primer sequence

<400> SEQUENCE: 190
tttttttttt ctagggcgct ggcaagtgtt tattagtaat aacatcactt tttttttttt    60

<210> SEQ ID NO 191
<211> LENGTH: 54
<212> TYPE: DNA
<213> ORGANISM: Artificial sequence
<220> FEATURE:
<223> OTHER INFORMATION: artificial primer sequence

<400> SEQUENCE: 191
tttttttttt cgcataggct ggctgattcg gtgtacagac caggttttttt tttt          54

<210> SEQ ID NO 192
<211> LENGTH: 54
<212> TYPE: DNA
<213> ORGANISM: Artificial sequence
<220> FEATURE:
<223> OTHER INFORMATION: artificial primer sequence

<400> SEQUENCE: 192
tttttttttt cctgtgtgaa attgttttat ggtcatagct gttttttttt tttt           54

<210> SEQ ID NO 193
<211> LENGTH: 54
<212> TYPE: DNA
<213> ORGANISM: Artificial sequence
<220> FEATURE:
<223> OTHER INFORMATION: artificial primer sequence

<400> SEQUENCE: 193
tttttttttt ccgtcaccga cttgagttta aaggtgaatt atcatttttt tttt           54

<210> SEQ ID NO 194
<211> LENGTH: 55
<212> TYPE: DNA
<213> ORGANISM: Artificial sequence
<220> FEATURE:
<223> OTHER INFORMATION: artificial primer sequence

<400> SEQUENCE: 194
tttttttttt ccgaaatcgg caaaatccct tataaattgg cgaaatttat ttact          55

<210> SEQ ID NO 195
<211> LENGTH: 55
<212> TYPE: DNA
<213> ORGANISM: Artificial sequence
<220> FEATURE:
<223> OTHER INFORMATION: artificial primer sequence

<400> SEQUENCE: 195
tttttttttt ccagaaggaa accgaggaaa cgcaatttag taagcttcaa tgaat          55

<210> SEQ ID NO 196
<211> LENGTH: 54
<212> TYPE: DNA
<213> ORGANISM: Artificial sequence
<220> FEATURE:
<223> OTHER INFORMATION: artificial primer sequence
```

```
<400> SEQUENCE: 196
tttttttttt ccaaaataac cccgcttttt atgacaatgt cccgttttt tttt          54

<210> SEQ ID NO 197
<211> LENGTH: 54
<212> TYPE: DNA
<213> ORGANISM: Artificial sequence
<220> FEATURE:
<223> OTHER INFORMATION: artificial primer sequence

<400> SEQUENCE: 197
tttttttttt catcaatata atcctgtttc agatgatggc aattttttt tttt          54

<210> SEQ ID NO 198
<211> LENGTH: 54
<212> TYPE: DNA
<213> ORGANISM: Artificial sequence
<220> FEATURE:
<223> OTHER INFORMATION: artificial primer sequence

<400> SEQUENCE: 198
tttttttttt cagtgccacg ctgagatttt aacaccgcct gcaattttt tttt          54

<210> SEQ ID NO 199
<211> LENGTH: 39
<212> TYPE: DNA
<213> ORGANISM: Artificial sequence
<220> FEATURE:
<223> OTHER INFORMATION: artificial primer sequence

<400> SEQUENCE: 199
tttttttttt cagaggcttt gaggactaat tgatattct                          39

<210> SEQ ID NO 200
<211> LENGTH: 60
<212> TYPE: DNA
<213> ORGANISM: Artificial sequence
<220> FEATURE:
<223> OTHER INFORMATION: artificial primer sequence

<400> SEQUENCE: 200
tttttttttt caataataag agcaagaaat tagatagccg aacaaagtta tttttttttt   60

<210> SEQ ID NO 201
<211> LENGTH: 60
<212> TYPE: DNA
<213> ORGANISM: Artificial sequence
<220> FEATURE:
<223> OTHER INFORMATION: artificial primer sequence

<400> SEQUENCE: 201
tttttttttt attagttgct attttgcact tacaagaatt gagttaagcc tttttttttt   60

<210> SEQ ID NO 202
<211> LENGTH: 54
<212> TYPE: DNA
<213> ORGANISM: Artificial sequence
<220> FEATURE:
<223> OTHER INFORMATION: artificial primer sequence

<400> SEQUENCE: 202
tttttttttt attacgaggc atagtattca taacgccaaa aggattttt tttt          54

<210> SEQ ID NO 203
<211> LENGTH: 39
```

```
<212> TYPE: DNA
<213> ORGANISM: Artificial sequence
<220> FEATURE:
<223> OTHER INFORMATION: artificial primer sequence

<400> SEQUENCE: 203
tttttttttt atcagaaaag ccccaaaaat tcgtaatct                    39

<210> SEQ ID NO 204
<211> LENGTH: 54
<212> TYPE: DNA
<213> ORGANISM: Artificial sequence
<220> FEATURE:
<223> OTHER INFORMATION: artificial primer sequence

<400> SEQUENCE: 204
tttttttttt ataaagctaa atcggtttaa taaagcctca gagcttttt tttt    54

<210> SEQ ID NO 205
<211> LENGTH: 54
<212> TYPE: DNA
<213> ORGANISM: Artificial sequence
<220> FEATURE:
<223> OTHER INFORMATION: artificial primer sequence

<400> SEQUENCE: 205
tttttttttt aggtcagacg attggcttga caggaggttg aggcttttt tttt    54

<210> SEQ ID NO 206
<211> LENGTH: 39
<212> TYPE: DNA
<213> ORGANISM: Artificial sequence
<220> FEATURE:
<223> OTHER INFORMATION: artificial primer sequence

<400> SEQUENCE: 206
tttttttttt aggcttttgc aaaagaagtt tgctatcat                    39

<210> SEQ ID NO 207
<211> LENGTH: 54
<212> TYPE: DNA
<213> ORGANISM: Artificial sequence
<220> FEATURE:
<223> OTHER INFORMATION: artificial primer sequence

<400> SEQUENCE: 207
tttttttttt agagaatata aagtactttt tcgagccagt aatatttttt tttt   54

<210> SEQ ID NO 208
<211> LENGTH: 54
<212> TYPE: DNA
<213> ORGANISM: Artificial sequence
<220> FEATURE:
<223> OTHER INFORMATION: artificial primer sequence

<400> SEQUENCE: 208
tttttttttt acgtcaccaa tgaaacttat tagcaaggcc ggaatttttt tttt   54

<210> SEQ ID NO 209
<211> LENGTH: 55
<212> TYPE: DNA
<213> ORGANISM: Artificial sequence
<220> FEATURE:
<223> OTHER INFORMATION: artificial primer sequence

<400> SEQUENCE: 209
```

-continued tttttttttt accagtacaa actacaacgc ctgtagttca tgtacttgag ccact    55

<210> SEQ ID NO 210
<211> LENGTH: 39
<212> TYPE: DNA
<213> ORGANISM: Artificial sequence
<220> FEATURE:
<223> OTHER INFORMATION: artificial primer sequence

<400> SEQUENCE: 210
tttttttttt accagaccgg aagcaaactt tattaagct    39

<210> SEQ ID NO 211
<211> LENGTH: 39
<212> TYPE: DNA
<213> ORGANISM: Artificial sequence
<220> FEATURE:
<223> OTHER INFORMATION: artificial primer sequence

<400> SEQUENCE: 211
tttttttttt aatacgtaat gccactacgt tagatgaat    39

<210> SEQ ID NO 212
<211> LENGTH: 60
<212> TYPE: DNA
<213> ORGANISM: Artificial sequence
<220> FEATURE:
<223> OTHER INFORMATION: artificial primer sequence

<400> SEQUENCE: 212
tttttttttt aagaaattgc gtagattttt tgtaaatcgt cgctattaat tttttttttt    60

<210> SEQ ID NO 213
<211> LENGTH: 54
<212> TYPE: DNA
<213> ORGANISM: Artificial sequence
<220> FEATURE:
<223> OTHER INFORMATION: artificial primer sequence

<400> SEQUENCE: 213
tttttttttt aaatcagata tagaagttgc gcccaatagc aagcttttt tttt    54

<210> SEQ ID NO 214
<211> LENGTH: 43
<212> TYPE: DNA
<213> ORGANISM: Artificial sequence
<220> FEATURE:
<223> OTHER INFORMATION: artificial primer sequence

<400> SEQUENCE: 214
tttcagcgga gtgagttaat ctccttaaga cagttttaga ctt    43

<210> SEQ ID NO 215
<211> LENGTH: 47
<212> TYPE: DNA
<213> ORGANISM: Artificial sequence
<220> FEATURE:
<223> OTHER INFORMATION: artificial primer sequence

<400> SEQUENCE: 215
ttctgtatgg gattttgctt ttttaatttt gcttttgttc ggggttt    47

<210> SEQ ID NO 216
<211> LENGTH: 43
<212> TYPE: DNA
<213> ORGANISM: Artificial sequence

```
<220> FEATURE:
<223> OTHER INFORMATION: artificial primer sequence

<400> SEQUENCE: 216
tgtctttcca gacgtttagg tgaattcggt cgcttccgtc gat           43

<210> SEQ ID NO 217
<211> LENGTH: 52
<212> TYPE: DNA
<213> ORGANISM: Artificial sequence
<220> FEATURE:
<223> OTHER INFORMATION: artificial primer sequence

<400> SEQUENCE: 217
tccctcatag ttagcgtaat tagttgcgcc gacaagtttt tcaagcccaa tt     52

<210> SEQ ID NO 218
<211> LENGTH: 75
<212> TYPE: DNA
<213> ORGANISM: Artificial sequence
<220> FEATURE:
<223> OTHER INFORMATION: artificial primer sequence

<400> SEQUENCE: 218
tgtatcggtt tttttatca gcttttacaa cattattttt ttacaggtat tatagaaatt     60
tttattcata tggtt                                                    75

<210> SEQ ID NO 219
<211> LENGTH: 72
<212> TYPE: DNA
<213> ORGANISM: Artificial sequence
<220> FEATURE:
<223> OTHER INFORMATION: artificial primer sequence

<400> SEQUENCE: 219
ttttcttaaa cttttagct tgattaaaat cttttttacg ttaataattg acaaagggt      60 ttttcgacat tt                                                       72

<210> SEQ ID NO 220
<211> LENGTH: 38
<212> TYPE: DNA
<213> ORGANISM: Artificial sequence
<220> FEATURE:
<223> OTHER INFORMATION: artificial primer sequence

<400> SEQUENCE: 220
tgggatatga caacaaccat tgaataggtt ggggtcat                 38

<210> SEQ ID NO 221
<211> LENGTH: 72
<212> TYPE: DNA
<213> ORGANISM: Artificial sequence
<220> FEATURE:
<223> OTHER INFORMATION: artificial primer sequence

<400> SEQUENCE: 221
tcctcaagag attttagga ttatttgcca tcttttttt tcataatttg acgagaaact      60
ttttaccaga at                                                       72

<210> SEQ ID NO 222
<211> LENGTH: 64
<212> TYPE: DNA
<213> ORGANISM: Artificial sequence
<220> FEATURE:
```

<223> OTHER INFORMATION: artificial primer sequence

<400> SEQUENCE: 222
tggattagtt cgggatcgtc acccttttt cagcagcgat taaaaaaag gttttctcc    60 aaat    64

<210> SEQ ID NO 223
<211> LENGTH: 66
<212> TYPE: DNA
<213> ORGANISM: Artificial sequence
<220> FEATURE:
<223> OTHER INFORMATION: artificial primer sequence

<400> SEQUENCE: 223
tcctattatt ctaaaacact catcttttt ttgaccccca ttgccggaac gagttttgc    60 gcagat    66

<210> SEQ ID NO 224
<211> LENGTH: 77
<212> TYPE: DNA
<213> ORGANISM: Artificial sequence
<220> FEATURE:
<223> OTHER INFORMATION: artificial primer sequence

<400> SEQUENCE: 224
tttaatgccc cctgcctatt tcggaatttt gctcatttt gtaccaggcg gttgcatttt    60
cggttttttc atagcct    77

<210> SEQ ID NO 225
<211> LENGTH: 59
<212> TYPE: DNA
<213> ORGANISM: Artificial sequence
<220> FEATURE:
<223> OTHER INFORMATION: artificial primer sequence

<400> SEQUENCE: 225
ttaaacagtt taccaagcgc gaaacaaagt acaatttcga aattttttcc gcgacctgt    59

<210> SEQ ID NO 226
<211> LENGTH: 77
<212> TYPE: DNA
<213> ORGANISM: Artificial sequence
<220> FEATURE:
<223> OTHER INFORMATION: artificial primer sequence

<400> SEQUENCE: 226
tgagtgtact ggtaataagt tttaactttg tatcactttt tcgtactcag gttccgtaat    60
cagtttttta gcgacat    77

<210> SEQ ID NO 227
<211> LENGTH: 67
<212> TYPE: DNA
<213> ORGANISM: Artificial sequence
<220> FEATURE:
<223> OTHER INFORMATION: artificial primer sequence

<400> SEQUENCE: 227
taaacgaaag aggcaaaatt ggaaccgttt ttaactgacc aattatcacc ggaattttc    60 cagagct    67

<210> SEQ ID NO 228
<211> LENGTH: 56

```
<212> TYPE: DNA
<213> ORGANISM: Artificial sequence
<220> FEATURE:
<223> OTHER INFORMATION: artificial primer sequence

<400> SEQUENCE: 228
tgaatacatt ttctgaaaca tgaattttta gtattaagag gctgcattca acctat          56

<210> SEQ ID NO 229
<211> LENGTH: 64
<212> TYPE: DNA
<213> ORGANISM: Artificial sequence
<220> FEATURE:
<223> OTHER INFORMATION: artificial primer sequence

<400> SEQUENCE: 229
tcggagattt gtgccttgag taactttta gtgcccgtat tgagggttga ttttttataa      60
gtat                                                                   64

<210> SEQ ID NO 230
<211> LENGTH: 82
<212> TYPE: DNA
<213> ORGANISM: Artificial sequence
<220> FEATURE:
<223> OTHER INFORMATION: artificial primer sequence

<400> SEQUENCE: 230
tttgtatcat taaagctttt tcagaatgga attacaaata aatttttcc tcatcgttcc       60 agaaccttt taccaccaga gt                                                82

<210> SEQ ID NO 231
<211> LENGTH: 70
<212> TYPE: DNA
<213> ORGANISM: Artificial sequence
<220> FEATURE:
<223> OTHER INFORMATION: artificial primer sequence

<400> SEQUENCE: 231
tcctcccttt tttcagagcc gccattaaca gccatattat ttatttcata aaattttac      60 agggaagcgt                                                             70

<210> SEQ ID NO 232
<211> LENGTH: 54
<212> TYPE: DNA
<213> ORGANISM: Artificial sequence
<220> FEATURE:
<223> OTHER INFORMATION: artificial primer sequence

<400> SEQUENCE: 232
tccctcagtt ttcatcgtta taagtgtttg aggcttgcag ggagttaaag gcct           54

<210> SEQ ID NO 233
<211> LENGTH: 72
<212> TYPE: DNA
<213> ORGANISM: Artificial sequence
<220> FEATURE:
<223> OTHER INFORMATION: artificial primer sequence

<400> SEQUENCE: 233
taccctcaga gttttccac cacttttcca gattttgcc taatttgtta ttaactgaat       60
ttttcaccct gt                                                          72

<210> SEQ ID NO 234
```

```
<211> LENGTH: 58
<212> TYPE: DNA
<213> ORGANISM: Artificial sequence
<220> FEATURE:
<223> OTHER INFORMATION: artificial primer sequence

<400> SEQUENCE: 234
tcctcagatt gtttgccttt agcccgtttc gcccacgcat aattttccg atatattt        58

<210> SEQ ID NO 235
<211> LENGTH: 72
<212> TYPE: DNA
<213> ORGANISM: Artificial sequence
<220> FEATURE:
<223> OTHER INFORMATION: artificial primer sequence

<400> SEQUENCE: 235
ttttagcgtt tttcagact gtattttgtg aattattttt ccttatgttt caggtctttt      60
ttttaccctg at                                                          72

<210> SEQ ID NO 236
<211> LENGTH: 70
<212> TYPE: DNA
<213> ORGANISM: Artificial sequence
<220> FEATURE:
<223> OTHER INFORMATION: artificial primer sequence

<400> SEQUENCE: 236
tggcttgatt tttgatggtt taatttagca aagcggattg catcttcaat acttttttgc     60
ggaatcgtct                                                             70

<210> SEQ ID NO 237
<211> LENGTH: 52
<212> TYPE: DNA
<213> ORGANISM: Artificial sequence
<220> FEATURE:
<223> OTHER INFORMATION: artificial primer sequence

<400> SEQUENCE: 237
tttaatcatt gcgcgtttta accgccttct ccatgttact tattgcgatt at              52

<210> SEQ ID NO 238
<211> LENGTH: 61
<212> TYPE: DNA
<213> ORGANISM: Artificial sequence
<220> FEATURE:
<223> OTHER INFORMATION: artificial primer sequence

<400> SEQUENCE: 238
tggctcattt ttttaaaatc accatttagc tatcttacga atgaccataa atttcagagg      60
t                                                                      61

<210> SEQ ID NO 239
<211> LENGTH: 52
<212> TYPE: DNA
<213> ORGANISM: Artificial sequence
<220> FEATURE:
<223> OTHER INFORMATION: artificial primer sequence

<400> SEQUENCE: 239
tcattacctt catcgatttc agcattttct tgatattcac aattagcgca gt              52

<210> SEQ ID NO 240
<211> LENGTH: 67
```

<212> TYPE: DNA
<213> ORGANISM: Artificial sequence
<220> FEATURE:
<223> OTHER INFORMATION: artificial primer sequence

<400> SEQUENCE: 240
tttgagattt tttttaggaa tactttccac ggaattttttt aagtttattg aaacgcaaag    60
acacgtt    67

<210> SEQ ID NO 241
<211> LENGTH: 52
<212> TYPE: DNA
<213> ORGANISM: Artificial sequence
<220> FEATURE:
<223> OTHER INFORMATION: artificial primer sequence

<400> SEQUENCE: 241
tgaaagattt taaattgttc ccttatttgg aaccgttcgg tcaatcataa gt    52

<210> SEQ ID NO 242
<211> LENGTH: 52
<212> TYPE: DNA
<213> ORGANISM: Artificial sequence
<220> FEATURE:
<223> OTHER INFORMATION: artificial primer sequence

<400> SEQUENCE: 242
tggacgtttt aagaactttg aatcaattgc cgccattcct gataaattgt gt    52

<210> SEQ ID NO 243
<211> LENGTH: 82
<212> TYPE: DNA
<213> ORGANISM: Artificial sequence
<220> FEATURE:
<223> OTHER INFORMATION: artificial primer sequence

<400> SEQUENCE: 243
tgagccagca ttttttacca gtcattaggg aaggtttttt aaatattgat tgaataccca    60
atttttaaga actggcatga tt    82

<210> SEQ ID NO 244
<211> LENGTH: 58
<212> TYPE: DNA
<213> ORGANISM: Artificial sequence
<220> FEATURE:
<223> OTHER INFORMATION: artificial primer sequence

<400> SEQUENCE: 244
tttaccagtt gaggggtta aatatcttgt caaaaatgaa aatagttttt cagccttt    58

<210> SEQ ID NO 245
<211> LENGTH: 59
<212> TYPE: DNA
<213> ORGANISM: Artificial sequence
<220> FEATURE:
<223> OTHER INFORMATION: artificial primer sequence

<400> SEQUENCE: 245
taaatacata catttttta aggtggcaac atttagcgtc ttaaaaagat tagaataat    59

<210> SEQ ID NO 246
<211> LENGTH: 53
<212> TYPE: DNA
<213> ORGANISM: Artificial sequence
<220> FEATURE:

<223> OTHER INFORMATION: artificial primer sequence

<400> SEQUENCE: 246
tccttattac gcagtatgtt agcaatttc attgttctat tatttcggga gat    53

<210> SEQ ID NO 247
<211> LENGTH: 61
<212> TYPE: DNA
<213> ORGANISM: Artificial sequence
<220> FEATURE:
<223> OTHER INFORMATION: artificial primer sequence

<400> SEQUENCE: 247
ttttgccatt acgacgattc actatcataa cccttcacat tcttttgccc tttcatgaca    60
t    61

<210> SEQ ID NO 248
<211> LENGTH: 72
<212> TYPE: DNA
<213> ORGANISM: Artificial sequence
<220> FEATURE:
<223> OTHER INFORMATION: artificial primer sequence

<400> SEQUENCE: 248
taatccccct cttttaaat gctttggaga cattttgtc aaatcactta tcataattat    60
ttttctagaa at    72

<210> SEQ ID NO 249
<211> LENGTH: 82
<212> TYPE: DNA
<213> ORGANISM: Artificial sequence
<220> FEATURE:
<223> OTHER INFORMATION: artificial primer sequence

<400> SEQUENCE: 249
tgttcagaaa acgacgtttt taagcccttt tttacaacgc cagttttat tcaaatttc    60 atatgctttt tgttatacaa at    82

<210> SEQ ID NO 250
<211> LENGTH: 72
<212> TYPE: DNA
<213> ORGANISM: Artificial sequence
<220> FEATURE:
<223> OTHER INFORMATION: artificial primer sequence

<400> SEQUENCE: 250
tgaagccctt tttgaaagac ttctttaata gtaaattttt atgtttattg agggtatttt    60
tgctattttt gt    72

<210> SEQ ID NO 251
<211> LENGTH: 55
<212> TYPE: DNA
<213> ORGANISM: Artificial sequence
<220> FEATURE:
<223> OTHER INFORMATION: artificial primer sequence

<400> SEQUENCE: 251
tttaagagtt cgagtagttt catcagttag gagccttaaa caactttcaa cagtt    55

<210> SEQ ID NO 252
<211> LENGTH: 52
<212> TYPE: DNA
<213> ORGANISM: Artificial sequence
<220> FEATURE:
<223> OTHER INFORMATION: artificial primer sequence

<400> SEQUENCE: 252
tagtcagatt ttcaactttt aacggattgc tttcgtttag taaatgaatt tt     52

<210> SEQ ID NO 253
<211> LENGTH: 55
<212> TYPE: DNA
<213> ORGANISM: Artificial sequence
<220> FEATURE:
<223> OTHER INFORMATION: artificial primer sequence

<400> SEQUENCE: 253
ttcaaaaatt cgatttttg ggaagattta ccgatttcga tctaaagttt tgtct     55

<210> SEQ ID NO 254
<211> LENGTH: 61
<212> TYPE: DNA
<213> ORGANISM: Artificial sequence
<220> FEATURE:
<223> OTHER INFORMATION: artificial primer sequence

<400> SEQUENCE: 254
tcagagagtt atagcaattg tagcacttgg aattattagg aaccttcatt ccacagacag     60
t     61

<210> SEQ ID NO 255
<211> LENGTH: 57
<212> TYPE: DNA
<213> ORGANISM: Artificial sequence
<220> FEATURE:
<223> OTHER INFORMATION: artificial primer sequence

<400> SEQUENCE: 255
tgaaacgatt ttttttttg tttaacgtca ttatggctta gagcttaatt gctgaat     57

<210> SEQ ID NO 256
<211> LENGTH: 66
<212> TYPE: DNA
<213> ORGANISM: Artificial sequence
<220> FEATURE:
<223> OTHER INFORMATION: artificial primer sequence

<400> SEQUENCE: 256
tcccaatctt ctgtagctca acatttttg ttttaaatat ttttcgcaaa tggttttttc     60
aataat     66

<210> SEQ ID NO 257
<211> LENGTH: 59
<212> TYPE: DNA
<213> ORGANISM: Artificial sequence
<220> FEATURE:
<223> OTHER INFORMATION: artificial primer sequence

<400> SEQUENCE: 257
tccagttatt aagtacggtg tctggaagtt tcatttcgag tagtttttat ttagtttgt     59

<210> SEQ ID NO 258
<211> LENGTH: 66
<212> TYPE: DNA
<213> ORGANISM: Artificial sequence
<220> FEATURE:
<223> OTHER INFORMATION: artificial primer sequence -continued

<400> SEQUENCE: 258
tgctaacgtt aacagttgat tttagttttt cgaacctccc ttctaagaac gcttttgag    60 gcgttt    66

<210> SEQ ID NO 259
<211> LENGTH: 70
<212> TYPE: DNA
<213> ORGANISM: Artificial sequence
<220> FEATURE:
<223> OTHER INFORMATION: artificial primer sequence

<400> SEQUENCE: 259
tatcctgaat cttaccaact tgtaattgat tttgcgcta atatttgtaa ttctgttttt    60
tccagacgat    70

<210> SEQ ID NO 260
<211> LENGTH: 52
<212> TYPE: DNA
<213> ORGANISM: Artificial sequence
<220> FEATURE:
<223> OTHER INFORMATION: artificial primer sequence

<400> SEQUENCE: 260
tcaatttttt ccgccgctta gcagcattag gtttattcac cctcattttc at    52

<210> SEQ ID NO 261
<211> LENGTH: 43
<212> TYPE: DNA
<213> ORGANISM: Artificial sequence
<220> FEATURE:
<223> OTHER INFORMATION: artificial primer sequence

<400> SEQUENCE: 261
ttttgcggtt ggattagttc aagagtaatc taattctttg aat    43

<210> SEQ ID NO 262
<211> LENGTH: 72
<212> TYPE: DNA
<213> ORGANISM: Artificial sequence
<220> FEATURE:
<223> OTHER INFORMATION: artificial primer sequence

<400> SEQUENCE: 262
tttttcattt tttttggggc gcgttagcat gtagattttt aaccaatttc gaattatttt    60
tttcatttca at    72

<210> SEQ ID NO 263
<211> LENGTH: 61
<212> TYPE: DNA
<213> ORGANISM: Artificial sequence
<220> FEATURE:
<223> OTHER INFORMATION: artificial primer sequence

<400> SEQUENCE: 263
tcggctgttt cctgtttagc tatatttata atgttcaaat aattcaccac ctttagcgtt    60
t    61

<210> SEQ ID NO 264
<211> LENGTH: 70
<212> TYPE: DNA
<213> ORGANISM: Artificial sequence
<220> FEATURE:
<223> OTHER INFORMATION: artificial primer sequence

<400> SEQUENCE: 264
tctttccttt tttatcatt ccaattttg ataccaagt tacattacaa aatttttta    60 attacatttt                                                       70

<210> SEQ ID NO 265
<211> LENGTH: 72
<212> TYPE: DNA
<213> ORGANISM: Artificial sequence
<220> FEATURE:
<223> OTHER INFORMATION: artificial primer sequence

<400> SEQUENCE: 265
tccaagtacc gttttcact catttgggag aattttaca ataacggtta attacctttt    60 ttttttaat gt                                                      72

<210> SEQ ID NO 266
<211> LENGTH: 70
<212> TYPE: DNA
<213> ORGANISM: Artificial sequence
<220> FEATURE:
<223> OTHER INFORMATION: artificial primer sequence

<400> SEQUENCE: 266 tccgttttt tttatttc atcgttgatg aatatacagt aacattatca atatttta    60 tgtgagtgat                                                       70

<210> SEQ ID NO 267
<211> LENGTH: 52
<212> TYPE: DNA
<213> ORGANISM: Artificial sequence
<220> FEATURE:
<223> OTHER INFORMATION: artificial primer sequence

<400> SEQUENCE: 267
ttaagaatta gcaaattcca acagttgcgt tttttataag gcttaactaa tt          52

<210> SEQ ID NO 268
<211> LENGTH: 72
<212> TYPE: DNA
<213> ORGANISM: Artificial sequence
<220> FEATURE:
<223> OTHER INFORMATION: artificial primer sequence

<400> SEQUENCE: 268
taatatcctt tttcatccta attttctgta atactttttt tttgcggtta acaaactttt    60
tggcggattg at                                                      72

<210> SEQ ID NO 269
<211> LENGTH: 70
<212> TYPE: DNA
<213> ORGANISM: Artificial sequence
<220> FEATURE:
<223> OTHER INFORMATION: artificial primer sequence

<400> SEQUENCE: 269
ttcaacaata gattttaa gtcctttcaa cgctttttaa ggataaaat tagcgagtaa    60 caacccgtct                                                       70

<210> SEQ ID NO 270
<211> LENGTH: 57
<212> TYPE: DNA

```
<213> ORGANISM: Artificial sequence
<220> FEATURE:
<223> OTHER INFORMATION: artificial primer sequence

<400> SEQUENCE: 270
taacgcgctt tattttttta aattaccatt agatacattt gcaactattc aaaatat        57

<210> SEQ ID NO 271
<211> LENGTH: 72
<212> TYPE: DNA
<213> ORGANISM: Artificial sequence
<220> FEATURE:
<223> OTHER INFORMATION: artificial primer sequence

<400> SEQUENCE: 271
tatgttcatt tttgctaatg cagttatata ttttattttt aatgcaattc tgtagctttt    60
tcagctttca tt                                                         72

<210> SEQ ID NO 272
<211> LENGTH: 61
<212> TYPE: DNA
<213> ORGANISM: Artificial sequence
<220> FEATURE:
<223> OTHER INFORMATION: artificial primer sequence

<400> SEQUENCE: 272 tttttagtt atgatattta taaatattac gtagattta ccagcgccaa attaacgaac       60
t                                                                      61

<210> SEQ ID NO 273
<211> LENGTH: 52
<212> TYPE: DNA
<213> ORGANISM: Artificial sequence
<220> FEATURE:
<223> OTHER INFORMATION: artificial primer sequence

<400> SEQUENCE: 273
ttgcctgatt aaaggccttt taaacattta agactttcaa ccgattgagg gt             52

<210> SEQ ID NO 274
<211> LENGTH: 61
<212> TYPE: DNA
<213> ORGANISM: Artificial sequence
<220> FEATURE:
<223> OTHER INFORMATION: artificial primer sequence

<400> SEQUENCE: 274
tgtaatgttt cgacaattta agcaagttcc caattctgcg aatttccata tttagcgtct    60
t                                                                      61

<210> SEQ ID NO 275
<211> LENGTH: 70
<212> TYPE: DNA
<213> ORGANISM: Artificial sequence
<220> FEATURE:
<223> OTHER INFORMATION: artificial primer sequence

<400> SEQUENCE: 275
tgtaggtaat ttttaacatg taatttatag cttagattat aattcgcgtc ttttacataa    60
ttgtaccttt                                                             70

<210> SEQ ID NO 276
<211> LENGTH: 61
```

```
<212> TYPE: DNA
<213> ORGANISM: Artificial sequence
<220> FEATURE:
<223> OTHER INFORMATION: artificial primer sequence

<400> SEQUENCE: 276
tttaggcatt atatttattt aagaaattaa taacgttcgg aaattattca tttccatttg    60
t                                                                   61

<210> SEQ ID NO 277
<211> LENGTH: 75
<212> TYPE: DNA
<213> ORGANISM: Artificial sequence
<220> FEATURE:
<223> OTHER INFORMATION: artificial primer sequence

<400> SEQUENCE: 277
ttcaaccgtt cttttttagc tgatttaaat aagttttgc gttaaataat taaacttttt    60
catttttaat atatt                                                    75

<210> SEQ ID NO 278
<211> LENGTH: 61
<212> TYPE: DNA
<213> ORGANISM: Artificial sequence
<220> FEATURE:
<223> OTHER INFORMATION: artificial primer sequence

<400> SEQUENCE: 278
taatcgcctt gaggcatttc gacaaattca ttaccttgct tatccggtat tttgacttgc    60
t                                                                   61

<210> SEQ ID NO 279
<211> LENGTH: 68
<212> TYPE: DNA
<213> ORGANISM: Artificial sequence
<220> FEATURE:
<223> OTHER INFORMATION: artificial primer sequence

<400> SEQUENCE: 279
taattaatgg ttttttttga aattttcttc tgacctaaat aactagcatt tattgtattt    60
ccgtaatt                                                            68

<210> SEQ ID NO 280
<211> LENGTH: 52
<212> TYPE: DNA
<213> ORGANISM: Artificial sequence
<220> FEATURE:
<223> OTHER INFORMATION: artificial primer sequence

<400> SEQUENCE: 280
taatttcatt accgaccgtg tgatttaaat taattcttta tttttgaaca at            52

<210> SEQ ID NO 281
<211> LENGTH: 77
<212> TYPE: DNA
<213> ORGANISM: Artificial sequence
<220> FEATURE:
<223> OTHER INFORMATION: artificial primer sequence

<400> SEQUENCE: 281
ttttagtttt ttaatatttg gattctttca agaaattaaa tcgcttaagc gccattcgcc    60
tttttattca ggctgct                                                  77
```

<210> SEQ ID NO 282
<211> LENGTH: 53
<212> TYPE: DNA
<213> ORGANISM: Artificial sequence
<220> FEATURE:
<223> OTHER INFORMATION: artificial primer sequence

<400> SEQUENCE: 282
tcaaatccaa tcgcaagaca aagaatttgt taaattcaac atttttcatt tgt      53

<210> SEQ ID NO 283
<211> LENGTH: 64
<212> TYPE: DNA
<213> ORGANISM: Artificial sequence
<220> FEATURE:
<223> OTHER INFORMATION: artificial primer sequence

<400> SEQUENCE: 283
tttgggttat attttttaac tatatgtaaa tttaacgcca tcaaaaaatt tttgacgctg      60
agat      64

<210> SEQ ID NO 284
<211> LENGTH: 72
<212> TYPE: DNA
<213> ORGANISM: Artificial sequence
<220> FEATURE:
<223> OTHER INFORMATION: artificial primer sequence

<400> SEQUENCE: 284
taagcaaata ttttttttaa attttacgga ggttttatc cccgggttta ccacagacat      60
ttttatattt tt      72

<210> SEQ ID NO 285
<211> LENGTH: 75
<212> TYPE: DNA
<213> ORGANISM: Artificial sequence
<220> FEATURE:
<223> OTHER INFORMATION: artificial primer sequence

<400> SEQUENCE: 285
ttttgttatt tttaaattcg cattttaag ctacgtgttt tgtgcttgt ttctttaatt      60 ttttgcgcga actgt      75

<210> SEQ ID NO 286
<211> LENGTH: 52
<212> TYPE: DNA
<213> ORGANISM: Artificial sequence
<220> FEATURE:
<223> OTHER INFORMATION: artificial primer sequence

<400> SEQUENCE: 286
taaatttttt cgcgagattg aataaacacc ggattcatca atttaaccct ct      52

<210> SEQ ID NO 287
<211> LENGTH: 72
<212> TYPE: DNA
<213> ORGANISM: Artificial sequence
<220> FEATURE:
<223> OTHER INFORMATION: artificial primer sequence

<400> SEQUENCE: 287
ttcagctcat tttttttttt aacttctcct ggttttttg gtgtaatttt cgccattaat      60
ttttaaatac ct      72

<210> SEQ ID NO 288
<211> LENGTH: 61
<212> TYPE: DNA
<213> ORGANISM: Artificial sequence
<220> FEATURE:
<223> OTHER INFORMATION: artificial primer sequence

<400> SEQUENCE: 288
tccgtgggtt gagaagcttt gccggattga ctggatttat aaaatttttt gtcacaatca    60
t                                                                    61

<210> SEQ ID NO 289
<211> LENGTH: 79
<212> TYPE: DNA
<213> ORGANISM: Artificial sequence
<220> FEATURE:
<223> OTHER INFORMATION: artificial primer sequence

<400> SEQUENCE: 289
ttttgagcaa aagaagattt tttgatgaaa ttgaagtatt tttttagact ttacttctgg    60
agtgactttt ttctatgat                                                 79

<210> SEQ ID NO 290
<211> LENGTH: 41
<212> TYPE: DNA
<213> ORGANISM: Artificial sequence
<220> FEATURE:
<223> OTHER INFORMATION: artificial primer sequence

<400> SEQUENCE: 290 tagggpgactt caggcaaggc aacgttagct gaaaaggtgg t                        41

<210> SEQ ID NO 291
<211> LENGTH: 59
<212> TYPE: DNA
<213> ORGANISM: Artificial sequence
<220> FEATURE:
<223> OTHER INFORMATION: artificial primer sequence

<400> SEQUENCE: 291
tttacctgtt cggcaccgct tctggtgccg gaaattcgac ggcttttttca gtgccaagt    59

<210> SEQ ID NO 292
<211> LENGTH: 83
<212> TYPE: DNA
<213> ORGANISM: Artificial sequence
<220> FEATURE:
<223> OTHER INFORMATION: artificial primer sequence

<400> SEQUENCE: 292
tattcgcctt tgggaaggg cgatcggtgc gggcttgatg tgcttttttg caaggcgatt    60
ttatcatttt tttttgcgga act                                            83

<210> SEQ ID NO 293
<211> LENGTH: 82
<212> TYPE: DNA
<213> ORGANISM: Artificial sequence
<220> FEATURE:
<223> OTHER INFORMATION: artificial primer sequence

<400> SEQUENCE: 293
tctattacgc agggtttttt tagaacctac cttacttctg aatttttaa tggacattaa    60

-continued

```
ggagcgtttt tgaattatca tt                                              82

<210> SEQ ID NO 294
<211> LENGTH: 61
<212> TYPE: DNA
<213> ORGANISM: Artificial sequence
<220> FEATURE:
<223> OTHER INFORMATION: artificial primer sequence

<400> SEQUENCE: 294
tacgacgttg taaaattcca ggcattgcag aggttcaata atttgaaaaa ttttacagag     60
t                                                                     61

<210> SEQ ID NO 295
<211> LENGTH: 70
<212> TYPE: DNA
<213> ORGANISM: Artificial sequence
<220> FEATURE:
<223> OTHER INFORMATION: artificial primer sequence

<400> SEQUENCE: 295
tgccagggtt ttttttttccc agtcttgaac gttttttttat taattttaat tacgagcacg    60
tataacgtgt                                                            70

<210> SEQ ID NO 296
<211> LENGTH: 61
<212> TYPE: DNA
<213> ORGANISM: Artificial sequence
<220> FEATURE:
<223> OTHER INFORMATION: artificial primer sequence

<400> SEQUENCE: 296
tttaagttgg gtaacttgca actgtttgat tgcttgaacg ggttctgttt attcattaga     60
t                                                                     61

<210> SEQ ID NO 297
<211> LENGTH: 61
<212> TYPE: DNA
<213> ORGANISM: Artificial sequence
<220> FEATURE:
<223> OTHER INFORMATION: artificial primer sequence

<400> SEQUENCE: 297
tgctggcgaa aggggttctc ttcgttttac atcttcgaga acttaaacaa cttaacaaag     60
t                                                                     61

<210> SEQ ID NO 298
<211> LENGTH: 52
<212> TYPE: DNA
<213> ORGANISM: Artificial sequence
<220> FEATURE:
<223> OTHER INFORMATION: artificial primer sequence

<400> SEQUENCE: 298
tattgtttgg attatttata tcaattaacg tcatttagga atttaggtaa at             52

<210> SEQ ID NO 299
<211> LENGTH: 41
<212> TYPE: DNA
<213> ORGANISM: Artificial sequence
<220> FEATURE:
<223> OTHER INFORMATION: artificial primer sequence

<400> SEQUENCE: 299
```

```
tcttaagtgt cctacttctt tctcaggaga attagctttc t                    41
```

<210> SEQ ID NO 300
<211> LENGTH: 71
<212> TYPE: DNA
<213> ORGANISM: Artificial sequence
<220> FEATURE:
<223> OTHER INFORMATION: artificial primer sequence

<400> SEQUENCE: 300

```
taattcgaca attttctcg tatttatcag agttttcgg gagctaaaca ggaattacta    60
ttaaagaacg t                                                       71
```

<210> SEQ ID NO 301
<211> LENGTH: 52
<212> TYPE: DNA
<213> ORGANISM: Artificial sequence
<220> FEATURE:
<223> OTHER INFORMATION: artificial primer sequence

<400> SEQUENCE: 301

```
taatagtgct gaattttctg ccagttggga tagttaaaac attttacaaa gt          52
```

<210> SEQ ID NO 302
<211> LENGTH: 61
<212> TYPE: DNA
<213> ORGANISM: Artificial sequence
<220> FEATURE:
<223> OTHER INFORMATION: artificial primer sequence

<400> SEQUENCE: 302

```
tagccgtcaa tatttttgat aatattccct gccttttat ctgtaagcat tcaccgcctg   60
t                                                                  61
```

<210> SEQ ID NO 303
<211> LENGTH: 65
<212> TYPE: DNA
<213> ORGANISM: Artificial sequence
<220> FEATURE:
<223> OTHER INFORMATION: artificial primer sequence

<400> SEQUENCE: 303

```
ttctttagtt tttgagcact aacttacgaa tatagttttt gggccttttc cagtgatttt  60
tgact                                                              65
```

<210> SEQ ID NO 304
<211> LENGTH: 77
<212> TYPE: DNA
<213> ORGANISM: Artificial sequence
<220> FEATURE:
<223> OTHER INFORMATION: artificial primer sequence

<400> SEQUENCE: 304

```
tttgaaagga attttttga ggaattattt cacattttt aagcatcact tctggtaata    60
tcccagggtg gtttttt                                                 77
```

<210> SEQ ID NO 305
<211> LENGTH: 61
<212> TYPE: DNA
<213> ORGANISM: Artificial sequence
<220> FEATURE:
<223> OTHER INFORMATION: artificial primer sequence

```
<400> SEQUENCE: 305
tgaatcggtt ctctgacttc aataggttgc tgatgttaag cctgtttagt attgggtgag      60
t                                                                     61

<210> SEQ ID NO 306
<211> LENGTH: 52
<212> TYPE: DNA
<213> ORGANISM: Artificial sequence
<220> FEATURE:
<223> OTHER INFORMATION: artificial primer sequence

<400> SEQUENCE: 306
tcttgctgtt gcaaatgtta gagtcattgc ttaggttttc ttaccagtat at              52

<210> SEQ ID NO 307
<211> LENGTH: 61
<212> TYPE: DNA
<213> ORGANISM: Artificial sequence
<220> FEATURE:
<223> OTHER INFORMATION: artificial primer sequence

<400> SEQUENCE: 307
ttcgaatttt caggaagttg tcaatctttg aacggtaatc gtttagagat ctttatgacc      60
t                                                                     61

<210> SEQ ID NO 308
<211> LENGTH: 74
<212> TYPE: DNA
<213> ORGANISM: Artificial sequence
<220> FEATURE:
<223> OTHER INFORMATION: artificial primer sequence

<400> SEQUENCE: 308
taaaaatcta attttttaatc atttttcaga agatttttta aaacagaggt taatggatta    60 tttttttttac attt                                                      74

<210> SEQ ID NO 309
<211> LENGTH: 34
<212> TYPE: DNA
<213> ORGANISM: Artificial sequence
<220> FEATURE:
<223> OTHER INFORMATION: artificial primer sequence

<400> SEQUENCE: 309
tcacaattcc acacattacc gagcttgctc gcct                                  34

<210> SEQ ID NO 310
<211> LENGTH: 52
<212> TYPE: DNA
<213> ORGANISM: Artificial sequence
<220> FEATURE:
<223> OTHER INFORMATION: artificial primer sequence

<400> SEQUENCE: 310
ttgaggcggt cagtattgcc agcattaacc tcatttggca aattctgatt at              52

<210> SEQ ID NO 311
<211> LENGTH: 53
<212> TYPE: DNA
<213> ORGANISM: Artificial sequence
<220> FEATURE:
<223> OTHER INFORMATION: artificial primer sequence

<400> SEQUENCE: 311
```
tcgtaagaat acgtggatac gagcctttaa ttgcttccca gcatttcagg cct             53

<210> SEQ ID NO 312
<211> LENGTH: 61
<212> TYPE: DNA
<213> ORGANISM: Artificial sequence
<220> FEATURE:
<223> OTHER INFORMATION: artificial primer sequence

<400> SEQUENCE: 312
tctgaaagtt tgaatggcta ttagttttac ctcttagtgc ggttcatttg attttttgccc    60
t                                                                     61

<210> SEQ ID NO 313
<211> LENGTH: 50
<212> TYPE: DNA
<213> ORGANISM: Artificial sequence
<220> FEATURE:
<223> OTHER INFORMATION: artificial primer sequence

<400> SEQUENCE: 313
tccaacagag attttttaga acccttctga cttgtcggga ttgagttgct                50

<210> SEQ ID NO 314
<211> LENGTH: 61
<212> TYPE: DNA
<213> ORGANISM: Artificial sequence
<220> FEATURE:
<223> OTHER INFORMATION: artificial primer sequence

<400> SEQUENCE: 314
tattctggtt atagccctaa aacattgagt aaattggtgg gcttaactaa tttagtaaca    60
t                                                                     61

<210> SEQ ID NO 315
<211> LENGTH: 44
<212> TYPE: DNA
<213> ORGANISM: Artificial sequence
<220> FEATURE:
<223> OTHER INFORMATION: artificial primer sequence

<400> SEQUENCE: 315
tcacacgacc agtaataaaa gggacttgaa tcggttagct gatt                      44

<210> SEQ ID NO 316
<211> LENGTH: 61
<212> TYPE: DNA
<213> ORGANISM: Artificial sequence
<220> FEATURE:
<223> OTHER INFORMATION: artificial primer sequence

<400> SEQUENCE: 316
tcaccagttt gaacgaacca ccagttctcc gaattctgac gcttggttat cttccaccag    60
t                                                                     61

<210> SEQ ID NO 317
<211> LENGTH: 53
<212> TYPE: DNA
<213> ORGANISM: Artificial sequence
<220> FEATURE:
<223> OTHER INFORMATION: artificial primer sequence

<400> SEQUENCE: 317

```
tggcagattt tgcgtattgg gcgcagaaca atattaccgc cagttcgtct gat        53
```

<210> SEQ ID NO 318
<211> LENGTH: 55
<212> TYPE: DNA
<213> ORGANISM: Artificial sequence
<220> FEATURE:
<223> OTHER INFORMATION: artificial primer sequence

<400> SEQUENCE: 318

```
tggtccactt tttgctggtt tgcttgttgc gctcattttt ctgcccgctt tccat     55
```

<210> SEQ ID NO 319
<211> LENGTH: 38
<212> TYPE: DNA
<213> ORGANISM: Artificial sequence
<220> FEATURE:
<223> OTHER INFORMATION: artificial primer sequence

<400> SEQUENCE: 319

```
tgccctgaga ttaacctgtc gtgccagctg cattaatt                        38
```

<210> SEQ ID NO 320
<211> LENGTH: 40
<212> TYPE: DNA
<213> ORGANISM: Artificial sequence
<220> FEATURE:
<223> OTHER INFORMATION: artificial primer sequence

<400> SEQUENCE: 320

```
tgggcaactt ccaacgcgcg tttttgggag aggcggtttt                      40
```

<210> SEQ ID NO 321
<211> LENGTH: 67
<212> TYPE: DNA
<213> ORGANISM: Artificial sequence
<220> FEATURE:
<223> OTHER INFORMATION: artificial primer sequence

<400> SEQUENCE: 321

```
tgattaaagg gttttattt tagacaggaa ttagcaagct ttaccgactt gataaagttg  60
taaacgt                                                          67
```

<210> SEQ ID NO 322
<211> LENGTH: 38
<212> TYPE: DNA
<213> ORGANISM: Artificial sequence
<220> FEATURE:
<223> OTHER INFORMATION: artificial primer sequence

<400> SEQUENCE: 322

```
tcggtacgtt ctttcctttg ggcgaaaaac cgtctatt                        38
```

<210> SEQ ID NO 323
<211> LENGTH: 54
<212> TYPE: DNA
<213> ORGANISM: Artificial sequence
<220> FEATURE:
<223> OTHER INFORMATION: artificial primer sequence

<400> SEQUENCE: 323

```
tccagaatcc tgagaagtgt ttttattttg ccctttact cgtcttcagg gctt       54
```

<210> SEQ ID NO 324
<211> LENGTH: 36

-continued

```
<212> TYPE: DNA
<213> ORGANISM: Artificial sequence
<220> FEATURE:
<223> OTHER INFORMATION: artificial primer sequence

<400> SEQUENCE: 324
taatcagttt ctatggtttc cctaaaggga gcccct                          36

<210> SEQ ID NO 325
<211> LENGTH: 38
<212> TYPE: DNA
<213> ORGANISM: Artificial sequence
<220> FEATURE:
<223> OTHER INFORMATION: artificial primer sequence

<400> SEQUENCE: 325
ttccatcatt ccgcgctttc ggggaaagcc ggcgaact                        38

<210> SEQ ID NO 326
<211> LENGTH: 64
<212> TYPE: DNA
<213> ORGANISM: Artificial sequence
<220> FEATURE:
<223> OTHER INFORMATION: artificial primer sequence

<400> SEQUENCE: 326
tccgctactt tttagggcgc gtattgaggc caccgttttt agtaaaagag tctgttcttt    60
tcat                                                                64

<210> SEQ ID NO 327
<211> LENGTH: 56
<212> TYPE: DNA
<213> ORGANISM: Artificial sequence
<220> FEATURE:
<223> OTHER INFORMATION: artificial primer sequence

<400> SEQUENCE: 327
tgcgtaacca ccacacccgt tcgcaaatta accgttgtag caatacttgg ccttgt        56

<210> SEQ ID NO 328
<211> LENGTH: 55
<212> TYPE: DNA
<213> ORGANISM: Artificial sequence
<220> FEATURE:
<223> OTHER INFORMATION: artificial primer sequence

<400> SEQUENCE: 328
ttggactcca acgtcaaatt cgttagattt aaatccttgg atttattcaa acatt          55

<210> SEQ ID NO 329
<211> LENGTH: 61
<212> TYPE: DNA
<213> ORGANISM: Artificial sequence
<220> FEATURE:
<223> OTHER INFORMATION: artificial primer sequence

<400> SEQUENCE: 329
tcaactaaat cggaatttgc tttgttaagt ttgttagatt agttaacaat tttaaatgtg    60
t                                                                   61

<210> SEQ ID NO 330
<211> LENGTH: 62
<212> TYPE: DNA
<213> ORGANISM: Artificial sequence
<220> FEATURE:
```

-continued

<223> OTHER INFORMATION: artificial primer sequence

<400> SEQUENCE: 330
tcgatttaga gcttgattta atgcgttaaa gaaatttaaa atattgaaac agttggcctt    60
ct    62

<210> SEQ ID NO 331
<211> LENGTH: 61
<212> TYPE: DNA
<213> ORGANISM: Artificial sequence
<220> FEATURE:
<223> OTHER INFORMATION: artificial primer sequence

<400> SEQUENCE: 331
tgtggcgaga aaggattacg ctgcttcata ttctttcaac agttataacc tttcatagcg    60
t    61

<210> SEQ ID NO 332
<211> LENGTH: 56
<212> TYPE: DNA
<213> ORGANISM: Artificial sequence
<220> FEATURE:
<223> OTHER INFORMATION: artificial primer sequence

<400> SEQUENCE: 332 tttttttacca gttttttaca aactacaacg cctgtagttc atgtacttga gccact    56

<210> SEQ ID NO 333
<211> LENGTH: 45
<212> TYPE: DNA
<213> ORGANISM: Artificial sequence
<220> FEATURE:
<223> OTHER INFORMATION: artificial primer sequence

<400> SEQUENCE: 333 tttttttgcga atttttttaat aatttttttt tttcattgca gatat    45

<210> SEQ ID NO 334
<211> LENGTH: 47
<212> TYPE: DNA
<213> ORGANISM: Artificial sequence
<220> FEATURE:
<223> OTHER INFORMATION: artificial primer sequence

<400> SEQUENCE: 334
tcgttgaatt aatagaaagg aacaactaaa gttttttgaat ttttttt    47

<210> SEQ ID NO 335
<211> LENGTH: 67
<212> TYPE: DNA
<213> ORGANISM: Artificial sequence
<220> FEATURE:
<223> OTHER INFORMATION: artificial primer sequence

<400> SEQUENCE: 335 tttttttctca gttttttaacc gccaccctca ttcgtaacat ttttctgagt ttttttttcgt    60 cttttttt    67

<210> SEQ ID NO 336
<211> LENGTH: 45
<212> TYPE: DNA
<213> ORGANISM: Artificial sequence
<220> FEATURE:
<223> OTHER INFORMATION: artificial primer sequence

<400> SEQUENCE: 336 tttttcaga gttttgctt tgattttgg actaattgat attct    45

<210> SEQ ID NO 337
<211> LENGTH: 61
<212> TYPE: DNA
<213> ORGANISM: Artificial sequence
<220> FEATURE:
<223> OTHER INFORMATION: artificial primer sequence

<400> SEQUENCE: 337
tgtaccgctt gatacagttt ctctgaattt accttttgt tccagttttt taagcttttt    60
t    61

<210> SEQ ID NO 338
<211> LENGTH: 67
<212> TYPE: DNA
<213> ORGANISM: Artificial sequence
<220> FEATURE:
<223> OTHER INFORMATION: artificial primer sequence

<400> SEQUENCE: 338 tttttgtca tttttacat ggcttttgat ttcaccctct ttttagaacc gtttttccac    60
cttttt    67

<210> SEQ ID NO 339
<211> LENGTH: 40
<212> TYPE: DNA
<213> ORGANISM: Artificial sequence
<220> FEATURE:
<223> OTHER INFORMATION: artificial primer sequence

<400> SEQUENCE: 339 tttttaata cttttgtaa tgccactacg ttagatgaat    40

<210> SEQ ID NO 340
<211> LENGTH: 61
<212> TYPE: DNA
<213> ORGANISM: Artificial sequence
<220> FEATURE:
<223> OTHER INFORMATION: artificial primer sequence

<400> SEQUENCE: 340
tagaggactt aaggcacttt gaggaagttt ccatttttt aaacgttttt ggtaatttt    60 t    61

<210> SEQ ID NO 341
<211> LENGTH: 56
<212> TYPE: DNA
<213> ORGANISM: Artificial sequence
<220> FEATURE:
<223> OTHER INFORMATION: artificial primer sequence

<400> SEQUENCE: 341 tttttaggt cagactttt gattggcttg acaggatttt tggttgaggc tttttt    56

<210> SEQ ID NO 342
<211> LENGTH: 51
<212> TYPE: DNA
<213> ORGANISM: Artificial sequence
<220> FEATURE:
<223> OTHER INFORMATION: artificial primer sequence

<400> SEQUENCE: 342 tttttcgca taggcttttt tggctgattc ggtgtacaga ccaggttttt t    51

<210> SEQ ID NO 343
<211> LENGTH: 45
<212> TYPE: DNA
<213> ORGANISM: Artificial sequence
<220> FEATURE:
<223> OTHER INFORMATION: artificial primer sequence

<400> SEQUENCE: 343
tccttcattt agagtacttt ttctttaatt tttttgctct ttttt    45

<210> SEQ ID NO 344
<211> LENGTH: 61
<212> TYPE: DNA
<213> ORGANISM: Artificial sequence
<220> FEATURE:
<223> OTHER INFORMATION: artificial primer sequence

<400> SEQUENCE: 344
tagaaccgtt agacttttc atcggaacga gggttttta gcaactttt ggctatttt    60
t    61

<210> SEQ ID NO 345
<211> LENGTH: 56
<212> TYPE: DNA
<213> ORGANISM: Artificial sequence
<220> FEATURE:
<223> OTHER INFORMATION: artificial primer sequence

<400> SEQUENCE: 345 tttttacgt caccattttt atgaaactta ttagcatttt taggccggaa tttttt    56

<210> SEQ ID NO 346
<211> LENGTH: 56
<212> TYPE: DNA
<213> ORGANISM: Artificial sequence
<220> FEATURE:
<223> OTHER INFORMATION: artificial primer sequence

<400> SEQUENCE: 346 ttttttaac aaagcttttt tgctcattta ttacccttt taaatcaacg tttttt    56

<210> SEQ ID NO 347
<211> LENGTH: 45
<212> TYPE: DNA
<213> ORGANISM: Artificial sequence
<220> FEATURE:
<223> OTHER INFORMATION: artificial primer sequence

<400> SEQUENCE: 347
ttcagtgatt aattcgattt ttgcttcaat ttttagcgat ttttt    45

<210> SEQ ID NO 348
<211> LENGTH: 56
<212> TYPE: DNA
<213> ORGANISM: Artificial sequence
<220> FEATURE:
<223> OTHER INFORMATION: artificial primer sequence

<400> SEQUENCE: 348 tttttccgt caccgttttt acttgagttt aaaggttttt tgaattatca tttttt    56

```
<210> SEQ ID NO 349
<211> LENGTH: 51
<212> TYPE: DNA
<213> ORGANISM: Artificial sequence
<220> FEATURE:
<223> OTHER INFORMATION: artificial primer sequence

<400> SEQUENCE: 349 tttttttatta cgaggcatag tattcataac gttttttccaa aaggattttt t          51

<210> SEQ ID NO 350
<211> LENGTH: 40
<212> TYPE: DNA
<213> ORGANISM: Artificial sequence
<220> FEATURE:
<223> OTHER INFORMATION: artificial primer sequence

<400> SEQUENCE: 350
tagagcaatt taaaaaccaa aatatttttg cgagtttttt                         40

<210> SEQ ID NO 351
<211> LENGTH: 61
<212> TYPE: DNA
<213> ORGANISM: Artificial sequence
<220> FEATURE:
<223> OTHER INFORMATION: artificial primer sequence

<400> SEQUENCE: 351 tttttttccag attttttagga aactttttcg aggaaacgca atttagtaag cttcaatgaa  60
t                                                                   61

<210> SEQ ID NO 352
<211> LENGTH: 45
<212> TYPE: DNA
<213> ORGANISM: Artificial sequence
<220> FEATURE:
<223> OTHER INFORMATION: artificial primer sequence

<400> SEQUENCE: 352 tttttttaggc tttttttttg caattttttaa gaagtttgct atcat                  45

<210> SEQ ID NO 353
<211> LENGTH: 67
<212> TYPE: DNA
<213> ORGANISM: Artificial sequence
<220> FEATURE:
<223> OTHER INFORMATION: artificial primer sequence

<400> SEQUENCE: 353 tttttttcaat atttttataa gagcaagaaa ttagatagct ttttcgaaca attttttagtt  60 atttttt                                                             67

<210> SEQ ID NO 354
<211> LENGTH: 45
<212> TYPE: DNA
<213> ORGANISM: Artificial sequence
<220> FEATURE:
<223> OTHER INFORMATION: artificial primer sequence

<400> SEQUENCE: 354 tttttttacca gttttttaccg gaatttttgc aaactttatt aagct                  45

<210> SEQ ID NO 355
<211> LENGTH: 61
<212> TYPE: DNA
```

<213> ORGANISM: Artificial sequence
<220> FEATURE:
<223> OTHER INFORMATION: artificial primer sequence

<400> SEQUENCE: 355

```
tataacccttt ccagctattg ggaggttttg aagttttcc ttaaatttt tcaagttttt      60
t                                                                     61
```

<210> SEQ ID NO 356
<211> LENGTH: 67
<212> TYPE: DNA
<213> ORGANISM: Artificial sequence
<220> FEATURE:
<223> OTHER INFORMATION: artificial primer sequence

<400> SEQUENCE: 356

```
tttttatta gttttttgc tattttgcac ttacaagaat tttttgagt tttttaagc        60
cttttt                                                                67
```

<210> SEQ ID NO 357
<211> LENGTH: 40
<212> TYPE: DNA
<213> ORGANISM: Artificial sequence
<220> FEATURE:
<223> OTHER INFORMATION: artificial primer sequence

<400> SEQUENCE: 357

```
tttttctttt tttttgata agaggtcatt ttcatcaatt                            40
```

<210> SEQ ID NO 358
<211> LENGTH: 56
<212> TYPE: DNA
<213> ORGANISM: Artificial sequence
<220> FEATURE:
<223> OTHER INFORMATION: artificial primer sequence

<400> SEQUENCE: 358

```
tttttaaat cagatttttt atagaagttg cgcccatttt tatagcaagc tttttt         56
```

<210> SEQ ID NO 359
<211> LENGTH: 51
<212> TYPE: DNA
<213> ORGANISM: Artificial sequence
<220> FEATURE:
<223> OTHER INFORMATION: artificial primer sequence

<400> SEQUENCE: 359

```
tttttgcat taacatttt tccaatattt ctactaatag tagtattttt t              51
```

<210> SEQ ID NO 360
<211> LENGTH: 45
<212> TYPE: DNA
<213> ORGANISM: Artificial sequence
<220> FEATURE:
<223> OTHER INFORMATION: artificial primer sequence

<400> SEQUENCE: 360

```
taatcatatt gacgacattt ttgtatcggt ttttcctcat ttttt                    45
```

<210> SEQ ID NO 361
<211> LENGTH: 56
<212> TYPE: DNA
<213> ORGANISM: Artificial sequence
<220> FEATURE:
<223> OTHER INFORMATION: artificial primer sequence

<400> SEQUENCE: 361 tttttagag aatatttttt aaagtactttt ttcgagtttt tccagtaata tttttt         56

<210> SEQ ID NO 362
<211> LENGTH: 56
<212> TYPE: DNA
<213> ORGANISM: Artificial sequence
<220> FEATURE:
<223> OTHER INFORMATION: artificial primer sequence

<400> SEQUENCE: 362 tttttttataa agctatttttt aatcggttta ataaagtttt tcctcagagc tttttt         56

<210> SEQ ID NO 363
<211> LENGTH: 45
<212> TYPE: DNA
<213> ORGANISM: Artificial sequence
<220> FEATURE:
<223> OTHER INFORMATION: artificial primer sequence

<400> SEQUENCE: 363
ttgtaccatt gtcacgtttt tttggtgtat ttttgatggt ttttt                       45

<210> SEQ ID NO 364
<211> LENGTH: 56
<212> TYPE: DNA
<213> ORGANISM: Artificial sequence
<220> FEATURE:
<223> OTHER INFORMATION: artificial primer sequence

<400> SEQUENCE: 364 tttttttgtag ggcttttttt aattgagtta agccaatttt tcgctcaaca tttttt         56

<210> SEQ ID NO 365
<211> LENGTH: 51
<212> TYPE: DNA
<213> ORGANISM: Artificial sequence
<220> FEATURE:
<223> OTHER INFORMATION: artificial primer sequence

<400> SEQUENCE: 365
tttttttctg gagcaaacaa gattggtcat tttttttgcct gagagttttt t              51

<210> SEQ ID NO 366
<211> LENGTH: 40
<212> TYPE: DNA
<213> ORGANISM: Artificial sequence
<220> FEATURE:
<223> OTHER INFORMATION: artificial primer sequence

<400> SEQUENCE: 366
tgaatcgatt atatgtaccc cggttttttt gatatttttt                             40

<210> SEQ ID NO 367
<211> LENGTH: 61
<212> TYPE: DNA
<213> ORGANISM: Artificial sequence
<220> FEATURE:
<223> OTHER INFORMATION: artificial primer sequence

<400> SEQUENCE: 367 tttttttctga gttttagac tactttttct ttttaacctc cgttatagtg attttgaaaa      60
t                                                                       61

```
<210> SEQ ID NO 368
<211> LENGTH: 45
<212> TYPE: DNA
<213> ORGANISM: Artificial sequence
<220> FEATURE:
<223> OTHER INFORMATION: artificial primer sequence

<400> SEQUENCE: 368 tttttatca gttttaaaa gcctttttcc aaaaattcgt aatct              45

<210> SEQ ID NO 369
<211> LENGTH: 67
<212> TYPE: DNA
<213> ORGANISM: Artificial sequence
<220> FEATURE:
<223> OTHER INFORMATION: artificial primer sequence

<400> SEQUENCE: 369
tttttttaat ttttttttcc cttagaatcc ttatttatct tttaaaatc atttttagg   60 tttttt                                                           67

<210> SEQ ID NO 370
<211> LENGTH: 45
<212> TYPE: DNA
<213> ORGANISM: Artificial sequence
<220> FEATURE:
<223> OTHER INFORMATION: artificial primer sequence

<400> SEQUENCE: 370 tttttgcgc atttttcgt aactttttcg tgcatttgtc aacct               45

<210> SEQ ID NO 371
<211> LENGTH: 61
<212> TYPE: DNA
<213> ORGANISM: Artificial sequence
<220> FEATURE:
<223> OTHER INFORMATION: artificial primer sequence

<400> SEQUENCE: 371
ttgcttcttt caggttttta attatttgca cgttttttaa aacagttttt aaatattttt   60
t                                                                 61

<210> SEQ ID NO 372
<211> LENGTH: 67
<212> TYPE: DNA
<213> ORGANISM: Artificial sequence
<220> FEATURE:
<223> OTHER INFORMATION: artificial primer sequence

<400> SEQUENCE: 372 tttttaaga atttttattg cgtagatttt ttgtaaatct ttttgtcgct atttttttaa   60
tttttt                                                           67

<210> SEQ ID NO 373
<211> LENGTH: 40
<212> TYPE: DNA
<213> ORGANISM: Artificial sequence
<220> FEATURE:
<223> OTHER INFORMATION: artificial primer sequence

<400> SEQUENCE: 373 tttttggaa gtttttatcg cactccagcc ttgccagggt            40
```

<210> SEQ ID NO 374
<211> LENGTH: 56
<212> TYPE: DNA
<213> ORGANISM: Artificial sequence
<220> FEATURE:
<223> OTHER INFORMATION: artificial primer sequence

<400> SEQUENCE: 374 tttttcatc aatattttt aatcctgttt cagatgtttt tatggcaatt tttttt          56

<210> SEQ ID NO 375
<211> LENGTH: 51
<212> TYPE: DNA
<213> ORGANISM: Artificial sequence
<220> FEATURE:
<223> OTHER INFORMATION: artificial primer sequence

<400> SEQUENCE: 375
tttttttggt tgtgatttt attcatgttt ggatgttctt ctaagttttt t               51

<210> SEQ ID NO 376
<211> LENGTH: 45
<212> TYPE: DNA
<213> ORGANISM: Artificial sequence
<220> FEATURE:
<223> OTHER INFORMATION: artificial primer sequence

<400> SEQUENCE: 376
tcgcacgatt gcccgagttt ttatagggtt ttttgagtt ttttt                      45

<210> SEQ ID NO 377
<211> LENGTH: 56
<212> TYPE: DNA
<213> ORGANISM: Artificial sequence
<220> FEATURE:
<223> OTHER INFORMATION: artificial primer sequence

<400> SEQUENCE: 377 ttttttcaa tatctttttt ggtcagttta atatcatttt taaccctcaa tttttt          56

<210> SEQ ID NO 378
<211> LENGTH: 56
<212> TYPE: DNA
<213> ORGANISM: Artificial sequence
<220> FEATURE:
<223> OTHER INFORMATION: artificial primer sequence

<400> SEQUENCE: 378 tttttccaa aataatttt ccccgctttt tatgactttt taatgtcccg tttttt           56

<210> SEQ ID NO 379
<211> LENGTH: 45
<212> TYPE: DNA
<213> ORGANISM: Artificial sequence
<220> FEATURE:
<223> OTHER INFORMATION: artificial primer sequence

<400> SEQUENCE: 379
ttctaatctt atcctgtttt ttttgatggt ttttggttt ttttt                      45

<210> SEQ ID NO 380
<211> LENGTH: 56
<212> TYPE: DNA
<213> ORGANISM: Artificial sequence
<220> FEATURE:
<223> OTHER INFORMATION: artificial primer sequence

<400> SEQUENCE: 380 tttttcagt gccactttt gctgagattt taacactttt tcgcctgcaa tttttt    56

<210> SEQ ID NO 381
<211> LENGTH: 51
<212> TYPE: DNA
<213> ORGANISM: Artificial sequence
<220> FEATURE:
<223> OTHER INFORMATION: artificial primer sequence

<400> SEQUENCE: 381
tttttccctg tgtgaaattg ttttatggtc atttttagc tgttttttt t    51

<210> SEQ ID NO 382
<211> LENGTH: 40
<212> TYPE: DNA
<213> ORGANISM: Artificial sequence
<220> FEATURE:
<223> OTHER INFORMATION: artificial primer sequence

<400> SEQUENCE: 382
tatccgcttt taaagtgtaa agccttttt ggggtttttt    40

<210> SEQ ID NO 383
<211> LENGTH: 61
<212> TYPE: DNA
<213> ORGANISM: Artificial sequence
<220> FEATURE:
<223> OTHER INFORMATION: artificial primer sequence

<400> SEQUENCE: 383 tttttgaaa ttttttacct acatttttt ttgacgctca atttccattg cttaactatc    60
t    61

<210> SEQ ID NO 384
<211> LENGTH: 52
<212> TYPE: DNA
<213> ORGANISM: Artificial sequence
<220> FEATURE:
<223> OTHER INFORMATION: artificial primer sequence

<400> SEQUENCE: 384 ttttttgcc ttttttaatg agttttttga gctaactcac atttggaagc at    52

<210> SEQ ID NO 385
<211> LENGTH: 62
<212> TYPE: DNA
<213> ORGANISM: Artificial sequence
<220> FEATURE:
<223> OTHER INFORMATION: artificial primer sequence

<400> SEQUENCE: 385 tttttgcct gttttagta gaagaactca ttaacaggaa aaacgctttt ttcatgtttt    60
tt    62

<210> SEQ ID NO 386
<211> LENGTH: 61
<212> TYPE: DNA
<213> ORGANISM: Artificial sequence
<220> FEATURE:
<223> OTHER INFORMATION: artificial primer sequence

<400> SEQUENCE: 386 tttttccga atttttatcg gcatttttaa atcccttata aattggcgaa atttatttac    60

```
t                                                             61

<210> SEQ ID NO 387
<211> LENGTH: 56
<212> TYPE: DNA
<213> ORGANISM: Artificial sequence
<220> FEATURE:
<223> OTHER INFORMATION: artificial primer sequence

<400> SEQUENCE: 387
tttctttgtt agcggtctta gggaagaaag cgaaaggagc tttttgggcg tttttt      56

<210> SEQ ID NO 388
<211> LENGTH: 62
<212> TYPE: DNA
<213> ORGANISM: Artificial sequence
<220> FEATURE:
<223> OTHER INFORMATION: artificial primer sequence

<400> SEQUENCE: 388 tttttctag gttttgcgc tggcaagtgt ttattagtaa taacattttt tcactttttt    60
tt                                                            62

<210> SEQ ID NO 389
<211> LENGTH: 47
<212> TYPE: DNA
<213> ORGANISM: Artificial sequence
<220> FEATURE:
<223> OTHER INFORMATION: artificial primer sequence

<400> SEQUENCE: 389 tttttgttg ttttttcca gtttggaaca agagtcctta agaatat                47

<210> SEQ ID NO 390
<211> LENGTH: 75
<212> TYPE: DNA
<213> ORGANISM: Artificial sequence
<220> FEATURE:
<223> OTHER INFORMATION: artificial primer sequence

<400> SEQUENCE: 390
tttttttttt gggtttgaga cggttgcgag tttttttttt aaaggttgtc gtgccttgag   60
gatccccggg ttttt                                              75

<210> SEQ ID NO 391
<211> LENGTH: 55
<212> TYPE: DNA
<213> ORGANISM: Artificial sequence
<220> FEATURE:
<223> OTHER INFORMATION: artificial primer sequence

<400> SEQUENCE: 391
tgccgtaaag cactaaattt tttttttcg gaaccttgga aagccggcga ttttt        55

<210> SEQ ID NO 392
<211> LENGTH: 58
<212> TYPE: DNA
<213> ORGANISM: Artificial sequence
<220> FEATURE:
<223> OTHER INFORMATION: artificial primer sequence

<400> SEQUENCE: 392
tgcaaaatct tagcccccgt tgcaggcgaa atcctgttta cgctggtttt gagagagt    58
```

```
<210> SEQ ID NO 393
<211> LENGTH: 50
<212> TYPE: DNA
<213> ORGANISM: Artificial sequence
<220> FEATURE:
<223> OTHER INFORMATION: artificial primer sequence

<400> SEQUENCE: 393
tcgaaatcgt tcctggccct tttgccccat tgagtaaaat ttaacatcat            50

<210> SEQ ID NO 394
<211> LENGTH: 60
<212> TYPE: DNA
<213> ORGANISM: Artificial sequence
<220> FEATURE:
<223> OTHER INFORMATION: artificial primer sequence

<400> SEQUENCE: 394
tttttagcgg tcctttttt tttttttga tggtggttct taatagccct tttgggcgct    60

<210> SEQ ID NO 395
<211> LENGTH: 61
<212> TYPE: DNA
<213> ORGANISM: Artificial sequence
<220> FEATURE:
<223> OTHER INFORMATION: artificial primer sequence

<400> SEQUENCE: 395
tttttacgtg ttgcaacagc tttgagaagt tttttccttt tttttttcag tcacgacgtt    60
t                                                                    61

<210> SEQ ID NO 396
<211> LENGTH: 50
<212> TYPE: DNA
<213> ORGANISM: Artificial sequence
<220> FEATURE:
<223> OTHER INFORMATION: artificial primer sequence

<400> SEQUENCE: 396
tcggccaact tcagggtggt ttgccaagct tgacaggaat tgccggaaat            50

<210> SEQ ID NO 397
<211> LENGTH: 60
<212> TYPE: DNA
<213> ORGANISM: Artificial sequence
<220> FEATURE:
<223> OTHER INFORMATION: artificial primer sequence

<400> SEQUENCE: 397
tgcgcggggt tacgtgcttt tcgccgctat tcagctttct taataggaat tttgcgggat    60

<210> SEQ ID NO 398
<211> LENGTH: 64
<212> TYPE: DNA
<213> ORGANISM: Artificial sequence
<220> FEATURE:
<223> OTHER INFORMATION: artificial primer sequence

<400> SEQUENCE: 398
tagaggcggt tttttttttt ttgcgtattg agtttttttt ttatagggtt gagtttaaag    60
aact                                                                64

<210> SEQ ID NO 399
<211> LENGTH: 80
```

<212> TYPE: DNA
<213> ORGANISM: Artificial sequence
<220> FEATURE:
<223> OTHER INFORMATION: artificial primer sequence

<400> SEQUENCE: 399
tggaaacctt taagggtttt tttttaaga aagcgaaagt tgtcacgctt tagctctttt    60 tttttgaat tcgtaatcat                                                80

<210> SEQ ID NO 400
<211> LENGTH: 60
<212> TYPE: DNA
<213> ORGANISM: Artificial sequence
<220> FEATURE:
<223> OTHER INFORMATION: artificial primer sequence

<400> SEQUENCE: 400
tttgcgttgt taatgagtgt ttaaagtgtt taattgttat taggaagatt tgataatcat    60

<210> SEQ ID NO 401
<211> LENGTH: 48
<212> TYPE: DNA
<213> ORGANISM: Artificial sequence
<220> FEATURE:
<223> OTHER INFORMATION: artificial primer sequence

<400> SEQUENCE: 401
tgctagggct tgaaaaacct taacaagagt ccactatttt gttgttct                 48

<210> SEQ ID NO 402
<211> LENGTH: 50
<212> TYPE: DNA
<213> ORGANISM: Artificial sequence
<220> FEATURE:
<223> OTHER INFORMATION: artificial primer sequence

<400> SEQUENCE: 402
tgggtgcctt tcgctcactt tgcttaatgt tttgcatgct tggtcacgtt               50

<210> SEQ ID NO 403
<211> LENGTH: 79
<212> TYPE: DNA
<213> ORGANISM: Artificial sequence
<220> FEATURE:
<223> OTHER INFORMATION: artificial primer sequence

<400> SEQUENCE: 403
tttttaactt tcgcgtcttt ttttttttga aatggatttc accatcttaa ctgttttttt    60
tttatagctt aaacattat                                                79

<210> SEQ ID NO 404
<211> LENGTH: 78
<212> TYPE: DNA
<213> ORGANISM: Artificial sequence
<220> FEATURE:
<223> OTHER INFORMATION: artificial primer sequence

<400> SEQUENCE: 404
tcgactctat tagctgcatt ttccagtcgt tcgtgaacct tgtctatcat tgggcgatgt    60 ttttttttg cccactat                                                  78

<210> SEQ ID NO 405
<211> LENGTH: 71
<212> TYPE: DNA

<213> ORGANISM: Artificial sequence
<220> FEATURE:
<223> OTHER INFORMATION: artificial primer sequence

<400> SEQUENCE: 405 tttttttaccg ttgcgcgtaa ttacaacccg ttaaattttt tttaaaaatt ttctgagtaa    60
tttttaatca t                                                          71

<210> SEQ ID NO 406
<211> LENGTH: 58
<212> TYPE: DNA
<213> ORGANISM: Artificial sequence
<220> FEATURE:
<223> OTHER INFORMATION: artificial primer sequence

<400> SEQUENCE: 406
tcccgccgct tgcccgcttt ttaatgaatt tcagtttggt tccttataaa tcaaaagt       58

<210> SEQ ID NO 407
<211> LENGTH: 82
<212> TYPE: DNA
<213> ORGANISM: Artificial sequence
<220> FEATURE:
<223> OTHER INFORMATION: artificial primer sequence

<400> SEQUENCE: 407
tcagggcgct tcggaagcat tagctaactt tttttttttc acattaattg tgttttttt      60 ttgactccaa cgtcaaaggg ct                                              82

<210> SEQ ID NO 408
<211> LENGTH: 60
<212> TYPE: DNA
<213> ORGANISM: Artificial sequence
<220> FEATURE:
<223> OTHER INFORMATION: artificial primer sequence

<400> SEQUENCE: 408 tggatttat ttcctcgttt tcgtgcatct ttggtgtagt tcaccagcat tctcagagct      60

<210> SEQ ID NO 409
<211> LENGTH: 50
<212> TYPE: DNA
<213> ORGANISM: Artificial sequence
<220> FEATURE:
<223> OTHER INFORMATION: artificial primer sequence

<400> SEQUENCE: 409
taggaggcct tcaaattaac cgtttttttt ttttgttcag ccatttttt                 50

<210> SEQ ID NO 410
<211> LENGTH: 57
<212> TYPE: DNA
<213> ORGANISM: Artificial sequence
<220> FEATURE:
<223> OTHER INFORMATION: artificial primer sequence

<400> SEQUENCE: 410
tttttaactt cagaggaatt ttttttttaa acgctcttca tcacctttca ttagatt        57

<210> SEQ ID NO 411
<211> LENGTH: 50
<212> TYPE: DNA
<213> ORGANISM: Artificial sequence
<220> FEATURE:
<223> OTHER INFORMATION: artificial primer sequence

<400> SEQUENCE: 411
tagtagaagt tgttgggtaa cgccttttt ttttagggtt tgtttttatt                50

<210> SEQ ID NO 412
<211> LENGTH: 68
<212> TYPE: DNA
<213> ORGANISM: Artificial sequence
<220> FEATURE:
<223> OTHER INFORMATION: artificial primer sequence

<400> SEQUENCE: 412
tcttctttga ttagtaattg agtctgtttg ggcgatcttc caggcaattc aataaccttc   60
agcagcat                                                            68

<210> SEQ ID NO 413
<211> LENGTH: 48
<212> TYPE: DNA
<213> ORGANISM: Artificial sequence
<220> FEATURE:
<223> OTHER INFORMATION: artificial primer sequence

<400> SEQUENCE: 413
tcgaaagggt ttacggtgtt tcatgttttt tgcggatggc ttagagct                48

<210> SEQ ID NO 414
<211> LENGTH: 60
<212> TYPE: DNA
<213> ORGANISM: Artificial sequence
<220> FEATURE:
<223> OTHER INFORMATION: artificial primer sequence

<400> SEQUENCE: 414
tccagctggt tcagctttct tgcgcgagct taacaccgct ttcctgattt ttagaacctt   60

<210> SEQ ID NO 415
<211> LENGTH: 82
<212> TYPE: DNA
<213> ORGANISM: Artificial sequence
<220> FEATURE:
<223> OTHER INFORMATION: artificial primer sequence

<400> SEQUENCE: 415
tctattacgt taatcagtgt tcagaatcct ttgattgcct tttcaccagt tgtcgaggtt   60
tatcacccaa atcaagtttt tt                                            82

<210> SEQ ID NO 416
<211> LENGTH: 58
<212> TYPE: DNA
<213> ORGANISM: Artificial sequence
<220> FEATURE:
<223> OTHER INFORMATION: artificial primer sequence

<400> SEQUENCE: 416
tggtgcgggt tgttgattct tgaaggttat tctttaggag cactaacttg ttttagct    58

<210> SEQ ID NO 417
<211> LENGTH: 54
<212> TYPE: DNA
<213> ORGANISM: Artificial sequence
<220> FEATURE:
<223> OTHER INFORMATION: artificial primer sequence

<400> SEQUENCE: 417
tttttgcaac ttgctagttt gacttatatc ttttttttttt tggtcagttg gcat    54

<210> SEQ ID NO 418
<211> LENGTH: 48
<212> TYPE: DNA
<213> ORGANISM: Artificial sequence
<220> FEATURE:
<223> OTHER INFORMATION: artificial primer sequence

<400> SEQUENCE: 418
tcttgctggt aatatccttg aattgagttc caattcttta ggtcaggt    48

<210> SEQ ID NO 419
<211> LENGTH: 54
<212> TYPE: DNA
<213> ORGANISM: Artificial sequence
<220> FEATURE:
<223> OTHER INFORMATION: artificial primer sequence

<400> SEQUENCE: 419
tagaacaatt tgttgggaat tccatcacgt tgattaaagt tttgcagcat tttt    54

<210> SEQ ID NO 420
<211> LENGTH: 60
<212> TYPE: DNA
<213> ORGANISM: Artificial sequence
<220> FEATURE:
<223> OTHER INFORMATION: artificial primer sequence

<400> SEQUENCE: 420
tgtatcggct tcggcggatt ttcagtattt tggcaaagat tgatgatgat tttaacaatt    60

<210> SEQ ID NO 421
<211> LENGTH: 50
<212> TYPE: DNA
<213> ORGANISM: Artificial sequence
<220> FEATURE:
<223> OTHER INFORMATION: artificial primer sequence

<400> SEQUENCE: 421
ttgccagttt tctgagagct ttgtttagct tattgcatct tattagagat    50

<210> SEQ ID NO 422
<211> LENGTH: 58
<212> TYPE: DNA
<213> ORGANISM: Artificial sequence
<220> FEATURE:
<223> OTHER INFORMATION: artificial primer sequence

<400> SEQUENCE: 422
tcttctggtt tcggtacgct taggccacct tatttagagc ttgacggttc taaagggt    58

<210> SEQ ID NO 423
<211> LENGTH: 60
<212> TYPE: DNA
<213> ORGANISM: Artificial sequence
<220> FEATURE:
<223> OTHER INFORMATION: artificial primer sequence

<400> SEQUENCE: 423
ttaaatgtgt tatgggatat tctgcaggtt tacggccagt tttttctttt tcttcaccgt    60

<210> SEQ ID NO 424
<211> LENGTH: 60
<212> TYPE: DNA
<213> ORGANISM: Artificial sequence

```
<220> FEATURE:
<223> OTHER INFORMATION: artificial primer sequence

<400> SEQUENCE: 424
tatcaacatt taataaagct tgaagataat tttgcacgtt tgatgatggt tcatcggaat    60

<210> SEQ ID NO 425
<211> LENGTH: 74
<212> TYPE: DNA
<213> ORGANISM: Artificial sequence
<220> FEATURE:
<223> OTHER INFORMATION: artificial primer sequence

<400> SEQUENCE: 425 tttttcaat tcgttgtac caattcctaa tttttttttt aacatcgcca ttattagatt    60
ttcttgagcg gaat                                                    74

<210> SEQ ID NO 426
<211> LENGTH: 56
<212> TYPE: DNA
<213> ORGANISM: Artificial sequence
<220> FEATURE:
<223> OTHER INFORMATION: artificial primer sequence

<400> SEQUENCE: 426
tttatttttt ttttaaattc gcattttcg gattcttaca ggcaatttag cattat       56

<210> SEQ ID NO 427
<211> LENGTH: 68
<212> TYPE: DNA
<213> ORGANISM: Artificial sequence
<220> FEATURE:
<223> OTHER INFORMATION: artificial primer sequence

<400> SEQUENCE: 427
taaacgttat taaactagct tttgagagat ttctggagct ttcattgaat cccctcttg    60 aatcgtct                                                           68

<210> SEQ ID NO 428
<211> LENGTH: 56
<212> TYPE: DNA
<213> ORGANISM: Artificial sequence
<220> FEATURE:
<223> OTHER INFORMATION: artificial primer sequence

<400> SEQUENCE: 428
ttaaattgtt ttggtcatag ctgtttcctg tgtgattaaa gcctgttttt taacct      56

<210> SEQ ID NO 429
<211> LENGTH: 60
<212> TYPE: DNA
<213> ORGANISM: Artificial sequence
<220> FEATURE:
<223> OTHER INFORMATION: artificial primer sequence

<400> SEQUENCE: 429
ttgtataagt tcaaaagggt tgaagccttt ttttttaatt tatttcaatt tcatatgcgt    60

<210> SEQ ID NO 430
<211> LENGTH: 45
<212> TYPE: DNA
<213> ORGANISM: Artificial sequence
<220> FEATURE:
<223> OTHER INFORMATION: artificial primer sequence
```

<400> SEQUENCE: 430
tcgccatcat tccaaaaact ttccgctcac aattccacac ttttt                45

<210> SEQ ID NO 431
<211> LENGTH: 60
<212> TYPE: DNA
<213> ORGANISM: Artificial sequence
<220> FEATURE:
<223> OTHER INFORMATION: artificial primer sequence

<400> SEQUENCE: 431
taaaataatt tatacgagct tgtactatgg ttttttttt ttgcttttt gacgcttttt      60

<210> SEQ ID NO 432
<211> LENGTH: 44
<212> TYPE: DNA
<213> ORGANISM: Artificial sequence
<220> FEATURE:
<223> OTHER INFORMATION: artificial primer sequence

<400> SEQUENCE: 432
ttctggccaa cagttatacg tggtttaatg ccgttgggaa gaat                 44

<210> SEQ ID NO 433
<211> LENGTH: 49
<212> TYPE: DNA
<213> ORGANISM: Artificial sequence
<220> FEATURE:
<223> OTHER INFORMATION: artificial primer sequence

<400> SEQUENCE: 433
ttctacaaat taagaactgt tttgtgaatt accttattta gaaattttt            49

<210> SEQ ID NO 434
<211> LENGTH: 58
<212> TYPE: DNA
<213> ORGANISM: Artificial sequence
<220> FEATURE:
<223> OTHER INFORMATION: artificial primer sequence

<400> SEQUENCE: 434
tagctatttt tatgtcaatt tcccttctgt taaacaagag aatcgatttc ctgagagt     58

<210> SEQ ID NO 435
<211> LENGTH: 50
<212> TYPE: DNA
<213> ORGANISM: Artificial sequence
<220> FEATURE:
<223> OTHER INFORMATION: artificial primer sequence

<400> SEQUENCE: 435
tgagagggtt ttaaagattt tcaaatattt tagctcattt tgctggcaat              50

<210> SEQ ID NO 436
<211> LENGTH: 38
<212> TYPE: DNA
<213> ORGANISM: Artificial sequence
<220> FEATURE:
<223> OTHER INFORMATION: artificial primer sequence

<400> SEQUENCE: 436
ttgataaatt tcacagacat tccacattca actaatgt                          38

<210> SEQ ID NO 437
<211> LENGTH: 60

```
<212> TYPE: DNA
<213> ORGANISM: Artificial sequence
<220> FEATURE:
<223> OTHER INFORMATION: artificial primer sequence

<400> SEQUENCE: 437
tttttggtca ttgttgaatt ttttttttcg gtaatcgtat tatattttgt ttgcaatgct    60

<210> SEQ ID NO 438
<211> LENGTH: 64
<212> TYPE: DNA
<213> ORGANISM: Artificial sequence
<220> FEATURE:
<223> OTHER INFORMATION: artificial primer sequence

<400> SEQUENCE: 438
tatatttttg aatggcttta ccagtaatta ttggcagatt caccattttt tttttgtcac    60
acgt                                                                 64

<210> SEQ ID NO 439
<211> LENGTH: 68
<212> TYPE: DNA
<213> ORGANISM: Artificial sequence
<220> FEATURE:
<223> OTHER INFORMATION: artificial primer sequence

<400> SEQUENCE: 439
tattagtctt taatttttttt ttttgcgcgt taatatgatt taacggaact ttgacgagaa   60
acaccagt                                                             68

<210> SEQ ID NO 440
<211> LENGTH: 55
<212> TYPE: DNA
<213> ORGANISM: Artificial sequence
<220> FEATURE:
<223> OTHER INFORMATION: artificial primer sequence

<400> SEQUENCE: 440
ttttagaact taattacatt taacaaacat tatcataatt tagtaccgac aaaat          55

<210> SEQ ID NO 441
<211> LENGTH: 54
<212> TYPE: DNA
<213> ORGANISM: Artificial sequence
<220> FEATURE:
<223> OTHER INFORMATION: artificial primer sequence

<400> SEQUENCE: 441
ttgagaaagt tgtaaattgt taaatctact taaagaagt tagcaacact atct            54

<210> SEQ ID NO 442
<211> LENGTH: 60
<212> TYPE: DNA
<213> ORGANISM: Artificial sequence
<220> FEATURE:
<223> OTHER INFORMATION: artificial primer sequence

<400> SEQUENCE: 442
ttgaggcggt ttgaccgtat tagcgagtat tccaccacat tgtgtagcgt tgagcgggct    60

<210> SEQ ID NO 443
<211> LENGTH: 70
<212> TYPE: DNA
<213> ORGANISM: Artificial sequence
<220> FEATURE:
```

<223> OTHER INFORMATION: artificial primer sequence

<400> SEQUENCE: 443

```
tttttaaat catttctctt tttttttgt gggaacaaat tctcaggaat taatagtagt    60
ttgaaaaggt                                                          70
```

<210> SEQ ID NO 444
<211> LENGTH: 50
<212> TYPE: DNA
<213> ORGANISM: Artificial sequence
<220> FEATURE:
<223> OTHER INFORMATION: artificial primer sequence

<400> SEQUENCE: 444

```
tcaaatggtt tagcgccatt tatcgtaact tagaatcagt tcacgtatat             50
```

<210> SEQ ID NO 445
<211> LENGTH: 67
<212> TYPE: DNA
<213> ORGANISM: Artificial sequence
<220> FEATURE:
<223> OTHER INFORMATION: artificial primer sequence

<400> SEQUENCE: 445

```
tctcaaatat tttttttttt ttcaaaccct caatcatttg ctgaacttac cagaagttag    60
gtttaat                                                              67
```

<210> SEQ ID NO 446
<211> LENGTH: 60
<212> TYPE: DNA
<213> ORGANISM: Artificial sequence
<220> FEATURE:
<223> OTHER INFORMATION: artificial primer sequence

<400> SEQUENCE: 446

```
ttagctcaat tctggaagtt tcttttgatt tctattatat tccatcctat tgtcctgaat    60
```

<210> SEQ ID NO 447
<211> LENGTH: 78
<212> TYPE: DNA
<213> ORGANISM: Artificial sequence
<220> FEATURE:
<223> OTHER INFORMATION: artificial primer sequence

<400> SEQUENCE: 447

```
tatttttttt tttttttaaa tatgcttttt ttttaacta aagttggatt ttttttttg     60
tgctgcaagg cgattaat                                                 78
```

<210> SEQ ID NO 448
<211> LENGTH: 60
<212> TYPE: DNA
<213> ORGANISM: Artificial sequence
<220> FEATURE:
<223> OTHER INFORMATION: artificial primer sequence

<400> SEQUENCE: 448

```
taattgctct tttcattcct tcatttgggt tcggcaccgt tcgacgacat tgtaaaacgt    60
```

<210> SEQ ID NO 449
<211> LENGTH: 68
<212> TYPE: DNA
<213> ORGANISM: Artificial sequence
<220> FEATURE:
<223> OTHER INFORMATION: artificial primer sequence

<400> SEQUENCE: 449
tccgtcaata gataatatta aggcttattc aatagcattg cgaataatta cagcttgtta    60
taataagt                                                            68

<210> SEQ ID NO 450
<211> LENGTH: 58
<212> TYPE: DNA
<213> ORGANISM: Artificial sequence
<220> FEATURE:
<223> OTHER INFORMATION: artificial primer sequence

<400> SEQUENCE: 450
tcatttgagt ttcgagcttc aaagcgatta atatcgcttc tgaggcttta ctaaagat     58

<210> SEQ ID NO 451
<211> LENGTH: 46
<212> TYPE: DNA
<213> ORGANISM: Artificial sequence
<220> FEATURE:
<223> OTHER INFORMATION: artificial primer sequence

<400> SEQUENCE: 451
taactttttt ttttaattcg acaactttt taaaattcat cgccct                   46

<210> SEQ ID NO 452
<211> LENGTH: 78
<212> TYPE: DNA
<213> ORGANISM: Artificial sequence
<220> FEATURE:
<223> OTHER INFORMATION: artificial primer sequence

<400> SEQUENCE: 452
tgattatcat taaaacagat ttaggcagat tttatacaat tgacctaaat tctatatgtt   60
tatcaataga aaattcat                                                 78

<210> SEQ ID NO 453
<211> LENGTH: 50
<212> TYPE: DNA
<213> ORGANISM: Artificial sequence
<220> FEATURE:
<223> OTHER INFORMATION: artificial primer sequence

<400> SEQUENCE: 453
tatcattttt ttttccattt tacgcataat tcgacaatgt ttagaaaggt              50

<210> SEQ ID NO 454
<211> LENGTH: 73
<212> TYPE: DNA
<213> ORGANISM: Artificial sequence
<220> FEATURE:
<223> OTHER INFORMATION: artificial primer sequence

<400> SEQUENCE: 454
tttttaaaat caggtctttt tggcatcatt ttttttttat tctactttga tttttttttt   60
tcgcactcca gct                                                      73

<210> SEQ ID NO 455
<211> LENGTH: 75
<212> TYPE: DNA
<213> ORGANISM: Artificial sequence
<220> FEATURE:
<223> OTHER INFORMATION: artificial primer sequence

<400> SEQUENCE: 455
ttaccctgat taagaggtct ttaaaccaat tttattttt ttttaatcaa gattattgca    60
gcctttacag ttttt    75

<210> SEQ ID NO 456
<211> LENGTH: 60
<212> TYPE: DNA
<213> ORGANISM: Artificial sequence
<220> FEATURE:
<223> OTHER INFORMATION: artificial primer sequence

<400> SEQUENCE: 456
tcaaagcggt ttatatttt tatataacat tcctcttcgt tctatcggct tcttgcctgt    60

<210> SEQ ID NO 457
<211> LENGTH: 60
<212> TYPE: DNA
<213> ORGANISM: Artificial sequence
<220> FEATURE:
<223> OTHER INFORMATION: artificial primer sequence

<400> SEQUENCE: 457
taaaaagatt tgcgggatct tcgagggtat tttgacccct tacggagatt tccctcagat    60

<210> SEQ ID NO 458
<211> LENGTH: 60
<212> TYPE: DNA
<213> ORGANISM: Artificial sequence
<220> FEATURE:
<223> OTHER INFORMATION: artificial primer sequence

<400> SEQUENCE: 458
ttaagaggat tatattcctt taatgaaaat tgaacgaact tatgggcgct tcctgtagct    60

<210> SEQ ID NO 459
<211> LENGTH: 60
<212> TYPE: DNA
<213> ORGANISM: Artificial sequence
<220> FEATURE:
<223> OTHER INFORMATION: artificial primer sequence

<400> SEQUENCE: 459
tagcccgaat tacatttcgt tgtagatttt tgcgcaactt tattaccgct ttagcaatat    60

<210> SEQ ID NO 460
<211> LENGTH: 68
<212> TYPE: DNA
<213> ORGANISM: Artificial sequence
<220> FEATURE:
<223> OTHER INFORMATION: artificial primer sequence

<400> SEQUENCE: 460
tagacttcat taccagacct taccgcgcct ttccggtatt tctaacgagc gtctttcttg    60
ccatattt    68

<210> SEQ ID NO 461
<211> LENGTH: 66
<212> TYPE: DNA
<213> ORGANISM: Artificial sequence
<220> FEATURE:
<223> OTHER INFORMATION: artificial primer sequence

<400> SEQUENCE: 461
tgcccgaacg ttattaattt cgtattattt aaacaacttt gaattttttg tcgtctttcc    60

```
agacgt                                                          66

<210> SEQ ID NO 462
<211> LENGTH: 46
<212> TYPE: DNA
<213> ORGANISM: Artificial sequence
<220> FEATURE:
<223> OTHER INFORMATION: artificial primer sequence

<400> SEQUENCE: 462
tgtttttttt ttttgagta acattttac ctttttgag gcgcat                 46

<210> SEQ ID NO 463
<211> LENGTH: 56
<212> TYPE: DNA
<213> ORGANISM: Artificial sequence
<220> FEATURE:
<223> OTHER INFORMATION: artificial primer sequence

<400> SEQUENCE: 463
ttcaagaaat taatgatttt tttttccat atttgaataa tttacatcca attttt    56

<210> SEQ ID NO 464
<211> LENGTH: 58
<212> TYPE: DNA
<213> ORGANISM: Artificial sequence
<220> FEATURE:
<223> OTHER INFORMATION: artificial primer sequence

<400> SEQUENCE: 464
taattattct tggaaacagt tttagattaa gacgctgttt tatataattt ttaatggt 58

<210> SEQ ID NO 465
<211> LENGTH: 78
<212> TYPE: DNA
<213> ORGANISM: Artificial sequence
<220> FEATURE:
<223> OTHER INFORMATION: artificial primer sequence

<400> SEQUENCE: 465
tggaagggtt tgtttggatt tatagataat tatttacgag catgttttt ttttagaaa 60 ccaatcatta cgggtatt                                              78

<210> SEQ ID NO 466
<211> LENGTH: 74
<212> TYPE: DNA
<213> ORGANISM: Artificial sequence
<220> FEATURE:
<223> OTHER INFORMATION: artificial primer sequence

<400> SEQUENCE: 466
tacatttttt ttttcggga gaaactttca ttaccttgta atcttgacaa gaattctgac 60
cttttgtaca gact                                                  74

<210> SEQ ID NO 467
<211> LENGTH: 48
<212> TYPE: DNA
<213> ORGANISM: Artificial sequence
<220> FEATURE:
<223> OTHER INFORMATION: artificial primer sequence

<400> SEQUENCE: 467
tggcttgaga tggtttatta attaccttttt atttcaatta attaagct           48
```

<210> SEQ ID NO 468
<211> LENGTH: 49
<212> TYPE: DNA
<213> ORGANISM: Artificial sequence
<220> FEATURE:
<223> OTHER INFORMATION: artificial primer sequence

<400> SEQUENCE: 468
tttttacgag ttacaaaatt ttcctcatat tttttttttt attttaaat          49

<210> SEQ ID NO 469
<211> LENGTH: 64
<212> TYPE: DNA
<213> ORGANISM: Artificial sequence
<220> FEATURE:
<223> OTHER INFORMATION: artificial primer sequence

<400> SEQUENCE: 469
ttacataaat taacgagtat tgccggagat tgttctagct tgaaaagcct ttaaaaggga    60
catt                                                                64

<210> SEQ ID NO 470
<211> LENGTH: 77
<212> TYPE: DNA
<213> ORGANISM: Artificial sequence
<220> FEATURE:
<223> OTHER INFORMATION: artificial primer sequence

<400> SEQUENCE: 470
ttcaatatat ttgaccctgt taaatcggtt tctggccttt tacctacatt tttgacgagt    60
tagcgggagc tattttt                                                  77

<210> SEQ ID NO 471
<211> LENGTH: 50
<212> TYPE: DNA
<213> ORGANISM: Artificial sequence
<220> FEATURE:
<223> OTHER INFORMATION: artificial primer sequence

<400> SEQUENCE: 471
ttgtgagtgt taagttacat tagccaacgt tatttaacat ttaaattgtt              50

<210> SEQ ID NO 472
<211> LENGTH: 58
<212> TYPE: DNA
<213> ORGANISM: Artificial sequence
<220> FEATURE:
<223> OTHER INFORMATION: artificial primer sequence

<400> SEQUENCE: 472
taataacctt ttcccttaga atccttgttc caatcgctta tattttatta gtaccagt     58

<210> SEQ ID NO 473
<211> LENGTH: 60
<212> TYPE: DNA
<213> ORGANISM: Artificial sequence
<220> FEATURE:
<223> OTHER INFORMATION: artificial primer sequence

<400> SEQUENCE: 473
ttaaatcgtt tccggatatt taataacggt tactgaccat tgacggtcat tgttacttat    60

<210> SEQ ID NO 474
<211> LENGTH: 42

```
<212> TYPE: DNA
<213> ORGANISM: Artificial sequence
<220> FEATURE:
<223> OTHER INFORMATION: artificial primer sequence

<400> SEQUENCE: 474 tcaattttt ttttatcaac gtaacaaagc tgctcattca gt                    42

<210> SEQ ID NO 475
<211> LENGTH: 56
<212> TYPE: DNA
<213> ORGANISM: Artificial sequence
<220> FEATURE:
<223> OTHER INFORMATION: artificial primer sequence

<400> SEQUENCE: 475
ttaacgccat tacctgaaag cgtaagatta gatagaattc atatgtaccc cggttt    56

<210> SEQ ID NO 476
<211> LENGTH: 44
<212> TYPE: DNA
<213> ORGANISM: Artificial sequence
<220> FEATURE:
<223> OTHER INFORMATION: artificial primer sequence

<400> SEQUENCE: 476
tttttaggta gaaagattca tcagtttacc agacgacgat tttt                44

<210> SEQ ID NO 477
<211> LENGTH: 68
<212> TYPE: DNA
<213> ORGANISM: Artificial sequence
<220> FEATURE:
<223> OTHER INFORMATION: artificial primer sequence

<400> SEQUENCE: 477
tgctcattat taatgtttat tataaatatt taaaggaatt acgaggcttc agatacatta  60
ggacgttt                                                          68

<210> SEQ ID NO 478
<211> LENGTH: 90
<212> TYPE: DNA
<213> ORGANISM: Artificial sequence
<220> FEATURE:
<223> OTHER INFORMATION: artificial primer sequence

<400> SEQUENCE: 478
tgactggata gcgtccattt tttttttata ctgcgttaaa tgctttaaac ttttttttt   60 agttcttgcg attttttggc tatcattttt                                  90

<210> SEQ ID NO 479
<211> LENGTH: 55
<212> TYPE: DNA
<213> ORGANISM: Artificial sequence
<220> FEATURE:
<223> OTHER INFORMATION: artificial primer sequence

<400> SEQUENCE: 479 tttttaaaa accaaaatag cgagaggctt tgcttgtta ataatttagg aatat        55

<210> SEQ ID NO 480
<211> LENGTH: 46
<212> TYPE: DNA
<213> ORGANISM: Artificial sequence
<220> FEATURE:
```

<223> OTHER INFORMATION: artificial primer sequence

<400> SEQUENCE: 480
tatagtaagt tttttgccag aggggtaat agtaatttac cagtct    46

<210> SEQ ID NO 481
<211> LENGTH: 64
<212> TYPE: DNA
<213> ORGANISM: Artificial sequence
<220> FEATURE:
<223> OTHER INFORMATION: artificial primer sequence

<400> SEQUENCE: 481
tataaccctc gttttttgag attttaacga actttattca accttcagtc aaattttatt    60
tact    64

<210> SEQ ID NO 482
<211> LENGTH: 56
<212> TYPE: DNA
<213> ORGANISM: Artificial sequence
<220> FEATURE:
<223> OTHER INFORMATION: artificial primer sequence

<400> SEQUENCE: 482
taatttatca aaatcatagg tcttttttt tttgagagac tacctttata aggcgt    56

<210> SEQ ID NO 483
<211> LENGTH: 80
<212> TYPE: DNA
<213> ORGANISM: Artificial sequence
<220> FEATURE:
<223> OTHER INFORMATION: artificial primer sequence

<400> SEQUENCE: 483
taaaacatat tcagtataat taaatcgcgt taattgcgtt taaaatacct tatctaaagt    60
tatggaaatt ttcgccattt    80

<210> SEQ ID NO 484
<211> LENGTH: 55
<212> TYPE: DNA
<213> ORGANISM: Artificial sequence
<220> FEATURE:
<223> OTHER INFORMATION: artificial primer sequence

<400> SEQUENCE: 484
tattaatttt ttgcttctgt ttgaataagg cttgcccta acattattac ttttt    55

<210> SEQ ID NO 485
<211> LENGTH: 68
<212> TYPE: DNA
<213> ORGANISM: Artificial sequence
<220> FEATURE:
<223> OTHER INFORMATION: artificial primer sequence

<400> SEQUENCE: 485
tgaacgcgat ttaggctggt tcgctattat tggaaccgat tattcgcctt tgaatataca    60
gtaacagt    68

<210> SEQ ID NO 486
<211> LENGTH: 50
<212> TYPE: DNA
<213> ORGANISM: Artificial sequence
<220> FEATURE:
<223> OTHER INFORMATION: artificial primer sequence

```
<400> SEQUENCE: 486
taaagcctgt tcaatagtgt tttcatttgt tatttcaact ttgtgtaggt                50

<210> SEQ ID NO 487
<211> LENGTH: 60
<212> TYPE: DNA
<213> ORGANISM: Artificial sequence
<220> FEATURE:
<223> OTHER INFORMATION: artificial primer sequence

<400> SEQUENCE: 487
ttttagtatt ttacctgagt taaaattatt taacagaggt tgtgccacgt ttgaggggat     60

<210> SEQ ID NO 488
<211> LENGTH: 48
<212> TYPE: DNA
<213> ORGANISM: Artificial sequence
<220> FEATURE:
<223> OTHER INFORMATION: artificial primer sequence

<400> SEQUENCE: 488
tactttgaaa gaggtttttt ttttacagat gaacggtttc atcaagat                  48

<210> SEQ ID NO 489
<211> LENGTH: 83
<212> TYPE: DNA
<213> ORGANISM: Artificial sequence
<220> FEATURE:
<223> OTHER INFORMATION: artificial primer sequence

<400> SEQUENCE: 489
tgaatataat ttactagaat ttgtgataat ttttaacct tcaaagacaa aattttttt       60 tgggttacc gacttgagtt ttt                                              83

<210> SEQ ID NO 490
<211> LENGTH: 60
<212> TYPE: DNA
<213> ORGANISM: Artificial sequence
<220> FEATURE:
<223> OTHER INFORMATION: artificial primer sequence

<400> SEQUENCE: 490
ttaataagat taccatatct tcaaaagaat tattagcaat tcgcaaggat tgttaaatct     60

<210> SEQ ID NO 491
<211> LENGTH: 58
<212> TYPE: DNA
<213> ORGANISM: Artificial sequence
<220> FEATURE:
<223> OTHER INFORMATION: artificial primer sequence

<400> SEQUENCE: 491
tggcattttt taaagtacat tcagcgattt tcccatgtat ttaccgaagc cctttttt       58

<210> SEQ ID NO 492
<211> LENGTH: 50
<212> TYPE: DNA
<213> ORGANISM: Artificial sequence
<220> FEATURE:
<223> OTHER INFORMATION: artificial primer sequence

<400> SEQUENCE: 492
tatgtaattt taataaagat tcagaggcgt tataaagctt ttaatactt                 50
```

```
<210> SEQ ID NO 493
<211> LENGTH: 58
<212> TYPE: DNA
<213> ORGANISM: Artificial sequence
<220> FEATURE:
<223> OTHER INFORMATION: artificial primer sequence

<400> SEQUENCE: 493
tatcgccatt tctcaacagt ttttcaaatt taagacaaat taagacacca cggaatat         58

<210> SEQ ID NO 494
<211> LENGTH: 78
<212> TYPE: DNA
<213> ORGANISM: Artificial sequence
<220> FEATURE:
<223> OTHER INFORMATION: artificial primer sequence

<400> SEQUENCE: 494
tggtaaagta attcttgcta atgcagaacg cgccttttttt ttttgtttta tcaacattta     60
tacttcttaa tcattttt                                                    78

<210> SEQ ID NO 495
<211> LENGTH: 60
<212> TYPE: DNA
<213> ORGANISM: Artificial sequence
<220> FEATURE:
<223> OTHER INFORMATION: artificial primer sequence

<400> SEQUENCE: 495
tcatgttcat ttgtccagat tctcattttt taataacggt ttcaccgtct tcgacattct     60

<210> SEQ ID NO 496
<211> LENGTH: 58
<212> TYPE: DNA
<213> ORGANISM: Artificial sequence
<220> FEATURE:
<223> OTHER INFORMATION: artificial primer sequence

<400> SEQUENCE: 496
taagaatact tgtacaaact tagcaagaaa caatgaattc cctgaacttt cacgttgt        58

<210> SEQ ID NO 497
<211> LENGTH: 60
<212> TYPE: DNA
<213> ORGANISM: Artificial sequence
<220> FEATURE:
<223> OTHER INFORMATION: artificial primer sequence

<400> SEQUENCE: 497
tagaggcaat tgtcgaaatt tgaggtttat tgcggataat ttagcggggt tgaaacgcat     60

<210> SEQ ID NO 498
<211> LENGTH: 58
<212> TYPE: DNA
<213> ORGANISM: Artificial sequence
<220> FEATURE:
<223> OTHER INFORMATION: artificial primer sequence

<400> SEQUENCE: 498
taaaacgaat tctttttcat taattgagat tcgtcagatt tgattgcttt gaatacct        58

<210> SEQ ID NO 499
<211> LENGTH: 50
<212> TYPE: DNA
<213> ORGANISM: Artificial sequence
```

```
<220> FEATURE:
<223> OTHER INFORMATION: artificial primer sequence

<400> SEQUENCE: 499
tacgaaggct tacagccctc atagttttt tttttagct tcccacaagt         50

<210> SEQ ID NO 500
<211> LENGTH: 60
<212> TYPE: DNA
<213> ORGANISM: Artificial sequence
<220> FEATURE:
<223> OTHER INFORMATION: artificial primer sequence

<400> SEQUENCE: 500
tctttgaggt ttgcagggat ttttcttaat ttaatttttt taaagtcagt tatttatcct         60

<210> SEQ ID NO 501
<211> LENGTH: 48
<212> TYPE: DNA
<213> ORGANISM: Artificial sequence
<220> FEATURE:
<223> OTHER INFORMATION: artificial primer sequence

<400> SEQUENCE: 501
taaacgggta aaatttttt ttttacgtaa tgccactttg ccggaact         48

<210> SEQ ID NO 502
<211> LENGTH: 66
<212> TYPE: DNA
<213> ORGANISM: Artificial sequence
<220> FEATURE:
<223> OTHER INFORMATION: artificial primer sequence

<400> SEQUENCE: 502 tgtcacccctt tgtatcggtt taggctccat tttagacggt ttgtttaacg tcaaaaatga         60
aaatat         66

<210> SEQ ID NO 503
<211> LENGTH: 66
<212> TYPE: DNA
<213> ORGANISM: Artificial sequence
<220> FEATURE:
<223> OTHER INFORMATION: artificial primer sequence

<400> SEQUENCE: 503
tccgatatat tgattttgct taatcctttt tgatttagaa gtattagact ttacatttta         60
gtaaat         66

<210> SEQ ID NO 504
<211> LENGTH: 68
<212> TYPE: DNA
<213> ORGANISM: Artificial sequence
<220> FEATURE:
<223> OTHER INFORMATION: artificial primer sequence

<400> SEQUENCE: 504
tgaggtgaat tgttaaaggt tgaatcattt tggaagcaat tgattagagt taatcaacag         60
ttgaaagt         68

<210> SEQ ID NO 505
<211> LENGTH: 58
<212> TYPE: DNA
<213> ORGANISM: Artificial sequence
<220> FEATURE:
```

<223> OTHER INFORMATION: artificial primer sequence

<400> SEQUENCE: 505
tgaacaagct tgtacctttt ttgaaatatt ttctaaatat aatgctgtta actcaaat            58

<210> SEQ ID NO 506
<211> LENGTH: 48
<212> TYPE: DNA
<213> ORGANISM: Artificial sequence
<220> FEATURE:
<223> OTHER INFORMATION: artificial primer sequence

<400> SEQUENCE: 506
taagccgttt tgaacctcct tcagctacaa ttttatcttc gatttttt                      48

<210> SEQ ID NO 507
<211> LENGTH: 58
<212> TYPE: DNA
<213> ORGANISM: Artificial sequence
<220> FEATURE:
<223> OTHER INFORMATION: artificial primer sequence

<400> SEQUENCE: 507
ttttattttt tcaaaaaaat tttatcagct tagctatctt tccgtaacac tgagtttt           58

<210> SEQ ID NO 508
<211> LENGTH: 48
<212> TYPE: DNA
<213> ORGANISM: Artificial sequence
<220> FEATURE:
<223> OTHER INFORMATION: artificial primer sequence

<400> SEQUENCE: 508
ttttcaacag tttctttttt ttttagcgga gtgagaatta caacaact                      48

<210> SEQ ID NO 509
<211> LENGTH: 59
<212> TYPE: DNA
<213> ORGANISM: Artificial sequence
<220> FEATURE:
<223> OTHER INFORMATION: artificial primer sequence

<400> SEQUENCE: 509
tttgaagcct tgtaccgcat tttccaagat tataatcggt ttaagcagat agccttttt          59

<210> SEQ ID NO 510
<211> LENGTH: 70
<212> TYPE: DNA
<213> ORGANISM: Artificial sequence
<220> FEATURE:
<223> OTHER INFORMATION: artificial primer sequence

<400> SEQUENCE: 510
tgttgctatt tccttatcat tctcatcgat tataatatct tgtcagaagt tcaatataat         60
tctgcaacat                                                                70

<210> SEQ ID NO 511
<211> LENGTH: 58
<212> TYPE: DNA
<213> ORGANISM: Artificial sequence
<220> FEATURE:
<223> OTHER INFORMATION: artificial primer sequence

<400> SEQUENCE: 511
ttaccaacgt ttctaagaac gcgaggctta actaatatta ctccaacttg cgaacgat           58

<210> SEQ ID NO 512
<211> LENGTH: 60
<212> TYPE: DNA
<213> ORGANISM: Artificial sequence
<220> FEATURE:
<223> OTHER INFORMATION: artificial primer sequence

<400> SEQUENCE: 512
tcagagcctt taaggaattt tagcaaatct tttcggtcgt tgttttaatt taagaaacct    60

<210> SEQ ID NO 513
<211> LENGTH: 58
<212> TYPE: DNA
<213> ORGANISM: Artificial sequence
<220> FEATURE:
<223> OTHER INFORMATION: artificial primer sequence

<400> SEQUENCE: 513
tcaatccaaa taagaaattc tgaatcttta aaatctcttc atcgtagttc cgcttttt     58

<210> SEQ ID NO 514
<211> LENGTH: 67
<212> TYPE: DNA
<213> ORGANISM: Artificial sequence
<220> FEATURE:
<223> OTHER INFORMATION: artificial primer sequence

<400> SEQUENCE: 514
tttttagaga ataacataaa aacaggttaa gaaaagttct gtcttttat aaacaattca    60 agaaaat                                                              67

<210> SEQ ID NO 515
<211> LENGTH: 58
<212> TYPE: DNA
<213> ORGANISM: Artificial sequence
<220> FEATURE:
<223> OTHER INFORMATION: artificial primer sequence

<400> SEQUENCE: 515
tgaagcgcat taaaggagct ttttgcacct tcgacttgcg ggaggttttt taattgct     58

<210> SEQ ID NO 516
<211> LENGTH: 58
<212> TYPE: DNA
<213> ORGANISM: Artificial sequence
<220> FEATURE:
<223> OTHER INFORMATION: artificial primer sequence

<400> SEQUENCE: 516
tgagaattaa ctgaacatta tagcaattt tgctttctta ctcatctttg caacggct     58

<210> SEQ ID NO 517
<211> LENGTH: 38
<212> TYPE: DNA
<213> ORGANISM: Artificial sequence
<220> FEATURE:
<223> OTHER INFORMATION: artificial primer sequence

<400> SEQUENCE: 517
tagggtaatt gagcgctttt aagcccatta taccgatt                            38

<210> SEQ ID NO 518
<211> LENGTH: 58
<212> TYPE: DNA

```
<213> ORGANISM: Artificial sequence
<220> FEATURE:
<223> OTHER INFORMATION: artificial primer sequence

<400> SEQUENCE: 518
tagagataat tgtaactttt tttttttgatc taaagttttt tagttacaaa ataaacat      58

<210> SEQ ID NO 519
<211> LENGTH: 60
<212> TYPE: DNA
<213> ORGANISM: Artificial sequence
<220> FEATURE:
<223> OTHER INFORMATION: artificial primer sequence

<400> SEQUENCE: 519
taattgagtt taatatcagt taacaactat taatttgcct tctgtatggt tagatatagt      60

<210> SEQ ID NO 520
<211> LENGTH: 59
<212> TYPE: DNA
<213> ORGANISM: Artificial sequence
<220> FEATURE:
<223> OTHER INFORMATION: artificial primer sequence

<400> SEQUENCE: 520
tttttgaaca ttcagggata gcaagcccct tccaccacctt cgacgacatt accgaccgt      59

<210> SEQ ID NO 521
<211> LENGTH: 58
<212> TYPE: DNA
<213> ORGANISM: Artificial sequence
<220> FEATURE:
<223> OTHER INFORMATION: artificial primer sequence

<400> SEQUENCE: 521
ttacaacgcc tgtagcattg tactcagttc cgcgaccttg aaaactttttt agggcttt      58

<210> SEQ ID NO 522
<211> LENGTH: 50
<212> TYPE: DNA
<213> ORGANISM: Artificial sequence
<220> FEATURE:
<223> OTHER INFORMATION: artificial primer sequence

<400> SEQUENCE: 522
tcctcagagt taataggaat tataccaagt tctttaattt tcagcagcgt                 50

<210> SEQ ID NO 523
<211> LENGTH: 50
<212> TYPE: DNA
<213> ORGANISM: Artificial sequence
<220> FEATURE:
<223> OTHER INFORMATION: artificial primer sequence

<400> SEQUENCE: 523
taaccgccat tttgtatcat tcatcttctt tattcttact tgcgatagct                 50

<210> SEQ ID NO 524
<211> LENGTH: 48
<212> TYPE: DNA
<213> ORGANISM: Artificial sequence
<220> FEATURE:
<223> OTHER INFORMATION: artificial primer sequence

<400> SEQUENCE: 524
tgtaccgcct taccaatgaa accatcgtta agtttgcttc ctattatt                   48
```

-continued

<210> SEQ ID NO 525
<211> LENGTH: 57
<212> TYPE: DNA
<213> ORGANISM: Artificial sequence
<220> FEATURE:
<223> OTHER INFORMATION: artificial primer sequence

<400> SEQUENCE: 525
taacgcaatt taagttacct ttttgggaat tagagccttt tagcgtttgc cattttt      57

<210> SEQ ID NO 526
<211> LENGTH: 60
<212> TYPE: DNA
<213> ORGANISM: Artificial sequence
<220> FEATURE:
<223> OTHER INFORMATION: artificial primer sequence

<400> SEQUENCE: 526
taaagaactt ttttgaaatt tcgcgaaact tcgagccagt taaagacagt tcaattcatt   60

<210> SEQ ID NO 527
<211> LENGTH: 58
<212> TYPE: DNA
<213> ORGANISM: Artificial sequence
<220> FEATURE:
<223> OTHER INFORMATION: artificial primer sequence

<400> SEQUENCE: 527
tggcatgatt taccgccact tgcaccatta ccattagttt ttcatcgttt aaacagtt     58

<210> SEQ ID NO 528
<211> LENGTH: 58
<212> TYPE: DNA
<213> ORGANISM: Artificial sequence
<220> FEATURE:
<223> OTHER INFORMATION: artificial primer sequence

<400> SEQUENCE: 528
ttaagactct tatagacggt tatattcatt tgagccgccg ccagcatttc gcctccct     58

<210> SEQ ID NO 529
<211> LENGTH: 60
<212> TYPE: DNA
<213> ORGANISM: Artificial sequence
<220> FEATURE:
<223> OTHER INFORMATION: artificial primer sequence

<400> SEQUENCE: 529
tgcagtatgt tgttaatttt ttcgcctgat tacgccaact ttacagaggt tttatcatct   60

<210> SEQ ID NO 530
<211> LENGTH: 68
<212> TYPE: DNA
<213> ORGANISM: Artificial sequence
<220> FEATURE:
<223> OTHER INFORMATION: artificial primer sequence

<400> SEQUENCE: 530
tgtgccgtcg agagggtttc aggcgcattt gctccattta tcataagttt gaggaagttg   60
cggaacat                                                           68

<210> SEQ ID NO 531
<211> LENGTH: 52
<212> TYPE: DNA

```
<213> ORGANISM: Artificial sequence
<220> FEATURE:
<223> OTHER INFORMATION: artificial primer sequence

<400> SEQUENCE: 531
ttgatataag tatattttt ttttgcccgg aataggttta ggctgagttt tt          52

<210> SEQ ID NO 532
<211> LENGTH: 58
<212> TYPE: DNA
<213> ORGANISM: Artificial sequence
<220> FEATURE:
<223> OTHER INFORMATION: artificial primer sequence

<400> SEQUENCE: 532
tgtgaattat taatacccat taccagcgct ttccggctta ggttgggtta gaagagtt   58

<210> SEQ ID NO 533
<211> LENGTH: 60
<212> TYPE: DNA
<213> ORGANISM: Artificial sequence
<220> FEATURE:
<223> OTHER INFORMATION: artificial primer sequence

<400> SEQUENCE: 533
tagagaaggt taccgtaatt tgtatcacct tttccacagt taccaacctt tagttgcgct  60

<210> SEQ ID NO 534
<211> LENGTH: 70
<212> TYPE: DNA
<213> ORGANISM: Artificial sequence
<220> FEATURE:
<223> OTHER INFORMATION: artificial primer sequence

<400> SEQUENCE: 534 ttttttactcc tcattatttt tttttttttaa gttcagtagc gacagaatct tatagcagct  60
tattaggatt                                                          70

<210> SEQ ID NO 535
<211> LENGTH: 71
<212> TYPE: DNA
<213> ORGANISM: Artificial sequence
<220> FEATURE:
<223> OTHER INFORMATION: artificial primer sequence

<400> SEQUENCE: 535
tttttccatt agaaggaatt ttttttttac cgaggatttt aaataagaat ttttttttt   60 aaacaccgga t                                                       71

<210> SEQ ID NO 536
<211> LENGTH: 58
<212> TYPE: DNA
<213> ORGANISM: Artificial sequence
<220> FEATURE:
<223> OTHER INFORMATION: artificial primer sequence

<400> SEQUENCE: 536
tcaaggccgt tcgtagaaat tcttattact tttgtcacat taaatgctga tgcaaatt    58

<210> SEQ ID NO 537
<211> LENGTH: 55
<212> TYPE: DNA
<213> ORGANISM: Artificial sequence
<220> FEATURE:
<223> OTHER INFORMATION: artificial primer sequence
```

<400> SEQUENCE: 537
tttttctttt tcataatctt ccttgatatt ttttttttt cacaaacaaa taaat                55

<210> SEQ ID NO 538
<211> LENGTH: 60
<212> TYPE: DNA
<213> ORGANISM: Artificial sequence
<220> FEATURE:
<223> OTHER INFORMATION: artificial primer sequence

<400> SEQUENCE: 538
tcctgcctat tttagcaaat tgaaacgtct taccctcagt tcgtcaccat tactaaaact         60

<210> SEQ ID NO 539
<211> LENGTH: 58
<212> TYPE: DNA
<213> ORGANISM: Artificial sequence
<220> FEATURE:
<223> OTHER INFORMATION: artificial primer sequence

<400> SEQUENCE: 539
tacgattggt taaaatcact tggttgaggt taaccgattg agggaggttt atggtttt           58

<210> SEQ ID NO 540
<211> LENGTH: 58
<212> TYPE: DNA
<213> ORGANISM: Artificial sequence
<220> FEATURE:
<223> OTHER INFORMATION: artificial primer sequence

<400> SEQUENCE: 540
tagtaacagt tgagccacct ttcctcattt tggtcatagc ccccttatta gcaaaatt           58

<210> SEQ ID NO 541
<211> LENGTH: 46
<212> TYPE: DNA
<213> ORGANISM: Artificial sequence
<220> FEATURE:
<223> OTHER INFORMATION: artificial primer sequence

<400> SEQUENCE: 541
tgtgccttgt ttcagagccg ccaccctcag aaccgttacc agaact                       46

<210> SEQ ID NO 542
<211> LENGTH: 58
<212> TYPE: DNA
<213> ORGANISM: Artificial sequence
<220> FEATURE:
<223> OTHER INFORMATION: artificial primer sequence

<400> SEQUENCE: 542
tcggggtcat ttaatgccct tcaccaccat tacataaagg tggcaactta gtttattt          58

<210> SEQ ID NO 543
<211> LENGTH: 46
<212> TYPE: DNA
<213> ORGANISM: Artificial sequence
<220> FEATURE:
<223> OTHER INFORMATION: artificial primer sequence

<400> SEQUENCE: 543
tgagtgtact tagagccact ttttttttc accctcagag ccgcct                        46

<210> SEQ ID NO 544

```
<211> LENGTH: 54
<212> TYPE: DNA
<213> ORGANISM: Artificial sequence
<220> FEATURE:
<223> OTHER INFORMATION: artificial primer sequence

<400> SEQUENCE: 544
tcatacatgg ctttttttt tttttgatga tacagtttct gaaacatgaa agtt        54

<210> SEQ ID NO 545
<211> LENGTH: 60
<212> TYPE: DNA
<213> ORGANISM: Artificial sequence
<220> FEATURE:
<223> OTHER INFORMATION: artificial primer sequence

<400> SEQUENCE: 545
tcaggtcagt taccggaact ttgacaggat tcggaaccat tcattaaagt tcaccagtat  60

<210> SEQ ID NO 546
<211> LENGTH: 56
<212> TYPE: DNA
<213> ORGANISM: Artificial sequence
<220> FEATURE:
<223> OTHER INFORMATION: artificial primer sequence

<400> SEQUENCE: 546
tccaccctct ttggtaataa gttttaattt ctgaattttt cagactgtag cgcgtt      56

<210> SEQ ID NO 547
<211> LENGTH: 66
<212> TYPE: DNA
<213> ORGANISM: Artificial sequence
<220> FEATURE:
<223> OTHER INFORMATION: artificial primer sequence

<400> SEQUENCE: 547
tgaaggtaat taaattattt ttgcccgtat tgcattttct taaagccaga atggaaagcg  60
cagtct                                                            66

<210> SEQ ID NO 548
<211> LENGTH: 60
<212> TYPE: DNA
<213> ORGANISM: Artificial sequence
<220> FEATURE:
<223> OTHER INFORMATION: artificial primer sequence

<400> SEQUENCE: 548
tatataaaat ttttgctctt tttcggaatt tctttagcgt ttaccgttcc agtaagcgtt  60

<210> SEQ ID NO 549
<211> LENGTH: 43
<212> TYPE: DNA
<213> ORGANISM: Artificial sequence
<220> FEATURE:
<223> OTHER INFORMATION: artificial primer sequence

<400> SEQUENCE: 549
tttttttttt tcagtattaa caccgcctgc aacagtcaga aga                   43

<210> SEQ ID NO 550
<211> LENGTH: 35
<212> TYPE: DNA
<213> ORGANISM: Artificial sequence
<220> FEATURE:
<223> OTHER INFORMATION: artificial primer sequence
```

```
<400> SEQUENCE: 550
gccacgcaat atccagaaca actgagaaca taaag                              35

<210> SEQ ID NO 551
<211> LENGTH: 35
<212> TYPE: DNA
<213> ORGANISM: Artificial sequence
<220> FEATURE:
<223> OTHER INFORMATION: artificial primer sequence

<400> SEQUENCE: 551
aaatgaacaa actatcggcc tagtgaggac acaac                              35

<210> SEQ ID NO 552
<211> LENGTH: 42
<212> TYPE: DNA
<213> ORGANISM: Artificial sequence
<220> FEATURE:
<223> OTHER INFORMATION: artificial primer sequence

<400> SEQUENCE: 552
accttgcact tgcctgagta gagtctgttt gttataccgc ct                      42

<210> SEQ ID NO 553
<211> LENGTH: 42
<212> TYPE: DNA
<213> ORGANISM: Artificial sequence
<220> FEATURE:
<223> OTHER INFORMATION: artificial primer sequence

<400> SEQUENCE: 553
tctttaagac aataatatcg atagcagcac cgtaagaata cg                      42

<210> SEQ ID NO 554
<211> LENGTH: 52
<212> TYPE: DNA
<213> ORGANISM: Artificial sequence
<220> FEATURE:
<223> OTHER INFORMATION: artificial primer sequence

<400> SEQUENCE: 554
tttttttttt atctggtggc tattagcaaa ccctcaatca atttttttttt tt          52

<210> SEQ ID NO 555
<211> LENGTH: 58
<212> TYPE: DNA
<213> ORGANISM: Artificial sequence
<220> FEATURE:
<223> OTHER INFORMATION: artificial primer sequence

<400> SEQUENCE: 555
tttttttttt cacacgacca gtaataaaat aaaacagagg tgaggcggtt tttttttt      58

<210> SEQ ID NO 556
<211> LENGTH: 43
<212> TYPE: DNA
<213> ORGANISM: Artificial sequence
<220> FEATURE:
<223> OTHER INFORMATION: artificial primer sequence

<400> SEQUENCE: 556
gggacataga tttacattgg cagattcacc agttttttttt ttt                    43

<210> SEQ ID NO 557
```

```
<211> LENGTH: 42
<212> TYPE: DNA
<213> ORGANISM: Artificial sequence
<220> FEATURE:
<223> OTHER INFORMATION: artificial primer sequence

<400> SEQUENCE: 557
atagaacttg cctttagcgt cagactgttc tggccccgga ag                    42

<210> SEQ ID NO 558
<211> LENGTH: 42
<212> TYPE: DNA
<213> ORGANISM: Artificial sequence
<220> FEATURE:
<223> OTHER INFORMATION: artificial primer sequence

<400> SEQUENCE: 558
aattgaggat ttagaagtat tagactttca acagttaccg ag                    42

<210> SEQ ID NO 559
<211> LENGTH: 49
<212> TYPE: DNA
<213> ORGANISM: Artificial sequence
<220> FEATURE:
<223> OTHER INFORMATION: artificial primer sequence

<400> SEQUENCE: 559
gaaggtttca cagttgagga tgccaccaga gggccgtttt caagcctcc             49

<210> SEQ ID NO 560
<211> LENGTH: 35
<212> TYPE: DNA
<213> ORGANISM: Artificial sequence
<220> FEATURE:
<223> OTHER INFORMATION: artificial primer sequence

<400> SEQUENCE: 560
atctaaaata tctttcaata gggaacaatg aacaa                            35

<210> SEQ ID NO 561
<211> LENGTH: 49
<212> TYPE: DNA
<213> ORGANISM: Artificial sequence
<220> FEATURE:
<223> OTHER INFORMATION: artificial primer sequence

<400> SEQUENCE: 561
tcagtagcga cagaatcaag tccttctgca attccccacc gagattaaa             49

<210> SEQ ID NO 562
<211> LENGTH: 47
<212> TYPE: DNA
<213> ORGANISM: Artificial sequence
<220> FEATURE:
<223> OTHER INFORMATION: artificial primer sequence

<400> SEQUENCE: 562
attcgacaac tcgttttttg acatggtcgt agcaatattt ttttttt               47

<210> SEQ ID NO 563
<211> LENGTH: 54
<212> TYPE: DNA
<213> ORGANISM: Artificial sequence
<220> FEATURE:
<223> OTHER INFORMATION: artificial primer sequence

<400> SEQUENCE: 563
```

```
tttttttttt taatagatta gagccgtagg agctcttcgc gtccgtgcgg tcat        54
```

<210> SEQ ID NO 564
<211> LENGTH: 52
<212> TYPE: DNA
<213> ORGANISM: Artificial sequence
<220> FEATURE:
<223> OTHER INFORMATION: artificial primer sequence

<400> SEQUENCE: 564

```
tttttttttt tttgacgctc aatcgtgcgg aaatacctac attttttttt tt         52
```

<210> SEQ ID NO 565
<211> LENGTH: 37
<212> TYPE: DNA
<213> ORGANISM: Artificial sequence
<220> FEATURE:
<223> OTHER INFORMATION: artificial primer sequence

<400> SEQUENCE: 565

```
tgaaacctaa atccttccgg aaagaaccgc caccctc                          37
```

<210> SEQ ID NO 566
<211> LENGTH: 42
<212> TYPE: DNA
<213> ORGANISM: Artificial sequence
<220> FEATURE:
<223> OTHER INFORMATION: artificial primer sequence

<400> SEQUENCE: 566

```
taattttgca ccatccaccc tcagagcccc ccgggtgaaa gg                    42
```

<210> SEQ ID NO 567
<211> LENGTH: 51
<212> TYPE: DNA
<213> ORGANISM: Artificial sequence
<220> FEATURE:
<223> OTHER INFORMATION: artificial primer sequence

<400> SEQUENCE: 567

```
atttatccct caaaaaggtt ttgtcatcgt ataatcggct gtcttgttca g          51
```

<210> SEQ ID NO 568
<211> LENGTH: 54
<212> TYPE: DNA
<213> ORGANISM: Artificial sequence
<220> FEATURE:
<223> OTHER INFORMATION: artificial primer sequence

<400> SEQUENCE: 568

```
cattttcggt cataatcaaa cagctggttt gcctgccgta cgatttagag cttg       54
```

<210> SEQ ID NO 569
<211> LENGTH: 42
<212> TYPE: DNA
<213> ORGANISM: Artificial sequence
<220> FEATURE:
<223> OTHER INFORMATION: artificial primer sequence

<400> SEQUENCE: 569

```
ccatttggaa ttatggttta ccagcgccaa gagcaagtca ga                    42
```

<210> SEQ ID NO 570
<211> LENGTH: 40
<212> TYPE: DNA

```
<213> ORGANISM: Artificial sequence
<220> FEATURE:
<223> OTHER INFORMATION: artificial primer sequence

<400> SEQUENCE: 570
attcctgatt atcagatgat ggcacgacca gaaggagcgg                    40

<210> SEQ ID NO 571
<211> LENGTH: 57
<212> TYPE: DNA
<213> ORGANISM: Artificial sequence
<220> FEATURE:
<223> OTHER INFORMATION: artificial primer sequence

<400> SEQUENCE: 571
tttttttttt tccagagcct aatttgccaa cagaaattag caattaagac gacaata    57

<210> SEQ ID NO 572
<211> LENGTH: 52
<212> TYPE: DNA
<213> ORGANISM: Artificial sequence
<220> FEATURE:
<223> OTHER INFORMATION: artificial primer sequence

<400> SEQUENCE: 572
tttttttttt cgctcatgtt tgccattgta aagccggaaa aatttttttt tt         52

<210> SEQ ID NO 573
<211> LENGTH: 47
<212> TYPE: DNA
<213> ORGANISM: Artificial sequence
<220> FEATURE:
<223> OTHER INFORMATION: artificial primer sequence

<400> SEQUENCE: 573
cttttcatag cccccttatt actgaaatgg attcgcgttt tcatcgg               47

<210> SEQ ID NO 574
<211> LENGTH: 35
<212> TYPE: DNA
<213> ORGANISM: Artificial sequence
<220> FEATURE:
<223> OTHER INFORMATION: artificial primer sequence

<400> SEQUENCE: 574
ggaaccagag ccacgttgag ttcctgtttc aagtt                            35

<210> SEQ ID NO 575
<211> LENGTH: 35
<212> TYPE: DNA
<213> ORGANISM: Artificial sequence
<220> FEATURE:
<223> OTHER INFORMATION: artificial primer sequence

<400> SEQUENCE: 575
caccggaccg ctcaacctga aaacatcgcc attaa                            35

<210> SEQ ID NO 576
<211> LENGTH: 57
<212> TYPE: DNA
<213> ORGANISM: Artificial sequence
<220> FEATURE:
<223> OTHER INFORMATION: artificial primer sequence

<400> SEQUENCE: 576
ccctcagaaa agaaaaatcg gctacgtgaa ggaagggaag aaagcgattt ttttttt     57
```

<210> SEQ ID NO 577
<211> LENGTH: 42
<212> TYPE: DNA
<213> ORGANISM: Artificial sequence
<220> FEATURE:
<223> OTHER INFORMATION: artificial primer sequence

<400> SEQUENCE: 577
tgtgaaacca tcacgcggga gacgtgctct agggcgctgg ca                42

<210> SEQ ID NO 578
<211> LENGTH: 35
<212> TYPE: DNA
<213> ORGANISM: Artificial sequence
<220> FEATURE:
<223> OTHER INFORMATION: artificial primer sequence

<400> SEQUENCE: 578
tcgtaatatc agttggcaaa tacaaacaac gttat                35

<210> SEQ ID NO 579
<211> LENGTH: 35
<212> TYPE: DNA
<213> ORGANISM: Artificial sequence
<220> FEATURE:
<223> OTHER INFORMATION: artificial primer sequence

<400> SEQUENCE: 579
ctcgaataga gccataccat tagcaaggtg cccga                35

<210> SEQ ID NO 580
<211> LENGTH: 41
<212> TYPE: DNA
<213> ORGANISM: Artificial sequence
<220> FEATURE:
<223> OTHER INFORMATION: artificial primer sequence

<400> SEQUENCE: 580
tttttttttt acgcgtgcct gtactaacaa cttttttttt t                41

<210> SEQ ID NO 581
<211> LENGTH: 52
<212> TYPE: DNA
<213> ORGANISM: Artificial sequence
<220> FEATURE:
<223> OTHER INFORMATION: artificial primer sequence

<400> SEQUENCE: 581
tttttttttt tgcaacatgg ggtgtctatt accgccagcc attttttttt tt                52

<210> SEQ ID NO 582
<211> LENGTH: 49
<212> TYPE: DNA
<213> ORGANISM: Artificial sequence
<220> FEATURE:
<223> OTHER INFORMATION: artificial primer sequence

<400> SEQUENCE: 582
gtgttttgaa cggtgctaca gccacacccg ccgcggagcc ccaagcact                49

<210> SEQ ID NO 583
<211> LENGTH: 35
<212> TYPE: DNA
<213> ORGANISM: Artificial sequence
<220> FEATURE:

<223> OTHER INFORMATION: artificial primer sequence

<400> SEQUENCE: 583
tataatctgc tggttgagag ccagcagcaa atacc                    35

<210> SEQ ID NO 584
<211> LENGTH: 56
<212> TYPE: DNA
<213> ORGANISM: Artificial sequence
<220> FEATURE:
<223> OTHER INFORMATION: artificial primer sequence

<400> SEQUENCE: 584
tttttttttt cttctttgat tagtaaaacc gttatagctg accctcacgt caccaa    56

<210> SEQ ID NO 585
<211> LENGTH: 49
<212> TYPE: DNA
<213> ORGANISM: Artificial sequence
<220> FEATURE:
<223> OTHER INFORMATION: artificial primer sequence

<400> SEQUENCE: 585
ggaggccgta aagaagaac taaatctaaa gcatcgccct aaagcgtaa       49

<210> SEQ ID NO 586
<211> LENGTH: 40
<212> TYPE: DNA
<213> ORGANISM: Artificial sequence
<220> FEATURE:
<223> OTHER INFORMATION: artificial primer sequence

<400> SEQUENCE: 586
ctaaacaggt tccgtagccc gaagagtcca ctattaaaga               40

<210> SEQ ID NO 587
<211> LENGTH: 47
<212> TYPE: DNA
<213> ORGANISM: Artificial sequence
<220> FEATURE:
<223> OTHER INFORMATION: artificial primer sequence

<400> SEQUENCE: 587
tttttttttt agaatcagag caaatttaac atctgaacct caaatat       47

<210> SEQ ID NO 588
<211> LENGTH: 43
<212> TYPE: DNA
<213> ORGANISM: Artificial sequence
<220> FEATURE:
<223> OTHER INFORMATION: artificial primer sequence

<400> SEQUENCE: 588
tttttttttt ctcacattaa ttgcgtttaa tgcgccacgc cag           43

<210> SEQ ID NO 589
<211> LENGTH: 51
<212> TYPE: DNA
<213> ORGANISM: Artificial sequence
<220> FEATURE:
<223> OTHER INFORMATION: artificial primer sequence

<400> SEQUENCE: 589
ttgctttcgg tcacgctgcg cacggggatt ttggggcgcg ggttttttct t    51

```
<210> SEQ ID NO 590
<211> LENGTH: 43
<212> TYPE: DNA
<213> ORGANISM: Artificial sequence
<220> FEATURE:
<223> OTHER INFORMATION: artificial primer sequence

<400> SEQUENCE: 590
gtaaccaggc gcgtactatg ggggatttgc gaaaagtgtg aga          43

<210> SEQ ID NO 591
<211> LENGTH: 41
<212> TYPE: DNA
<213> ORGANISM: Artificial sequence
<220> FEATURE:
<223> OTHER INFORMATION: artificial primer sequence

<400> SEQUENCE: 591
tttttttttt aaggagcggg cgttcctcgt tttttttttt t            41

<210> SEQ ID NO 592
<211> LENGTH: 52
<212> TYPE: DNA
<213> ORGANISM: Artificial sequence
<220> FEATURE:
<223> OTHER INFORMATION: artificial primer sequence

<400> SEQUENCE: 592
tttttttttt ctttccaccc taaaggctgc gctcactgcc cgttttttttt tt   52

<210> SEQ ID NO 593
<211> LENGTH: 35
<212> TYPE: DNA
<213> ORGANISM: Artificial sequence
<220> FEATURE:
<223> OTHER INFORMATION: artificial primer sequence

<400> SEQUENCE: 593
aagccggcga acgtagtgta ggacgagcac gtata                   35

<210> SEQ ID NO 594
<211> LENGTH: 50
<212> TYPE: DNA
<213> ORGANISM: Artificial sequence
<220> FEATURE:
<223> OTHER INFORMATION: artificial primer sequence

<400> SEQUENCE: 594
ggcgagaaac catcgtaaag ggcgaaaaac cgtctatcag tttttttttt    50

<210> SEQ ID NO 595
<211> LENGTH: 41
<212> TYPE: DNA
<213> ORGANISM: Artificial sequence
<220> FEATURE:
<223> OTHER INFORMATION: artificial primer sequence

<400> SEQUENCE: 595
tttttttttt ggcgatggcc cacaaaatcc cttttttttt t            41

<210> SEQ ID NO 596
<211> LENGTH: 52
<212> TYPE: DNA
<213> ORGANISM: Artificial sequence
<220> FEATURE:
<223> OTHER INFORMATION: artificial primer sequence
```

-continued

<400> SEQUENCE: 596
tttttttttt aacctgtcgt gccagcaaat cggaagtcgg gatttttttt tt    52

<210> SEQ ID NO 597
<211> LENGTH: 42
<212> TYPE: DNA
<213> ORGANISM: Artificial sequence
<220> FEATURE:
<223> OTHER INFORMATION: artificial primer sequence

<400> SEQUENCE: 597
tgcattaatg aatcggccaa cgtcgaggcc agcagtagac ag    42

<210> SEQ ID NO 598
<211> LENGTH: 40
<212> TYPE: DNA
<213> ORGANISM: Artificial sequence
<220> FEATURE:
<223> OTHER INFORMATION: artificial primer sequence

<400> SEQUENCE: 598
acgtggactc caacgtcatt gggcgcttgg aacagatagg    40

<210> SEQ ID NO 599
<211> LENGTH: 40
<212> TYPE: DNA
<213> ORGANISM: Artificial sequence
<220> FEATURE:
<223> OTHER INFORMATION: artificial primer sequence

<400> SEQUENCE: 599
ctgattgctt tgaataccat tactagtgtg atatgctgat    40

<210> SEQ ID NO 600
<211> LENGTH: 51
<212> TYPE: DNA
<213> ORGANISM: Artificial sequence
<220> FEATURE:
<223> OTHER INFORMATION: artificial primer sequence

<400> SEQUENCE: 600
ttcaccatgt tccagtcagg gtggagaggc ggtttgcacc caaatgatgg t    51

<210> SEQ ID NO 601
<211> LENGTH: 32
<212> TYPE: DNA
<213> ORGANISM: Artificial sequence
<220> FEATURE:
<223> OTHER INFORMATION: artificial primer sequence

<400> SEQUENCE: 601
aattattcat ttcaacaaat cgcgcagagg cg    32

<210> SEQ ID NO 602
<211> LENGTH: 41
<212> TYPE: DNA
<213> ORGANISM: Artificial sequence
<220> FEATURE:
<223> OTHER INFORMATION: artificial primer sequence

<400> SEQUENCE: 602
cgggcaaatc accatacgag aacagaggaa cgaaccacca g    41

<210> SEQ ID NO 603
<211> LENGTH: 54

```
<212> TYPE: DNA
<213> ORGANISM: Artificial sequence
<220> FEATURE:
<223> OTHER INFORMATION: artificial primer sequence

<400> SEQUENCE: 603
tttttttttt ttataaatca gccgcctttc ctgtggcaca tgcgcgaact gata      54

<210> SEQ ID NO 604
<211> LENGTH: 58
<212> TYPE: DNA
<213> ORGANISM: Artificial sequence
<220> FEATURE:
<223> OTHER INFORMATION: artificial primer sequence

<400> SEQUENCE: 604
tttttttttt agagttgcag caagcggtca acctaatgag tgagctaatt tttttttt   58

<210> SEQ ID NO 605
<211> LENGTH: 43
<212> TYPE: DNA
<213> ORGANISM: Artificial sequence
<220> FEATURE:
<223> OTHER INFORMATION: artificial primer sequence

<400> SEQUENCE: 605
cacgctgatt gcccttcacc gcctggccct gagttttttt ttt                   43

<210> SEQ ID NO 606
<211> LENGTH: 35
<212> TYPE: DNA
<213> ORGANISM: Artificial sequence
<220> FEATURE:
<223> OTHER INFORMATION: artificial primer sequence

<400> SEQUENCE: 606
tgagcgctta agcccaataa taaagacata ttcat                            35

<210> SEQ ID NO 607
<211> LENGTH: 35
<212> TYPE: DNA
<213> ORGANISM: Artificial sequence
<220> FEATURE:
<223> OTHER INFORMATION: artificial primer sequence

<400> SEQUENCE: 607
gggtaatcat tatcgagcca gcaaaatccg gaaat                            35

<210> SEQ ID NO 608
<211> LENGTH: 50
<212> TYPE: DNA
<213> ORGANISM: Artificial sequence
<220> FEATURE:
<223> OTHER INFORMATION: artificial primer sequence

<400> SEQUENCE: 608
aacacccaga aaccacttga gaccgggggt ttctgccagc tttttttttt            50

<210> SEQ ID NO 609
<211> LENGTH: 42
<212> TYPE: DNA
<213> ORGANISM: Artificial sequence
<220> FEATURE:
<223> OTHER INFORMATION: artificial primer sequence

<400> SEQUENCE: 609
```

```
gggagaagct atcttaccgc ctttgtcaaa tcctgattgt tt                          42
```

<210> SEQ ID NO 610
<211> LENGTH: 43
<212> TYPE: DNA
<213> ORGANISM: Artificial sequence
<220> FEATURE:
<223> OTHER INFORMATION: artificial primer sequence

<400> SEQUENCE: 610

```
tttttttttt acaatttat cctgaatctt accagagatt agt                         43
```

<210> SEQ ID NO 611
<211> LENGTH: 41
<212> TYPE: DNA
<213> ORGANISM: Artificial sequence
<220> FEATURE:
<223> OTHER INFORMATION: artificial primer sequence

<400> SEQUENCE: 611

```
tttttttttt acccacaaga accgattgag gttttttttt t                          41
```

<210> SEQ ID NO 612
<211> LENGTH: 37
<212> TYPE: DNA
<213> ORGANISM: Artificial sequence
<220> FEATURE:
<223> OTHER INFORMATION: artificial primer sequence

<400> SEQUENCE: 612

```
agaaacaatg aaatttcata tcaccgtcac attcatc                               37
```

<210> SEQ ID NO 613
<211> LENGTH: 42
<212> TYPE: DNA
<213> ORGANISM: Artificial sequence
<220> FEATURE:
<223> OTHER INFORMATION: artificial primer sequence

<400> SEQUENCE: 613

```
gttttagaga gaataacata aaaacaggta agaacgatat ag                         42
```

<210> SEQ ID NO 614
<211> LENGTH: 54
<212> TYPE: DNA
<213> ORGANISM: Artificial sequence
<220> FEATURE:
<223> OTHER INFORMATION: artificial primer sequence

<400> SEQUENCE: 614

```
tagcaagcaa atcagcgagg cgacaccaac ttctgttatt accttttttt tttt            54
```

<210> SEQ ID NO 615
<211> LENGTH: 42
<212> TYPE: DNA
<213> ORGANISM: Artificial sequence
<220> FEATURE:
<223> OTHER INFORMATION: artificial primer sequence

<400> SEQUENCE: 615

```
cgcccaacga gcatgtagaa agcctgttca ataatgagtg aa                         42
```

<210> SEQ ID NO 616
<211> LENGTH: 54
<212> TYPE: DNA
<213> ORGANISM: Artificial sequence

```
<220> FEATURE:
<223> OTHER INFORMATION: artificial primer sequence

<400> SEQUENCE: 616
aggaatcatt accgcccgac taacatatta gaaccaatat actaacggat tcgc        54

<210> SEQ ID NO 617
<211> LENGTH: 43
<212> TYPE: DNA
<213> ORGANISM: Artificial sequence
<220> FEATURE:
<223> OTHER INFORMATION: artificial primer sequence

<400> SEQUENCE: 617
acaagcatca ttccaagaac gggtattaaa ccattttttt ttt                    43

<210> SEQ ID NO 618
<211> LENGTH: 58
<212> TYPE: DNA
<213> ORGANISM: Artificial sequence
<220> FEATURE:
<223> OTHER INFORMATION: artificial primer sequence

<400> SEQUENCE: 618
tttttttttt agtaccgcac tcatcgagat gctattttgc acccagcttt tttttttt    58

<210> SEQ ID NO 619
<211> LENGTH: 52
<212> TYPE: DNA
<213> ORGANISM: Artificial sequence
<220> FEATURE:
<223> OTHER INFORMATION: artificial primer sequence

<400> SEQUENCE: 619
tttttttttt ttttaagaaa agtaaaaagg cttataagcc cttttttttt tt          52

<210> SEQ ID NO 620
<211> LENGTH: 47
<212> TYPE: DNA
<213> ORGANISM: Artificial sequence
<220> FEATURE:
<223> OTHER INFORMATION: artificial primer sequence

<400> SEQUENCE: 620
ataatatccc atccaagtcc tcagaaggta aatcgtcttt ttttttt                47

<210> SEQ ID NO 621
<211> LENGTH: 35
<212> TYPE: DNA
<213> ORGANISM: Artificial sequence
<220> FEATURE:
<223> OTHER INFORMATION: artificial primer sequence

<400> SEQUENCE: 621
aacaacattc cttaagccgt ttttatttaa gcctt                             35

<210> SEQ ID NO 622
<211> LENGTH: 52
<212> TYPE: DNA
<213> ORGANISM: Artificial sequence
<220> FEATURE:
<223> OTHER INFORMATION: artificial primer sequence

<400> SEQUENCE: 622
tttttttttt attctgtcca gacgactcct tattataaag tatttttttt tt          52
```

<210> SEQ ID NO 623
<211> LENGTH: 59
<212> TYPE: DNA
<213> ORGANISM: Artificial sequence
<220> FEATURE:
<223> OTHER INFORMATION: artificial primer sequence

<400> SEQUENCE: 623
tttttttttt agccgaacaa gtttatggta ttcgaagcgc attagacaat tatcatcat    59

<210> SEQ ID NO 624
<211> LENGTH: 49
<212> TYPE: DNA
<213> ORGANISM: Artificial sequence
<220> FEATURE:
<223> OTHER INFORMATION: artificial primer sequence

<400> SEQUENCE: 624
aagaactagt acatattaca ttaaatttat gcgttataca aattcttac               49

<210> SEQ ID NO 625
<211> LENGTH: 47
<212> TYPE: DNA
<213> ORGANISM: Artificial sequence
<220> FEATURE:
<223> OTHER INFORMATION: artificial primer sequence

<400> SEQUENCE: 625
aaagggcgac attcaattga gtaatatcag agagatattt tttttt                  47

<210> SEQ ID NO 626
<211> LENGTH: 42
<212> TYPE: DNA
<213> ORGANISM: Artificial sequence
<220> FEATURE:
<223> OTHER INFORMATION: artificial primer sequence

<400> SEQUENCE: 626
aggtggctgc gggatgaaaa tagcagcctt tacagcgaac ct                      42

<210> SEQ ID NO 627
<211> LENGTH: 35
<212> TYPE: DNA
<213> ORGANISM: Artificial sequence
<220> FEATURE:
<223> OTHER INFORMATION: artificial primer sequence

<400> SEQUENCE: 627
tacataatac ccaactaatg cagaacgccc aatca                              35

<210> SEQ ID NO 628
<211> LENGTH: 49
<212> TYPE: DNA
<213> ORGANISM: Artificial sequence
<220> FEATURE:
<223> OTHER INFORMATION: artificial primer sequence

<400> SEQUENCE: 628
aaatacatat ttgctttcag gtttaacgaa aattaaaatc aatagcgat               49

<210> SEQ ID NO 629
<211> LENGTH: 51
<212> TYPE: DNA
<213> ORGANISM: Artificial sequence
<220> FEATURE:
<223> OTHER INFORMATION: artificial primer sequence

<400> SEQUENCE: 629
acgtagaaaa tcaatttttt gtttaacgaa tccaaaataa acagccatat t    51

<210> SEQ ID NO 630
<211> LENGTH: 52
<212> TYPE: DNA
<213> ORGANISM: Artificial sequence
<220> FEATURE:
<223> OTHER INFORMATION: artificial primer sequence

<400> SEQUENCE: 630
tttttttttt caaaaggcgc agtatgtaat ataaagtacc gattttttt tt    52

<210> SEQ ID NO 631
<211> LENGTH: 50
<212> TYPE: DNA
<213> ORGANISM: Artificial sequence
<220> FEATURE:
<223> OTHER INFORMATION: artificial primer sequence

<400> SEQUENCE: 631
tttttttttt gagggaaggt aaatattgaa ccagtaaaaa gtttgagtaa    50

<210> SEQ ID NO 632
<211> LENGTH: 35
<212> TYPE: DNA
<213> ORGANISM: Artificial sequence
<220> FEATURE:
<223> OTHER INFORMATION: artificial primer sequence

<400> SEQUENCE: 632
taaaggtgga attaattttg cataatacat ttgag    35

<210> SEQ ID NO 633
<211> LENGTH: 33
<212> TYPE: DNA
<213> ORGANISM: Artificial sequence
<220> FEATURE:
<223> OTHER INFORMATION: artificial primer sequence

<400> SEQUENCE: 633
aatatcaatc aatagaaaaa gcaatattaa ctg    33

<210> SEQ ID NO 634
<211> LENGTH: 47
<212> TYPE: DNA
<213> ORGANISM: Artificial sequence
<220> FEATURE:
<223> OTHER INFORMATION: artificial primer sequence

<400> SEQUENCE: 634
ggattatcgg aataaagtta cgaacaagaa agcagatttt ttttttt    47

<210> SEQ ID NO 635
<211> LENGTH: 42
<212> TYPE: DNA
<213> ORGANISM: Artificial sequence
<220> FEATURE:
<223> OTHER INFORMATION: artificial primer sequence

<400> SEQUENCE: 635
gaagggtaaa agaaggaaac gtatcaacaa tagattaatt ta    42

<210> SEQ ID NO 636

```
<211> LENGTH: 50
<212> TYPE: DNA
<213> ORGANISM: Artificial sequence
<220> FEATURE:
<223> OTHER INFORMATION: artificial primer sequence

<400> SEQUENCE: 636
acgtaaagtt acaaataaga aacacgctaa cgagcgtctt tttttttttt          50

<210> SEQ ID NO 637
<211> LENGTH: 72
<212> TYPE: DNA
<213> ORGANISM: Artificial sequence
<220> FEATURE:
<223> OTHER INFORMATION: artificial primer sequence

<400> SEQUENCE: 637
tttttttttt gagccagtaa taagagaaag aaattgtttc atttgaatgc agaggcattt   60
tctttttttt tt                                                       72

<210> SEQ ID NO 638
<211> LENGTH: 41
<212> TYPE: DNA
<213> ORGANISM: Artificial sequence
<220> FEATURE:
<223> OTHER INFORMATION: artificial primer sequence

<400> SEQUENCE: 638
tttttttttt gagcaaaagc gttaaataag atttttttt t                    41

<210> SEQ ID NO 639
<211> LENGTH: 42
<212> TYPE: DNA
<213> ORGANISM: Artificial sequence
<220> FEATURE:
<223> OTHER INFORMATION: artificial primer sequence

<400> SEQUENCE: 639
tgaaacataa ccttcccttta gaatccttag actacgcaaa tc                 42

<210> SEQ ID NO 640
<211> LENGTH: 42
<212> TYPE: DNA
<213> ORGANISM: Artificial sequence
<220> FEATURE:
<223> OTHER INFORMATION: artificial primer sequence

<400> SEQUENCE: 640
aacatcaccg accgaaaaag cctgtttagt atcataatgg tt                  42

<210> SEQ ID NO 641
<211> LENGTH: 72
<212> TYPE: DNA
<213> ORGANISM: Artificial sequence
<220> FEATURE:
<223> OTHER INFORMATION: artificial primer sequence

<400> SEQUENCE: 641
tttttttttt aacatgtaat ttagtacctt ttttaacgct gagaaccata tttaacaacg   60 ccttttttt tt                                                       72

<210> SEQ ID NO 642
<211> LENGTH: 41
<212> TYPE: DNA
<213> ORGANISM: Artificial sequence
```

```
<220> FEATURE:
<223> OTHER INFORMATION: artificial primer sequence

<400> SEQUENCE: 642
tttttttttt gctattaatg cttaggttgg gttttttttt t                    41

<210> SEQ ID NO 643
<211> LENGTH: 49
<212> TYPE: DNA
<213> ORGANISM: Artificial sequence
<220> FEATURE:
<223> OTHER INFORMATION: artificial primer sequence

<400> SEQUENCE: 643
agcttagtat caaaagaacg cgagaaaatc tgaccttaac aacgtagat           49

<210> SEQ ID NO 644
<211> LENGTH: 42
<212> TYPE: DNA
<213> ORGANISM: Artificial sequence
<220> FEATURE:
<223> OTHER INFORMATION: artificial primer sequence

<400> SEQUENCE: 644 cttttaacc tccgtaattt tgcttctgaa accgaacgca aa                   42

<210> SEQ ID NO 645
<211> LENGTH: 52
<212> TYPE: DNA
<213> ORGANISM: Artificial sequence
<220> FEATURE:
<223> OTHER INFORMATION: artificial primer sequence

<400> SEQUENCE: 645
tttttttttt ttaattgaga atcggaaaat atattgtagg gctttttttt tt       52

<210> SEQ ID NO 646
<211> LENGTH: 57
<212> TYPE: DNA
<213> ORGANISM: Artificial sequence
<220> FEATURE:
<223> OTHER INFORMATION: artificial primer sequence

<400> SEQUENCE: 646
tttttttttt ttatataact atatgtaaaa ataaggaaga tgagtacctt aataatg  57

<210> SEQ ID NO 647
<211> LENGTH: 42
<212> TYPE: DNA
<213> ORGANISM: Artificial sequence
<220> FEATURE:
<223> OTHER INFORMATION: artificial primer sequence

<400> SEQUENCE: 647
caatcgctga aataagaaaa ctcagatgta ccatatcaaa at                  42

<210> SEQ ID NO 648
<211> LENGTH: 42
<212> TYPE: DNA
<213> ORGANISM: Artificial sequence
<220> FEATURE:
<223> OTHER INFORMATION: artificial primer sequence

<400> SEQUENCE: 648
aagacaaatc ataggtctga ggaaaacata tatgtaacgg aa                  42
```

<210> SEQ ID NO 649
<211> LENGTH: 49
<212> TYPE: DNA
<213> ORGANISM: Artificial sequence
<220> FEATURE:
<223> OTHER INFORMATION: artificial primer sequence

<400> SEQUENCE: 649
ttcatctctt tttcgtcaat agtgaattat taagatggaa acggcatga                49

<210> SEQ ID NO 650
<211> LENGTH: 52
<212> TYPE: DNA
<213> ORGANISM: Artificial sequence
<220> FEATURE:
<223> OTHER INFORMATION: artificial primer sequence

<400> SEQUENCE: 650
tttttttttt ctcaacatta gttaatcagt ataaagccaa cgttttttttt tt            52

<210> SEQ ID NO 651
<211> LENGTH: 57
<212> TYPE: DNA
<213> ORGANISM: Artificial sequence
<220> FEATURE:
<223> OTHER INFORMATION: artificial primer sequence

<400> SEQUENCE: 651
tttttttttt ataaacaccg gaatcataaa gttacaatcg ggagaaacaa agtaaca        57

<210> SEQ ID NO 652
<211> LENGTH: 43
<212> TYPE: DNA
<213> ORGANISM: Artificial sequence
<220> FEATURE:
<223> OTHER INFORMATION: artificial primer sequence

<400> SEQUENCE: 652
cagggatcgc caccctcaga accgccaccc tcattttttt ttt                      43

<210> SEQ ID NO 653
<211> LENGTH: 58
<212> TYPE: DNA
<213> ORGANISM: Artificial sequence
<220> FEATURE:
<223> OTHER INFORMATION: artificial primer sequence

<400> SEQUENCE: 653
tttttttttt gagccaccac cctcattttg atgcctattt cggaacctttt tttttttt     58

<210> SEQ ID NO 654
<211> LENGTH: 54
<212> TYPE: DNA
<213> ORGANISM: Artificial sequence
<220> FEATURE:
<223> OTHER INFORMATION: artificial primer sequence

<400> SEQUENCE: 654
tttttttttt acaacgcgac atcagacact aaaagaaaaa tgccctgacg agaa          54

<210> SEQ ID NO 655
<211> LENGTH: 35
<212> TYPE: DNA
<213> ORGANISM: Artificial sequence
<220> FEATURE:
<223> OTHER INFORMATION: artificial primer sequence

<400> SEQUENCE: 655
tcagaacagc aagcaacaac tgaaaatctc caaaa                                35

<210> SEQ ID NO 656
<211> LENGTH: 40
<212> TYPE: DNA
<213> ORGANISM: Artificial sequence
<220> FEATURE:
<223> OTHER INFORMATION: artificial primer sequence

<400> SEQUENCE: 656
attagataca tttcgcaaac aatgccactg gatatcaggt                           40

<210> SEQ ID NO 657
<211> LENGTH: 50
<212> TYPE: DNA
<213> ORGANISM: Artificial sequence
<220> FEATURE:
<223> OTHER INFORMATION: artificial primer sequence

<400> SEQUENCE: 657
atataagtat agcctagcgt atagtaaatg aattttctgt ttttttttt                 50

<210> SEQ ID NO 658
<211> LENGTH: 54
<212> TYPE: DNA
<213> ORGANISM: Artificial sequence
<220> FEATURE:
<223> OTHER INFORMATION: artificial primer sequence

<400> SEQUENCE: 658
tcgagagggt tggtactcac agcggtcccc cagataccag aacgagtagt aaat           54

<210> SEQ ID NO 659
<211> LENGTH: 58
<212> TYPE: DNA
<213> ORGANISM: Artificial sequence
<220> FEATURE:
<223> OTHER INFORMATION: artificial primer sequence

<400> SEQUENCE: 659
attttcatta catccatgtc tggcttagag aaccagaccg gaagaagatt aaccataa       58

<210> SEQ ID NO 660
<211> LENGTH: 32
<212> TYPE: DNA
<213> ORGANISM: Artificial sequence
<220> FEATURE:
<223> OTHER INFORMATION: artificial primer sequence

<400> SEQUENCE: 660
agacagccct catagtcgct gtagcattcc ac                                   32

<210> SEQ ID NO 661
<211> LENGTH: 49
<212> TYPE: DNA
<213> ORGANISM: Artificial sequence
<220> FEATURE:
<223> OTHER INFORMATION: artificial primer sequence

<400> SEQUENCE: 661
tttgctcagt accaagaaag gccaatagac agaggtttcc atacggggt                 49

<210> SEQ ID NO 662

```
<211> LENGTH: 52
<212> TYPE: DNA
<213> ORGANISM: Artificial sequence
<220> FEATURE:
<223> OTHER INFORMATION: artificial primer sequence

<400> SEQUENCE: 662
tttttttttt agaaggatta ggattattgc gaatacctca agttttttt tt      52

<210> SEQ ID NO 663
<211> LENGTH: 41
<212> TYPE: DNA
<213> ORGANISM: Artificial sequence
<220> FEATURE:
<223> OTHER INFORMATION: artificial primer sequence

<400> SEQUENCE: 663
tttttttttt atgggatttt gcgtacaaac tttttttttt t                 41

<210> SEQ ID NO 664
<211> LENGTH: 49
<212> TYPE: DNA
<213> ORGANISM: Artificial sequence
<220> FEATURE:
<223> OTHER INFORMATION: artificial primer sequence

<400> SEQUENCE: 664
tgagaatggc ggataagtgt cgtctttcca gtttctaaca ctggaacga         49

<210> SEQ ID NO 665
<211> LENGTH: 40
<212> TYPE: DNA
<213> ORGANISM: Artificial sequence
<220> FEATURE:
<223> OTHER INFORMATION: artificial primer sequence

<400> SEQUENCE: 665
ttaattgctt tcaacagacg tacgatctaa agttttgccg                   40

<210> SEQ ID NO 666
<211> LENGTH: 52
<212> TYPE: DNA
<213> ORGANISM: Artificial sequence
<220> FEATURE:
<223> OTHER INFORMATION: artificial primer sequence

<400> SEQUENCE: 666
tttttttttt tgagactata attttacaa gtattaagag gcttttttt tt       52

<210> SEQ ID NO 667
<211> LENGTH: 41
<212> TYPE: DNA
<213> ORGANISM: Artificial sequence
<220> FEATURE:
<223> OTHER INFORMATION: artificial primer sequence

<400> SEQUENCE: 667
tttttttttt tttcgaggtg aagatcgtca cttttttttt t                 41

<210> SEQ ID NO 668
<211> LENGTH: 42
<212> TYPE: DNA
<213> ORGANISM: Artificial sequence
<220> FEATURE:
<223> OTHER INFORMATION: artificial primer sequence

<400> SEQUENCE: 668
```

```
caatgacaac aaccatcgcc ctcacgttaa aggaagcggg gt          42
```

<210> SEQ ID NO 669
<211> LENGTH: 35
<212> TYPE: DNA
<213> ORGANISM: Artificial sequence
<220> FEATURE:
<223> OTHER INFORMATION: artificial primer sequence

<400> SEQUENCE: 669

```
agttaaaggc cgctcagcat cgagtttcta tcacc                 35
```

<210> SEQ ID NO 670
<211> LENGTH: 43
<212> TYPE: DNA
<213> ORGANISM: Artificial sequence
<220> FEATURE:
<223> OTHER INFORMATION: artificial primer sequence

<400> SEQUENCE: 670

```
tttttttttt attattctga aacatgagca taaccggact aaa        43
```

<210> SEQ ID NO 671
<211> LENGTH: 62
<212> TYPE: DNA
<213> ORGANISM: Artificial sequence
<220> FEATURE:
<223> OTHER INFORMATION: artificial primer sequence

<400> SEQUENCE: 671

```
tttttttttt cctcagcaga ccaaccatgg ctttaacaaa gctgctcatt cattttttt    60 tt                                                                   62
```

<210> SEQ ID NO 672
<211> LENGTH: 35
<212> TYPE: DNA
<213> ORGANISM: Artificial sequence
<220> FEATURE:
<223> OTHER INFORMATION: artificial primer sequence

<400> SEQUENCE: 672

```
aacggctgaa cccatagtac cgccaccccc atgtt                 35
```

<210> SEQ ID NO 673
<211> LENGTH: 31
<212> TYPE: DNA
<213> ORGANISM: Artificial sequence
<220> FEATURE:
<223> OTHER INFORMATION: artificial primer sequence

<400> SEQUENCE: 673

```
tttttttttt atttaccgtt ccagtaagcg t                     31
```

<210> SEQ ID NO 674
<211> LENGTH: 41
<212> TYPE: DNA
<213> ORGANISM: Artificial sequence
<220> FEATURE:
<223> OTHER INFORMATION: artificial primer sequence

<400> SEQUENCE: 674

```
catactaaaa cgaaagaagc gcagtctctg atttttttt t           41
```

<210> SEQ ID NO 675

```
<211> LENGTH: 57
<212> TYPE: DNA
<213> ORGANISM: Artificial sequence
<220> FEATURE:
<223> OTHER INFORMATION: artificial primer sequence

<400> SEQUENCE: 675
ttgagtattt tcataacgga gatccgcggc agacggtcaa tcataagttt tttttt        57

<210> SEQ ID NO 676
<211> LENGTH: 35
<212> TYPE: DNA
<213> ORGANISM: Artificial sequence
<220> FEATURE:
<223> OTHER INFORMATION: artificial primer sequence

<400> SEQUENCE: 676
acgtaatgtg tacttattca ttacccaaac accag                                35

<210> SEQ ID NO 677
<211> LENGTH: 42
<212> TYPE: DNA
<213> ORGANISM: Artificial sequence
<220> FEATURE:
<223> OTHER INFORMATION: artificial primer sequence

<400> SEQUENCE: 677
gtaaaatggg tagctgcagg ggatagttgc gccgaaaaag gc                        42

<210> SEQ ID NO 678
<211> LENGTH: 52
<212> TYPE: DNA
<213> ORGANISM: Artificial sequence
<220> FEATURE:
<223> OTHER INFORMATION: artificial primer sequence

<400> SEQUENCE: 678 ttttttttt cagttaatgc cccctacag tgcccgtata aattttttt tt                52

<210> SEQ ID NO 679
<211> LENGTH: 41
<212> TYPE: DNA
<213> ORGANISM: Artificial sequence
<220> FEATURE:
<223> OTHER INFORMATION: artificial primer sequence

<400> SEQUENCE: 679 ttttttttt acaggaggtt gaacattcaa cttttttttt t                          41

<210> SEQ ID NO 680
<211> LENGTH: 42
<212> TYPE: DNA
<213> ORGANISM: Artificial sequence
<220> FEATURE:
<223> OTHER INFORMATION: artificial primer sequence

<400> SEQUENCE: 680
aagaatacga tccagcgcag tgtcactgag aatggacgaa ct                        42

<210> SEQ ID NO 681
<211> LENGTH: 42
<212> TYPE: DNA
<213> ORGANISM: Artificial sequence
<220> FEATURE:
<223> OTHER INFORMATION: artificial primer sequence

<400> SEQUENCE: 681
```

-continued acactcacga aggccgaaag atttgcggtt tcttaaacag ct                              42

<210> SEQ ID NO 682
<211> LENGTH: 42
<212> TYPE: DNA
<213> ORGANISM: Artificial sequence
<220> FEATURE:
<223> OTHER INFORMATION: artificial primer sequence

<400> SEQUENCE: 682
gcgaaacgat tttagagatg gtttaattat caagacagtg cc                              42

<210> SEQ ID NO 683
<211> LENGTH: 42
<212> TYPE: DNA
<213> ORGANISM: Artificial sequence
<220> FEATURE:
<223> OTHER INFORMATION: artificial primer sequence

<400> SEQUENCE: 683
aaagtacgag gaagctttga gatatattcg gtcgctgagg ct                              42

<210> SEQ ID NO 684
<211> LENGTH: 42
<212> TYPE: DNA
<213> ORGANISM: Artificial sequence
<220> FEATURE:
<223> OTHER INFORMATION: artificial primer sequence

<400> SEQUENCE: 684
ctgtggtaaa taaaattaca ggtagaaaca ttgcacagca cc                              42

<210> SEQ ID NO 685
<211> LENGTH: 57
<212> TYPE: DNA
<213> ORGANISM: Artificial sequence
<220> FEATURE:
<223> OTHER INFORMATION: artificial primer sequence

<400> SEQUENCE: 685
ccccctgata ggtggtcacc ataaacaata tcggtttatc agcttgcttt tttttt            57

<210> SEQ ID NO 686
<211> LENGTH: 49
<212> TYPE: DNA
<213> ORGANISM: Artificial sequence
<220> FEATURE:
<223> OTHER INFORMATION: artificial primer sequence

<400> SEQUENCE: 686
ctgcagcgga ggtttgtacc gagcggagtc caaaaggagc cttgatacc                    49

<210> SEQ ID NO 687
<211> LENGTH: 52
<212> TYPE: DNA
<213> ORGANISM: Artificial sequence
<220> FEATURE:
<223> OTHER INFORMATION: artificial primer sequence

<400> SEQUENCE: 687
tttttttttt gataaattgt gtcgaaattt gtatcatcgc cttttttttt tt                52

<210> SEQ ID NO 688
<211> LENGTH: 52
<212> TYPE: DNA

```
<213> ORGANISM: Artificial sequence
<220> FEATURE:
<223> OTHER INFORMATION: artificial primer sequence

<400> SEQUENCE: 688 ttttttttt  aaaggctatc  aggtcatttt  tgagagatct  acttttttt  tt            52

<210> SEQ ID NO 689
<211> LENGTH: 66
<212> TYPE: DNA
<213> ORGANISM: Artificial sequence
<220> FEATURE:
<223> OTHER INFORMATION: artificial primer sequence

<400> SEQUENCE: 689
aagagcaacg  cttttggcca  gcactcaccg  cagtgccaag  ctttcagagg  tggagctttt    60
tttttt                                                                  66

<210> SEQ ID NO 690
<211> LENGTH: 49
<212> TYPE: DNA
<213> ORGANISM: Artificial sequence
<220> FEATURE:
<223> OTHER INFORMATION: artificial primer sequence

<400> SEQUENCE: 690
ctcataacca  gaatgcggca  ccaccaccgg  ccagatttcg  tccgtaaaa               49

<210> SEQ ID NO 691
<211> LENGTH: 44
<212> TYPE: DNA
<213> ORGANISM: Artificial sequence
<220> FEATURE:
<223> OTHER INFORMATION: artificial primer sequence

<400> SEQUENCE: 691
atgccggtta  gccggatcgt  taatctttgc  tcgtcatctt  atgc                    44

<210> SEQ ID NO 692
<211> LENGTH: 33
<212> TYPE: DNA
<213> ORGANISM: Artificial sequence
<220> FEATURE:
<223> OTHER INFORMATION: artificial primer sequence

<400> SEQUENCE: 692
taaattaatg  ccggagaggc  caaaaagacg  aca                                 33

<210> SEQ ID NO 693
<211> LENGTH: 35
<212> TYPE: DNA
<213> ORGANISM: Artificial sequence
<220> FEATURE:
<223> OTHER INFORMATION: artificial primer sequence

<400> SEQUENCE: 693
ataacgctca  gctcaaacgg  cggattgagg  ttgtg                               35

<210> SEQ ID NO 694
<211> LENGTH: 40
<212> TYPE: DNA
<213> ORGANISM: Artificial sequence
<220> FEATURE:
<223> OTHER INFORMATION: artificial primer sequence

<400> SEQUENCE: 694
```

```
tctggtcagc agccgggcgc ggttgctaat aaaaaggcaa                          40
```

<210> SEQ ID NO 695
<211> LENGTH: 50
<212> TYPE: DNA
<213> ORGANISM: Artificial sequence
<220> FEATURE:
<223> OTHER INFORMATION: artificial primer sequence

<400> SEQUENCE: 695

```
tttttttttt ggaaccgcac tggtgtgttc agcaaaacga ggcacctgct              50
```

<210> SEQ ID NO 696
<211> LENGTH: 54
<212> TYPE: DNA
<213> ORGANISM: Artificial sequence
<220> FEATURE:
<223> OTHER INFORMATION: artificial primer sequence

<400> SEQUENCE: 696

```
tttttttttt taatgcaacg gctggagaat accggcaggt cagacgattg gcct          54
```

<210> SEQ ID NO 697
<211> LENGTH: 54
<212> TYPE: DNA
<213> ORGANISM: Artificial sequence
<220> FEATURE:
<223> OTHER INFORMATION: artificial primer sequence

<400> SEQUENCE: 697

```
tcgcactcaa catttcctca ttaaagcccg cgcctaacgt cagcgtggtg ctgg          54
```

<210> SEQ ID NO 698
<211> LENGTH: 35
<212> TYPE: DNA
<213> ORGANISM: Artificial sequence
<220> FEATURE:
<223> OTHER INFORMATION: artificial primer sequence

<400> SEQUENCE: 698

```
cagttgagat ttagggtgtc ccccacgcag gaacg                              35
```

<210> SEQ ID NO 699
<211> LENGTH: 35
<212> TYPE: DNA
<213> ORGANISM: Artificial sequence
<220> FEATURE:
<223> OTHER INFORMATION: artificial primer sequence

<400> SEQUENCE: 699

```
gattcattga tattcacaaa cgctgcggcg gaacg                              35
```

<210> SEQ ID NO 700
<211> LENGTH: 42
<212> TYPE: DNA
<213> ORGANISM: Artificial sequence
<220> FEATURE:
<223> OTHER INFORMATION: artificial primer sequence

<400> SEQUENCE: 700

```
aacggaacaa tccgcaaccg caagaatgct tgtaggtgca ct                      42
```

<210> SEQ ID NO 701
<211> LENGTH: 42
<212> TYPE: DNA

```
<213> ORGANISM: Artificial sequence
<220> FEATURE:
<223> OTHER INFORMATION: artificial primer sequence

<400> SEQUENCE: 701
tcaggacgcc ctgcggctgg taatgggtgc tcattcgatt at                    42

<210> SEQ ID NO 702
<211> LENGTH: 72
<212> TYPE: DNA
<213> ORGANISM: Artificial sequence
<220> FEATURE:
<223> OTHER INFORMATION: artificial primer sequence

<400> SEQUENCE: 702
tttttttttt gaaagaggac agatattgtg aattacaaac atcccttaaa ctgaccaact    60
tttttttttt tt                                                       72

<210> SEQ ID NO 703
<211> LENGTH: 57
<212> TYPE: DNA
<213> ORGANISM: Artificial sequence
<220> FEATURE:
<223> OTHER INFORMATION: artificial primer sequence

<400> SEQUENCE: 703
tttttttttt gtgaataagg cttctacgtg gtatgagccg ggtcactgtt gttggga       57

<210> SEQ ID NO 704
<211> LENGTH: 42
<212> TYPE: DNA
<213> ORGANISM: Artificial sequence
<220> FEATURE:
<223> OTHER INFORMATION: artificial primer sequence

<400> SEQUENCE: 704
atcaacgttg atgatacagg agccactatc tttgagccgg tg                      42

<210> SEQ ID NO 705
<211> LENGTH: 42
<212> TYPE: DNA
<213> ORGANISM: Artificial sequence
<220> FEATURE:
<223> OTHER INFORMATION: artificial primer sequence

<400> SEQUENCE: 705
aaccggaggt aataagtttt ataaacggac caagcacgtt ac                      42

<210> SEQ ID NO 706
<211> LENGTH: 44
<212> TYPE: DNA
<213> ORGANISM: Artificial sequence
<220> FEATURE:
<223> OTHER INFORMATION: artificial primer sequence

<400> SEQUENCE: 706
gtaatcttga caagtgggct tagaactgaa aggttcggca tcag                    44

<210> SEQ ID NO 707
<211> LENGTH: 72
<212> TYPE: DNA
<213> ORGANISM: Artificial sequence
<220> FEATURE:
<223> OTHER INFORMATION: artificial primer sequence

<400> SEQUENCE: 707
```
tttttttttt ccaggcgcat aggctggctg accttctcaa ctttaatcga acggtgtaca     60
gatttttttt tt                                                        72

<210> SEQ ID NO 708
<211> LENGTH: 50
<212> TYPE: DNA
<213> ORGANISM: Artificial sequence
<220> FEATURE:
<223> OTHER INFORMATION: artificial primer sequence

<400> SEQUENCE: 708
tttttttttt acgagtagat ttagcaattc tactaaataa cagagaggtc               50

<210> SEQ ID NO 709
<211> LENGTH: 52
<212> TYPE: DNA
<213> ORGANISM: Artificial sequence
<220> FEATURE:
<223> OTHER INFORMATION: artificial primer sequence

<400> SEQUENCE: 709
tttttttttt aagcaataca tgttttaaga attagcaaaa tttttttttt tt            52

<210> SEQ ID NO 710
<211> LENGTH: 42
<212> TYPE: DNA
<213> ORGANISM: Artificial sequence
<220> FEATURE:
<223> OTHER INFORMATION: artificial primer sequence

<400> SEQUENCE: 710
agtacggata aatcatacag gcaaggcaaa atatgataat gc                       42

<210> SEQ ID NO 711
<211> LENGTH: 35
<212> TYPE: DNA
<213> ORGANISM: Artificial sequence
<220> FEATURE:
<223> OTHER INFORMATION: artificial primer sequence

<400> SEQUENCE: 711
aagtttcaat actgatatat tagattcaaa agggt                               35

<210> SEQ ID NO 712
<211> LENGTH: 44
<212> TYPE: DNA
<213> ORGANISM: Artificial sequence
<220> FEATURE:
<223> OTHER INFORMATION: artificial primer sequence

<400> SEQUENCE: 712
attccattag tagtagcatt atggggcgta acctgtttag ctat                     44

<210> SEQ ID NO 713
<211> LENGTH: 54
<212> TYPE: DNA
<213> ORGANISM: Artificial sequence
<220> FEATURE:
<223> OTHER INFORMATION: artificial primer sequence

<400> SEQUENCE: 713
cttaattgct gaatcaacta aatattcaat aaaaagccgg agcgttctag ctga          54

<210> SEQ ID NO 714

```
<211> LENGTH: 69
<212> TYPE: DNA
<213> ORGANISM: Artificial sequence
<220> FEATURE:
<223> OTHER INFORMATION: artificial primer sequence

<400> SEQUENCE: 714
tttttttttt ttaattgctc cttttgatat tgattctgtt tagtgtgcca gagggggtat      60
tttttttt                                                               69

<210> SEQ ID NO 715
<211> LENGTH: 52
<212> TYPE: DNA
<213> ORGANISM: Artificial sequence
<220> FEATURE:
<223> OTHER INFORMATION: artificial primer sequence

<400> SEQUENCE: 715
tttttttttt cagagcataa agctgttgta gctcaaaagc cttttttttt tt              52

<210> SEQ ID NO 716
<211> LENGTH: 35
<212> TYPE: DNA
<213> ORGANISM: Artificial sequence
<220> FEATURE:
<223> OTHER INFORMATION: artificial primer sequence

<400> SEQUENCE: 716
tttaattcga gcttagactt cacagttcgt gagag                                 35

<210> SEQ ID NO 717
<211> LENGTH: 49
<212> TYPE: DNA
<213> ORGANISM: Artificial sequence
<220> FEATURE:
<223> OTHER INFORMATION: artificial primer sequence

<400> SEQUENCE: 717
caacaggtca ggatagcaaa gcttacctc ggcgatctgc tctggtgta                   49

<210> SEQ ID NO 718
<211> LENGTH: 35
<212> TYPE: DNA
<213> ORGANISM: Artificial sequence
<220> FEATURE:
<223> OTHER INFORMATION: artificial primer sequence

<400> SEQUENCE: 718
cggattgcat caaacaaact cattttttgcg gatgg                                35

<210> SEQ ID NO 719
<211> LENGTH: 41
<212> TYPE: DNA
<213> ORGANISM: Artificial sequence
<220> FEATURE:
<223> OTHER INFORMATION: artificial primer sequence

<400> SEQUENCE: 719
tttttttttt atagtcagat agagagtacc tttttttttt t                          41

<210> SEQ ID NO 720
<211> LENGTH: 58
<212> TYPE: DNA
<213> ORGANISM: Artificial sequence
<220> FEATURE:
<223> OTHER INFORMATION: artificial primer sequence
```

<400> SEQUENCE: 720
tttttttttt aacattatga ccctcaaatc ccctgtaata cttttgcgtt tttttttt    58

<210> SEQ ID NO 721
<211> LENGTH: 43
<212> TYPE: DNA
<213> ORGANISM: Artificial sequence
<220> FEATURE:
<223> OTHER INFORMATION: artificial primer sequence

<400> SEQUENCE: 721
gctttaaaaa tatcgcaaat cggttgtacc aaattttttt ttt    43

<210> SEQ ID NO 722
<211> LENGTH: 41
<212> TYPE: DNA
<213> ORGANISM: Artificial sequence
<220> FEATURE:
<223> OTHER INFORMATION: artificial primer sequence

<400> SEQUENCE: 722
tttttttttt atagtaaaac caattctgcg atttttttt t    41

<210> SEQ ID NO 723
<211> LENGTH: 43
<212> TYPE: DNA
<213> ORGANISM: Artificial sequence
<220> FEATURE:
<223> OTHER INFORMATION: artificial primer sequence

<400> SEQUENCE: 723
tttttttttt ggagaagcct ttatttcaac gcaaggttga atc    43

<210> SEQ ID NO 724
<211> LENGTH: 42
<212> TYPE: DNA
<213> ORGANISM: Artificial sequence
<220> FEATURE:
<223> OTHER INFORMATION: artificial primer sequence

<400> SEQUENCE: 724
aaccctccgg aatcgagaat gagaggaagc ccgaacaaag cg    42

<210> SEQ ID NO 725
<211> LENGTH: 40
<212> TYPE: DNA
<213> ORGANISM: Artificial sequence
<220> FEATURE:
<223> OTHER INFORMATION: artificial primer sequence

<400> SEQUENCE: 725
ttaaatgtgg tcaacgagct gaaaaggtgg cattttgacc    40

<210> SEQ ID NO 726
<211> LENGTH: 49
<212> TYPE: DNA
<213> ORGANISM: Artificial sequence
<220> FEATURE:
<223> OTHER INFORMATION: artificial primer sequence

<400> SEQUENCE: 726
caaaagaagt ttagtaatgt gttaaattaa cgtacacgac gttgtaaaa    49

<210> SEQ ID NO 727

```
<211> LENGTH: 37
<212> TYPE: DNA
<213> ORGANISM: Artificial sequence
<220> FEATURE:
<223> OTHER INFORMATION: artificial primer sequence

<400> SEQUENCE: 727
caaaatagcg agagactatc aaattacgag gcatagt                        37

<210> SEQ ID NO 728
<211> LENGTH: 35
<212> TYPE: DNA
<213> ORGANISM: Artificial sequence
<220> FEATURE:
<223> OTHER INFORMATION: artificial primer sequence

<400> SEQUENCE: 728
taaaaactac atcgacataa atgggaacat ttttt                          35

<210> SEQ ID NO 729
<211> LENGTH: 35
<212> TYPE: DNA
<213> ORGANISM: Artificial sequence
<220> FEATURE:
<223> OTHER INFORMATION: artificial primer sequence

<400> SEQUENCE: 729
tccgtttgca catcgtgcca tagcatcagc ggggt                          35

<210> SEQ ID NO 730
<211> LENGTH: 54
<212> TYPE: DNA
<213> ORGANISM: Artificial sequence
<220> FEATURE:
<223> OTHER INFORMATION: artificial primer sequence

<400> SEQUENCE: 730
tccggcaggc ctttagtgat gcaacatttg gccttcctgt agcctttttt tttt     54

<210> SEQ ID NO 731
<211> LENGTH: 50
<212> TYPE: DNA
<213> ORGANISM: Artificial sequence
<220> FEATURE:
<223> OTHER INFORMATION: artificial primer sequence

<400> SEQUENCE: 731 ttttttttt aaacgatgct gattgccgtt gccggaccaa cggggcgctt           50

<210> SEQ ID NO 732
<211> LENGTH: 52
<212> TYPE: DNA
<213> ORGANISM: Artificial sequence
<220> FEATURE:
<223> OTHER INFORMATION: artificial primer sequence

<400> SEQUENCE: 732
tttttttttt tgagagtgtg aagggaaatc accatcattg ccttttttt tt        52

<210> SEQ ID NO 733
<211> LENGTH: 35
<212> TYPE: DNA
<213> ORGANISM: Artificial sequence
<220> FEATURE:
<223> OTHER INFORMATION: artificial primer sequence

<400> SEQUENCE: 733
```

```
tagctctata gacttgcaag gcgattaagg cgaaa                               35
```

<210> SEQ ID NO 734
<211> LENGTH: 42
<212> TYPE: DNA
<213> ORGANISM: Artificial sequence
<220> FEATURE:
<223> OTHER INFORMATION: artificial primer sequence

<400> SEQUENCE: 734

```
cacggaaagg ggaccaggaa gattgtataa gcaaacatct gc                      42
```

<210> SEQ ID NO 735
<211> LENGTH: 35
<212> TYPE: DNA
<213> ORGANISM: Artificial sequence
<220> FEATURE:
<223> OTHER INFORMATION: artificial primer sequence

<400> SEQUENCE: 735

```
cgcagaacag tcccaacgcc agggttttct cttcg                              35
```

<210> SEQ ID NO 736
<211> LENGTH: 35
<212> TYPE: DNA
<213> ORGANISM: Artificial sequence
<220> FEATURE:
<223> OTHER INFORMATION: artificial primer sequence

<400> SEQUENCE: 736

```
aaagccgaac aacccatca aaataatgt cggtg                                35
```

<210> SEQ ID NO 737
<211> LENGTH: 49
<212> TYPE: DNA
<213> ORGANISM: Artificial sequence
<220> FEATURE:
<223> OTHER INFORMATION: artificial primer sequence

<400> SEQUENCE: 737

```
tgtttacaca gcggaaccgt gtatttaaat tgtaaacgtt aagatgggc               49
```

<210> SEQ ID NO 738
<211> LENGTH: 50
<212> TYPE: DNA
<213> ORGANISM: Artificial sequence
<220> FEATURE:
<223> OTHER INFORMATION: artificial primer sequence

<400> SEQUENCE: 738

```
tttttttttt cgccacggga acggataacg ttgggcccgt aataaatttt              50
```

<210> SEQ ID NO 739
<211> LENGTH: 52
<212> TYPE: DNA
<213> ORGANISM: Artificial sequence
<220> FEATURE:
<223> OTHER INFORMATION: artificial primer sequence

<400> SEQUENCE: 739

```
tttttttttt aaacaagaga atcggcttct ccgtgctgga gctttttttt tt           52
```

<210> SEQ ID NO 740
<211> LENGTH: 35
<212> TYPE: DNA

```
<213> ORGANISM: Artificial sequence
<220> FEATURE:
<223> OTHER INFORMATION: artificial primer sequence

<400> SEQUENCE: 740
ggaagggaaa ccaggcaaag cgtcacgtat ttgcc                              35

<210> SEQ ID NO 741
<211> LENGTH: 62
<212> TYPE: DNA
<213> ORGANISM: Artificial sequence
<220> FEATURE:
<223> OTHER INFORMATION: artificial primer sequence

<400> SEQUENCE: 741 ttttttttt tcaggctgcg caactgttgc gacggcgaaa caactgacta tttttttttt   60
tt                                                                 62

<210> SEQ ID NO 742
<211> LENGTH: 58
<212> TYPE: DNA
<213> ORGANISM: Artificial sequence
<220> FEATURE:
<223> OTHER INFORMATION: artificial primer sequence

<400> SEQUENCE: 742 ttttttttt aactagcatg tcaaggcctg tatctcatat gtaccccgtt tttttttt     58

<210> SEQ ID NO 743
<211> LENGTH: 43
<212> TYPE: DNA
<213> ORGANISM: Artificial sequence
<220> FEATURE:
<223> OTHER INFORMATION: artificial primer sequence

<400> SEQUENCE: 743
caggaagggg ggatgtatga acggtaatcg taatttttt ttt                     43

<210> SEQ ID NO 744
<211> LENGTH: 42
<212> TYPE: DNA
<213> ORGANISM: Artificial sequence
<220> FEATURE:
<223> OTHER INFORMATION: artificial primer sequence

<400> SEQUENCE: 744
atcgcactcc agcccagttt gaaagagaga gaaagttttt ag                     42

<210> SEQ ID NO 745
<211> LENGTH: 49
<212> TYPE: DNA
<213> ORGANISM: Artificial sequence
<220> FEATURE:
<223> OTHER INFORMATION: artificial primer sequence

<400> SEQUENCE: 745
agctttccta ttacgccagc tgttgggtgg aatttagaaa acgtcataa              49

<210> SEQ ID NO 746
<211> LENGTH: 35
<212> TYPE: DNA
<213> ORGANISM: Artificial sequence
<220> FEATURE:
<223> OTHER INFORMATION: artificial primer sequence

<400> SEQUENCE: 746
```

-continued cggcaccgct tctggcatcg tatcaaacta ggtaa                                    35

<210> SEQ ID NO 747
<211> LENGTH: 49
<212> TYPE: DNA
<213> ORGANISM: Artificial sequence
<220> FEATURE:
<223> OTHER INFORMATION: artificial primer sequence

<400> SEQUENCE: 747
gtgccggcga tcggtgcggg ccccagtcag cgccaatcaa aaagcgtcc                    49

<210> SEQ ID NO 748
<211> LENGTH: 35
<212> TYPE: DNA
<213> ORGANISM: Artificial sequence
<220> FEATURE:
<223> OTHER INFORMATION: artificial primer sequence

<400> SEQUENCE: 748
cgtcggattc tccgaaaatc ctcgtcgctg gacga                                   35

<210> SEQ ID NO 749
<211> LENGTH: 41
<212> TYPE: DNA
<213> ORGANISM: Artificial sequence
<220> FEATURE:
<223> OTHER INFORMATION: artificial primer sequence

<400> SEQUENCE: 749
tttttttttt agctttcata agggtaaagt tttttttttt t                            41

<210> SEQ ID NO 750
<211> LENGTH: 57
<212> TYPE: DNA
<213> ORGANISM: Artificial sequence
<220> FEATURE:
<223> OTHER INFORMATION: artificial primer sequence

<400> SEQUENCE: 750
tttttttttt gttgataatc agaaaagccg tagctaatat gatattcaac acagtca          57

<210> SEQ ID NO 751
<211> LENGTH: 50
<212> TYPE: DNA
<213> ORGANISM: Artificial sequence
<220> FEATURE:
<223> OTHER INFORMATION: artificial primer sequence

<400> SEQUENCE: 751
tattttgtta aaattcgcat tgggataggc cattcgccat tttttttttt                   50

<210> SEQ ID NO 752
<211> LENGTH: 42
<212> TYPE: DNA
<213> ORGANISM: Artificial sequence
<220> FEATURE:
<223> OTHER INFORMATION: artificial primer sequence

<400> SEQUENCE: 752
tgttaaacaa aaggtaaccc tcgtttacca gacgcttgat ac                           42

<210> SEQ ID NO 753
<211> LENGTH: 50
<212> TYPE: DNA

<213> ORGANISM: Artificial sequence
<220> FEATURE:
<223> OTHER INFORMATION: artificial primer sequence

<400> SEQUENCE: 753
aaccaataac cagcagcctc cagagccgcc gccagcattg tttttttttt          50

<210> SEQ ID NO 754
<211> LENGTH: 35
<212> TYPE: DNA
<213> ORGANISM: Artificial sequence
<220> FEATURE:
<223> OTHER INFORMATION: artificial primer sequence

<400> SEQUENCE: 754
tcgcgtcaaa tgtgagcgag tcacaggcaa cgcgg                          35

<210> SEQ ID NO 755
<211> LENGTH: 40
<212> TYPE: DNA
<213> ORGANISM: Artificial sequence
<220> FEATURE:
<223> OTHER INFORMATION: artificial primer sequence

<400> SEQUENCE: 755
tttttttttt actaaagact ttttcataca gagggagcct                     40

<210> SEQ ID NO 756
<211> LENGTH: 44
<212> TYPE: DNA
<213> ORGANISM: Artificial sequence
<220> FEATURE:
<223> OTHER INFORMATION: artificial primer sequence

<400> SEQUENCE: 756
tttttttttt acagaccagg cgagctgctc attctttttt tttt                44

<210> SEQ ID NO 757
<211> LENGTH: 50
<212> TYPE: DNA
<213> ORGANISM: Artificial sequence
<220> FEATURE:
<223> OTHER INFORMATION: artificial primer sequence

<400> SEQUENCE: 757
cataggctgg ctgatttgaa agaggacaga tgaacggtgt tttttttttt          50

<210> SEQ ID NO 758
<211> LENGTH: 49
<212> TYPE: DNA
<213> ORGANISM: Artificial sequence
<220> FEATURE:
<223> OTHER INFORMATION: artificial primer sequence

<400> SEQUENCE: 758
ggcttgcgac aacataaaca agtctttcca gacgttagta aagtatggg           49

<210> SEQ ID NO 759
<211> LENGTH: 49
<212> TYPE: DNA
<213> ORGANISM: Artificial sequence
<220> FEATURE:
<223> OTHER INFORMATION: artificial primer sequence

<400> SEQUENCE: 759
ctcagcagaa tttcaacaac tcagacagcc ctcatagtta gctgagaat           49

<210> SEQ ID NO 760
<211> LENGTH: 49
<212> TYPE: DNA
<213> ORGANISM: Artificial sequence
<220> FEATURE:
<223> OTHER INFORMATION: artificial primer sequence

<400> SEQUENCE: 760
agggtagcaa cggctgagga agtttccatt aaacgcggaa cgttatcag          49

<210> SEQ ID NO 761
<211> LENGTH: 49
<212> TYPE: DNA
<213> ORGANISM: Artificial sequence
<220> FEATURE:
<223> OTHER INFORMATION: artificial primer sequence

<400> SEQUENCE: 761
gttgcgccga caatagggag tcagagcccg ttttcgtgaa ttatcacaa          49

<210> SEQ ID NO 762
<211> LENGTH: 42
<212> TYPE: DNA
<213> ORGANISM: Artificial sequence
<220> FEATURE:
<223> OTHER INFORMATION: artificial primer sequence

<400> SEQUENCE: 762
accgataagc ggaggtaacg atctaaagtt ttgtcctttc aa                 42

<210> SEQ ID NO 763
<211> LENGTH: 38
<212> TYPE: DNA
<213> ORGANISM: Artificial sequence
<220> FEATURE:
<223> OTHER INFORMATION: artificial primer sequence

<400> SEQUENCE: 763
tttttttttt gctccaaaag ctttgaggtt tttttttt                      38

<210> SEQ ID NO 764
<211> LENGTH: 44
<212> TYPE: DNA
<213> ORGANISM: Artificial sequence
<220> FEATURE:
<223> OTHER INFORMATION: artificial primer sequence

<400> SEQUENCE: 764
tttttttttt agtgaataag gcgaattacc ttatttttttt tttt              44

<210> SEQ ID NO 765
<211> LENGTH: 35
<212> TYPE: DNA
<213> ORGANISM: Artificial sequence
<220> FEATURE:
<223> OTHER INFORMATION: artificial primer sequence

<400> SEQUENCE: 765
taataattac aacgtttcag ggatagcata ccgcc                         35

<210> SEQ ID NO 766
<211> LENGTH: 40
<212> TYPE: DNA
<213> ORGANISM: Artificial sequence
<220> FEATURE:

<223> OTHER INFORMATION: artificial primer sequence

<400> SEQUENCE: 766
aatctccagt tcgtaggaa cccatgtacc tttttttttt                40

<210> SEQ ID NO 767
<211> LENGTH: 42
<212> TYPE: DNA
<213> ORGANISM: Artificial sequence
<220> FEATURE:
<223> OTHER INFORMATION: artificial primer sequence

<400> SEQUENCE: 767
actttaatca ttgtttgccc taattacgcg tttacgaagc aa            42

<210> SEQ ID NO 768
<211> LENGTH: 35
<212> TYPE: DNA
<213> ORGANISM: Artificial sequence
<220> FEATURE:
<223> OTHER INFORMATION: artificial primer sequence

<400> SEQUENCE: 768
tgaatgggct tgagatggtt tgaacgagca gatac                    35

<210> SEQ ID NO 769
<211> LENGTH: 49
<212> TYPE: DNA
<213> ORGANISM: Artificial sequence
<220> FEATURE:
<223> OTHER INFORMATION: artificial primer sequence

<400> SEQUENCE: 769
cctgtagcat tccaaaagga agggtcagaa agcgccgagg aaaaagaca     49

<210> SEQ ID NO 770
<211> LENGTH: 42
<212> TYPE: DNA
<213> ORGANISM: Artificial sequence
<220> FEATURE:
<223> OTHER INFORMATION: artificial primer sequence

<400> SEQUENCE: 770
tcaccagtac aaactttttc atactggtcc gttccacaaa gt            42

<210> SEQ ID NO 771
<211> LENGTH: 38
<212> TYPE: DNA
<213> ORGANISM: Artificial sequence
<220> FEATURE:
<223> OTHER INFORMATION: artificial primer sequence

<400> SEQUENCE: 771
tttttttttt gtaacactga aaaaaagtt tttttttt                  38

<210> SEQ ID NO 772
<211> LENGTH: 36
<212> TYPE: DNA
<213> ORGANISM: Artificial sequence
<220> FEATURE:
<223> OTHER INFORMATION: artificial primer sequence

<400> SEQUENCE: 772
tttttttttt ccgtactcag gaggtttaga gcccaa                   36

-continued

```
<210> SEQ ID NO 773
<211> LENGTH: 36
<212> TYPE: DNA
<213> ORGANISM: Artificial sequence
<220> FEATURE:
<223> OTHER INFORMATION: artificial primer sequence

<400> SEQUENCE: 773
tttttttttt gcgattttaa gaactggctt aacgga                                    36

<210> SEQ ID NO 774
<211> LENGTH: 38
<212> TYPE: DNA
<213> ORGANISM: Artificial sequence
<220> FEATURE:
<223> OTHER INFORMATION: artificial primer sequence

<400> SEQUENCE: 774
tttttttttt tagaaagatg taagagcatt tttttttt                                  38

<210> SEQ ID NO 775
<211> LENGTH: 42
<212> TYPE: DNA
<213> ORGANISM: Artificial sequence
<220> FEATURE:
<223> OTHER INFORMATION: artificial primer sequence

<400> SEQUENCE: 775
ttgagattta ggaacaaaag ggacgagaaa tcaacgtaac aa                             42

<210> SEQ ID NO 776
<211> LENGTH: 49
<212> TYPE: DNA
<213> ORGANISM: Artificial sequence
<220> FEATURE:
<223> OTHER INFORMATION: artificial primer sequence

<400> SEQUENCE: 776
gggttttgct cagtattaga caattgagtt ttattcaaga aatcatttg                      49

<210> SEQ ID NO 777
<211> LENGTH: 42
<212> TYPE: DNA
<213> ORGANISM: Artificial sequence
<220> FEATURE:
<223> OTHER INFORMATION: artificial primer sequence

<400> SEQUENCE: 777
gagagggttt aacgttgcga acttgctttc gaggtgcgaa ag                             42

<210> SEQ ID NO 778
<211> LENGTH: 42
<212> TYPE: DNA
<213> ORGANISM: Artificial sequence
<220> FEATURE:
<223> OTHER INFORMATION: artificial primer sequence

<400> SEQUENCE: 778
aagtataagc agccagcaat atattaaaac caatcaaaca aa                             42

<210> SEQ ID NO 779
<211> LENGTH: 35
<212> TYPE: DNA
<213> ORGANISM: Artificial sequence
<220> FEATURE:
<223> OTHER INFORMATION: artificial primer sequence
```

<400> SEQUENCE: 779
gcccggaagg agtgcgttga attaattgta tcggt                    35

<210> SEQ ID NO 780
<211> LENGTH: 40
<212> TYPE: DNA
<213> ORGANISM: Artificial sequence
<220> FEATURE:
<223> OTHER INFORMATION: artificial primer sequence

<400> SEQUENCE: 780
aggcatatca tcagacaaca ttattacagg tttttttttt              40

<210> SEQ ID NO 781
<211> LENGTH: 42
<212> TYPE: DNA
<213> ORGANISM: Artificial sequence
<220> FEATURE:
<223> OTHER INFORMATION: artificial primer sequence

<400> SEQUENCE: 781
tctgaaacat gatgtagtaa agaaccggat attcacaaga gt           42

<210> SEQ ID NO 782
<211> LENGTH: 42
<212> TYPE: DNA
<213> ORGANISM: Artificial sequence
<220> FEATURE:
<223> OTHER INFORMATION: artificial primer sequence

<400> SEQUENCE: 782
ctattatggc aggtcaatat cgcgtttttt tgcggatggc gt           42

<210> SEQ ID NO 783
<211> LENGTH: 42
<212> TYPE: DNA
<213> ORGANISM: Artificial sequence
<220> FEATURE:
<223> OTHER INFORMATION: artificial primer sequence

<400> SEQUENCE: 783
tcggaacatt ttgcaccatc gcccacgcat aacaattttt ct           42

<210> SEQ ID NO 784
<211> LENGTH: 42
<212> TYPE: DNA
<213> ORGANISM: Artificial sequence
<220> FEATURE:
<223> OTHER INFORMATION: artificial primer sequence

<400> SEQUENCE: 784
gcccccttga tatttgatta aagaaaatca gacgaagtat ca           42

<210> SEQ ID NO 785
<211> LENGTH: 42
<212> TYPE: DNA
<213> ORGANISM: Artificial sequence
<220> FEATURE:
<223> OTHER INFORMATION: artificial primer sequence

<400> SEQUENCE: 785
gtgcccgtcc tcatgaatac cggcaacaaa aaggtattct ta           42

<210> SEQ ID NO 786
<211> LENGTH: 44

<212> TYPE: DNA
<213> ORGANISM: Artificial sequence
<220> FEATURE:
<223> OTHER INFORMATION: artificial primer sequence

<400> SEQUENCE: 786
tttttttttt ttttgatgat acataggtgt atcatttttt tttt         44

<210> SEQ ID NO 787
<211> LENGTH: 38
<212> TYPE: DNA
<213> ORGANISM: Artificial sequence
<220> FEATURE:
<223> OTHER INFORMATION: artificial primer sequence

<400> SEQUENCE: 787
tttttttttt acactatcaa ctggatagtt tttttttt               38

<210> SEQ ID NO 788
<211> LENGTH: 49
<212> TYPE: DNA
<213> ORGANISM: Artificial sequence
<220> FEATURE:
<223> OTHER INFORMATION: artificial primer sequence

<400> SEQUENCE: 788
cagacgacga taaataacg ctaccacatt aataaaacga accattata    49

<210> SEQ ID NO 789
<211> LENGTH: 49
<212> TYPE: DNA
<213> ORGANISM: Artificial sequence
<220> FEATURE:
<223> OTHER INFORMATION: artificial primer sequence

<400> SEQUENCE: 789
aaccaaaata gcgacaaaag aaatcttgaa gggaaccgaa ctgaccaac   49

<210> SEQ ID NO 790
<211> LENGTH: 42
<212> TYPE: DNA
<213> ORGANISM: Artificial sequence
<220> FEATURE:
<223> OTHER INFORMATION: artificial primer sequence

<400> SEQUENCE: 790
gaatttaaat aagtttgata taccctcaga accgcccctc at          42

<210> SEQ ID NO 791
<211> LENGTH: 42
<212> TYPE: DNA
<213> ORGANISM: Artificial sequence
<220> FEATURE:
<223> OTHER INFORMATION: artificial primer sequence

<400> SEQUENCE: 791
agttttgatc ccctgacca taaatcaaaa aaagattaag ag           42

<210> SEQ ID NO 792
<211> LENGTH: 49
<212> TYPE: DNA
<213> ORGANISM: Artificial sequence
<220> FEATURE:
<223> OTHER INFORMATION: artificial primer sequence

<400> SEQUENCE: 792

```
gccgccattg gcctgcctat tagagaagga ttaggaacac ccatcagag          49
```

<210> SEQ ID NO 793
<211> LENGTH: 42
<212> TYPE: DNA
<213> ORGANISM: Artificial sequence
<220> FEATURE:
<223> OTHER INFORMATION: artificial primer sequence

<400> SEQUENCE: 793

```
cctcagattg ccatgaggga gggaaggtga aacgcacgca at                 42
```

<210> SEQ ID NO 794
<211> LENGTH: 44
<212> TYPE: DNA
<213> ORGANISM: Artificial sequence
<220> FEATURE:
<223> OTHER INFORMATION: artificial primer sequence

<400> SEQUENCE: 794

```
tttttttttt gaaccgcctc ccgtcataca tggcttttttt tttt              44
```

<210> SEQ ID NO 795
<211> LENGTH: 40
<212> TYPE: DNA
<213> ORGANISM: Artificial sequence
<220> FEATURE:
<223> OTHER INFORMATION: artificial primer sequence

<400> SEQUENCE: 795

```
tttttttttt cgtccaatac tgcggatgtt tagtaaccct                    40
```

<210> SEQ ID NO 796
<211> LENGTH: 36
<212> TYPE: DNA
<213> ORGANISM: Artificial sequence
<220> FEATURE:
<223> OTHER INFORMATION: artificial primer sequence

<400> SEQUENCE: 796

```
atcgtcagtc tttaccctga ctattatttt tttttt                        36
```

<210> SEQ ID NO 797
<211> LENGTH: 63
<212> TYPE: DNA
<213> ORGANISM: Artificial sequence
<220> FEATURE:
<223> OTHER INFORMATION: artificial primer sequence

<400> SEQUENCE: 797

```
cattagcgtc agacgataaa tttagccgga actaaaacac tcttgtatca tcgccttgta   60
gcg                                                            63
```

<210> SEQ ID NO 798
<211> LENGTH: 49
<212> TYPE: DNA
<213> ORGANISM: Artificial sequence
<220> FEATURE:
<223> OTHER INFORMATION: artificial primer sequence

<400> SEQUENCE: 798

```
attaaagatc ggcacggaga tatctttgac ccccactaaa accgctttt          49
```

<210> SEQ ID NO 799
<211> LENGTH: 42

```
<212> TYPE: DNA
<213> ORGANISM: Artificial sequence
<220> FEATURE:
<223> OTHER INFORMATION: artificial primer sequence

<400> SEQUENCE: 799
aagggcgaca ttcaataagt ttaccagaat gaaattttac ag                    42

<210> SEQ ID NO 800
<211> LENGTH: 40
<212> TYPE: DNA
<213> ORGANISM: Artificial sequence
<220> FEATURE:
<223> OTHER INFORMATION: artificial primer sequence

<400> SEQUENCE: 800
tttttttttt tggtttacca gcgccacaat agaaagcaga                       40

<210> SEQ ID NO 801
<211> LENGTH: 44
<212> TYPE: DNA
<213> ORGANISM: Artificial sequence
<220> FEATURE:
<223> OTHER INFORMATION: artificial primer sequence

<400> SEQUENCE: 801
tttttttttt tagtcagaag caactccaac aggttttttt tttt                  44

<210> SEQ ID NO 802
<211> LENGTH: 50
<212> TYPE: DNA
<213> ORGANISM: Artificial sequence
<220> FEATURE:
<223> OTHER INFORMATION: artificial primer sequence

<400> SEQUENCE: 802
aagcggagga gaaggaaccc taaatcacca tcaatatgat tttttttttt            50

<210> SEQ ID NO 803
<211> LENGTH: 49
<212> TYPE: DNA
<213> ORGANISM: Artificial sequence
<220> FEATURE:
<223> OTHER INFORMATION: artificial primer sequence

<400> SEQUENCE: 803
ttgcatcaaa tcagtaaata ttcattgacc agaggggta atagtaaaa              49

<210> SEQ ID NO 804
<211> LENGTH: 42
<212> TYPE: DNA
<213> ORGANISM: Artificial sequence
<220> FEATURE:
<223> OTHER INFORMATION: artificial primer sequence

<400> SEQUENCE: 804
caaacgtgac tcctcgctaa ttgaacaaag tcagactcct ca                    42

<210> SEQ ID NO 805
<211> LENGTH: 50
<212> TYPE: DNA
<213> ORGANISM: Artificial sequence
<220> FEATURE:
<223> OTHER INFORMATION: artificial primer sequence

<400> SEQUENCE: 805
```
tattttgtca caataagaca aggaaccaga gccaccaccg ttttttttt    50

<210> SEQ ID NO 806
<211> LENGTH: 49
<212> TYPE: DNA
<213> ORGANISM: Artificial sequence
<220> FEATURE:
<223> OTHER INFORMATION: artificial primer sequence

<400> SEQUENCE: 806
aattcgagct tcaaagcgaa ctccttttct gtagctcaac atgttttaa    49

<210> SEQ ID NO 807
<211> LENGTH: 49
<212> TYPE: DNA
<213> ORGANISM: Artificial sequence
<220> FEATURE:
<223> OTHER INFORMATION: artificial primer sequence

<400> SEQUENCE: 807
actggcacac aaacccacca ctaaaggcga aagaggcaaa agaatacac    49

<210> SEQ ID NO 808
<211> LENGTH: 49
<212> TYPE: DNA
<213> ORGANISM: Artificial sequence
<220> FEATURE:
<223> OTHER INFORMATION: artificial primer sequence

<400> SEQUENCE: 808
caaaagacca caaggggaga attaactgat tagcgagtta atcagtttc    49

<210> SEQ ID NO 809
<211> LENGTH: 49
<212> TYPE: DNA
<213> ORGANISM: Artificial sequence
<220> FEATURE:
<223> OTHER INFORMATION: artificial primer sequence

<400> SEQUENCE: 809
aggaaacagt ctctccgcca cacagcatgg taaaatacgt aatgccact    49

<210> SEQ ID NO 810
<211> LENGTH: 38
<212> TYPE: DNA
<213> ORGANISM: Artificial sequence
<220> FEATURE:
<223> OTHER INFORMATION: artificial primer sequence

<400> SEQUENCE: 810
tttttttttt aagaaaagta aattcatatt tttttttt    38

<210> SEQ ID NO 811
<211> LENGTH: 44
<212> TYPE: DNA
<213> ORGANISM: Artificial sequence
<220> FEATURE:
<223> OTHER INFORMATION: artificial primer sequence

<400> SEQUENCE: 811
tttttttttt caggattaga gaatatgcaa ctaattttt tttt    44

<210> SEQ ID NO 812
<211> LENGTH: 42
<212> TYPE: DNA
<213> ORGANISM: Artificial sequence

```
<220> FEATURE:
<223> OTHER INFORMATION: artificial primer sequence

<400> SEQUENCE: 812
gtaccttcaa taaaaagcaa tcaagagata gctgataaat ta                42

<210> SEQ ID NO 813
<211> LENGTH: 42
<212> TYPE: DNA
<213> ORGANISM: Artificial sequence
<220> FEATURE:
<223> OTHER INFORMATION: artificial primer sequence

<400> SEQUENCE: 813
caataataaa cagggaagcg caccaggcag taacaagaaa gg                42

<210> SEQ ID NO 814
<211> LENGTH: 40
<212> TYPE: DNA
<213> ORGANISM: Artificial sequence
<220> FEATURE:
<223> OTHER INFORMATION: artificial primer sequence

<400> SEQUENCE: 814
taccgaatca aaaataaga aacgattttt tttttttttt                    40

<210> SEQ ID NO 815
<211> LENGTH: 42
<212> TYPE: DNA
<213> ORGANISM: Artificial sequence
<220> FEATURE:
<223> OTHER INFORMATION: artificial primer sequence

<400> SEQUENCE: 815
ggttagagct taattgctga aaaaagtatt aagaggctga ga                42

<210> SEQ ID NO 816
<211> LENGTH: 38
<212> TYPE: DNA
<213> ORGANISM: Artificial sequence
<220> FEATURE:
<223> OTHER INFORMATION: artificial primer sequence

<400> SEQUENCE: 816
tttttttttt tgtttaacgg cccttttttt tttttttt                     38

<210> SEQ ID NO 817
<211> LENGTH: 43
<212> TYPE: DNA
<213> ORGANISM: Artificial sequence
<220> FEATURE:
<223> OTHER INFORMATION: artificial primer sequence

<400> SEQUENCE: 817
tttttttttt tacaatttta tcctgaatca atccaatgaa aat               43

<210> SEQ ID NO 818
<211> LENGTH: 43
<212> TYPE: DNA
<213> ORGANISM: Artificial sequence
<220> FEATURE:
<223> OTHER INFORMATION: artificial primer sequence

<400> SEQUENCE: 818
tttttttttt agtacggtgt ctggaagttg accatttagc tat               43
```

<210> SEQ ID NO 819
<211> LENGTH: 35
<212> TYPE: DNA
<213> ORGANISM: Artificial sequence
<220> FEATURE:
<223> OTHER INFORMATION: artificial primer sequence

<400> SEQUENCE: 819
atattattta tcccttacca aagattagag ggtta                          35

<210> SEQ ID NO 820
<211> LENGTH: 38
<212> TYPE: DNA
<213> ORGANISM: Artificial sequence
<220> FEATURE:
<223> OTHER INFORMATION: artificial primer sequence

<400> SEQUENCE: 820 ttttttttt tggtcaatag gcaaggcatt tttttttt                        38

<210> SEQ ID NO 821
<211> LENGTH: 40
<212> TYPE: DNA
<213> ORGANISM: Artificial sequence
<220> FEATURE:
<223> OTHER INFORMATION: artificial primer sequence

<400> SEQUENCE: 821
tcatacaacc tgttagatac atttcgcaaa tttttttttt                     40

<210> SEQ ID NO 822
<211> LENGTH: 42
<212> TYPE: DNA
<213> ORGANISM: Artificial sequence
<220> FEATURE:
<223> OTHER INFORMATION: artificial primer sequence

<400> SEQUENCE: 822
gcaaatcatg cagaatacaa aggctatcag aaaagcccca aa                  42

<210> SEQ ID NO 823
<211> LENGTH: 35
<212> TYPE: DNA
<213> ORGANISM: Artificial sequence
<220> FEATURE:
<223> OTHER INFORMATION: artificial primer sequence

<400> SEQUENCE: 823
cattacccaa caatatggaa accttgctaa aaata                          35

<210> SEQ ID NO 824
<211> LENGTH: 42
<212> TYPE: DNA
<213> ORGANISM: Artificial sequence
<220> FEATURE:
<223> OTHER INFORMATION: artificial primer sequence

<400> SEQUENCE: 824
ttcatcgcgt tttagcgaac cagaaataaa taacgctaaa at                  42

<210> SEQ ID NO 825
<211> LENGTH: 35
<212> TYPE: DNA
<213> ORGANISM: Artificial sequence
<220> FEATURE:
<223> OTHER INFORMATION: artificial primer sequence

<400> SEQUENCE: 825
catcgagcta atttaattaa tgaatccttg aaaac                                    35

<210> SEQ ID NO 826
<211> LENGTH: 42
<212> TYPE: DNA
<213> ORGANISM: Artificial sequence
<220> FEATURE:
<223> OTHER INFORMATION: artificial primer sequence

<400> SEQUENCE: 826
ccaagtataa atcacgctaa cgagcgtcaa cagccagaga at                           42

<210> SEQ ID NO 827
<211> LENGTH: 49
<212> TYPE: DNA
<213> ORGANISM: Artificial sequence
<220> FEATURE:
<223> OTHER INFORMATION: artificial primer sequence

<400> SEQUENCE: 827
gaacggggct atcttagccg aagtaagctc agagccgcca ccctcagaa                    49

<210> SEQ ID NO 828
<211> LENGTH: 44
<212> TYPE: DNA
<213> ORGANISM: Artificial sequence
<220> FEATURE:
<223> OTHER INFORMATION: artificial primer sequence

<400> SEQUENCE: 828
tttttttttt ttatcattcc aatttgcacc cagcttttttt tttt                        44

<210> SEQ ID NO 829
<211> LENGTH: 38
<212> TYPE: DNA
<213> ORGANISM: Artificial sequence
<220> FEATURE:
<223> OTHER INFORMATION: artificial primer sequence

<400> SEQUENCE: 829
tttttttttt aagaattagt tcaacgcatt tttttttt                                38

<210> SEQ ID NO 830
<211> LENGTH: 42
<212> TYPE: DNA
<213> ORGANISM: Artificial sequence
<220> FEATURE:
<223> OTHER INFORMATION: artificial primer sequence

<400> SEQUENCE: 830
aataatatac cgactataaa aaaatattcc ccttattagc gt                           42

<210> SEQ ID NO 831
<211> LENGTH: 49
<212> TYPE: DNA
<213> ORGANISM: Artificial sequence
<220> FEATURE:
<223> OTHER INFORMATION: artificial primer sequence

<400> SEQUENCE: 831
acgagcacag taatccacgg aaccgattct tttcataatc aaaatcacc                    49

<210> SEQ ID NO 832

```
<211> LENGTH: 42
<212> TYPE: DNA
<213> ORGANISM: Artificial sequence
<220> FEATURE:
<223> OTHER INFORMATION: artificial primer sequence

<400> SEQUENCE: 832
tgaccctgca atgctgagaa aggccggaat gccgggagtc tg                          42

<210> SEQ ID NO 833
<211> LENGTH: 49
<212> TYPE: DNA
<213> ORGANISM: Artificial sequence
<220> FEATURE:
<223> OTHER INFORMATION: artificial primer sequence

<400> SEQUENCE: 833
aacattagaa gcccacgaga atcaaatgct ttaaattttt tggaggcga                   49

<210> SEQ ID NO 834
<211> LENGTH: 35
<212> TYPE: DNA
<213> ORGANISM: Artificial sequence
<220> FEATURE:
<223> OTHER INFORMATION: artificial primer sequence

<400> SEQUENCE: 834
cgacaattgt ttatgcgccc acggtattct aagaa                                  35

<210> SEQ ID NO 835
<211> LENGTH: 42
<212> TYPE: DNA
<213> ORGANISM: Artificial sequence
<220> FEATURE:
<223> OTHER INFORMATION: artificial primer sequence

<400> SEQUENCE: 835
aagagaaacg ctcaaacctc cggcttagtc ccttatacat tt                          42

<210> SEQ ID NO 836
<211> LENGTH: 44
<212> TYPE: DNA
<213> ORGANISM: Artificial sequence
<220> FEATURE:
<223> OTHER INFORMATION: artificial primer sequence

<400> SEQUENCE: 836
tttttttttt caacatgtaa ttggctgtct ttcctttttt tttt                        44

<210> SEQ ID NO 837
<211> LENGTH: 40
<212> TYPE: DNA
<213> ORGANISM: Artificial sequence
<220> FEATURE:
<223> OTHER INFORMATION: artificial primer sequence

<400> SEQUENCE: 837
tttttttttt aggataaaaa tttttacctt tatcaaaatt                             40

<210> SEQ ID NO 838
<211> LENGTH: 63
<212> TYPE: DNA
<213> ORGANISM: Artificial sequence
<220> FEATURE:
<223> OTHER INFORMATION: artificial primer sequence

<400> SEQUENCE: 838
```

```
ggtactagaa aaagcgtcac ctagcgacag cgtcaccgac ttagcaaggc cggaaacctg    60
ttt                                                                  63
```

<210> SEQ ID NO 839
<211> LENGTH: 35
<212> TYPE: DNA
<213> ORGANISM: Artificial sequence
<220> FEATURE:
<223> OTHER INFORMATION: artificial primer sequence

<400> SEQUENCE: 839

```
ttgagaaggt ctgagagact aatagcgaca tcaag                               35
```

<210> SEQ ID NO 840
<211> LENGTH: 42
<212> TYPE: DNA
<213> ORGANISM: Artificial sequence
<220> FEATURE:
<223> OTHER INFORMATION: artificial primer sequence

<400> SEQUENCE: 840

```
gacagtccat atattttaaa tgtaatacca gagcagtagc at                       42
```

<210> SEQ ID NO 841
<211> LENGTH: 42
<212> TYPE: DNA
<213> ORGANISM: Artificial sequence
<220> FEATURE:
<223> OTHER INFORMATION: artificial primer sequence

<400> SEQUENCE: 841

```
ataagaagac cgtgtagtta atttcatcat ggattccgaa cg                       42
```

<210> SEQ ID NO 842
<211> LENGTH: 49
<212> TYPE: DNA
<213> ORGANISM: Artificial sequence
<220> FEATURE:
<223> OTHER INFORMATION: artificial primer sequence

<400> SEQUENCE: 842

```
gcgttaatat gcgttaccat tgagccattt gggaaattat tctaaaggt                49
```

<210> SEQ ID NO 843
<211> LENGTH: 35
<212> TYPE: DNA
<213> ORGANISM: Artificial sequence
<220> FEATURE:
<223> OTHER INFORMATION: artificial primer sequence

<400> SEQUENCE: 843

```
tatataacta taagatcgtc gaattaccga gaaac                               35
```

<210> SEQ ID NO 844
<211> LENGTH: 35
<212> TYPE: DNA
<213> ORGANISM: Artificial sequence
<220> FEATURE:
<223> OTHER INFORMATION: artificial primer sequence

<400> SEQUENCE: 844

```
ccttttttaca gtagggctta attcgagctg tagaa                              35
```

<210> SEQ ID NO 845

```
<211> LENGTH: 40
<212> TYPE: DNA
<213> ORGANISM: Artificial sequence
<220> FEATURE:
<223> OTHER INFORMATION: artificial primer sequence

<400> SEQUENCE: 845
tttttttttt atagtgaatt tatcaaacgc tgaaaagaa                             40

<210> SEQ ID NO 846
<211> LENGTH: 44
<212> TYPE: DNA
<213> ORGANISM: Artificial sequence
<220> FEATURE:
<223> OTHER INFORMATION: artificial primer sequence

<400> SEQUENCE: 846
tttttttttt attcaaccgt tcatcgatga acggttttttt tttt                     44

<210> SEQ ID NO 847
<211> LENGTH: 49
<212> TYPE: DNA
<213> ORGANISM: Artificial sequence
<220> FEATURE:
<223> OTHER INFORMATION: artificial primer sequence

<400> SEQUENCE: 847
agctattaaa agggctgagt aatgtgtagc ccaaattgta taagatcaa                 49

<210> SEQ ID NO 848
<211> LENGTH: 49
<212> TYPE: DNA
<213> ORGANISM: Artificial sequence
<220> FEATURE:
<223> OTHER INFORMATION: artificial primer sequence

<400> SEQUENCE: 848
tagcttacaa tattgataga aagaagtgtt tttatggagc tagaaagga                 49

<210> SEQ ID NO 849
<211> LENGTH: 43
<212> TYPE: DNA
<213> ORGANISM: Artificial sequence
<220> FEATURE:
<223> OTHER INFORMATION: artificial primer sequence

<400> SEQUENCE: 849
gattaagaat catatcgcca tatttaacaa cgctttttttt ttt                      43

<210> SEQ ID NO 850
<211> LENGTH: 49
<212> TYPE: DNA
<213> ORGANISM: Artificial sequence
<220> FEATURE:
<223> OTHER INFORMATION: artificial primer sequence

<400> SEQUENCE: 850
aggtcattgc ctgaagaggg taaccaggca gctggtgggt aacgccagg                 49

<210> SEQ ID NO 851
<211> LENGTH: 38
<212> TYPE: DNA
<213> ORGANISM: Artificial sequence
<220> FEATURE:
<223> OTHER INFORMATION: artificial primer sequence

<400> SEQUENCE: 851
```
tttttttttt tacctgagcg aagagtcatt tttttttt                      38

<210> SEQ ID NO 852
<211> LENGTH: 44
<212> TYPE: DNA
<213> ORGANISM: Artificial sequence
<220> FEATURE:
<223> OTHER INFORMATION: artificial primer sequence

<400> SEQUENCE: 852
tttttttttt taatcgtaaa acatttgtt aaaattttt tttt                 44

<210> SEQ ID NO 853
<211> LENGTH: 35
<212> TYPE: DNA
<213> ORGANISM: Artificial sequence
<220> FEATURE:
<223> OTHER INFORMATION: artificial primer sequence

<400> SEQUENCE: 853
tatgtacatt taaactcatt ttttaaccgg ccttc                         35

<210> SEQ ID NO 854
<211> LENGTH: 35
<212> TYPE: DNA
<213> ORGANISM: Artificial sequence
<220> FEATURE:
<223> OTHER INFORMATION: artificial primer sequence

<400> SEQUENCE: 854
acatcggttt tttaagataa gttctgtcac ataca                         35

<210> SEQ ID NO 855
<211> LENGTH: 49
<212> TYPE: DNA
<213> ORGANISM: Artificial sequence
<220> FEATURE:
<223> OTHER INFORMATION: artificial primer sequence

<400> SEQUENCE: 855
ctgattgttt gcacgtaaaa ctcccgacaa gccgtttaag ccaataacg          49

<210> SEQ ID NO 856
<211> LENGTH: 49
<212> TYPE: DNA
<213> ORGANISM: Artificial sequence
<220> FEATURE:
<223> OTHER INFORMATION: artificial primer sequence

<400> SEQUENCE: 856
ttacaaagaa cctaagatga tggcaattcc agaagttaaa agtttgagt          49

<210> SEQ ID NO 857
<211> LENGTH: 42
<212> TYPE: DNA
<213> ORGANISM: Artificial sequence
<220> FEATURE:
<223> OTHER INFORMATION: artificial primer sequence

<400> SEQUENCE: 857
atcgcgccag ttggcacctt gagaaagcaa caggaggccg at                 42

<210> SEQ ID NO 858
<211> LENGTH: 36
<212> TYPE: DNA

```
<213> ORGANISM: Artificial sequence
<220> FEATURE:
<223> OTHER INFORMATION: artificial primer sequence

<400> SEQUENCE: 858
aattattttc tgaaataatc ctgattgttt tttttt                              36

<210> SEQ ID NO 859
<211> LENGTH: 35
<212> TYPE: DNA
<213> ORGANISM: Artificial sequence
<220> FEATURE:
<223> OTHER INFORMATION: artificial primer sequence

<400> SEQUENCE: 859
cgttaattag catggtgcat cctcaggacc ggaat                               35

<210> SEQ ID NO 860
<211> LENGTH: 35
<212> TYPE: DNA
<213> ORGANISM: Artificial sequence
<220> FEATURE:
<223> OTHER INFORMATION: artificial primer sequence

<400> SEQUENCE: 860
ttgtaaaatt ttcataacat ctaattgcca gaccg                               35

<210> SEQ ID NO 861
<211> LENGTH: 49
<212> TYPE: DNA
<213> ORGANISM: Artificial sequence
<220> FEATURE:
<223> OTHER INFORMATION: artificial primer sequence

<400> SEQUENCE: 861
ggtttaacgt cagagcttat catagcaaaa ttgagtatta cgcagacga                49

<210> SEQ ID NO 862
<211> LENGTH: 42
<212> TYPE: DNA
<213> ORGANISM: Artificial sequence
<220> FEATURE:
<223> OTHER INFORMATION: artificial primer sequence

<400> SEQUENCE: 862
attttcaacc tttttaacaa ctattaaccc acaccactat gg                       42

<210> SEQ ID NO 863
<211> LENGTH: 35
<212> TYPE: DNA
<213> ORGANISM: Artificial sequence
<220> FEATURE:
<223> OTHER INFORMATION: artificial primer sequence

<400> SEQUENCE: 863
aagaaattgc gtagcgcgag gtaggaatag ataac                               35

<210> SEQ ID NO 864
<211> LENGTH: 38
<212> TYPE: DNA
<213> ORGANISM: Artificial sequence
<220> FEATURE:
<223> OTHER INFORMATION: artificial primer sequence

<400> SEQUENCE: 864
tttttttttt ggattatacc atttcaattt tttttttt                            38
```

<210> SEQ ID NO 865
<211> LENGTH: 50
<212> TYPE: DNA
<213> ORGANISM: Artificial sequence
<220> FEATURE:
<223> OTHER INFORMATION: artificial primer sequence

<400> SEQUENCE: 865
tttttttttt ttgcggaaca aagaaaccac atcaattaat ggattgctat            50

<210> SEQ ID NO 866
<211> LENGTH: 43
<212> TYPE: DNA
<213> ORGANISM: Artificial sequence
<220> FEATURE:
<223> OTHER INFORMATION: artificial primer sequence

<400> SEQUENCE: 866
tttttttttt ttcgcattaa attttgttc atcaactctc cgt                     43

<210> SEQ ID NO 867
<211> LENGTH: 38
<212> TYPE: DNA
<213> ORGANISM: Artificial sequence
<220> FEATURE:
<223> OTHER INFORMATION: artificial primer sequence

<400> SEQUENCE: 867
tttttttttt taacaaccct tgaggggatt tttttttt                          38

<210> SEQ ID NO 868
<211> LENGTH: 42
<212> TYPE: DNA
<213> ORGANISM: Artificial sequence
<220> FEATURE:
<223> OTHER INFORMATION: artificial primer sequence

<400> SEQUENCE: 868
cgtaatggga taataataca tcaacgtccc cactaggcca ga                     42

<210> SEQ ID NO 869
<211> LENGTH: 35
<212> TYPE: DNA
<213> ORGANISM: Artificial sequence
<220> FEATURE:
<223> OTHER INFORMATION: artificial primer sequence

<400> SEQUENCE: 869
taaatccttt gccccgagat atcggaacag tgtaa                             35

<210> SEQ ID NO 870
<211> LENGTH: 40
<212> TYPE: DNA
<213> ORGANISM: Artificial sequence
<220> FEATURE:
<223> OTHER INFORMATION: artificial primer sequence

<400> SEQUENCE: 870
tgccagtgtc ggatattaaa tgtgagcgag tttttttttt                        40

<210> SEQ ID NO 871
<211> LENGTH: 35
<212> TYPE: DNA
<213> ORGANISM: Artificial sequence
<220> FEATURE:

```
<223> OTHER INFORMATION: artificial primer sequence

<400> SEQUENCE: 871
gtagatgcca gcttacagcg ccgccacgcg gggtc                                    35

<210> SEQ ID NO 872
<211> LENGTH: 49
<212> TYPE: DNA
<213> ORGANISM: Artificial sequence
<220> FEATURE:
<223> OTHER INFORMATION: artificial primer sequence

<400> SEQUENCE: 872
cgtcaataaa cagacggaaa caatcggcgc gatggaaagg gcgaaaaac                     49

<210> SEQ ID NO 873
<211> LENGTH: 42
<212> TYPE: DNA
<213> ORGANISM: Artificial sequence
<220> FEATURE:
<223> OTHER INFORMATION: artificial primer sequence

<400> SEQUENCE: 873
atctggtaga ggcggatgat gaataatcta ggcagaggca tt                            42

<210> SEQ ID NO 874
<211> LENGTH: 44
<212> TYPE: DNA
<213> ORGANISM: Artificial sequence
<220> FEATURE:
<223> OTHER INFORMATION: artificial primer sequence

<400> SEQUENCE: 874 ttttttttt ccctcaatca ataacattat cattttttt tttt                            44

<210> SEQ ID NO 875
<211> LENGTH: 38
<212> TYPE: DNA
<213> ORGANISM: Artificial sequence
<220> FEATURE:
<223> OTHER INFORMATION: artificial primer sequence

<400> SEQUENCE: 875
tttttttttt cgacgacagc aactgttgtt tttttttt                                 38

<210> SEQ ID NO 876
<211> LENGTH: 42
<212> TYPE: DNA
<213> ORGANISM: Artificial sequence
<220> FEATURE:
<223> OTHER INFORMATION: artificial primer sequence

<400> SEQUENCE: 876
actccagggc gcataacggc gctgtagcca gctttaaatc ag                            42

<210> SEQ ID NO 877
<211> LENGTH: 42
<212> TYPE: DNA
<213> ORGANISM: Artificial sequence
<220> FEATURE:
<223> OTHER INFORMATION: artificial primer sequence

<400> SEQUENCE: 877
ggtgaggaac caccatgtga gcggaatcat aattaaagat tc                            42
```

-continued

```
<210> SEQ ID NO 878
<211> LENGTH: 49
<212> TYPE: DNA
<213> ORGANISM: Artificial sequence
<220> FEATURE:
<223> OTHER INFORMATION: artificial primer sequence

<400> SEQUENCE: 878
cggtcagtaa tagatttaga agtattagac tattacaaat cataattgc            49

<210> SEQ ID NO 879
<211> LENGTH: 49
<212> TYPE: DNA
<213> ORGANISM: Artificial sequence
<220> FEATURE:
<223> OTHER INFORMATION: artificial primer sequence

<400> SEQUENCE: 879
tgccacgcgg tcacacgtat atttcacggt taacggcatc agatgccgg             49

<210> SEQ ID NO 880
<211> LENGTH: 42
<212> TYPE: DNA
<213> ORGANISM: Artificial sequence
<220> FEATURE:
<223> OTHER INFORMATION: artificial primer sequence

<400> SEQUENCE: 880
ctgagaggaa ctgattaatt tgttgggtcc agtataaagc ca                    42

<210> SEQ ID NO 881
<211> LENGTH: 49
<212> TYPE: DNA
<213> ORGANISM: Artificial sequence
<220> FEATURE:
<223> OTHER INFORMATION: artificial primer sequence

<400> SEQUENCE: 881
caaatgacta gggcttagaa tggccagagt tacctgcagc cagcggtgc             49

<210> SEQ ID NO 882
<211> LENGTH: 42
<212> TYPE: DNA
<213> ORGANISM: Artificial sequence
<220> FEATURE:
<223> OTHER INFORMATION: artificial primer sequence

<400> SEQUENCE: 882
aaaacatgca acagatcttt aaaacaattc gacaatccag tt                    42

<210> SEQ ID NO 883
<211> LENGTH: 44
<212> TYPE: DNA
<213> ORGANISM: Artificial sequence
<220> FEATURE:
<223> OTHER INFORMATION: artificial primer sequence

<400> SEQUENCE: 883
tttttttttt taagaatacg tgtcaaatat caaattttttt tttt                 44

<210> SEQ ID NO 884
<211> LENGTH: 40
<212> TYPE: DNA
<213> ORGANISM: Artificial sequence
<220> FEATURE:
<223> OTHER INFORMATION: artificial primer sequence
```

<400> SEQUENCE: 884
tttttttttt ggaagggcga tcggtgggct gcgtatcggc        40

<210> SEQ ID NO 885
<211> LENGTH: 36
<212> TYPE: DNA
<213> ORGANISM: Artificial sequence
<220> FEATURE:
<223> OTHER INFORMATION: artificial primer sequence

<400> SEQUENCE: 885
cgggcctcag tcacgacgtt gtaaaatttt tttttt        36

<210> SEQ ID NO 886
<211> LENGTH: 42
<212> TYPE: DNA
<213> ORGANISM: Artificial sequence
<220> FEATURE:
<223> OTHER INFORMATION: artificial primer sequence

<400> SEQUENCE: 886
atttacacgt tgtagcaatt aggcgcgtcg ccgcgcatca cc        42

<210> SEQ ID NO 887
<211> LENGTH: 56
<212> TYPE: DNA
<213> ORGANISM: Artificial sequence
<220> FEATURE:
<223> OTHER INFORMATION: artificial primer sequence

<400> SEQUENCE: 887
ttggcagtat attttgataa atatgtaaat gctgaaaaac ttttcaaaa ttcacc        56

<210> SEQ ID NO 888
<211> LENGTH: 35
<212> TYPE: DNA
<213> ORGANISM: Artificial sequence
<220> FEATURE:
<223> OTHER INFORMATION: artificial primer sequence

<400> SEQUENCE: 888
gaggccaccg agtattcctc ggctggcaca ctaaa        35

<210> SEQ ID NO 889
<211> LENGTH: 36
<212> TYPE: DNA
<213> ORGANISM: Artificial sequence
<220> FEATURE:
<223> OTHER INFORMATION: artificial primer sequence

<400> SEQUENCE: 889
aatcctgccc ttctgacctg aaagcgtttt tttttt        36

<210> SEQ ID NO 890
<211> LENGTH: 40
<212> TYPE: DNA
<213> ORGANISM: Artificial sequence
<220> FEATURE:
<223> OTHER INFORMATION: artificial primer sequence

<400> SEQUENCE: 890
tttttttttt aggaacggta cgccagtaaa ggggagaaag        40

<210> SEQ ID NO 891
<211> LENGTH: 44

```
<212> TYPE: DNA
<213> ORGANISM: Artificial sequence
<220> FEATURE:
<223> OTHER INFORMATION: artificial primer sequence

<400> SEQUENCE: 891
tttttttttt cgacggccag tgttgtgaga gatatttttt tttt          44

<210> SEQ ID NO 892
<211> LENGTH: 42
<212> TYPE: DNA
<213> ORGANISM: Artificial sequence
<220> FEATURE:
<223> OTHER INFORMATION: artificial primer sequence

<400> SEQUENCE: 892
ccaagctcgc actcgtcact gttgccctgc ggctgattgc ag            42

<210> SEQ ID NO 893
<211> LENGTH: 35
<212> TYPE: DNA
<213> ORGANISM: Artificial sequence
<220> FEATURE:
<223> OTHER INFORMATION: artificial primer sequence

<400> SEQUENCE: 893
ttcagaggtt ttcccttcgc tattacgcca aagcg                    35

<210> SEQ ID NO 894
<211> LENGTH: 49
<212> TYPE: DNA
<213> ORGANISM: Artificial sequence
<220> FEATURE:
<223> OTHER INFORMATION: artificial primer sequence

<400> SEQUENCE: 894
gtggagccat gttttctcac ggaaaatccg gaacgtcggt ggtgccatc     49

<210> SEQ ID NO 895
<211> LENGTH: 49
<212> TYPE: DNA
<213> ORGANISM: Artificial sequence
<220> FEATURE:
<223> OTHER INFORMATION: artificial primer sequence

<400> SEQUENCE: 895
gacgagcgct gcgctggggt ctggaacaag agtccacttt acggagcac     49

<210> SEQ ID NO 896
<211> LENGTH: 42
<212> TYPE: DNA
<213> ORGANISM: Artificial sequence
<220> FEATURE:
<223> OTHER INFORMATION: artificial primer sequence

<400> SEQUENCE: 896
gaaacgttcc ggcaccgctt aagggtcacg ttggtgataa tc            42

<210> SEQ ID NO 897
<211> LENGTH: 38
<212> TYPE: DNA
<213> ORGANISM: Artificial sequence
<220> FEATURE:
<223> OTHER INFORMATION: artificial primer sequence

<400> SEQUENCE: 897
```

```
tttttttttt gaacgtggca ttttagactt tttttttt                            38
```

<210> SEQ ID NO 898
<211> LENGTH: 44
<212> TYPE: DNA
<213> ORGANISM: Artificial sequence
<220> FEATURE:
<223> OTHER INFORMATION: artificial primer sequence

<400> SEQUENCE: 898

```
tttttttttt gactttctcc gtttaaattt ctgcttttt tttt                      44
```

<210> SEQ ID NO 899
<211> LENGTH: 35
<212> TYPE: DNA
<213> ORGANISM: Artificial sequence
<220> FEATURE:
<223> OTHER INFORMATION: artificial primer sequence

<400> SEQUENCE: 899

```
agttttgta accaaccgcc tcgccatttc tgtaa                                35
```

<210> SEQ ID NO 900
<211> LENGTH: 35
<212> TYPE: DNA
<213> ORGANISM: Artificial sequence
<220> FEATURE:
<223> OTHER INFORMATION: artificial primer sequence

<400> SEQUENCE: 900

```
gaggtgcaat gagtaggatc cccgggtagg gccgt                               35
```

<210> SEQ ID NO 901
<211> LENGTH: 42
<212> TYPE: DNA
<213> ORGANISM: Artificial sequence
<220> FEATURE:
<223> OTHER INFORMATION: artificial primer sequence

<400> SEQUENCE: 901

```
cctaaaggcg ggcgaaaatc tggctattag tctttaggga ca                       42
```

<210> SEQ ID NO 902
<211> LENGTH: 49
<212> TYPE: DNA
<213> ORGANISM: Artificial sequence
<220> FEATURE:
<223> OTHER INFORMATION: artificial primer sequence

<400> SEQUENCE: 902

```
ggagccctca aaagtggttt gccccagcgc aacaggcgta ttgggcgcc                49
```

<210> SEQ ID NO 903
<211> LENGTH: 40
<212> TYPE: DNA
<213> ORGANISM: Artificial sequence
<220> FEATURE:
<223> OTHER INFORMATION: artificial primer sequence

<400> SEQUENCE: 903

```
gacggggatc ggcaaatcct gtttgatggt tttttttttt                          40
```

<210> SEQ ID NO 904
<211> LENGTH: 42
<212> TYPE: DNA
<213> ORGANISM: Artificial sequence

```
<220> FEATURE:
<223> OTHER INFORMATION: artificial primer sequence

<400> SEQUENCE: 904
atcaaacggt gaagaacgtc aagaatgcca acggcgcgct tt                              42

<210> SEQ ID NO 905
<211> LENGTH: 49
<212> TYPE: DNA
<213> ORGANISM: Artificial sequence
<220> FEATURE:
<223> OTHER INFORMATION: artificial primer sequence

<400> SEQUENCE: 905
acagcggggg aacacgtaac ctcaatcaga gcaaaaaagc cttttttgcg                      49

<210> SEQ ID NO 906
<211> LENGTH: 49
<212> TYPE: DNA
<213> ORGANISM: Artificial sequence
<220> FEATURE:
<223> OTHER INFORMATION: artificial primer sequence

<400> SEQUENCE: 906
aagaacgtgg actcttgagg attagagcta tacagtaaat caacgcgcc                       49

<210> SEQ ID NO 907
<211> LENGTH: 42
<212> TYPE: DNA
<213> ORGANISM: Artificial sequence
<220> FEATURE:
<223> OTHER INFORMATION: artificial primer sequence

<400> SEQUENCE: 907
gggttgagtg ttgtctcgta taggttatga ttcgcaacaa tt                              42

<210> SEQ ID NO 908
<211> LENGTH: 42
<212> TYPE: DNA
<213> ORGANISM: Artificial sequence
<220> FEATURE:
<223> OTHER INFORMATION: artificial primer sequence

<400> SEQUENCE: 908
aaatccctta taaaccgatt tacatacgag ctgtttcctg tg                              42

<210> SEQ ID NO 909
<211> LENGTH: 38
<212> TYPE: DNA
<213> ORGANISM: Artificial sequence
<220> FEATURE:
<223> OTHER INFORMATION: artificial primer sequence

<400> SEQUENCE: 909
tttttttttt ggttccgaaa aagccggctt tttttttt                                   38

<210> SEQ ID NO 910
<211> LENGTH: 36
<212> TYPE: DNA
<213> ORGANISM: Artificial sequence
<220> FEATURE:
<223> OTHER INFORMATION: artificial primer sequence

<400> SEQUENCE: 910
tttttttttt cttttcacca gtgagacgga ggcgaa                                     36
```

<210> SEQ ID NO 911
<211> LENGTH: 50
<212> TYPE: DNA
<213> ORGANISM: Artificial sequence
<220> FEATURE:
<223> OTHER INFORMATION: artificial primer sequence

<400> SEQUENCE: 911
tttttttttt tcatttgccg ccagcagttc ggccttttgc cgttccggca            50

<210> SEQ ID NO 912
<211> LENGTH: 42
<212> TYPE: DNA
<213> ORGANISM: Artificial sequence
<220> FEATURE:
<223> OTHER INFORMATION: artificial primer sequence

<400> SEQUENCE: 912
tccacgcaat agccgaacgt tacagttgta ccaagaaaac aa                    42

<210> SEQ ID NO 913
<211> LENGTH: 35
<212> TYPE: DNA
<213> ORGANISM: Artificial sequence
<220> FEATURE:
<223> OTHER INFORMATION: artificial primer sequence

<400> SEQUENCE: 913
gtaatatcca gaactccctt aagcacgcgt gcccg                            35

<210> SEQ ID NO 914
<211> LENGTH: 38
<212> TYPE: DNA
<213> ORGANISM: Artificial sequence
<220> FEATURE:
<223> OTHER INFORMATION: artificial primer sequence

<400> SEQUENCE: 914
tttttttttt agttaaacgg ctggtctgtt tttttttt                         38

<210> SEQ ID NO 915
<211> LENGTH: 49
<212> TYPE: DNA
<213> ORGANISM: Artificial sequence
<220> FEATURE:
<223> OTHER INFORMATION: artificial primer sequence

<400> SEQUENCE: 915
tcgtcgctgg cagcctgccc gctttccagt cgggaaacct gtctcacat             49

<210> SEQ ID NO 916
<211> LENGTH: 42
<212> TYPE: DNA
<213> ORGANISM: Artificial sequence
<220> FEATURE:
<223> OTHER INFORMATION: artificial primer sequence

<400> SEQUENCE: 916
cgtgccagct gcattaatga aggtgcctcg taaagagtgt ag                    42

<210> SEQ ID NO 917
<211> LENGTH: 40
<212> TYPE: DNA
<213> ORGANISM: Artificial sequence
<220> FEATURE:
<223> OTHER INFORMATION: artificial primer sequence -continued

<400> SEQUENCE: 917
gcgtggtatg ctgatagtga tgaagggtaa ttttttttttt                                40

<210> SEQ ID NO 918
<211> LENGTH: 42
<212> TYPE: DNA
<213> ORGANISM: Artificial sequence
<220> FEATURE:
<223> OTHER INFORMATION: artificial primer sequence

<400> SEQUENCE: 918
cttgtaggga tagcaccagt cagatcgccc attcgccatt ca                              42

<210> SEQ ID NO 919
<211> LENGTH: 35
<212> TYPE: DNA
<213> ORGANISM: Artificial sequence
<220> FEATURE:
<223> OTHER INFORMATION: artificial primer sequence

<400> SEQUENCE: 919
ccacacaaga gcttgaaggg actgaaccgc acaga                                      35

<210> SEQ ID NO 920
<211> LENGTH: 44
<212> TYPE: DNA
<213> ORGANISM: Artificial sequence
<220> FEATURE:
<223> OTHER INFORMATION: artificial primer sequence

<400> SEQUENCE: 920
tttttttttt ccgctcacaa ttagggtggt tttttttttt tttt                            44

<210> SEQ ID NO 921
<211> LENGTH: 38
<212> TYPE: DNA
<213> ORGANISM: Artificial sequence
<220> FEATURE:
<223> OTHER INFORMATION: artificial primer sequence

<400> SEQUENCE: 921
tttttttttt gtcagcagcc gggcgcggtt tttttttt                                   38

<210> SEQ ID NO 922
<211> LENGTH: 42
<212> TYPE: DNA
<213> ORGANISM: Artificial sequence
<220> FEATURE:
<223> OTHER INFORMATION: artificial primer sequence

<400> SEQUENCE: 922
agcaccgtgc cggaaacgcg gaaaagccgc acaggggcg gt                               42

<210> SEQ ID NO 923
<211> LENGTH: 49
<212> TYPE: DNA
<213> ORGANISM: Artificial sequence
<220> FEATURE:
<223> OTHER INFORMATION: artificial primer sequence

<400> SEQUENCE: 923
accagcttat gttcttcgcg tgttgcgctc actcccgtga accttaatg                       49

<210> SEQ ID NO 924

```
<211> LENGTH: 35
<212> TYPE: DNA
<213> ORGANISM: Artificial sequence
<220> FEATURE:
<223> OTHER INFORMATION: artificial primer sequence

<400> SEQUENCE: 924
ccgtgagcct cctccggggg tttgctttaa ttaac                              35

<210> SEQ ID NO 925
<211> LENGTH: 49
<212> TYPE: DNA
<213> ORGANISM: Artificial sequence
<220> FEATURE:
<223> OTHER INFORMATION: artificial primer sequence

<400> SEQUENCE: 925
cgaattcgta atcagtgctg ccagagcgaa tcagtttctg gccaacaga               49

<210> SEQ ID NO 926
<211> LENGTH: 49
<212> TYPE: DNA
<213> ORGANISM: Artificial sequence
<220> FEATURE:
<223> OTHER INFORMATION: artificial primer sequence

<400> SEQUENCE: 926
gcatcaggga acggattaag tcgaaagggg gatgtgatct ggtgccgga               49

<210> SEQ ID NO 927
<211> LENGTH: 49
<212> TYPE: DNA
<213> ORGANISM: Artificial sequence
<220> FEATURE:
<223> OTHER INFORMATION: artificial primer sequence

<400> SEQUENCE: 927
ttctgcccac tggtgtgttc acttgctgag taataacatc actcacgca               49

<210> SEQ ID NO 928
<211> LENGTH: 42
<212> TYPE: DNA
<213> ORGANISM: Artificial sequence
<220> FEATURE:
<223> OTHER INFORMATION: artificial primer sequence

<400> SEQUENCE: 928
ctctgtgtgg tcatagccgg agcggtttct gattgccctt ca                      42

<210> SEQ ID NO 929
<211> LENGTH: 50
<212> TYPE: DNA
<213> ORGANISM: Artificial sequence
<220> FEATURE:
<223> OTHER INFORMATION: artificial primer sequence

<400> SEQUENCE: 929
tgcgcgcctg tgcacggtgc cccctgcatc agacgatcca tttttttttt              50

<210> SEQ ID NO 930
<211> LENGTH: 44
<212> TYPE: DNA
<213> ORGANISM: Artificial sequence
<220> FEATURE:
<223> OTHER INFORMATION: artificial primer sequence

<400> SEQUENCE: 930
```
tttttttttt gcgcagtgtc actgaaattg ttatttttt tttt        44

<210> SEQ ID NO 931
<211> LENGTH: 40
<212> TYPE: DNA
<213> ORGANISM: Artificial sequence
<220> FEATURE:
<223> OTHER INFORMATION: artificial primer sequence

<400> SEQUENCE: 931
tttttttttt ttgcggtatg agccggaatc cgcaaccgca        40

<210> SEQ ID NO 932
<211> LENGTH: 42
<212> TYPE: DNA
<213> ORGANISM: Artificial sequence
<220> FEATURE:
<223> OTHER INFORMATION: artificial primer sequence

<400> SEQUENCE: 932
gtaatgggta aaggtttctt tgtgtccacc acgcagcaca tc        42

<210> SEQ ID NO 933
<211> LENGTH: 42
<212> TYPE: DNA
<213> ORGANISM: Artificial sequence
<220> FEATURE:
<223> OTHER INFORMATION: artificial primer sequence

<400> SEQUENCE: 933
gctcgtcata aacaaatatt aggaaatacc acttctttga tt        42

<210> SEQ ID NO 934
<211> LENGTH: 54
<212> TYPE: DNA
<213> ORGANISM: Artificial sequence
<220> FEATURE:
<223> OTHER INFORMATION: artificial primer sequence

<400> SEQUENCE: 934
ttaaacagct tgatgcggga tagccgcctc atagcgacgg aattagagcc agca        54

<210> SEQ ID NO 935
<211> LENGTH: 47
<212> TYPE: DNA
<213> ORGANISM: Artificial sequence
<220> FEATURE:
<223> OTHER INFORMATION: artificial primer sequence

<400> SEQUENCE: 935
agcgcgaaac aaagtacaat tttcggacca gaaaataaa tataaac        47

<210> SEQ ID NO 936
<211> LENGTH: 37
<212> TYPE: DNA
<213> ORGANISM: Artificial sequence
<220> FEATURE:
<223> OTHER INFORMATION: artificial primer sequence

<400> SEQUENCE: 936
acctgctccc aatcataccg atatattcgg caggagg        37

<210> SEQ ID NO 937
<211> LENGTH: 47
<212> TYPE: DNA

```
<213> ORGANISM: Artificial sequence
<220> FEATURE:
<223> OTHER INFORMATION: artificial primer sequence

<400> SEQUENCE: 937
taaagccccc tcagcgtcac cacgaaggca ccaacgcgat tatacca         47

<210> SEQ ID NO 938
<211> LENGTH: 51
<212> TYPE: DNA
<213> ORGANISM: Artificial sequence
<220> FEATURE:
<223> OTHER INFORMATION: artificial primer sequence

<400> SEQUENCE: 938
gcattgatcg ctgagaggcg cagacggtat gttactgtgt cgaaatccgc g     51

<210> SEQ ID NO 939
<211> LENGTH: 40
<212> TYPE: DNA
<213> ORGANISM: Artificial sequence
<220> FEATURE:
<223> OTHER INFORMATION: artificial primer sequence

<400> SEQUENCE: 939
aaatcaccag tagcaccatt atacaaaaag taatcctgaa                  40

<210> SEQ ID NO 940
<211> LENGTH: 37
<212> TYPE: DNA
<213> ORGANISM: Artificial sequence
<220> FEATURE:
<223> OTHER INFORMATION: artificial primer sequence

<400> SEQUENCE: 940
gcagcaccgt cagaaagaaa gacttcaagt atgttca                     37

<210> SEQ ID NO 941
<211> LENGTH: 51
<212> TYPE: DNA
<213> ORGANISM: Artificial sequence
<220> FEATURE:
<223> OTHER INFORMATION: artificial primer sequence

<400> SEQUENCE: 941
aaacaacatg ttagtcaagt ttgcctgtta atcagaatga aaccatcgat a     51

<210> SEQ ID NO 942
<211> LENGTH: 47
<212> TYPE: DNA
<213> ORGANISM: Artificial sequence
<220> FEATURE:
<223> OTHER INFORMATION: artificial primer sequence

<400> SEQUENCE: 942
tttgagagat ctatagcaga agccaatcgt ctgaattctg acctaaa          47

<210> SEQ ID NO 943
<211> LENGTH: 40
<212> TYPE: DNA
<213> ORGANISM: Artificial sequence
<220> FEATURE:
<223> OTHER INFORMATION: artificial primer sequence

<400> SEQUENCE: 943
ctattaatag ccctagtcac actgtccatt gcctgagtag                  40
```

<210> SEQ ID NO 944
<211> LENGTH: 37
<212> TYPE: DNA
<213> ORGANISM: Artificial sequence
<220> FEATURE:
<223> OTHER INFORMATION: artificial primer sequence

<400> SEQUENCE: 944
agacaaagat aataaaaatg cgcccagcag ttgagga      37

<210> SEQ ID NO 945
<211> LENGTH: 47
<212> TYPE: DNA
<213> ORGANISM: Artificial sequence
<220> FEATURE:
<223> OTHER INFORMATION: artificial primer sequence

<400> SEQUENCE: 945
tttaatggtt tgaaataccT aaacactgaa taacagtaca taacagt      47

<210> SEQ ID NO 946
<211> LENGTH: 44
<212> TYPE: DNA
<213> ORGANISM: Artificial sequence
<220> FEATURE:
<223> OTHER INFORMATION: artificial primer sequence

<400> SEQUENCE: 946
gctacagcat tttgacgctt gcgctcatcc gccagccatt gcaa      44

<210> SEQ ID NO 947
<211> LENGTH: 44
<212> TYPE: DNA
<213> ORGANISM: Artificial sequence
<220> FEATURE:
<223> OTHER INFORMATION: artificial primer sequence

<400> SEQUENCE: 947
acgtgctaaa gagtcgacca gacgcgagtg caaatccaat cgca      44

<210> SEQ ID NO 948
<211> LENGTH: 47
<212> TYPE: DNA
<213> ORGANISM: Artificial sequence
<220> FEATURE:
<223> OTHER INFORMATION: artificial primer sequence

<400> SEQUENCE: 948
aagaactcaa actatcggcg caaatcgtca tacacagttg gagctaa      47

<210> SEQ ID NO 949
<211> LENGTH: 37
<212> TYPE: DNA
<213> ORGANISM: Artificial sequence
<220> FEATURE:
<223> OTHER INFORMATION: artificial primer sequence

<400> SEQUENCE: 949
caggaaaaac aaggcgataa cctcaccgcc gctggag      37

<210> SEQ ID NO 950
<211> LENGTH: 47
<212> TYPE: DNA
<213> ORGANISM: Artificial sequence
<220> FEATURE:

<223> OTHER INFORMATION: artificial primer sequence

<400> SEQUENCE: 950
ccttcattta cccaaacacc aaatttcacc agtcaggacg ttgggaa          47

<210> SEQ ID NO 951
<211> LENGTH: 54
<212> TYPE: DNA
<213> ORGANISM: Artificial sequence
<220> FEATURE:
<223> OTHER INFORMATION: artificial primer sequence

<400> SEQUENCE: 951
gaaaaatcta cgttcaactt ataatggata agaaatagta taaagctaaa tcgg    54

<210> SEQ ID NO 952
<211> LENGTH: 44
<212> TYPE: DNA
<213> ORGANISM: Artificial sequence
<220> FEATURE:
<223> OTHER INFORMATION: artificial primer sequence

<400> SEQUENCE: 952
accctcagag ccaccacacc ctctgccgtc aacataaaag agca             44

<210> SEQ ID NO 953
<211> LENGTH: 37
<212> TYPE: DNA
<213> ORGANISM: Artificial sequence
<220> FEATURE:
<223> OTHER INFORMATION: artificial primer sequence

<400> SEQUENCE: 953
gccaccaaga atggtgcctt gggataagag aaccgcc                     37

<210> SEQ ID NO 954
<211> LENGTH: 33
<212> TYPE: DNA
<213> ORGANISM: Artificial sequence
<220> FEATURE:
<223> OTHER INFORMATION: artificial primer sequence

<400> SEQUENCE: 954
attctgcgaa cgcgcgagca gcaaatcccg gtt                         33

<210> SEQ ID NO 955
<211> LENGTH: 51
<212> TYPE: DNA
<213> ORGANISM: Artificial sequence
<220> FEATURE:
<223> OTHER INFORMATION: artificial primer sequence

<400> SEQUENCE: 955
tgccagttac aaaatatttc cagaggtttt aaaattactt tgaaaaagga a      51

<210> SEQ ID NO 956
<211> LENGTH: 47
<212> TYPE: DNA
<213> ORGANISM: Artificial sequence
<220> FEATURE:
<223> OTHER INFORMATION: artificial primer sequence

<400> SEQUENCE: 956
tttggggagt agatttagtt ttcattccat ataacagttg attccca          47

```
<210> SEQ ID NO 957
<211> LENGTH: 37
<212> TYPE: DNA
<213> ORGANISM: Artificial sequence
<220> FEATURE:
<223> OTHER INFORMATION: artificial primer sequence

<400> SEQUENCE: 957
gtggcatata gaagtgaaaa caggaagaac gccatca                              37

<210> SEQ ID NO 958
<211> LENGTH: 37
<212> TYPE: DNA
<213> ORGANISM: Artificial sequence
<220> FEATURE:
<223> OTHER INFORMATION: artificial primer sequence

<400> SEQUENCE: 958
tataaagtcc catcaacaag cttgcgggag cctaatt                              37

<210> SEQ ID NO 959
<211> LENGTH: 51
<212> TYPE: DNA
<213> ORGANISM: Artificial sequence
<220> FEATURE:
<223> OTHER INFORMATION: artificial primer sequence

<400> SEQUENCE: 959
aaaataattc gcgtctaata ggattgtata tgaaaagttc tactggtcat t              51

<210> SEQ ID NO 960
<211> LENGTH: 40
<212> TYPE: DNA
<213> ORGANISM: Artificial sequence
<220> FEATURE:
<223> OTHER INFORMATION: artificial primer sequence

<400> SEQUENCE: 960
ttcctgatta tcccatatcg aagcctccgc actagaaaca                           40

<210> SEQ ID NO 961
<211> LENGTH: 40
<212> TYPE: DNA
<213> ORGANISM: Artificial sequence
<220> FEATURE:
<223> OTHER INFORMATION: artificial primer sequence

<400> SEQUENCE: 961
gattgaccga gagacgcaga atgtgtacat cgacataaaa                           40

<210> SEQ ID NO 962
<211> LENGTH: 47
<212> TYPE: DNA
<213> ORGANISM: Artificial sequence
<220> FEATURE:
<223> OTHER INFORMATION: artificial primer sequence

<400> SEQUENCE: 962
tttgaataaa gcatcaaatc aattaattga gcggaattat catcata                   47

<210> SEQ ID NO 963
<211> LENGTH: 40
<212> TYPE: DNA
<213> ORGANISM: Artificial sequence
<220> FEATURE:
<223> OTHER INFORMATION: artificial primer sequence
```

```
<400> SEQUENCE: 963
aaatcccgta aatccgtttt ttcgtcctca taatatcagg                          40

<210> SEQ ID NO 964
<211> LENGTH: 44
<212> TYPE: DNA
<213> ORGANISM: Artificial sequence
<220> FEATURE:
<223> OTHER INFORMATION: artificial primer sequence

<400> SEQUENCE: 964
gagttgcagc aagcggccgc ctgacgcgcg gggagagagc ataa                     44

<210> SEQ ID NO 965
<211> LENGTH: 37
<212> TYPE: DNA
<213> ORGANISM: Artificial sequence
<220> FEATURE:
<223> OTHER INFORMATION: artificial primer sequence

<400> SEQUENCE: 965
atgcggcccg agctagcctg gtcggccagc cctgaga                             37
```

METHOD FOR STABILIZING NUCLEIC ACID NANOSTRUCTURES

RELATED APPLICATIONS

This patent application is the U.S. National Stage filing under 35 U.S.C. 371 of International Patent Application No. PCT/EP2019/064707 entitled "NOVEL METHOD FOR STABILIZING NUCLEIC ACID NANOSTRUCTURES," filed Jun. 5, 2019, which claims priority to DE 102018004454.9, filed Jun. 5, 2018, each of which is incorporated herein by reference in its entirety.

FIELD OF THE INVENTION

The present invention relates to a novel method for stabilizing nucleic acid nanostructures by curing with ultraviolet light, particularly by crosslinking pyrimidine nucleotides.

BACKGROUND OF THE INVENTION

This invention relates to a novel method for stabilizing nucleic acid nanostructures, which results in nanostructures having advantageous properties, particularly high structural stability.

DNA nanotechnology[1-4] enables the bottom-up self-assembly of discrete three-dimensional (3D) objects with sub-nanometer precise features and overall dimensions ranging from the nanometer- to the micrometer-scale[5-16] and with molecular weights up to the gigadalton scale[17,18]. The resulting objects may be site-specifically functionalized and modified with chemical groups and biomolecules[19-21], and objects can be constructed that may also include mechanisms to yield machine-like behavior[22-24]. Custom DNA objects have been developed and successfully used in diverse applications in basic research, thereby delivering new scientific insights and underlining the capacity of DNA nanotechnology to yield objects with utility. Examples range from structural biology[25-27], biophysics[28-33], photonics[34-37], plasmonics[38-42], to molecular electronics[19,43-45]. First steps have also been taken to explore uses of designed DNA objects as programmable agents in medical therapy[24,46]. Scalable biotechnological approaches for producing single-stranded DNA help pave the way to fabricate DNA objects at the quantities required for materials and health-care applications[47]. To find use in different contexts, designed DNA objects must remain stable at the target conditions for sufficient time so that the desired application effects can be achieved. Commonly, applications in low ionic strength solutions such as in physiological fluids, in other solvents, in air or vacuum, and at elevated temperatures beyond 50° C. are not accessible. Researchers have therefore sought for ways to expand the range of conditions under which designed DNA objects remain stable. Additional covalent bonds have been introduced in exemplary structures between correspondingly modified strand termini via chemical[48,49] or enzymatic ligation[50]. DNA nanostructures may also be further stabilized by the addition of cofactors such as 8-methoxypsoralen[62] or oligolysine and oligolysine-PEG copolymers[51,52]. Despite these advances, it remains desirable to establish complementary, generally applicable approaches for the covalent stabilization of DNA nanostructures that do not require costly chemically modified strands or the addition of cofactors. The possibility of creating additional covalent connections at user-defined sites in DNA nanostructures would enable the rational stabilization of entire structures or parts of them for uses in a broader scope of environmental conditions. Moreover, it may enable the stable trapping of conformational states in mechanisms and in higher-order assemblies. Here, we present a general and scalable method for site-selectively introducing additional covalent bonds in DNA nanostructures. The target bonding sites are specified in the sequences of DNA strands alone and do not require the introduction of chemical modifications. Our method is generally applicable to the diverse range of DNA nanostructures, and it functions regardless whether the DNA strands have been produced via solid-phase chemical synthesis or using a biotechnological process[47].

To find use in different contexts, designed DNA objects must remain stable at the target conditions for sufficient time so that the desired application effects can be achieved. Commonly, applications in low ionic strength solutions such as in physiological fluids, in other solvents, in air or vacuum, and at elevated temperatures beyond 50° C. are not accessible. Researchers have therefore sought for ways to expand the range of conditions under which designed DNA objects remain stable. Additional covalent bonds have been introduced in exemplary structures between correspondingly modified strand termini via chemical[48,49] or enzymatic ligation[50]. DNA nanostructures may also be further stabilized by the addition of cofactors such as oligolysine and oligolysine-PEG copolymers[51,52]. Despite these advances, it remains desirable to establish complementary, generally applicable approaches for the covalent stabilization of DNA nanostructures that do not require costly chemically modified strands or the addition of cofactors. The possibility to create additional covalent connections at user-defined sites in DNA nanostructures would enable the rational stabilization of entire structures or parts of them for uses in a broader scope of environmental conditions. Moreover, it may enable the stable trapping of conformational states in mechanisms and in higher-order assemblies. Here, we present a general and scalable method for site-selectively introducing additional covalent bonds in DNA nanostructures. The target bonding sites are specified in the sequences of DNA strands alone and do not require the introduction of chemical modifications. Our method is generally applicable to the diverse range of DNA nanostructures, and it functions regardless whether the DNA strands have been produced via solid-phase chemical synthesis or using a biotechnological process[47].

Thus, despite that fact that many attempts have already been made to address the issue of increasing the stability of nucleic acid nanostructures, there still remains a large unmet need to develop novel approaches that result in the formation of constructs with increased stability.

The solution for this problem that has been provided by the present invention, i.e. the curing of nucleic acid nanostructures by ultraviolet light-induced crosslinking of pyrimidine nucleotides, has so far not been achieved or suggested by the prior art.

SUMMARY OF THE INVENTION

The present invention relates to a novel method for stabilizing nucleic acid nanostructures by curing with ultraviolet light, particularly by crosslinking pyrimidine nucleotides.

Thus, in a first aspect, the present invention relates to a method for increasing the stability of a non-naturally occurring nucleic acid nanostructure, wherein said nanostructure comprises at least one single-chain nucleic acid sequence binding to at least two non-contiguous sequence stretches present on one or more complementary nucleic acid sequences, wherein said method is characterized by a step of exposing said nucleic acid nanostructure to UV irradiation, wherein said step of exposing said nucleic acid nanostructure to UV irradiation results in the formation of at least one chemical bond between two pyrimidine nucleotides, wherein at least one of the two pyrimidine nucleotides is not part of a complementary nucleotide pair comprised in a double-helical substructure.

In a second aspect, the present invention relates to a method for increasing the stability of a non-naturally occurring nucleic acid nanostructure, wherein said nanostructure comprises at least one single-chain nucleic acid sequence binding to at least two non-contiguous sequence stretches present on one or more complementary nucleic acid sequences, wherein said method is characterized by a step of exposing said nucleic acid nanostructure to UV irradiation.

In a third aspect, the present invention relates to a method for increasing the stability of a non-naturally occurring nucleic acid nanostructure, wherein said nanostructure comprises at least two double-helical substructures, wherein said method is characterized by a step of exposing said nucleic acid nanostructure to UV irradiation.

In a fourth aspect, the present invention relates to a method for increasing the stability of a non-naturally occurring nucleic acid nanostructure comprising a multiplicity of double-helical substructures, wherein said nanostructure comprises at least one single-chain nucleic acid sequence being part of at least two different double-helical substructures, wherein said method is characterized by a step of exposing said nucleic acid nanostructure to UV irradiation.

In a fifth aspect, the present invention relates to a kit for the generation of a nucleic acid nanostructure comprising one or more copies of at least a first single-stranded polynucleotide, and a set of single-stranded polynucleotides, wherein each of the single-stranded polynucleotides consists of an n-specific sequence consisting of n core sequences, with n being an integer independently selected from the range of 1 to 40, wherein each of said n core sequences consists of (i) a sequence that is complementary to a region on said first single-stranded polynucleotide, wherein the region complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In a sixth aspect, the present invention relates to a kit for the generation of a nucleic acid nanostructure comprising a set of single-stranded oligonucleotides, wherein each of the single-stranded polynucleotides consists of an n-specific sequence consisting of n core sequences, with n being an integer independently selected from the range of 1 to 40, wherein each of said n core sequences consists of (i) a sequence that is complementary to the sequence of another member of said set of single-stranded polynucleotides, wherein the region on said another member complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In a seventh aspect, the present invention relates to a nucleic acid nanostructure comprising one or more copies of at least a first single-stranded polynucleotide, and a set of single-stranded polynucleotides, wherein each of the single-stranded polynucleotides consists of an n-specific sequence consisting of n core sequences, with n being an integer selected from the range of 1 to 40, wherein each of said n core sequences consists of (i) a sequence that is complementary to a region on said first single-stranded polynucleotide, wherein the region complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In an eighth aspect, the present invention relates to a nucleic acid nanostructure comprising a set of single-stranded oligonucleotides, wherein each of the single-stranded polynucleotides consists of an n-specific sequence consisting of n core sequences, with n being independently selected from 1, 2, 3, . . . , 40, wherein each of said n core sequences consists of (i) a sequence that is complementary to the sequence of another member of said set of single-stranded polynucleotides, wherein the region on said another member complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is independently selected from 1, 2, 3, . . . , 40, and wherein each P is independently selected from a thymidine and a cytosine residue.

In a ninth aspect, the present invention relates to a complex nucleic acid nanostructure resulting from assembly of two or more nucleic acid nanostructures according to the present invention.

DETAILED DESCRIPTION OF THE INVENTION

Figure 1:
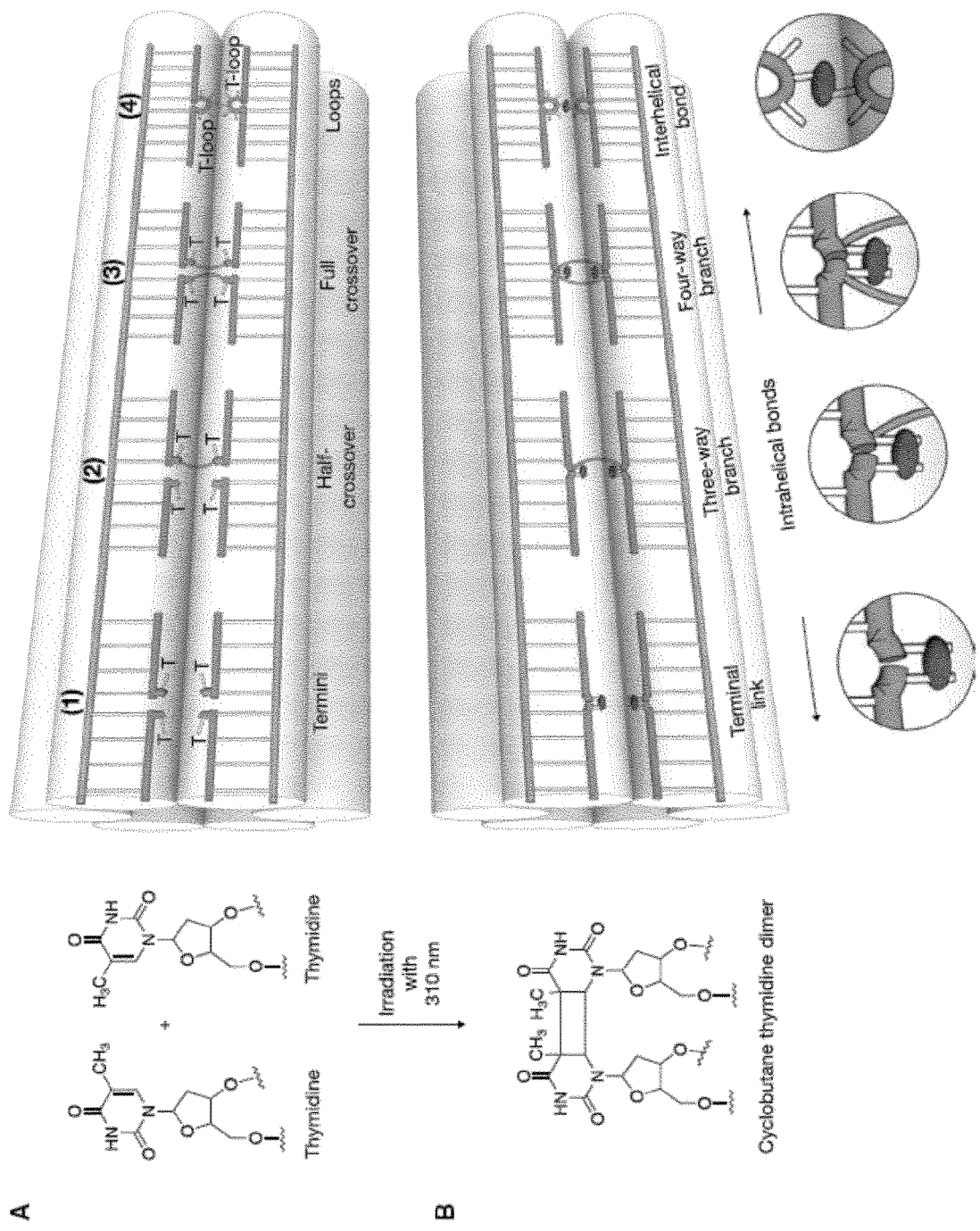
FIG. 1 shows proximal thymidines as sites for crosslinking in DNA nanostructures. (A) Left: chemical structures of two proximal thymidines before UV irradiation. Right: Schematic illustration of a six-helix bundle DNA nanostructure featuring single-stranded thymidines at strand termini (1); at half crossovers (2); at full crossovers (3); and thymidine loops (4) before UV irradiation. (B) As in (A), but after exposure to light with 310 nm wavelength. CPD bonds are indicated as ellipsoids.

The present invention relates to a novel method for stabilizing nucleic acid nanostructures by curing with ultraviolet light, particularly by crosslinking pyrimidine nucleotides.

Unless defined otherwise, all technical and scientific terms used herein have the same meaning as commonly understood by those of ordinary skill in the art to which this invention pertains.

Thus, in a first aspect, the present invention relates to a method for increasing the stability of a non-naturally occurring nucleic acid nanostructure, wherein said nanostructure comprises at least one single-chain nucleic acid sequence binding to at least two non-contiguous sequence stretches present on one or more complementary nucleic acid sequences, wherein said method is characterized by a step of exposing said nucleic acid nanostructure to UV irradiation, wherein said step of exposing said nucleic acid nanostructure to UV irradiation results in the formation of at least one chemical bond between two pyrimidine nucleotides, wherein at least one of the two pyrimidine nucleotides is not part of a complementary nucleotide pair comprised in a double-helical substructure.

In a second aspect, the present invention relates to a method for increasing the stability of a non-naturally occurring nucleic acid nanostructure, wherein said nanostructure comprises at least one single-chain nucleic acid sequence binding to at least two non-contiguous sequence stretches present on one or more complementary nucleic acid sequences, wherein said method is characterized by a step of exposing said nucleic acid nanostructure to UV irradiation.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

In the context of the present invention, the term "nanostructure" relates to a three-dimensional structure that is formed from a complex and at least in part regular arrangement of smaller sub-structures. In the context of the present invention, the smaller sub-structures comprise double-helical substructures. In particular embodiments, the double-helical substructures are arranged in more complex nanostructures by regular connections between different double-helical substructures, wherein said connections are formed by single-chain nucleic acid sequences forming cross-overs between different double-helical substructures by being complementary to at least two different sequences stretches on different nucleic sequence counterparts.

In the context of the present invention, the term "single-chain nucleic acid sequence" relates to a single chain of nucleic acid monomer units (nucleosides) linked by a phosphate group, by a modified phosphate group, or by a phosphate analogue (together the nucleosides and the phosphate-based linking group are called nucleotides). In the case of deoxyribonucleic acid-based nucleic acid sequences, the nucleic acid monomers are formed from (i) a nucleoside comprising a nucleobase selected from the four nitrogen-containing nucleobases cytosine [C], guanine [G], adenine [A] or thymine [T]), and a sugar called deoxyribose, and (ii) a phosphate group. In the case of ribonucleic acid-based nucleic acid sequences, the nucleic acid monomers are formed from (i) a nucleoside comprising a nucleobase selected from the four nitrogen-containing nucleobases cytosine [C], guanine [G], adenine [A] or thymine [T]), and a sugar called ribose, and (ii) a phosphate group.

In particular embodiments, the single-chain nucleic acid sequence are based on deoxyribonucleic acid-based nucleic acid sequences.

In the context of the present invention, the term "non-contiguous sequence stretches" relates to stretches of nucleic acid sequences that are not directly linked. Non-contiguous sequences stretches may be located on different nucleic acid sequences, or may be on one nucleic acid sequence, provided that there is at least one nucleotide located between said non-contiguous sequence stretches that is not part of either of said non-contiguous sequence stretches In the context of the present invention, the term "at least one single-chain nucleic acid sequence binding to at least two non-contiguous sequence stretches" refers to binding via the formation of hydrogen bonds between complementary bases contained in said at least one single-chain nucleic acid sequence on one side, and in said at least two non-contiguous sequence stretches on the other side. Said binding may further be enhanced by covalent bonds formed between said at least one single-chain nucleic acid sequence and one, both or all of said at least two non-contiguous sequence stretches after UV irradiation in accordance with the present invention.

In a third aspect, the present invention relates to a method for increasing the stability of a non-naturally occurring nucleic acid nanostructure, wherein said nanostructure comprises at least two double-helical substructures, wherein said method is characterized by a step of exposing said nucleic acid nanostructure to UV irradiation.

In the context of the present invention, the term "double-helical substructure" relates to a subpart of the nanostructures according to the present invention that are in a double-helical arrangement formed by two complementary nucleic acid sequence stretches. The ends of a double-helical substructure may result from the termination of the region of complementarity due to the fact (i) that one of the two complementary nucleic acid sequence stretches reaches its 3' or 5'-end, or (ii) that one of the two complementary nucleic acid sequence stretches continues to form another double-helical substructure by complementarity to a second, non-contiguous sequence stretch on the other or a different nucleic acid sequence.

In a fourth aspect, the present invention relates to a method for increasing the stability of a non-naturally occurring nucleic acid nanostructure comprising a multiplicity of double-helical substructures, wherein said nanostructure comprises at least one single-chain nucleic acid sequence being part of at least two different double-helical substructures, wherein said method is characterized by a step of exposing said nucleic acid nanostructure to UV irradiation.

In a particular embodiment said non-naturally occurring nucleic acid nanostructure comprises either a two- or a three-dimensional arrangement of double-helical substructures.

In a particular embodiment said non-naturally occurring nucleic acid nanostructure is a structure, wherein said double-helical substructures each consist of between 10 and 5,000 complementary nucleotide pairs, wherein said double-helical substructures can make connections to neighboring double-helical substructures every seven, eight or nine bases, wherein one or more of the single-stranded oligonucleotides forming the double-helical substructures are either part of the same or at least of two different double-helical substructures.

In a particular embodiment said connections between said double-helical substructures results in a honeycomb-, square-, or hexagonal-packing geometry or a combination of those.

In a particular embodiment, at least 85% of the single-stranded oligonucleotides forming the double-helical substructures are part of at least two different double-helical substructures.

In a particular embodiment said step of exposing said nucleic acid nanostructure to UV irradiation results in the formation of at least one chemical bond between two pyrimidine nucleotides.

In a particular embodiment, wherein at least one of the two pyrimidine nucleotides is not part of a complementary nucleotide pair comprised in a double-helical substructure.

In a particular embodiment said nucleic acid nanostructure comprises one or more copies of at least a first single-stranded polynucleotide, and a set of second single-stranded polynucleotides, wherein each of the second single-stranded polynucleotides consists of an n-specific sequence consisting of n core sequences, with n being an integer independently selected from the range of 1 to 40, wherein each of said n core sequences consists of (i) a sequence that is complementary to a region on said first single-stranded polynucleotide, wherein the region on said first single-stranded polynucleotide complementary to the $n^{th}$ core sequence is not contiguous with the regions on said first single-stranded polynucleotide complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In the context of the present invention, said first single-stranded polynucleotide can be regarded as a scaffolding or backbone polynucleotide.

In the context of the present invention, a value of m=0 indicates that the core sequence is not flanked by a pyrimidine nucleotide stretch $P_m$ at the corresponding end of the nucleic acid sequence. In particular embodiments, at least 50% of the second single-stranded polynucleotides of said set have at least one pyrimidine nucleotide stretch at either the 3'- or the 5'-end. In particular embodiments, at least 75%, particularly at least 80%, at least 85% or at least 90% have at least one pyrimidine nucleotide stretch at either the 3'- or the 5'-end. In particular embodiments, at least 35% of the second single-stranded polynucleotides of said set have two pyrimidine nucleotide stretches at both the 3'- and the 5'-end. In particular embodiments, at least 50%, particularly at least 75%, at least 80% or at least 85% have two pyrimidine nucleotide stretches at both the 3'- and the 5'-end.

In a particular embodiment, the first single-stranded polynucleotide comprises at least 100 nucleotides.

In a particular embodiment, the first single-stranded polynucleotide has at least 70% sequence identity to the DNA of a filamentous bacteriophage. In particular embodiments, the single-stranded polynucleotide has at least 80% sequence identity, particularly at least 85%, more particularly at least 90%, and most particularly at least 95% sequence identity.

In a particular embodiment said filamentous bacteriophage is M13, particularly M13mp18.

In a particular embodiment said nucleic acid nanostructure comprises a set of single-stranded oligonucleotides,
  wherein each of the single-stranded polynucleotides consists of an n-specific sequence consisting of n core sequences, with n being an integer independently selected from the range of 1 to 40, wherein each of said n core sequences consists of (i) a sequence that is complementary to the sequence of another member of said set of single-stranded polynucleotides, wherein the region on said another member complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$,
  wherein each m is an integer independently selected from the range of 0 to 40, and
  wherein each P is independently selected from a thymidine and a cytosine residue.

In particular embodiments, each m is an integer independently selected from the range of 0 to 5.

In a particular embodiment, for each of said pyrimidine nucleotide stretches $P_m$ at the 3' ends and at the 5' ends m is either 0 or 1 and P is a thymidine residue.

In particular embodiments, said nucleic acid nanostructure comprises one or more insertions of a pyrimidine nucleotide stretch $P_m$, wherein m is independently selected from the range of 1 to 5, particularly wherein m is independently selected from 1, 3 and 5.

In a particular embodiment, each of said core sequences consists of x nucleotides, with x being independently selected from an integer that is a multiple of 7, 8 or 16.

In the context of the present invention, the values for x are determined by the geometry of the DNA double helix. One of skill in the art is able to determine the size of the double helices and the number of nucleotides that have to be present in order to permit a regular arrangement of the double-helical substructures in the nanostructures to be stabilized in accordance with the present invention.

In a particular embodiment said UV irradiation is performed with UV light of a wavelength in the range between 250 nm and 350 nm.

In a particular embodiment said UV irradiation is performed using the following parameters: volume of the sample between about 5 and 2,000 μl, concentration of the nucleic acid nanostructure in the sample between about 1 and 500 nM, in the temperature range between about 0 and 25° C., in a TRIS-buffered solution, with a Xenon light source (MAX 303 from Asahi Spectra) using a light guide to couple the light beam into the sample (with a distance of less than about 5 cm between the solution surface of the sample and the terminus of the light guide). The sample is exposed to UV-irradiation for between about 1 and 6 hours with an intensity of the UV-light of between about 1 and 10 mW/cm².

In the context of the present invention, the term "about" in combination with values or ranges of values indicates that the given value or range of values is not excluding values close to the value or range of values specifically listed. In particular, depending on the context, the term "about" includes values that are within a range of plus or minus 10% of the specified value. In particular embodiments, the term "about" is disregarded, and the values or ranges of values are used as written.

In a particular embodiment said step of exposing said nucleic acid nanostructure to UV irradiation is performed for the duration required for the reference DNA nanostructure of Example 2, treated under identical conditions, to reach stability, wherein said stability is identified in a gel electrophoresis assay as described in Example 2, wherein said reference DNA nanostructure is incubated (i) either untreated under reference conditions at 25° C. in 5 mM TRIS, 5 mM NaCl, 1 mM EDTA, 5 mM MgCl$_2$. and (ii) after UV treatment, at the target condition needed e.g. at elevated temperatures such as 90° C., in pure water, under physiological conditions, or in vacuum wherein stability is reached as soon as the band for the reference DNA nanostructure exhibits the same electrophoretic mobility after UV treatment as under reference condition.

In a fifth aspect, the present invention relates to a kit for the generation of a nucleic acid nanostructure comprising one or more copies of at least a first single-stranded polynucleotide, and a set of single-stranded polynucleotides, wherein each of the single-stranded polynucleotides consists of an n-specific sequence consisting of n core sequences, with n being an integer independently selected from the range of 1 to 40, wherein each of said n core sequences consists of (i) a sequence that is complementary to a region on said first single-stranded polynucleotide, wherein the region complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In particular embodiments, each m is an integer independently selected from the range of 0 to 5.

In a particular embodiment, for each of said pyrimidine nucleotide stretches $P_m$ at the 3' ends and at the 5' ends m is either 0 or 1 and P is a thymidine residue.

In particular embodiments, said nucleic acid nanostructure comprises one or more insertions of a pyrimidine nucleotide stretch $P_m$, wherein m is independently selected from the range of 1 to 5, particularly wherein m is independently selected from 1, 3 and 5.

In a sixth aspect, the present invention relates to a kit for the generation of a nucleic acid nanostructure comprising a set of single-stranded oligonucleotides, wherein each of the single-stranded polynucleotides consists of an n-specific sequence consisting of n core sequences, with n being an integer independently selected from the range of 1 to 40, wherein each of said n core sequences consists of (i) a sequence that is complementary to the sequence of another member of said set of single-stranded polynucleotides, wherein the region on said another member complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In particular embodiments, each m is an integer independently selected from the range of 0 to 5.

In a particular embodiment, for each of said pyrimidine nucleotide stretches $P_m$ at the 3' ends and at the 5' ends m is either 0 or 1 and P is a thymidine residue.

In particular embodiments, said nucleic acid nanostructure comprises one or more insertions of a pyrimidine nucleotide stretch $P_m$, wherein m is independently selected from the range of 1 to 5, particularly wherein m is independently selected from 1, 3 and 5.

In a seventh aspect, the present invention relates to a nucleic acid nanostructure comprising one or more copies of at least a first single-stranded polynucleotide, and a set of single-stranded polynucleotides, wherein each of the single-stranded polynucleotides consists of an n-specific sequence consisting of n core sequences, with n being an integer selected from the range of 1 to 40, wherein each of said n core sequences consists of (i) a sequence that is complementary to a region on said first single-stranded polynucleotide, wherein the region complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In particular embodiments, each m is an integer independently selected from the range of 0 to 5.

In a particular embodiment, for each of said pyrimidine nucleotide stretches $P_m$ at the 3' ends and at the 5' ends m is either 0 or 1 and P is a thymidine residue.

In particular embodiments, said nucleic acid nanostructure comprises one or more insertions of a pyrimidine nucleotide stretch $P_m$, wherein m is independently selected from the range of 1 to 5, particularly wherein m is independently selected from 1, 3 and 5.

In an eighth aspect, the present invention relates to a nucleic acid nanostructure comprising a set of single-stranded oligonucleotides, wherein each of the single-stranded polynucleotides consists of an n-specific sequence consisting of n core sequences, with n being independently selected from the range of 1 to 40, wherein each of said n core sequences consists of (i) a sequence that is complementary to the sequence of another member of said set of single-stranded polynucleotides, wherein the region on said another member complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and (iv) optionally, one or more insertions of a pyrimidine nucleotide stretch $P_m$, wherein each m is an integer independently selected from the range of 0 to 40, and wherein each P is independently selected from a thymidine and a cytosine residue.

In particular embodiments, each m is an integer independently selected from the range of 0 to 5.

In a particular embodiment, for each of said pyrimidine nucleotide stretches $P_m$ at the 3' ends and at the 5' ends m is either 0 or 1 and P is a thymidine residue.

In particular embodiments, said nucleic acid nanostructure comprises one or more insertions of a pyrimidine nucleotide stretch $P_m$, wherein m is independently selected from the range of 1 to 5, particularly wherein m is independently selected from 1, 3 and 5.

In a particular embodiment, said nucleic acid nanostructure comprises one or more UV-induced bridges between spatially adjacent thymidine and/or cytosine residues.

In a particular embodiment, said one or more bridges comprise a pyrimidine dimer selected from a cyclobutane pyrimidine dimer and a (6,4) pyrimidine-pyrimidone.

In a particular embodiment, said one or more bridges are between thymidine and/or cytosine residues comprised in a $P_m$ stretch at the 3' end of a single-stranded oligonucleotide or core sequence, at the 5' end of a single-stranded oligonucleotide or core sequence, and/or a thymidine of one of said optional $P_m$ insertions.

In a particular embodiment, one or more of said bridges are intrahelical bridges between the thymidine or cytosine residues at the 3' and 5' ends of two adjacent single-stranded oligonucleotides or core sequences being part of the same or a different double-helical substructure of said nucleic acid nanostructure.

In a particular embodiment, one or more of said bridges are interhelical bridges between thymidine or cytosine residues comprised in single-stranded oligonucleotides or parts of such single-stranded oligonucleotides that are part of two different double-helical substructures of said nucleic acid nanostructure, particularly between two thymidine residues comprised in two of said optional insertions.

In a particular embodiment, the crosslinking is from the list of 3'-end of polynucleotide A to 5'-end of polynucleotide B, 3'-end of polynucleotide A to 3'-end of polynucleotide B, 5'-end of polynucleotide A to 5'-end of polynucleotide B, 3'-end of polynucleotide A to insertion in core sequence of polynucleotide B, 5'-end of polynucleotide A to insertion in core sequence of polynucleotide B, and insertion in core sequence of polynucleotide A to insertion in core sequence of polynucleotide B.

In a ninth aspect, the present invention relates to a complex nucleic acid nanostructure resulting from assembly of two or more nucleic acid nanostructures according to the present invention.

In a particular embodiment, said assembly comprises one or more UV-induced bridges between two or more of said nucleic acid nanostructures according to the present invention.

EXAMPLES

The following examples illustrate the invention without limiting its scope.

Bottom-up fabrication of custom nanostructures using the methods of DNA nanotechnology has great potential for applications in many areas of science and technology. One important obstacle to applications concerns the constrained environmental conditions at which DNA objects retain their structure. Here, we present a general, site-selective, and scalable method for introducing additional covalent bonds to increase the structural stability of DNA nanostructures. The key concept is the user-defined placement of thymidines in close proximity within DNA nanostructures to rationally create sites for introducing covalent cyclobutane pyrimidine dimer (CPD) bonds via UV irradiation. These additional bonds may be used in a sequence-programmable fashion to link free strand termini, to remove strand breaks that occur at crossover sites, i.e. to bridge strand breaks at crossover sites, and to create additional inter-helical connections. As a result, one obtains objects that are covalently crosslinked at user-programmable sites without the need for chemical modifications. Accordingly designed multi-layer DNA origami objects preserve their global shape, and thus can remain stable, at temperatures up to 90° C. and in pure double-distilled water with no additional cations present. In addition, these objects show substantially enhanced lifetimes, i.e. enhanced resistance, against nuclease activity. Cryo-electron microscopy (cryo-EM) structural analysis of non-crosslinked and crosslinked objects indicated that the global shape and the internal network of crossovers are preserved after irradiation. A cryo-EM map of a CPD-stabilized multilayer DNA origami object determined at physiological ionic strength reveals a substantial swelling behavior, presumably caused by repulsive electrostatic forces that, without covalent stabilization, would cause disassembly at low ionic strength. Our method opens new avenues for applications of DNA nanostructures in a wider range of conditions and thus in a variety of fields.

Example 1: General Description of the Approach and of the Results Achieved

Pyrimidine dimers are molecular lesions produced by photochemical reactions in DNA[53]. Ultraviolet light induces the formation of covalent bonds through reactions at the C=C double bonds in thymine (T) or cytosine (C) bases (FIG. 1, left). Common products are cyclobutane-pyrimidine dimers (CPDs), including thymine dimers. Minor by-products, such as (6-4) pyrimidine-pyrimidone and Dewar isomers, may also form upon UV irradiation. These lesions can arrest DNA replication and transcription and thus are cancerogenic and represent targets of the cellular DNA repair machinery[54]. In 1982 Lewis and Hanawalt reported that CPDs can also form from adjacent terminal thymines in separate DNA strands that are brought together by a templating complementary DNA strand[55]. However, the potential of this finding for solving the stability problem in DNA nanotechnology has remained unrecognized thus far. The key concept in our work is the user-defined placement of thymidines in close proximity within DNA nanostructures to rationally create sites for introducing covalent CPD bonds via UV irradiation. These additional bonds may be used to link free strand termini, to remove strand breaks that occur at crossover sites, and to create additional inter-helical connections (FIG. 1, right). The fundamental building blocks of DNA nanotechnology are double-helical DNA domains. In DNA origami objects[3,4,56] these domains form by hybridization of a set of short single-stranded staple oligonucleotides to a long single-stranded scaffold molecule. In other types of DNA nanostructures such as DNA tile-brick objects[16], the double-helical domains are formed only between single-stranded oligonucleotides. DNA origami and tile brick objects contain hundreds of single-strand breaks, which represent weak points. This is because free ends enable not only the formation but also the dissolution of plectonemic double-helical domains. To create the option for removing the single-strand breaks after self-assembly of a target object, we prepare DNA strands with additional thymidines at both strand termini (FIG. 1A, motif 1). Even though the added bases will not be involved in forming Watson-Crick base pairs, the thymidines will come into close proximity at single-strand break sites in the folded object, which allows forming CPD bonds between the two thymidines through irradiation with light of wavelength 310 nm. In DNA objects, double-helical domains are connected to neighboring double-helical domains by interhelical connections typically formed by antiparallel single-strand crossovers including both half crossovers and double crossovers (FIG. 1A, motif 2 vs. motif 3). For example, DNA tile brick objects are almost exclusively connected via half crossovers, while in DNA origami objects both types of interhelical connections may occur. The crossover positions also represent weak points in DNA nanostructures due to the interrupted backbone bonds in the helical direction. To create the option for closing the weak links after self-assembly, we may add additional unpaired thymidine bases in the staple strands at crossover positions as indicated in FIG. 1A (motifs 2 and 3). Through proximity, irradiation with 310 nm light again may induce formation of CPD bonds which covalently connect the strands along the helical direction (FIG. 1B, motifs 2 and 3), thereby creating another topological hindrance for helical unwinding. When designing DNA objects, strand crossovers are typically placed between neighboring double-helical domains at positions where the helical backbones come close together. Complementary to strand crossovers, we may also exploit the light-induced CPD dimer bonds to create additional interhelical linkages after self-assembly of an object. To this end, we place single-stranded thymidine loops (T-loops) at positions where the backbones of neighboring DNA helices roughly align (FIG. 1A, motif 4). Irradiation at 310 nm can then induce the creation of covalent inter-helical linkages (FIG. 1B, motif 4).

Proof-of-Concept: High-Temperature and Low-Salt Stability

Figure 2:
FIG. 2 shows the proof-of-concept of UV crosslinking with multi-layer DNA origami. (A) From left to right: model of the brick-like DNA origami object featuring additional thymidines at all strand termini and at all strand crossover positions; laser-scanned fluorescent images of 2.0% agarose gels stained with ethidium bromide. Irradiated (135 min at 310 nm) and non-irradiated samples were either incubated for 30 min at different temperatures or incubated for 3 h at room temperature in double-distilled water containing successively lower concentrations of monovalent sodium chloride, respectively. p: pocket; u: unfolded species; f: folded species; c: crosslinked staple strands; s: un-crosslinked staple strands; L: 1 KB ladder; NI and I: non-irradiated and irradiated reference samples in folding buffer with 5 mM MgCl$_2$, respectively. The images of the gels were autoleveled and highlighted regions were auto-leveled twice; average 2D particle micrograph of the irradiated sample in double distilled water. (B) and (C) as in (A), but with the brick-like DNA origami object featuring additional thymidines at all strand termini, at all strand crossover positions, and 5-T loops and the pointer object featuring additional thymidines at all strand termini and at all strand crossover positions, respectively. See FIG. 29 for globally autoleveled gel images.
Figure 6:
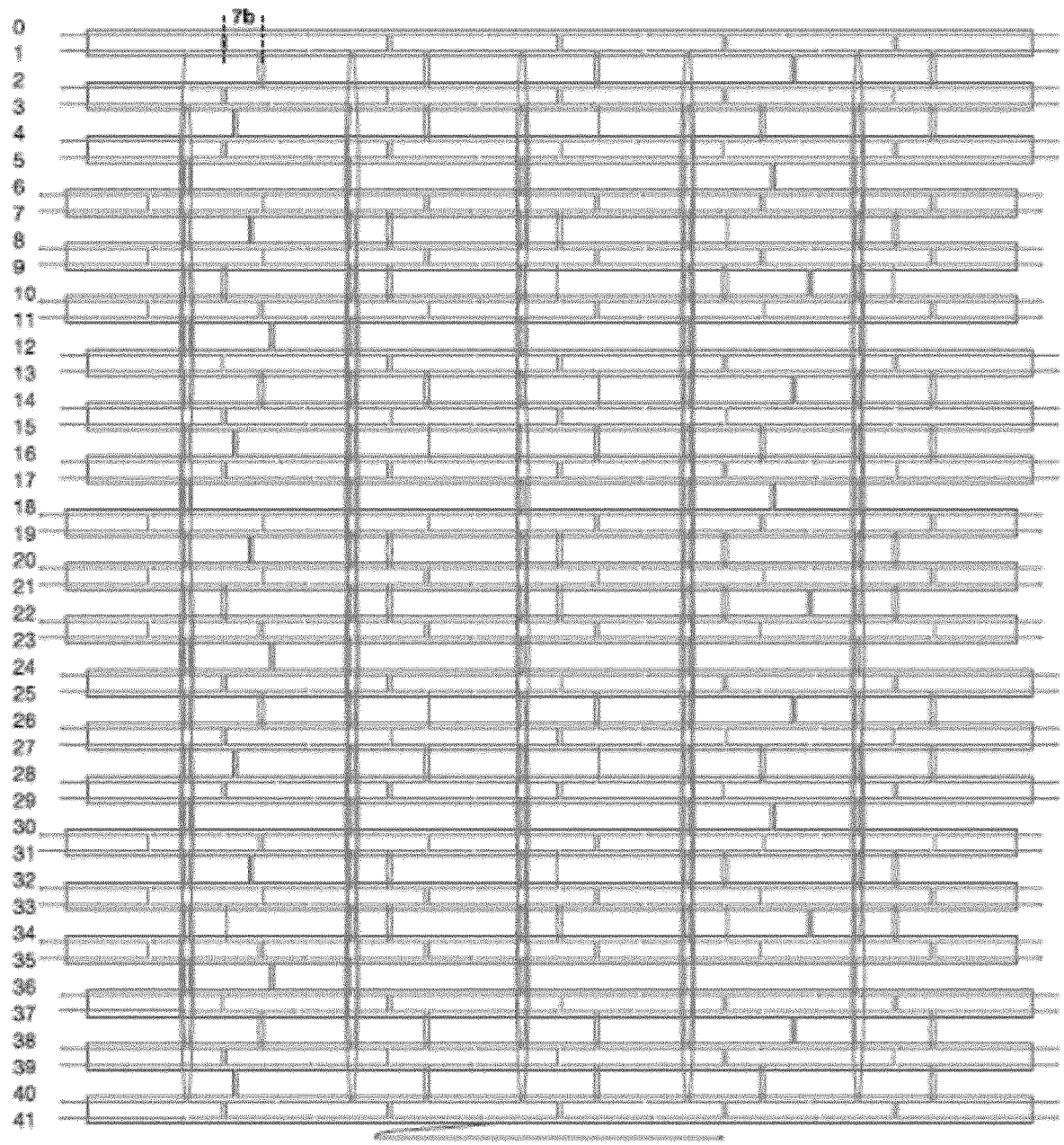
FIG. 6 shows the design diagram of the brick-like (TT motifs 1 to 3) object prepared using caDNAno[66]. The object features 1-thymine-long overhangs at all staple termini. In addition, TT motifs were inserted at all crossover sites per strand. Interfaces were passivated with poly-thymine overhangs. Inset upper right: Cross-section of the object designed in honeycomb lattice.
Figure 6:
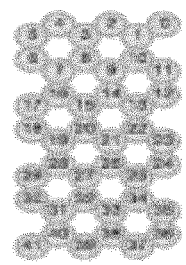
Figure 7:
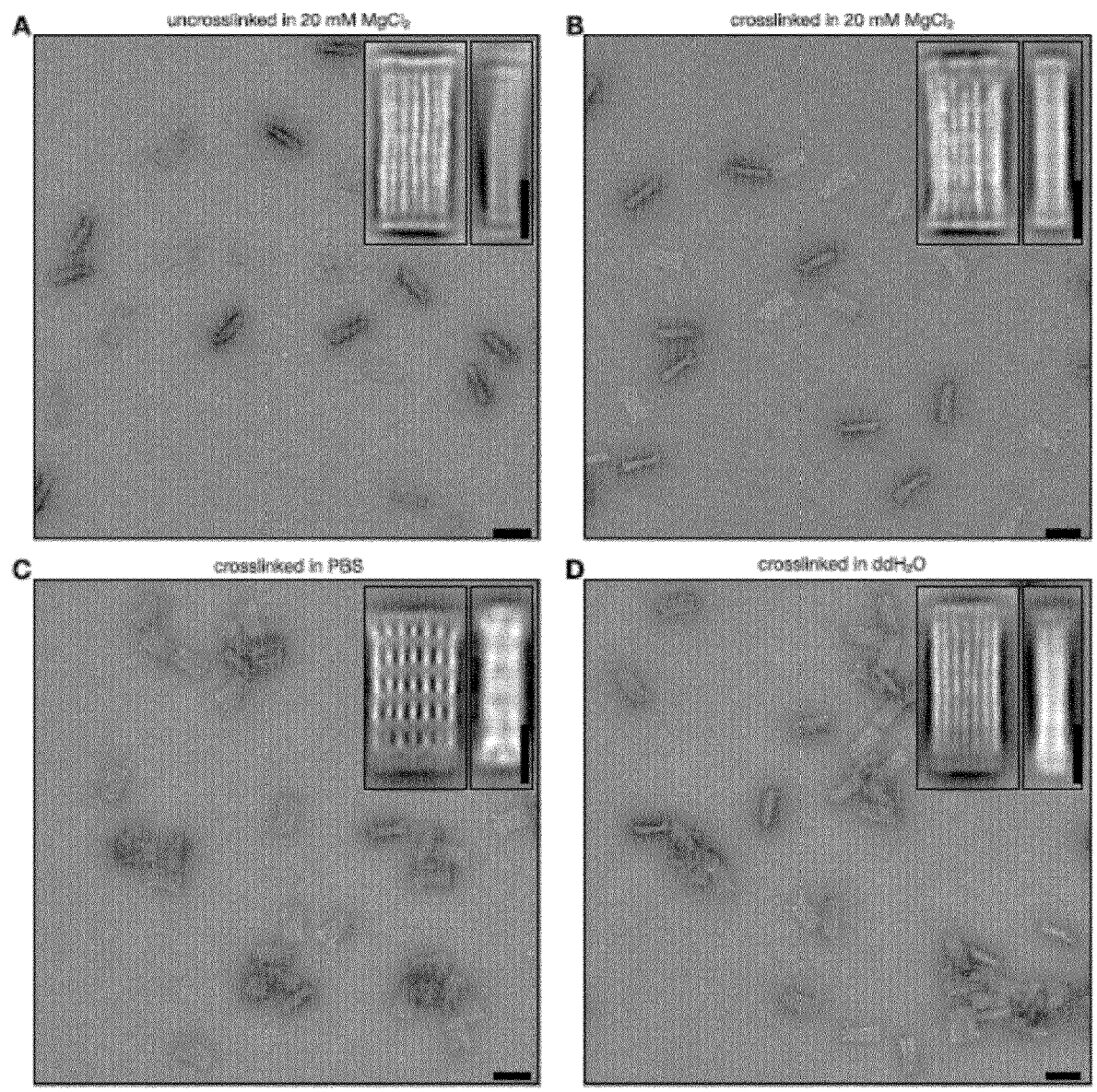
FIG. 7 shows the exemplary negative-stained TEM micrographs of the brick-like object (TT-motifs 1 to 4) in different buffers/solvents. Images were high-pass filtered to reduce staining gradients. Insets: corresponding average 2D particle micrographs. Scale bars: 20 nm.
Figure 8:
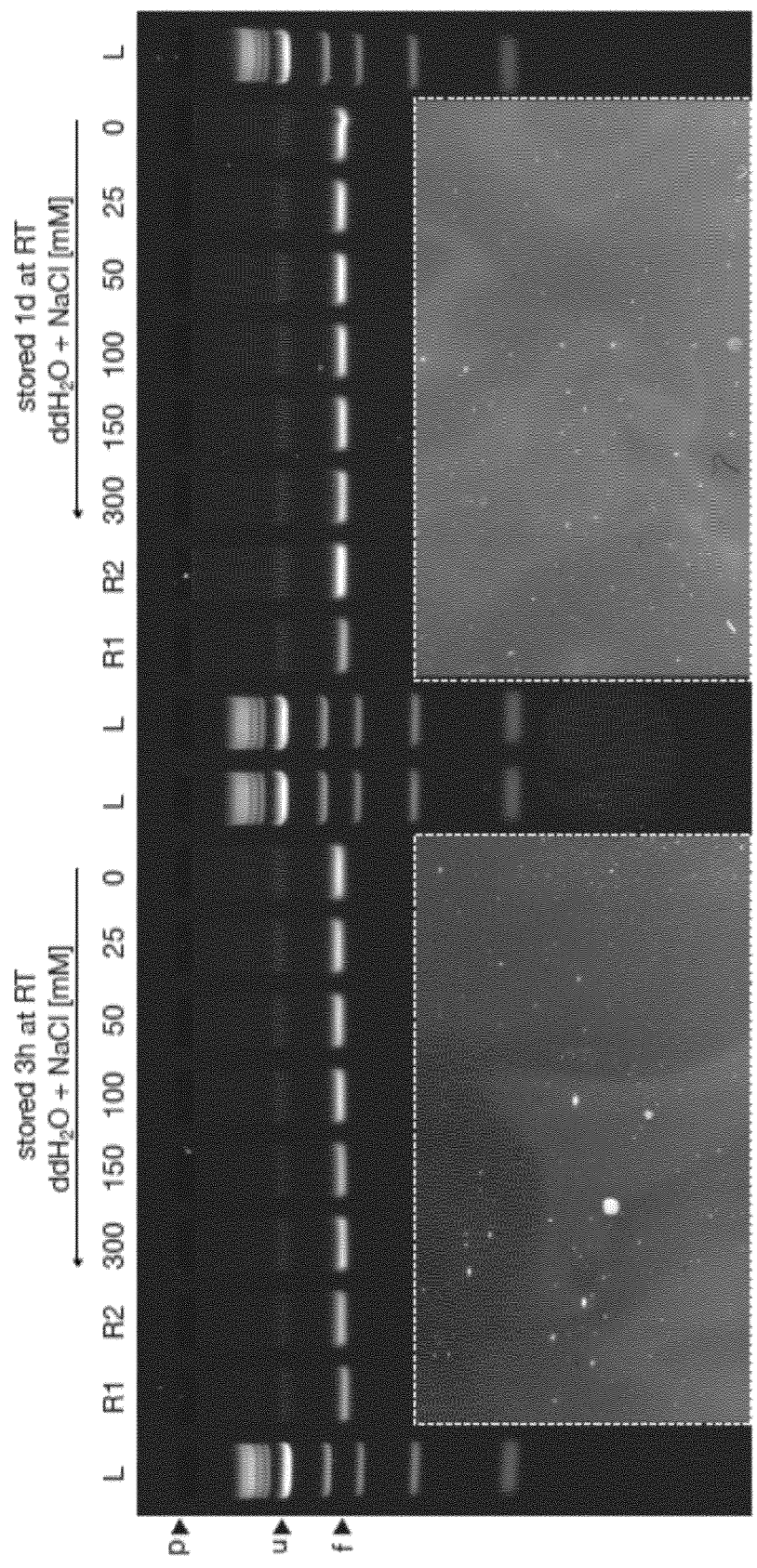
FIG. 8 shows the laser-scanned fluorescent image of a 2.0% agarose gel that was run in an ice-cooled water bath. The brick-like object with TT-motifs 1 to 3 dissolved in different solvents were loaded on the gel. p: pocket; u: unfolded species; f: folded species; L: 1 KB ladder; R1: non-irradiated reference in folding buffer with 30 mM MgCl$_2$; R2: reference that was irradiated at 310 nm for 135 min in folding buffer with 30 mM MgCl$_2$. The image of the gel was auto-leveled and highlighted regions were auto-leveled again.
Figure 9:
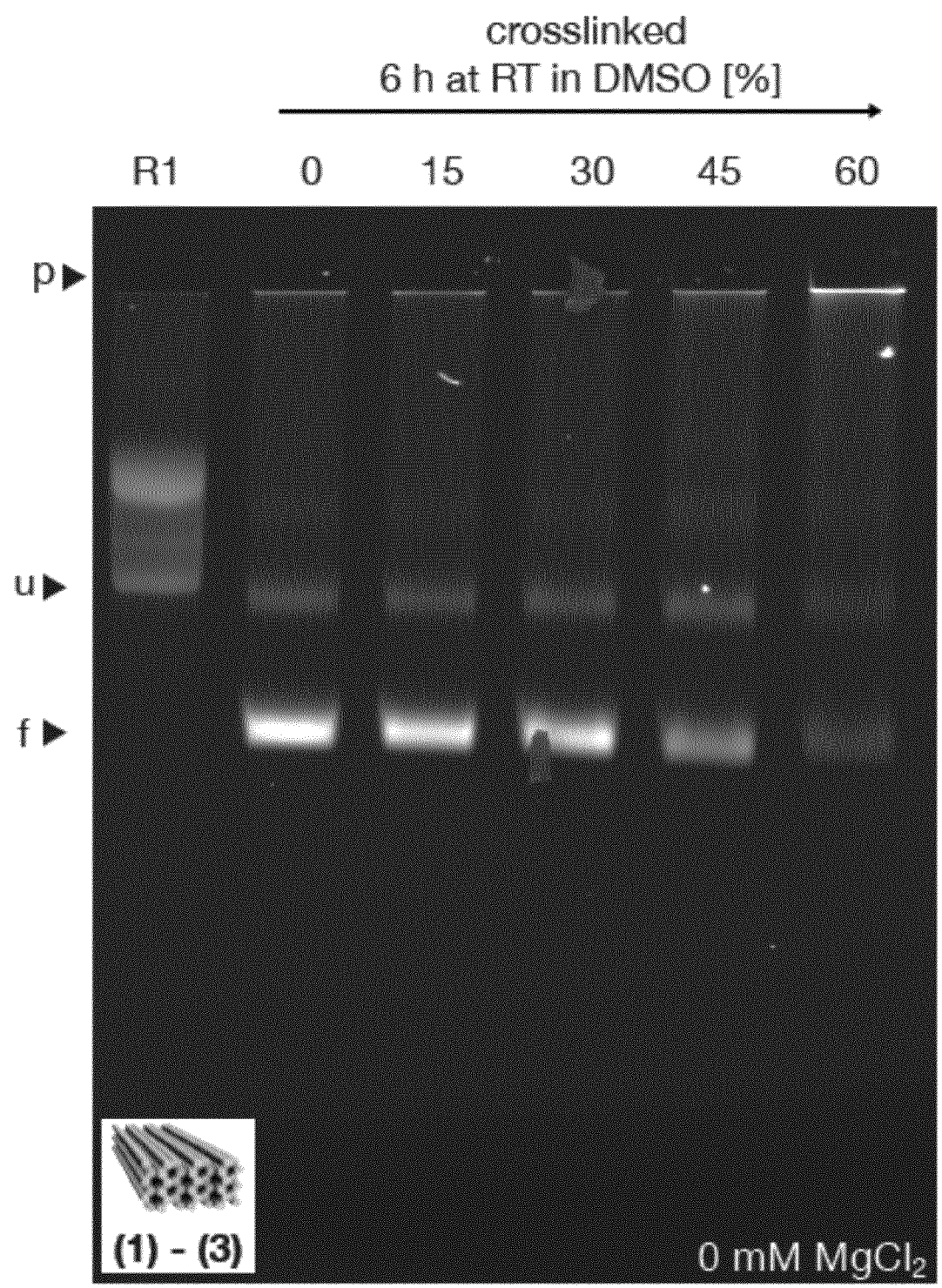
FIG. 9 shows the laser-scanned fluorescent image of a 2.0% agarose gel that was run in an ambient temperature water bath. The gel and the running buffer contained 0.5× TBE with no MgCl$_2$. Samples of the brick-like object with TT motifs 1 to 3 in the presence of different percentages of DMSO were loaded on the gel. p: pocket; u: unfolded species; f: folded species; R1: non-irradiated reference in folding buffer with 30 mM MgCl$_2$. The image of the gel was auto-leveled.
Figure 10:
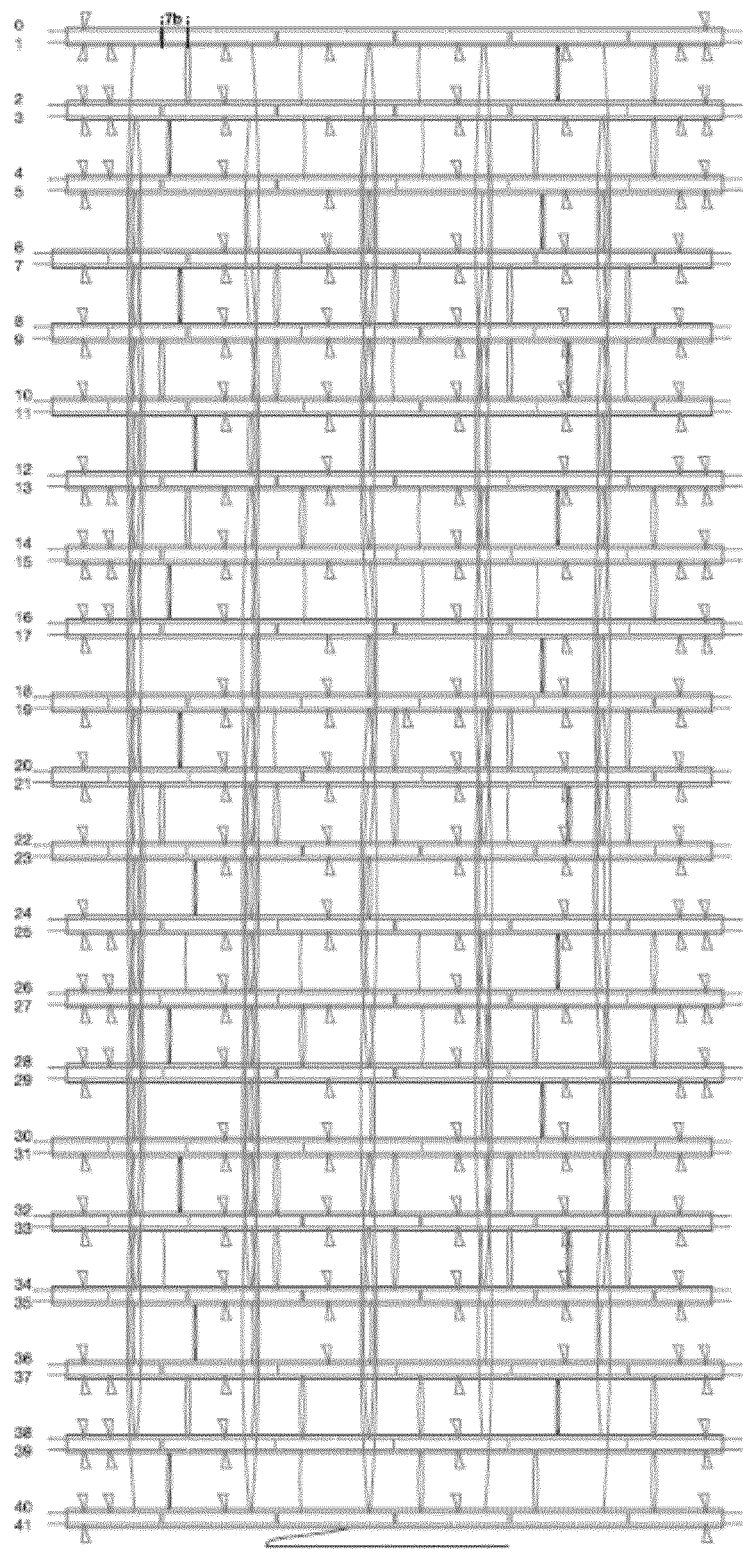
FIG. 10 shows the design diagram of the brick-like (TT-motifs 1 to 4) object prepared using caDNAno[66]. The object features 1-thymine-long overhangs at all staple termini. TT motifs were inserted at all crossover sites per strand. In addition, helices feature 5-thymine-long loops for inter-helical crosslinking. Interfaces are passivated with poly-thymine overhangs. Inset upper right: Cross-section of the object designed in honeycomb lattice.
Figure 10:
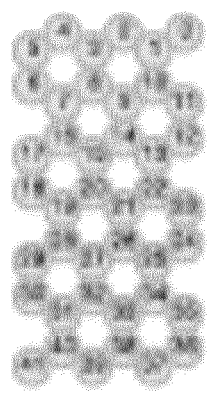
Figure 11:
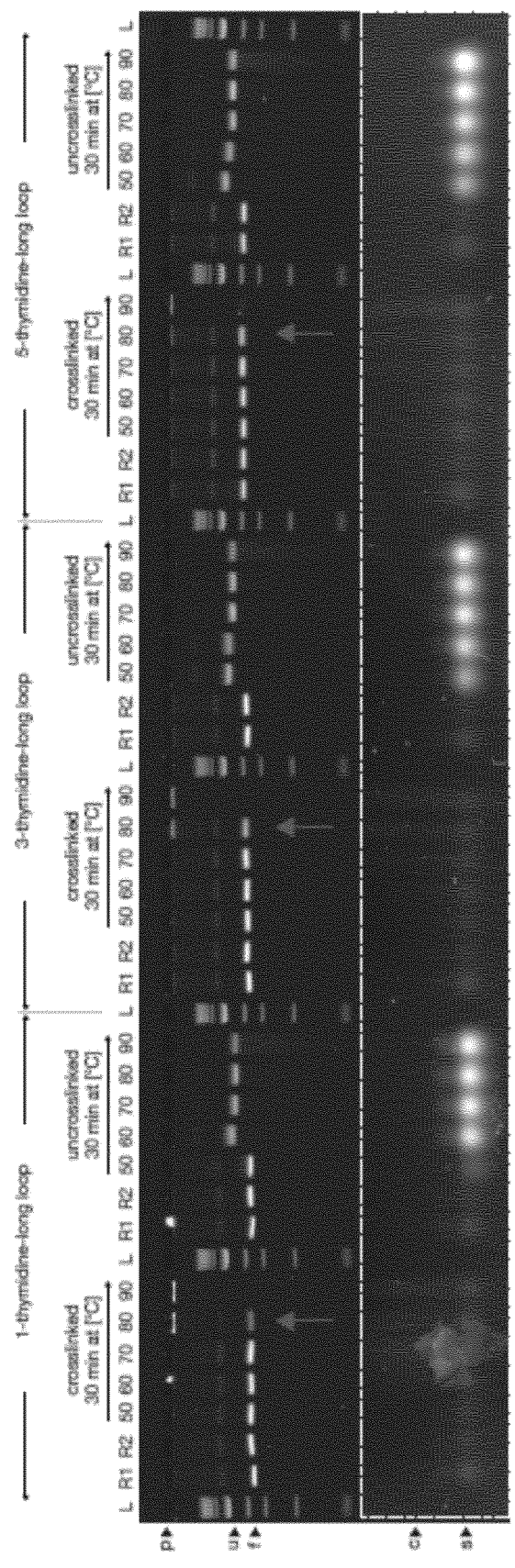
FIG. 11 shows the laser-scanned fluorescent image of a 2.0% agarose gel placed in an ice-cooled water bath. Irradiated (135 min at 310 nm) and non-irradiated samples of different variants of the brick-like object with TT motifs 1 to 4 featuring 1-T, 3-T, and 5-T loops were incubated at different temperatures and loaded on the gel. p: pocket; u: unfolded species; f: folded species; c: crosslinked staples; s: un-crosslinked staples; L: 1 KB ladder; R1: non-irradiated brick-like object with TT-motifs 1 to 3 in folding buffer with 30 mM MgCl$_2$; R2: irradiated (135 min at 310 nm) brick-like object with TT-motifs 1 to 3 in folding buffer with 30 mM MgCl$_2$. The image of the gel was auto-leveled and highlighted regions were auto-leveled again. The arrows indicate the band whose intensity increases for longer loop lengths.
Figure 12:
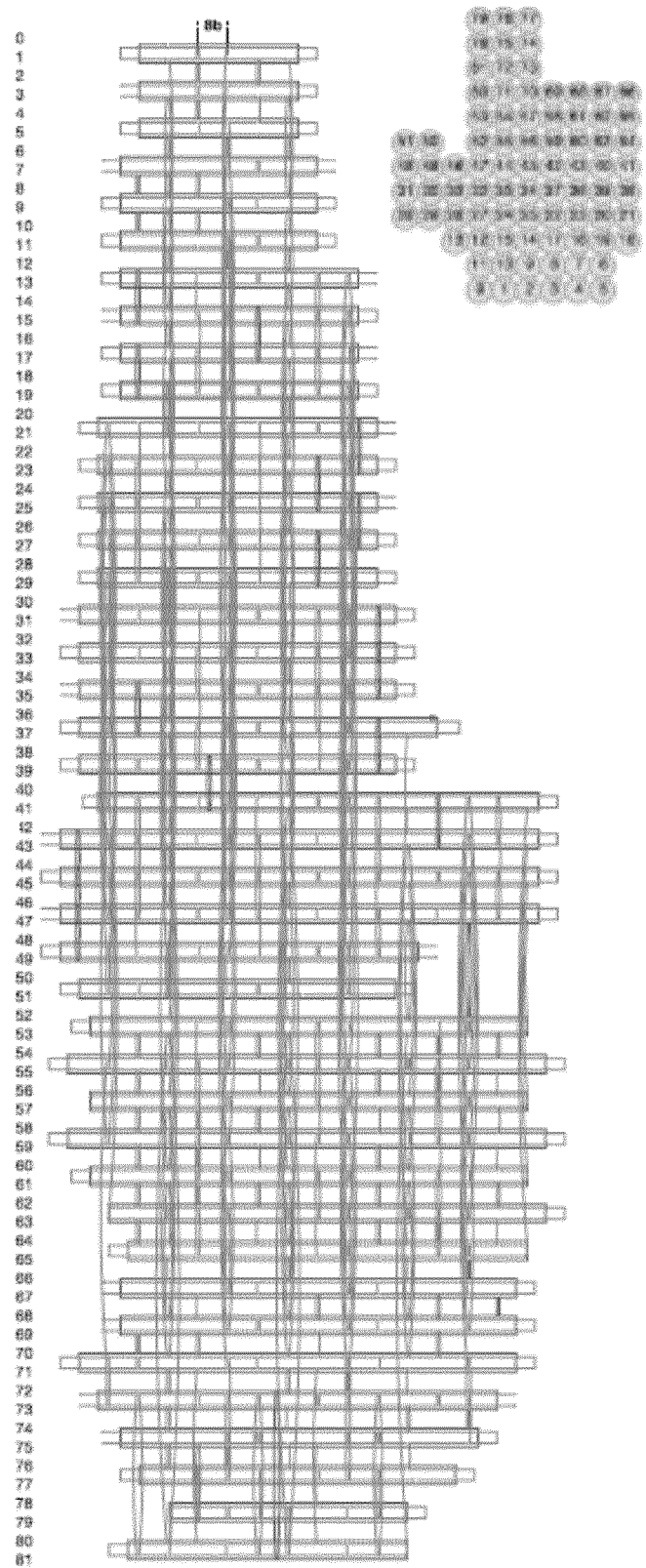
FIG. 12 shows the design diagram of the pointer object prepared using caDNAno[66]. The object features 1-thymine-long overhangs at all staple termini. TT motifs were inserted at all crossover sites per strand. Interfaces are passivated with poly-thymine overhangs. Inset upper right: Cross-section of the object designed in square lattice.
Figure 13:
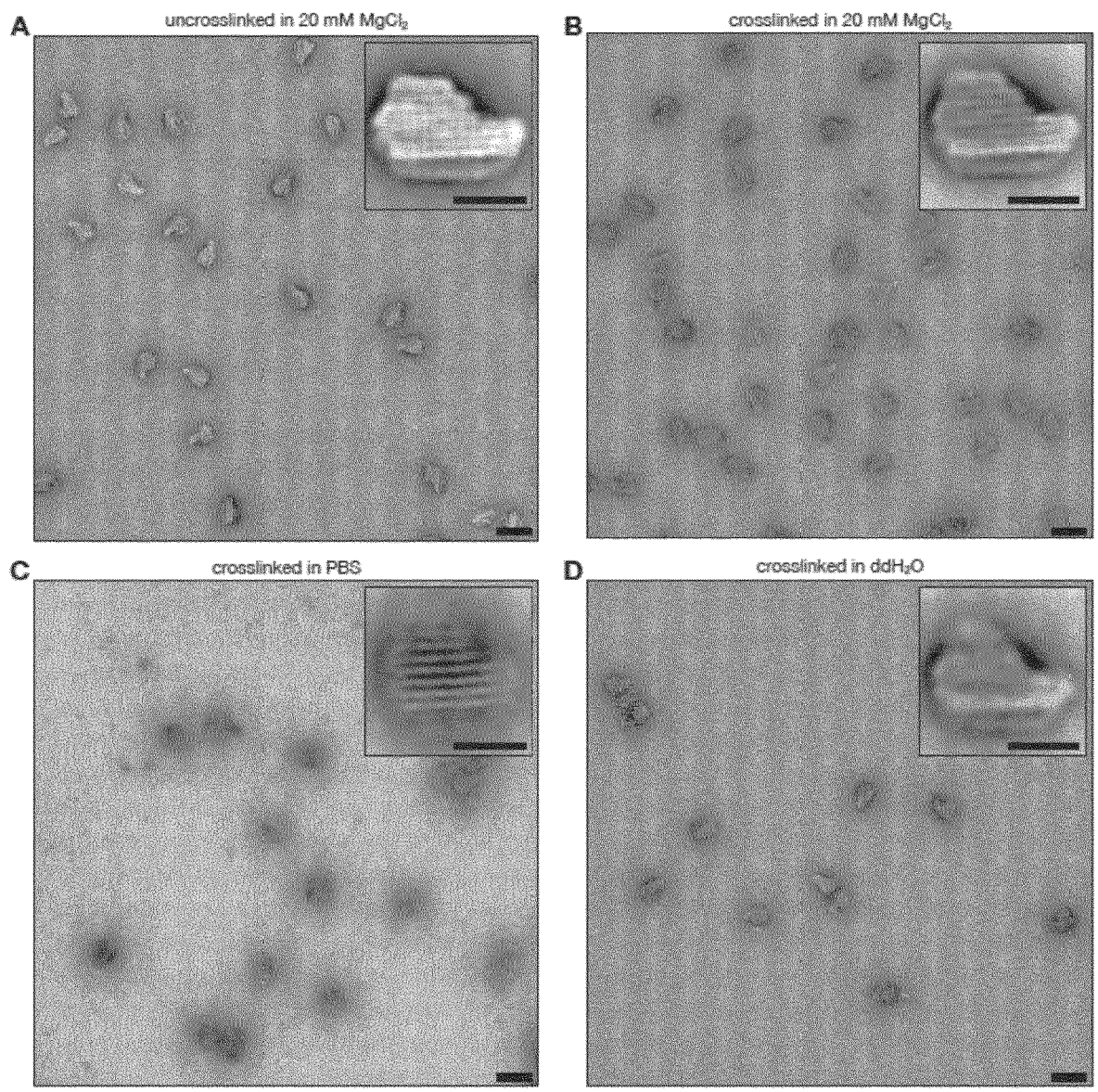
FIG. 13 shows the exemplary negative-stained TEM micrographs of the pointer object in different buffers/solvents. Images were high-pass filtered to reduce staining gradients. Insets: corresponding average 2D particle micrographs. Scale bars: 20 nm.
Figure 14:
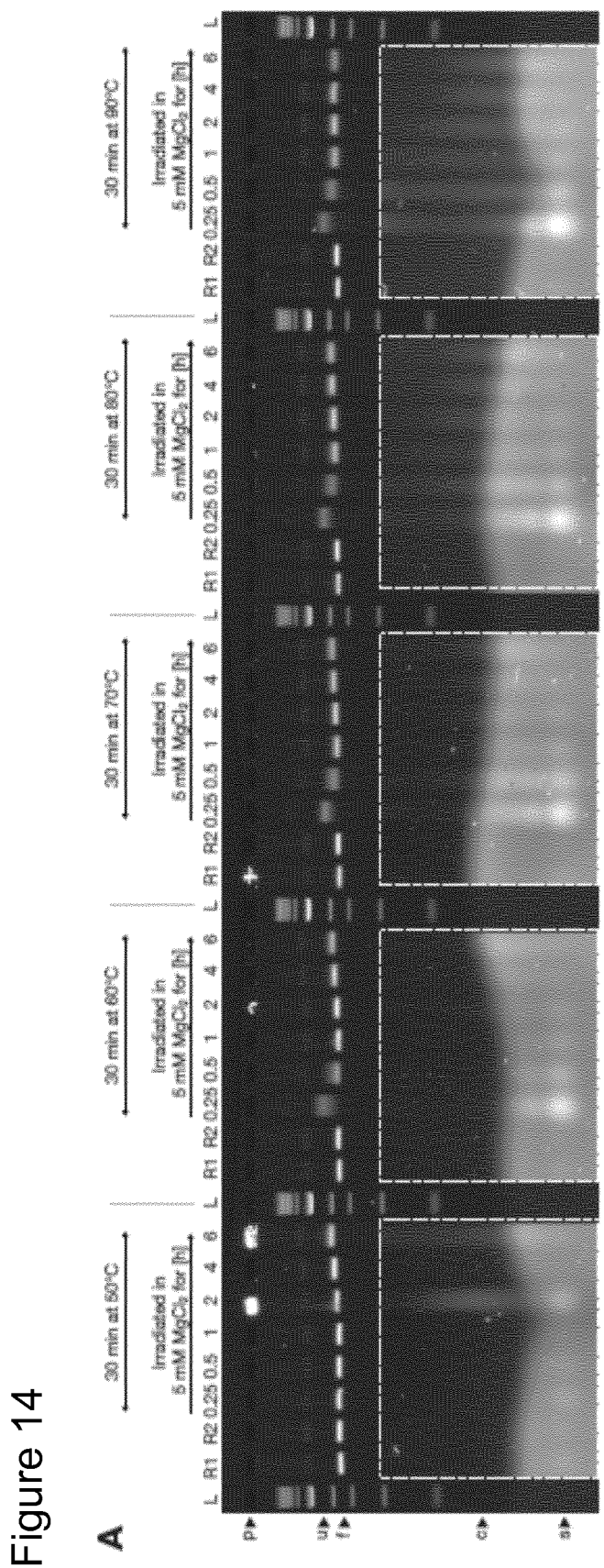
FIG. 14 shows the laser-scanned fluorescent image of a 2.0% agarose gel placed in a water bath. The brick-like object with TT-motifs 1 to 3 irradiated for different periods of time and incubated at different temperatures were loaded on the gel. p: pocket; u: unfolded species; f: folded species; c: crosslinked staples; s: un-crosslinked staples; L: 1 KB ladder; R1: non-irradiated reference in folding buffer with 30 mM $MgCl_2$; R2: reference that was irradiated at 310 nm for 135 min in folding buffer with 30 mM $MgCl_2$. The image of the gel was auto-leveled and highlighted regions were auto-leveled again. (A) Samples were irradiated in the presence of 5 mM $MgCl_2$. (B) and (C) Samples were irradiated in the presence of 30 mM $MgCl_2$.
Figure 15:
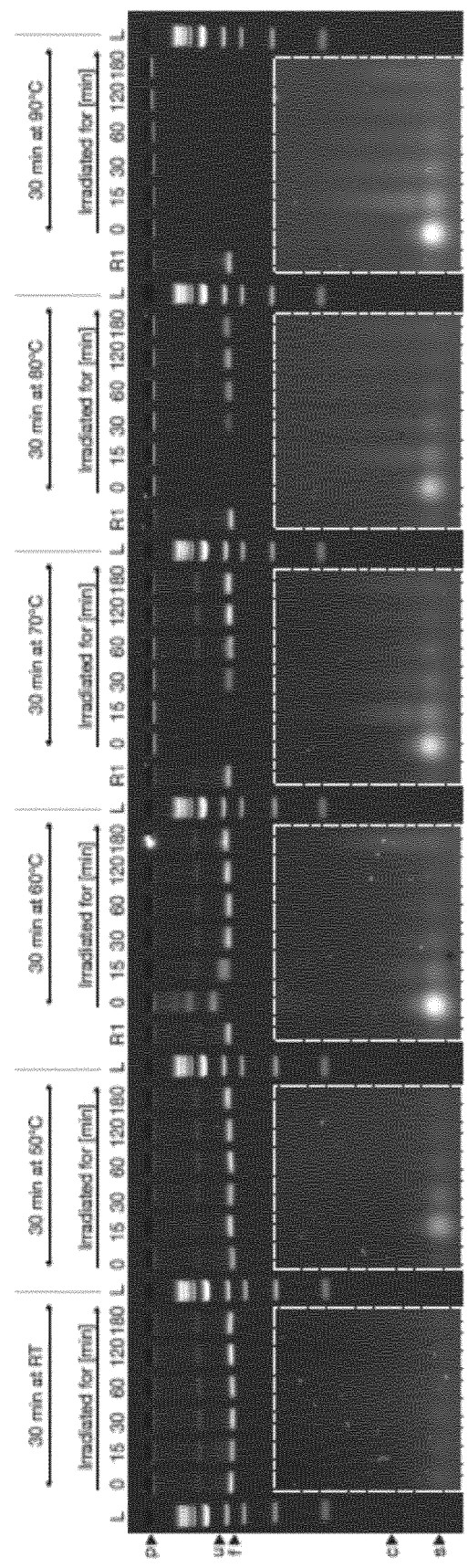
FIG. 15 shows the laser-scanned fluorescent image of a 2.0% agarose gel placed in a water bath. The brick-like object with TT motifs 1 to 4 irradiated for different periods of time and incubated at different temperatures were loaded on the gel. p: pocket; u: unfolded species; f: folded species; c: crosslinked staples; s: un-crosslinked staples; L: 1 KB ladder; R1: non-irradiated reference in folding buffer with 30 mM $MgCl_2$. The image of the gel was auto-leveled and highlighted regions were auto-leveled again.
Figure 16:
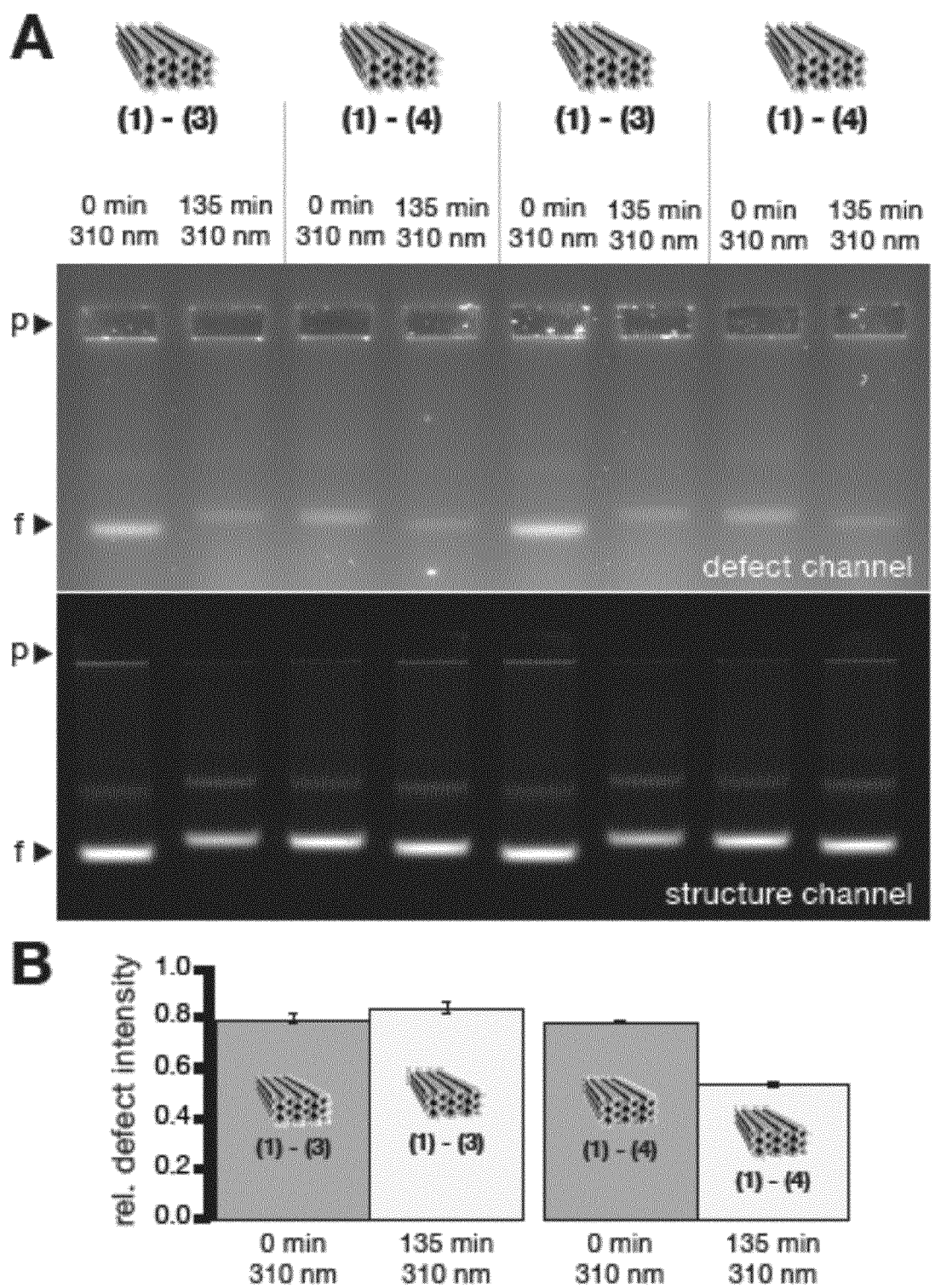
FIG. 16 shows the laser-scanned fluorescent image of a 2.0% agarose gel placed in an ice-cooled water bath. The gel and running buffer included 10 mM $MgCl_2$. Cyanine 5-labeled brick-like objects with TT motifs 1 to 3 and TT motifs 1 to 4 were subjected to a defect analysis using the de-Bruijn assay[58]. Non-irradiated and irradiated samples were mixed with two cyanine 3-modified oligonucleotides (de-Bruijn probes; final concentration of 16 μM) prior to loading on the gel. (A) The gel was laser-scanned in two channels. Top gel: defect channel; excitation of the cyanine 3 fluorophores at 532 nm and collecting the emission between 560 and 580 nm. Bottom gel: structure channel; excitation of the cyanine 5 fluorophores at 635 nm and collecting the emission above 665 nm. p: pocket and f: folded species. The images of the gel were globally auto-leveled. (B) Plot of the relative defect intensity (i.e. ratio of the band intensity between defect and structure channel) calculated from the gel in (A).
Figure 17:
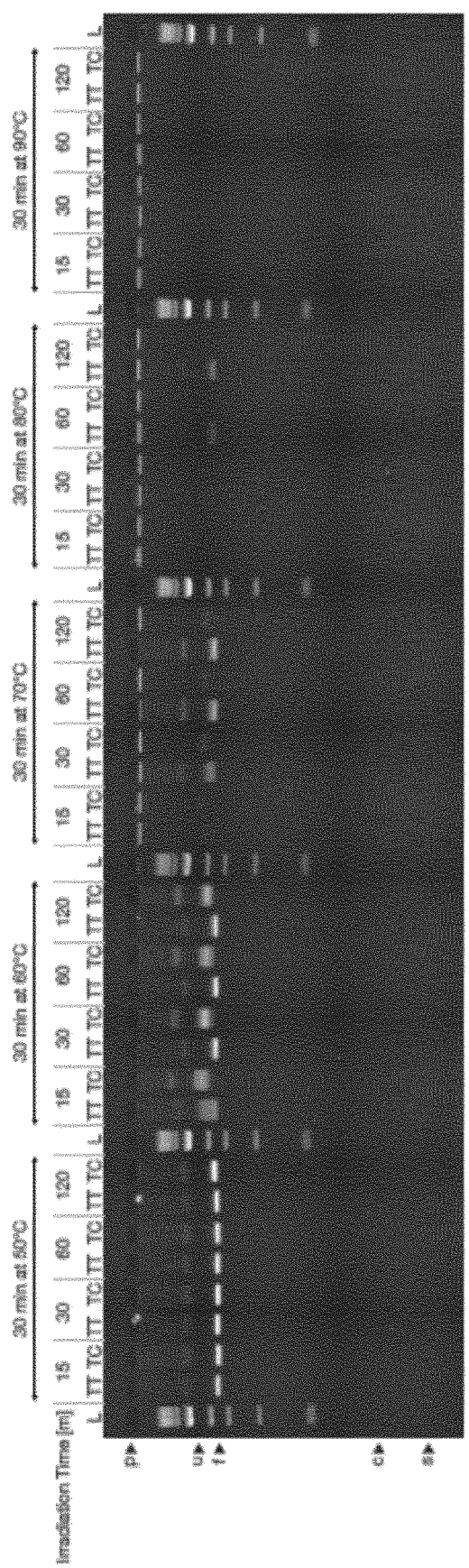
FIG. 17 shows the laser-scanned fluorescent image of a 2.0% agarose gel placed in a water bath. The brick-like object with TT or TC motifs 1 to 3 irradiated for different periods of time and incubated at different temperatures were loaded on the gel. p: pocket; u: unfolded species; f: folded species; c: crosslinked staples; s: un-crosslinked staples; L: 1 KB ladder. The image of the gel was auto-leveled.
Figure 18:
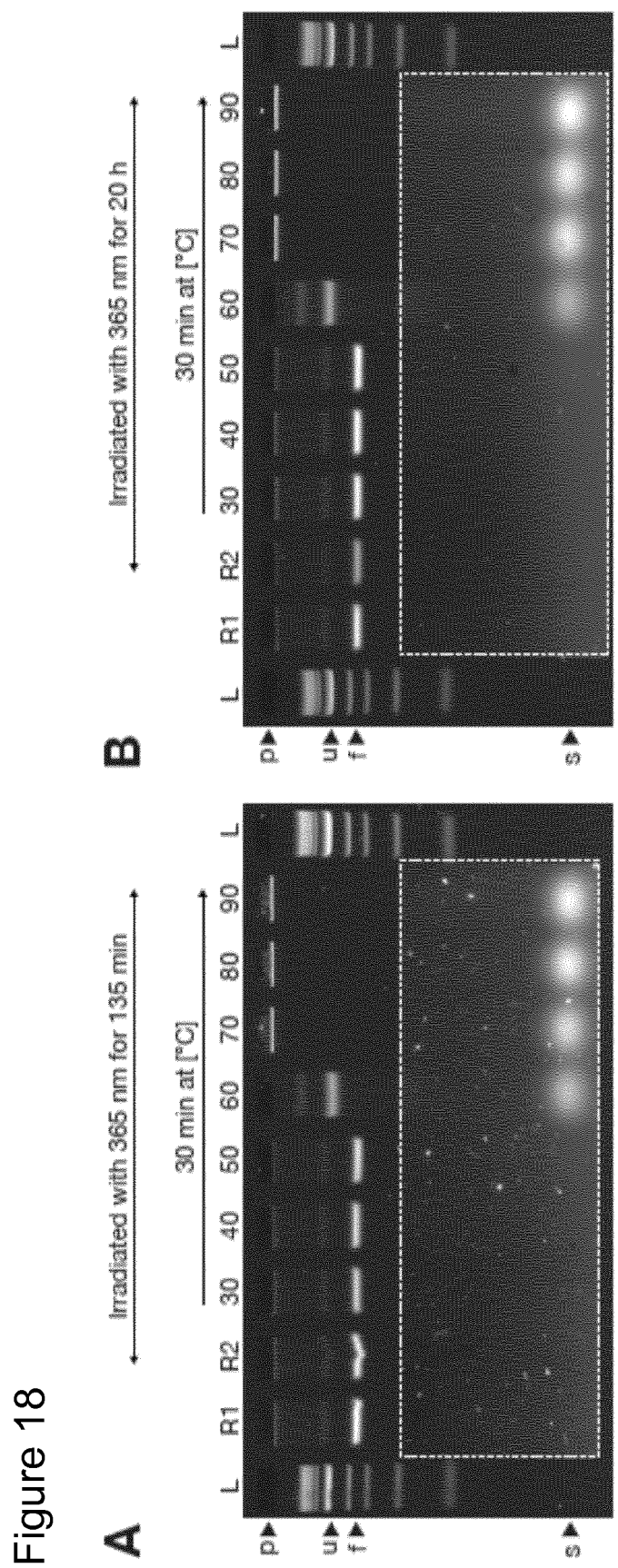
FIG. 18 shows the laser-scanned fluorescent image of a 2.0% agarose gel placed in a water bath. The brick-like object with TT motifs 1 to 3 irradiated for (A) 135 min (B) 20 h at 365 nm and incubated at different temperatures were loaded on the gel. p: pocket; u: unfolded species; f: folded species; s: un-crosslinked staples; L: 1 KB ladder; R1: non-irradiated reference in folding buffer with 30 mM $MgCl_2$; R2: reference that was irradiated at 365 nm for (A) 135 min (B) 20 h in folding buffer containing 30 mM $MgCl_2$. The image of the gel was auto-leveled and highlighted regions were auto-leveled separately.

To test our method, we implemented the design alterations shown in FIG. 1 in several variants of multilayer DNA origami objects. We tested the stability of the resulting objects after irradiation with light of wavelength 310 nm in melting experiments (FIG. 2, left) and in experiments in which we removed cations from solution (FIG. 2, right). We modified a brick-like multi-layer DNA origami[57] object in honeycomb-packing geometry (FIG. 6) by inserting additional thymidines both at all strand termini and at all strand crossover positions. We found that the non-irradiated control sample disassembled ("unfolded") around 50° C. as seen in gel electrophoresis by disappearance of the band indicating folded objects and appearance of free staple strands (FIG. 2A, left gel). By contrast, the irradiated sample preserved its global shape up to 90° C. judging by the fact that the electrophoretic mobility of the folded species remains largely unaltered. A slight smear at high electrophoretic mobilities shows that some strands still separate from the folded objects at high temperatures. However, the strands that separated had much lower electrophoretic mobilities and thus higher mass than the staple strands that emerged from the molten non-irradiated control sample. The high-temperature resistance of the irradiated object and the emergence of higher-mass strands provide evidence for the successful introduction of covalent crosslinks at the designed thymidines sites upon UV irradiation. We also tested the stability of the irradiated versus non-irradiated sample when removing cations from solution. Using filtration, we exchanged buffers and dissolved the samples in double-distilled water containing successively lower concentrations of monovalent sodium chloride (FIG. 2A, right). The irradiated sample remained folded even in double-distilled water containing zero added cations, whereas the non-irradiated control disassembled between 300 and 150 mM sodium chloride (NaCl), as seen by strong mobility shifts and the emergence of single-strands with high mobility. Transmission electron microscopy (TEM) imaging of the irradiated sample dissolved in pure water revealed particles with the expected shape (FIG. 7). The degree of heterogeneity of the sample in pure water was somewhat higher than at high-salt conditions. Electrophoretic analysis after up to one day of storage in pure water showed no changes in electrophoretic mobility, and we could not detect any staple strands that separate from the folded objects (FIG. 8). Therefore, simple design alterations and UV irradiation allow the stabilization of the normally quite cation-sensitive multi-layer DNA origami for uses under physiological (~150 mM NaCl) and even lower ionic strength conditions. Many other harsh environments may also be accessible after UV stabilization. As a simple demonstration we dissolved the crosslinked objects in aqueous mixtures of dimethyl sulfoxide (DMSO; an organic solvent) without added cations (FIG. 9). As a second example we prepared and tested a variant of the brick-like object in which we also inserted single-stranded T-loops (motif 4 in FIG. 1), in addition to extra thymidines at all strand termini and at all crossover positions (FIG. 10). The extent of thermal and cationic stabilization after irradiation (FIG. 2B) was similar compared to the design variant lacking the single-stranded T-loops. We tested loops containing 1, 3, and 5 thymidines. The variant with 5-T loops showed incrementally greater extent of stabilization at high temperatures (80° C.), judging by gel-electrophoretic band intensity (FIG. 11). We note that the irradiation of the brick variant with additional 5-T loops for inter-helical bonds also leads to a slight electrophoretic mobility increase compared to the non-irradiated control (FIG. 2B, lane R2 vs. lane R1), which suggests that the additional inter-helical bonds may lead to some degree of compaction or mechanical stabilization. As a third example, we chose the previously described "pointer" object[13], which is a multi-layer DNA origami in square-lattice packing geometry, and added additional thymidines at all strand termini and at all crossover positions (FIG. 12). As for the brick variants, irradiation with UV light stabilized this object against exposure of temperatures up to 90° C. and the pointer object may now be dissolved in pure water without any cations (FIG. 2C). The non-irradiated control pointer sample already disassembled between 45° C. and 50° C. and required more than 300 mM NaCl in solution to remain folded as seen by electrophoretic mobility analysis (FIG. 2C) and TEM imaging (FIG. 13). In the course of establishing our method, we tested several parameters such as time of exposure to UV irradiation. In addition, we performed a defect analysis using the de-Bruijn assay[58] to evaluate the structural integrity of double-helical domains in DNA objects upon UV irradiation. Approximately two hours of exposure at our UV setup lead to most efficient stabilization for all structures tested (FIG. 14 and FIG. 15) without signs of structural degradation (FIG. 16). For shorter irradiation times, the crosslinking was not complete, meaning that structures did not survive exposure to temperatures substantially above the melting temperatures prior to UV treatment. For irradiation times longer than the optimal, structural radiation damages accumulated as reflected in successively lower electrophoretic mobilities of the objects. Therefore, the exposure to UV irradiation follows a Goldilocks principle. Since the optimal irradiation time will depend on details of the UV light source and other parameters, our optimal irradiation times will not necessarily hold up in other contexts. However, users can identify the optimum irradiation time by using screens similar to those we performed. As outlined in the introduction, our method relies on cyclobutane-pyrimidine dimers, which could form between T-T but also between, for example, T-C contacts. As an example, we compared the efficiency of crosslinking for brick variants prepared with T-T versus T-C at all strand termini and at all strand crossover positions (FIG. 17). Based on the amount of structures that survive exposure to high temperatures after UV exposure, T-T bonds form significantly more efficiently than the T-C contacts, and lead to complete stabilization. The crosslinking worked successfully through exposure to 310 nm light. Longer wavelengths such as 365 nm did not lead to stabilization in our hands (FIG. 18), even though it has been reported that CPD bonds may also form through exposure to 365 nm UVA light[59].

Stability at Physiological Conditions

Figure 19:
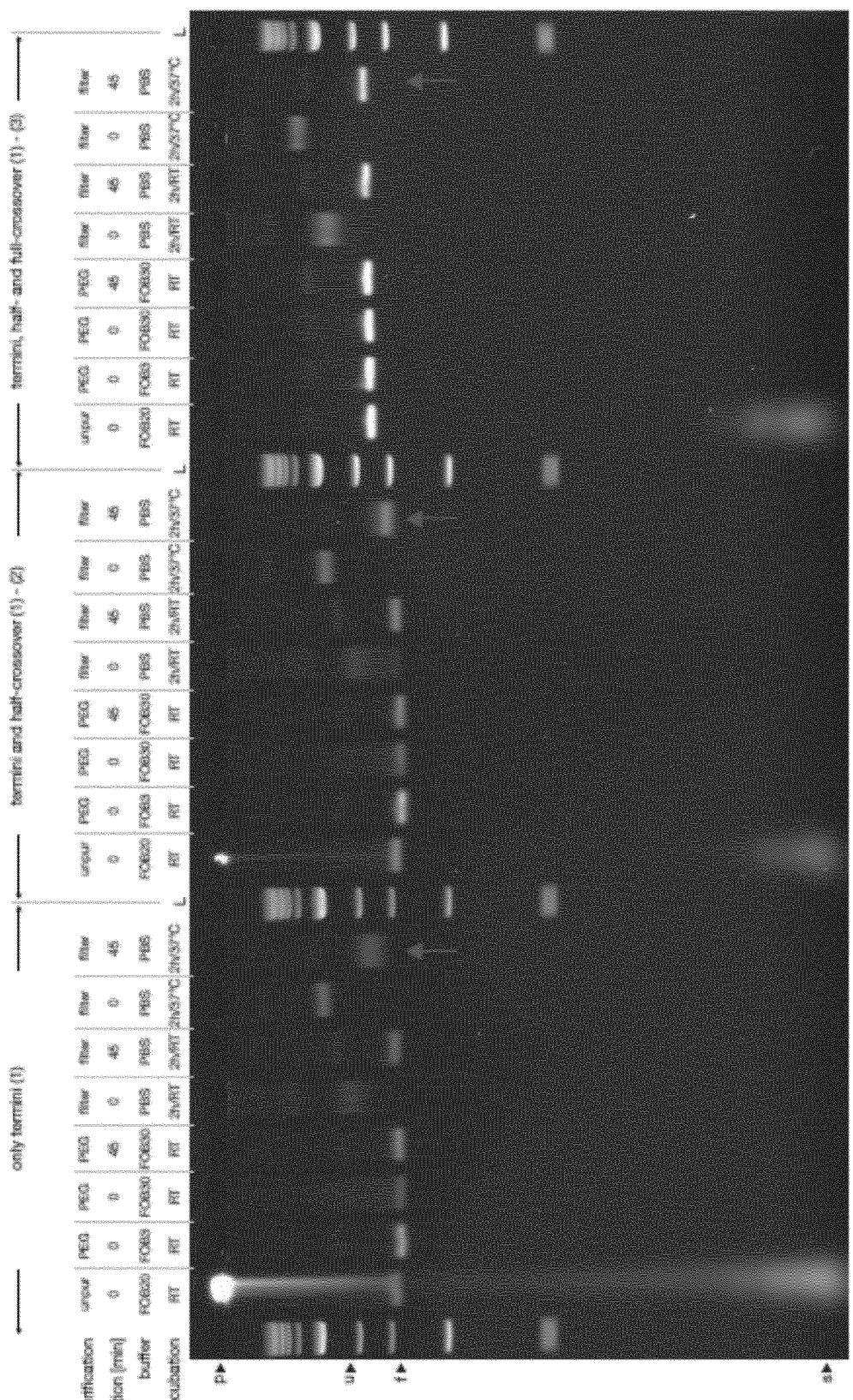
FIG. 19 shows the laser-scanned fluorescent image of a 2.0% agarose gel placed in a water bath. Different variants of the brick-like object with TT motifs 1, 1 to 2, and 1 to 3 were loaded on the gel. p: pocket; u: unfolded species; f: folded species; s: un-crosslinked staples; L: 1 KB ladder. The arrows indicate the bands with increasing electrophoretic mobility when including more TT motifs in the design. The image of the gel was auto-leveled.
Figure 20:
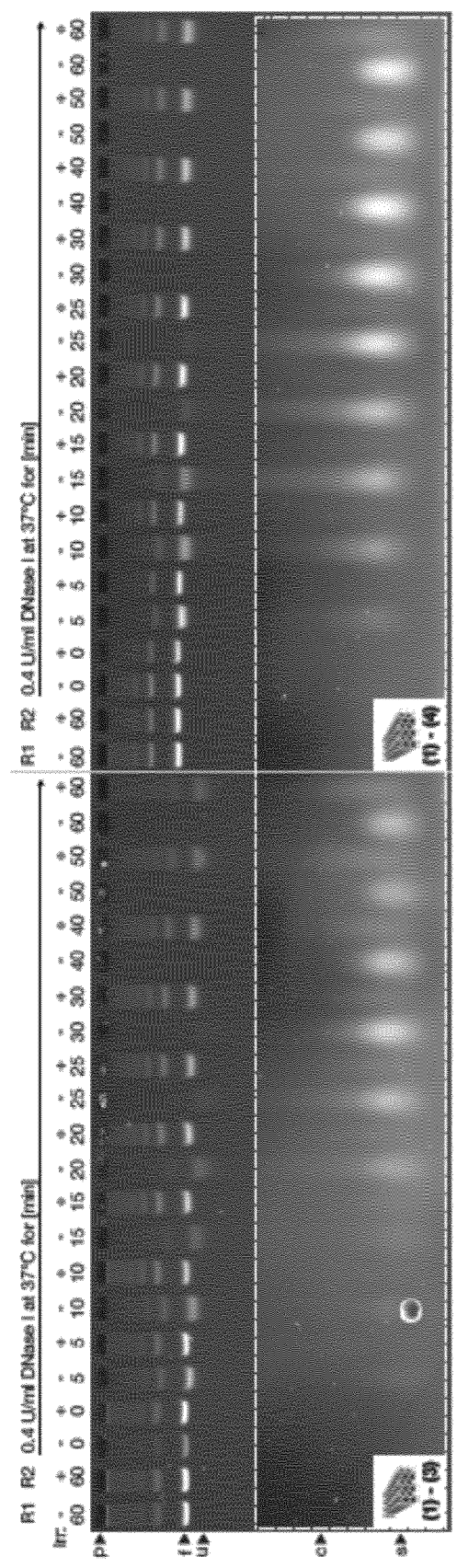
FIG. 20 shows the laser-scanned fluorescent image of a 2.0% agarose gel placed in a water bath. The brick-like object with TT motifs 1 to 3 (left) and with TT motifs 1 to 4 (right) incubated for different periods of time with 0.4 U/ml DNase I diluted in DNase I reaction buffer were loaded on the gel. p: pocket; u: unfolded species; f: folded species; c: crosslinked staples; s: un-crosslinked staples; R1: non-irradiated reference; R2: reference that was irradiated at 310 nm for 135 min. The reference samples R1 and R2 were dissolved in DNase I buffer in the absence of DNase I. The image of the gel was auto-leveled and highlighted regions were auto-leveled again.

Our UV-crosslinking method may be employed to substantially enhance the stability of DNA nanostructures, and in particular multi-layer DNA origami objects, for applications under physiological conditions. As a demonstration, we dissolved the brick-like multi-layer DNA origami object which contained additional T's at all staple termini and at all crossover positions in physiological phosphate buffered saline solution (PBS) and incubated the objects at the physiological temperature of 37° C. Even after two days of storage in PBS at 37° C., there was no detectable degradation of the irradiated and covalently crosslinked sample (FIG. 3A). By contrast, the non-irradiated control disassembled within minutes after exposure to these conditions. Judging by the extent of which irradiated design variants of the brick sample remained stable at physiological temperature and ionic strength, the stabilization appeared complete for the design variant that had additional T bases to all strand termini, and at all half- and full crossover positions. Ligating only the free strand termini and a subset of crossovers was not sufficiently effective in preserving the full structure (FIG. 19). In 10% fetal bovine serum (FBS) at 37° C., the irradiated brick sample survived for several hours and substantially longer than a non-irradiated control (FIG. 3B). In serum, presumably the loss of folded structures was caused by enzyme activity rather than the low ionic strength of the solution. Biological fluids, such as serum, contain a variety of exo- and endonucleases for digesting DNA molecules. To elucidate the activity of various nucleases, we exposed the brick-like multi-layer DNA origami object featuring Ts at strand termini, at all crossover positions, and T loops to a panel of such enzymes (FIG. 3C). Some enzymes such as Exo VIII and T7 Exo, by default, appear inactive on the brick sample regardless whether it was irradiated or not. However, for others (such as Exo I e, Exo T, T7 Endo, and Exo III), introduction of the additional covalent bonds through irradiation substantially enhanced the lifetime of the crosslinked object compared to the non-irradiated control sample. The most active DNA degrading enzyme was deoxyribonuclease I (DNase I). A kinetic analysis of the digestion of the brick-like object using DNase I at blood plasma activity levels 60 revealed that the irradiated and thus stabilized brick sample was digested much more slowly than the non-irradiated control. Analysis of the band intensities reveals an approximately five- to six-fold life-span expansion from 10 min to 60 min under the conditions tested through crosslinking (FIG. 3D). The brick variant featuring only extra Ts at strand termini and at all crossover positions (lacking inter-helical T loops) showed somewhat weaker resilience against DNase I digestion (FIG. 20).

Cryo-EM Structural Analysis of UV-Crosslinked Multi-Layer DNA Origami Objects

Figure 4:
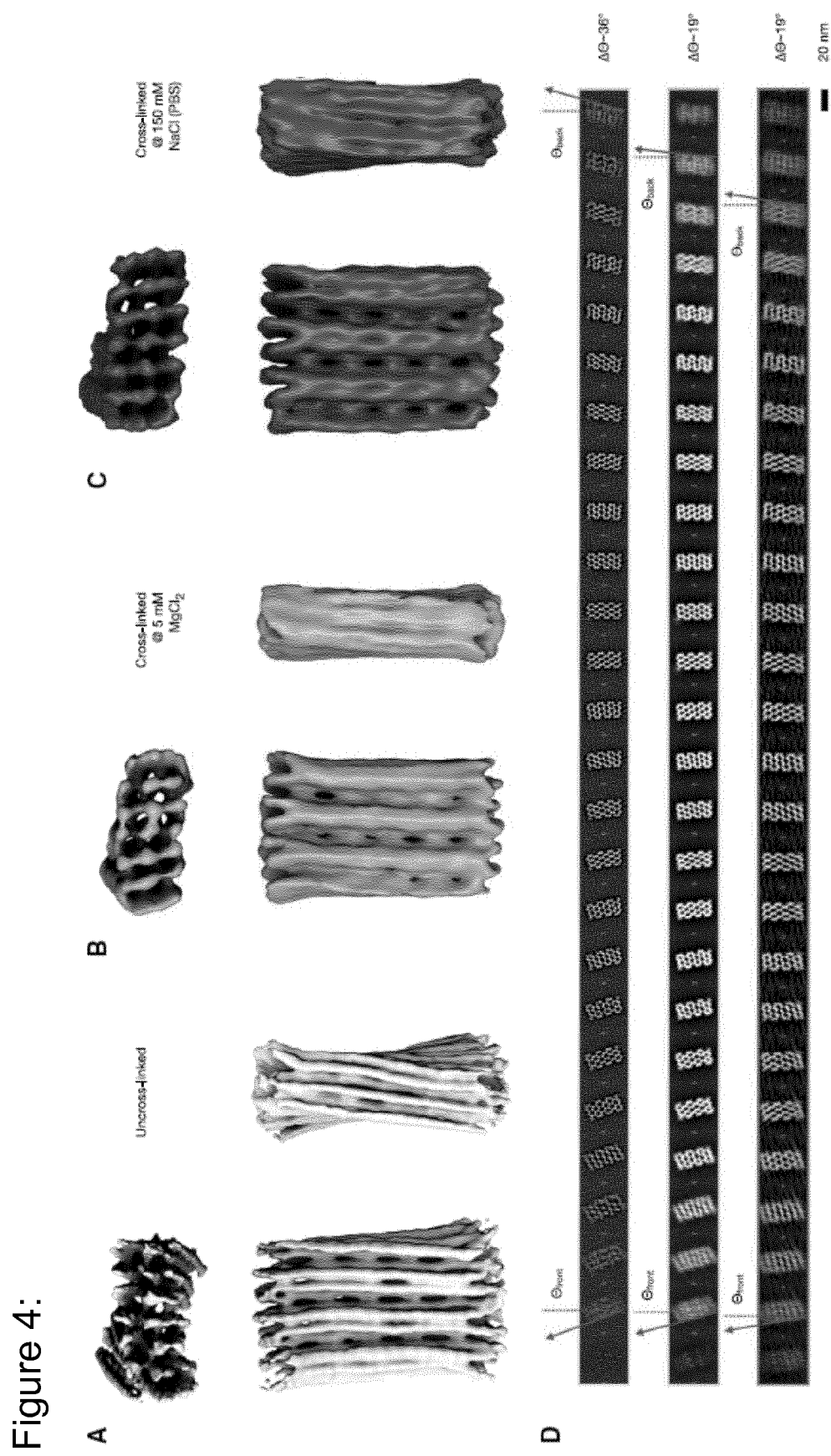
FIG. 4 shows a cryo-EM structural analysis before and after UV irradiation. (A) Cryo-EM density map of the non-irradiated brick-like object with TT-motifs 1 to 3 (ElectronMicroscopy Data Bank Identifier EMD-4354). (B) and (C) Cryo-EM density map of the irradiated (135 min at 310 nm) brick-like object with TT-motifs 1 to 3 in buffer containing 5 mM MgCl$_2$ or in physiological phosphate buffered saline (PBS) buffer, respectively. The electron density thresholds are chosen in such a way that all crossovers in the top layer are visible as seen in the side view (ElectronMicroscopy Data Bank identifier EMD-0027 and EMD-0028, respectively). (D) Slices along the z-direction obtained from the three density maps shown in (A) to (C) from top to bottom. To determine the twist angle delta Theta, the first and last slices were chosen. (E) Slices showing the three crossover layers in the reconstructions shown in (A) to (C). (F) Comparison of the global dimensions of the un-crosslinked variant in 5 mM MgCl$_2$ buffer and the cross-linked variant in PBS buffer.
Figure 4:
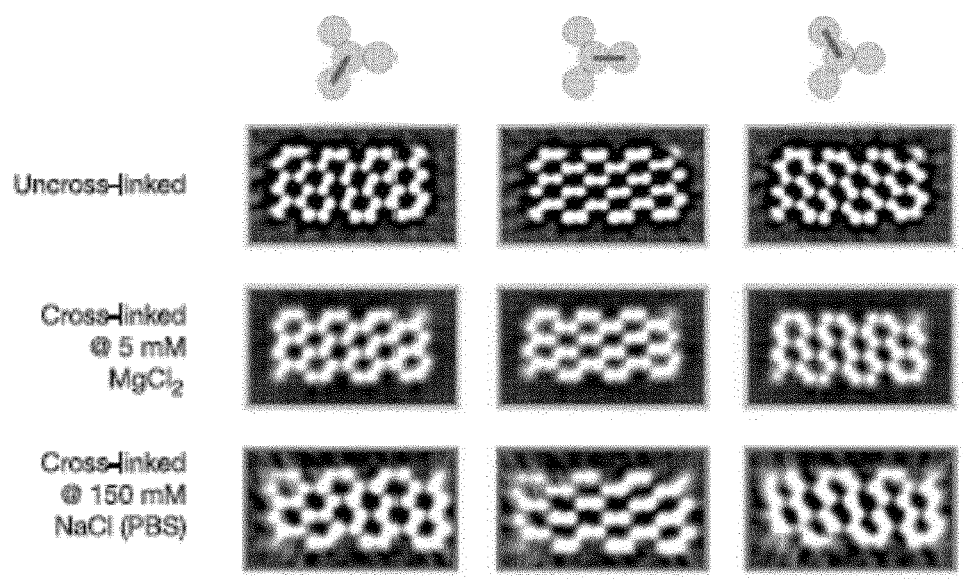
Figure 4:
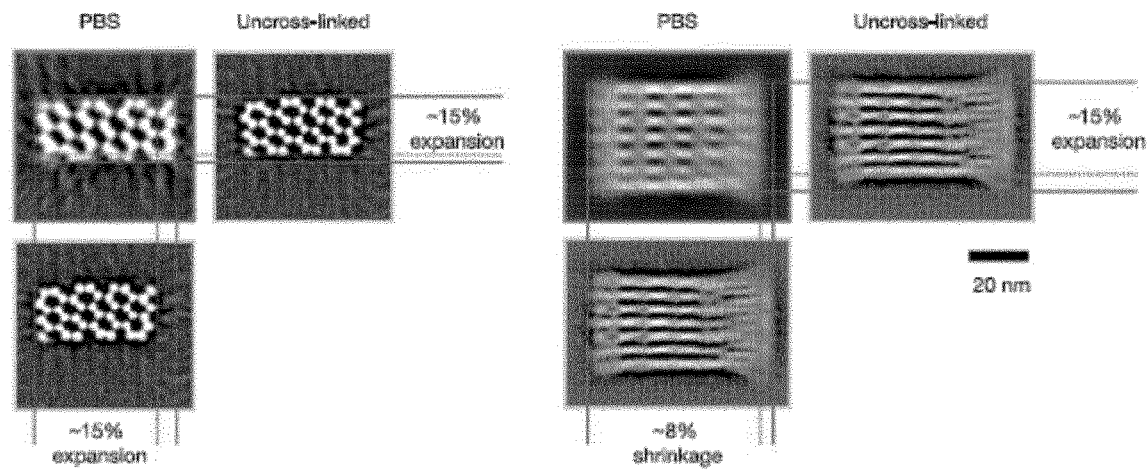
Figure 21:
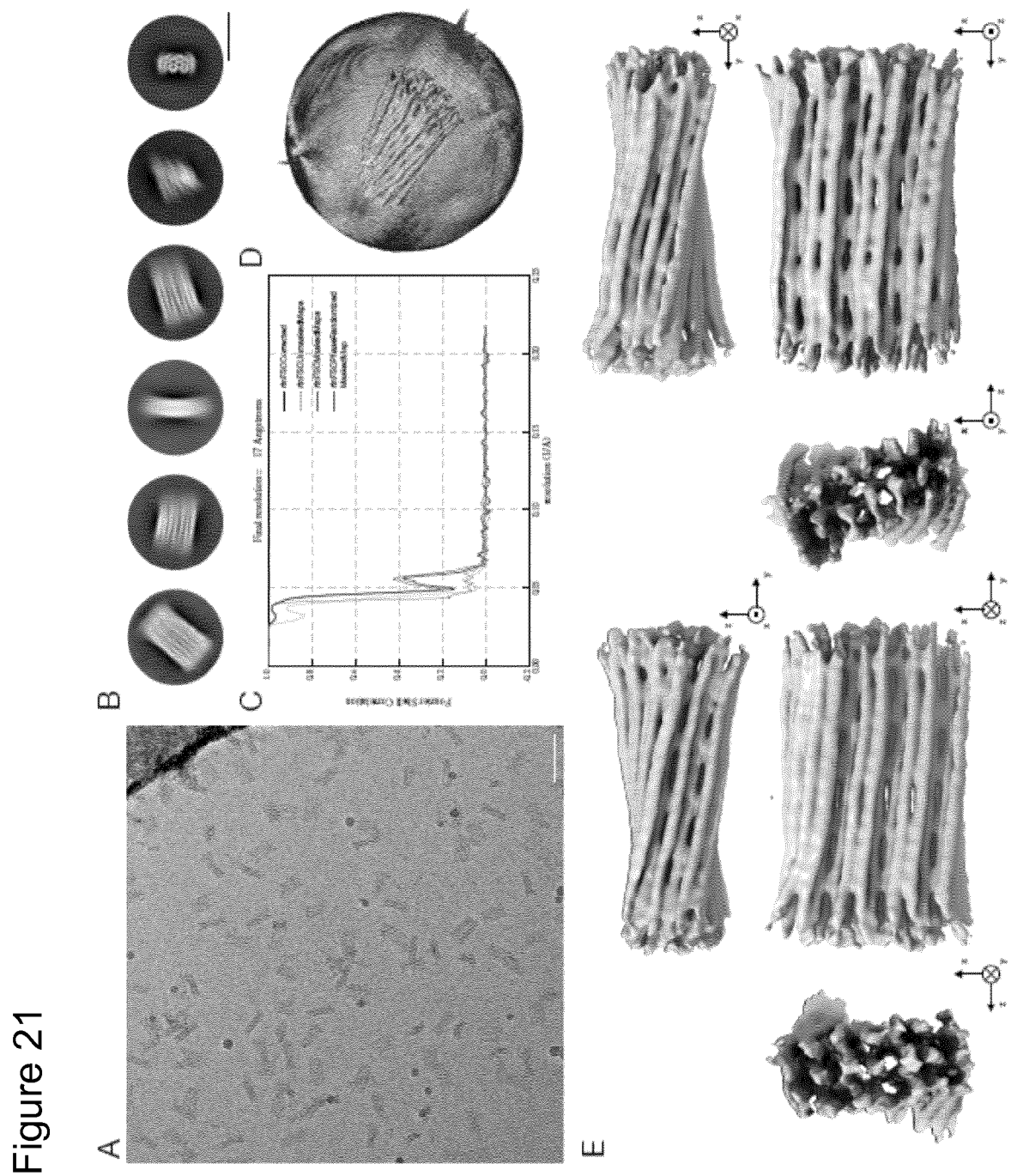
FIG. 21 shows cryo-EM data of the brick-like object with TT motifs 1 to 3 before crosslinking in folding buffer: (A) Motion corrected and dose weighted cryo-EM micrograph of the dataset with the brick-like object with TT motifs 1 to 3 before crosslinking in folding buffer with 5 mM $MgCl_2$. Scale bar represents 100 nm. Dose fractionated movies with 15 frames were acquired on a FEI Titan Krios G2 operated at 300 kV at a magnified pixel size of 2.3 Å and a total dose of 60 $e^-/Å^2$. (B) Representative two dimensional class averages showing different orientations. Scale bar represents 40 nm. (C) Graph of different FSC curves showing the resolution after sharpening. (D) Three dimensional histogram representing the orientational distribution of the particles. (E) Six different views of the sharpened final map reconstructed from 165 k individual particles. A B factor of −1,000 was used for sharpening.
Figure 22:
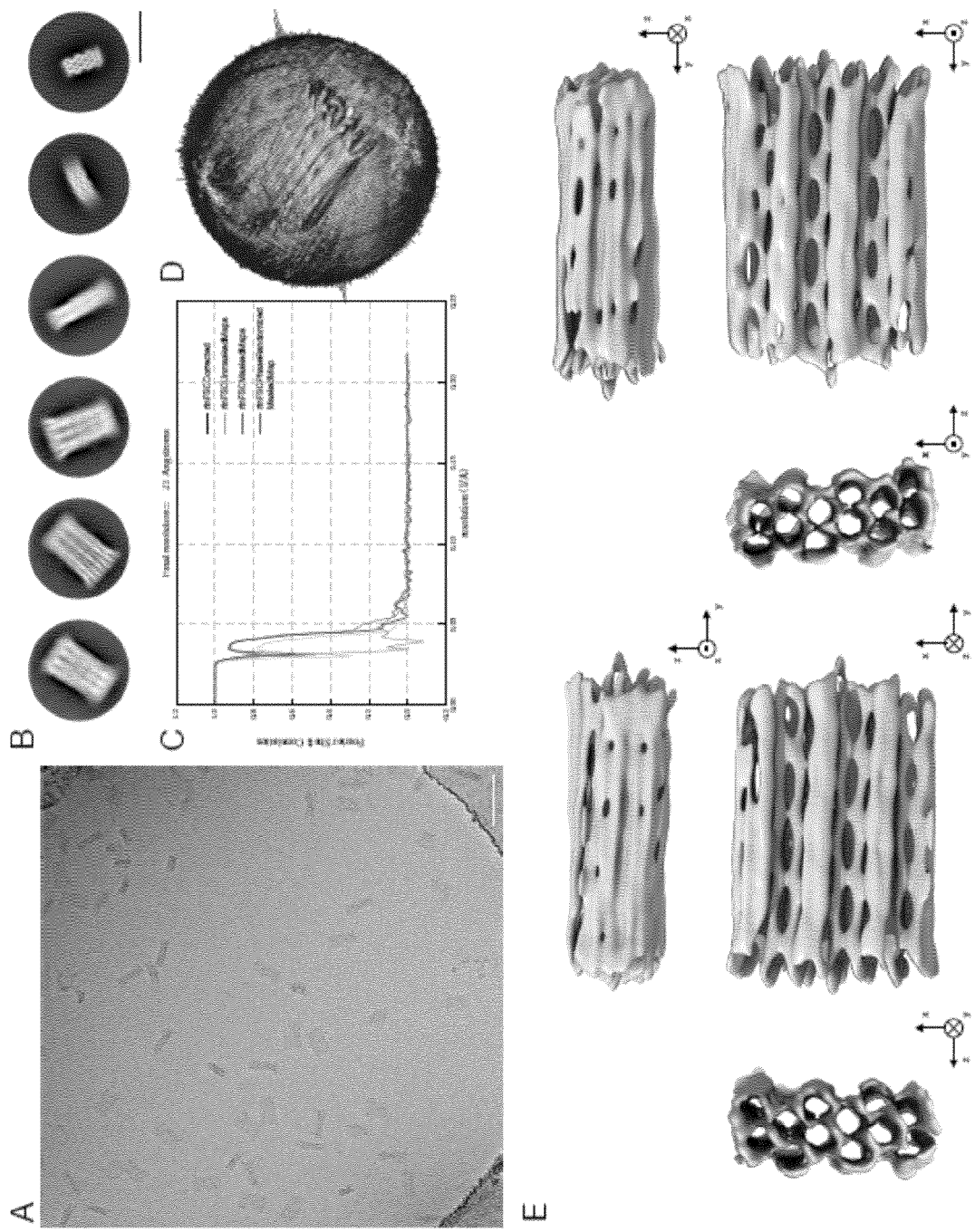
FIG. 22 shows cryo-EM data of the brick-like object with TT motifs 1 to 3 after crosslinking in folding buffer. (A) Motion corrected and dose weighted cryo-EM micrograph of the dataset with the brick-like object with TT motifs 1 to 3 after crosslinking in folding buffer with 5 mM $MgCl_2$. Scale bar represents 100 nm. Dose fractionated movies with 15 frames were acquired on a FEI Titan Krios G2 operated at 300 kV at a magnified pixel size of 2.3 Å and a total dose of 60 $e^-/Å^2$. (B) Representative two dimensional class averages showing different orientations. Scale bar represents 40 nm. (C) Graph of different FSC curves showing the resolution after sharpening. (D) Three dimensional histogram representing the orientational distribution of the particles. (E) Six different views of the sharpened final map reconstructed from 95 k individual particles. A B factor of −1,000 was used for sharpening.
Figure 23:
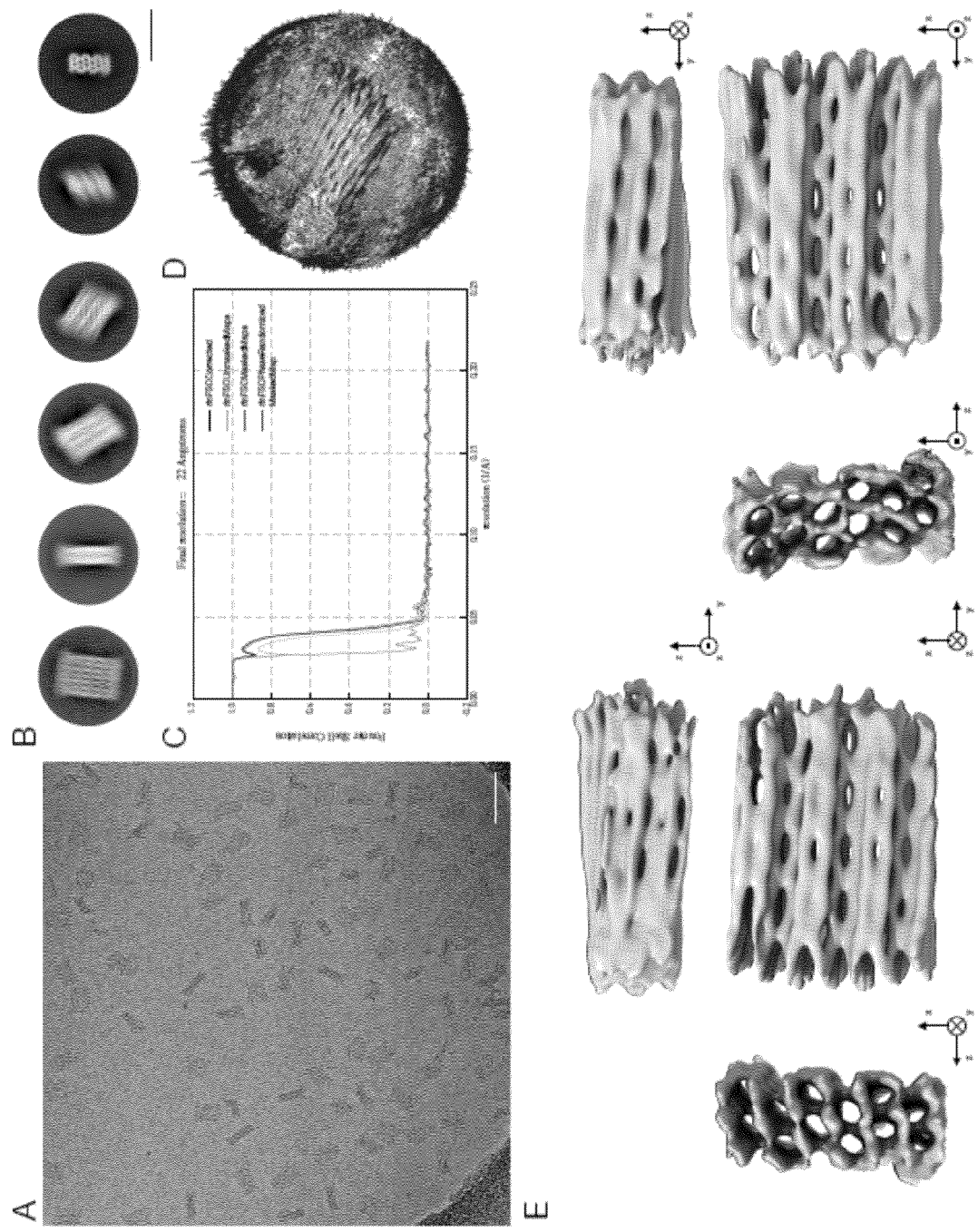
FIG. 23 shows cryo-EM data of the brick-like object with TT motifs 1 to 3 after crosslinking in phosphate-buffered saline. (A) Motion corrected and dose weighted cryo-EM micrograph of the dataset with the brick-like object with TT motifs 1 to 3 after crosslinking in PBS buffer. Scale bar represents 100 nm. Dose fractionated movies with 15 frames were acquired on a FEI Titan Krios G2 operated at 300 kV at a magnified pixel size of 2.3 Å and a total dose of 60 $e^-/Å^2$. (B) Representative two dimensional class averages showing different orientations. Scale bar represents 40 nm. (C) Graph of different FSC curves showing the resolution after sharpening. (D) Three dimensional histogram representing the orientational distribution of the particles. (E) Six different views of the sharpened final map reconstructed from 57 k individual particles. A B factor of −1,000 was used for sharpening.
Figure 24:
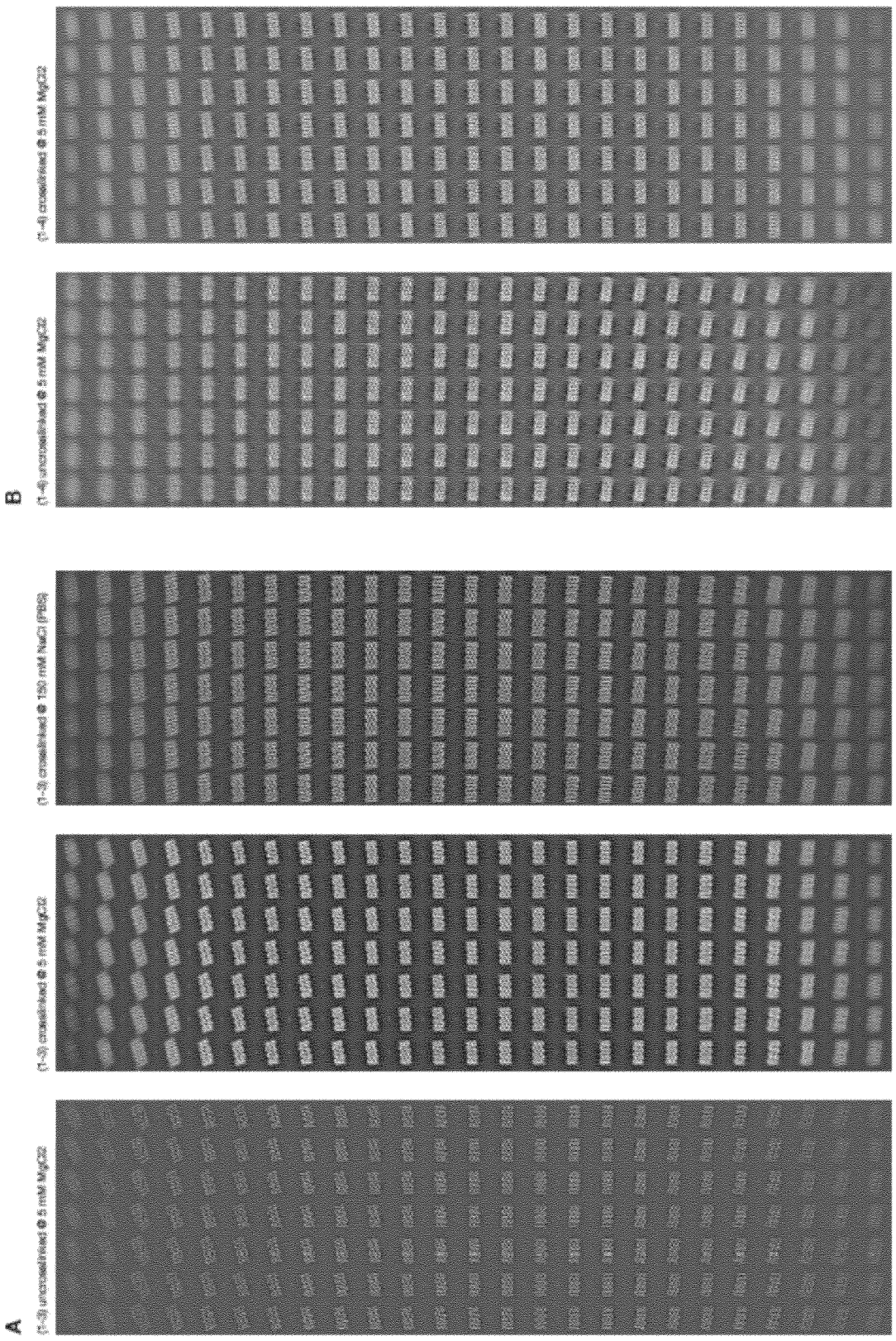
FIG. 24 shows the slice-by-slice visualization of cryo-EM maps determined from brick samples. The 3D volumes were rotated so that the helical axis was orthogonal to the figure plane (which we denote as z direction). The original volumes had 400×400×400 pixel with size 2.3 Å per pixel. For the slice analysis, the volumes were cropped to 200×200 in xy plane, and binned in z direction so that each slice has 3.35 Å thickness, which corresponds to the contribution of one base pair along the helical direction. Image J was used to create the montages of the 3D volumes. (A) brick variant with thymines at all staple termini and with TT motifs at all crossover sites per strand. (B) brick variant that had in addition 5-T loops to create inter-helical bonds.
Figure 25:
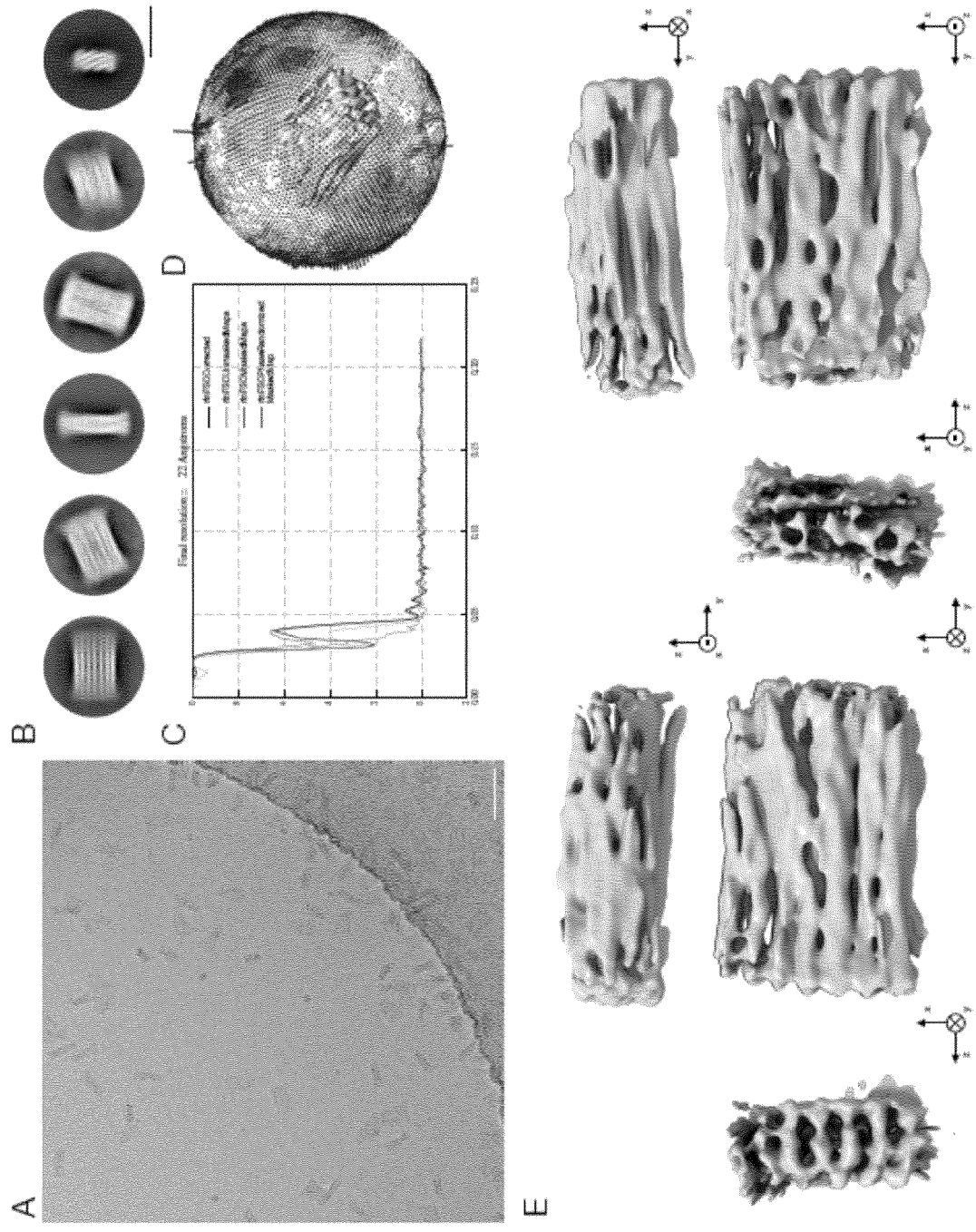
FIG. 25 shows cryo-EM data of the brick-like object with TT motifs 1 to 4 before crosslinking in folding buffer. (A) Motion corrected and dose weighted cryo-EM micrograph of the dataset with the brick-like object with TT motifs 1 to 4 before crosslinking in folding buffer with 5 mM $MgCl_2$. Scale bar represents 100 nm. Dose fractionated movies with 15 frames were acquired on a FEI Titan Krios G2 operated at 300 kV at a magnified pixel size of 2.3 Å and a total dose of 60 $e^-/Å^2$. (B) Representative two dimensional class averages showing different orientations. Scale bar represents 40 nm. (C) Graph of different FSC curves showing the resolution after sharpening. (D) Three dimensional histogram representing the orientational distribution of the particles. (E) Six different views of the sharpened final map reconstructed from 33 k individual particles. A B factor of −1,000 was used for sharpening.
Figure 26:
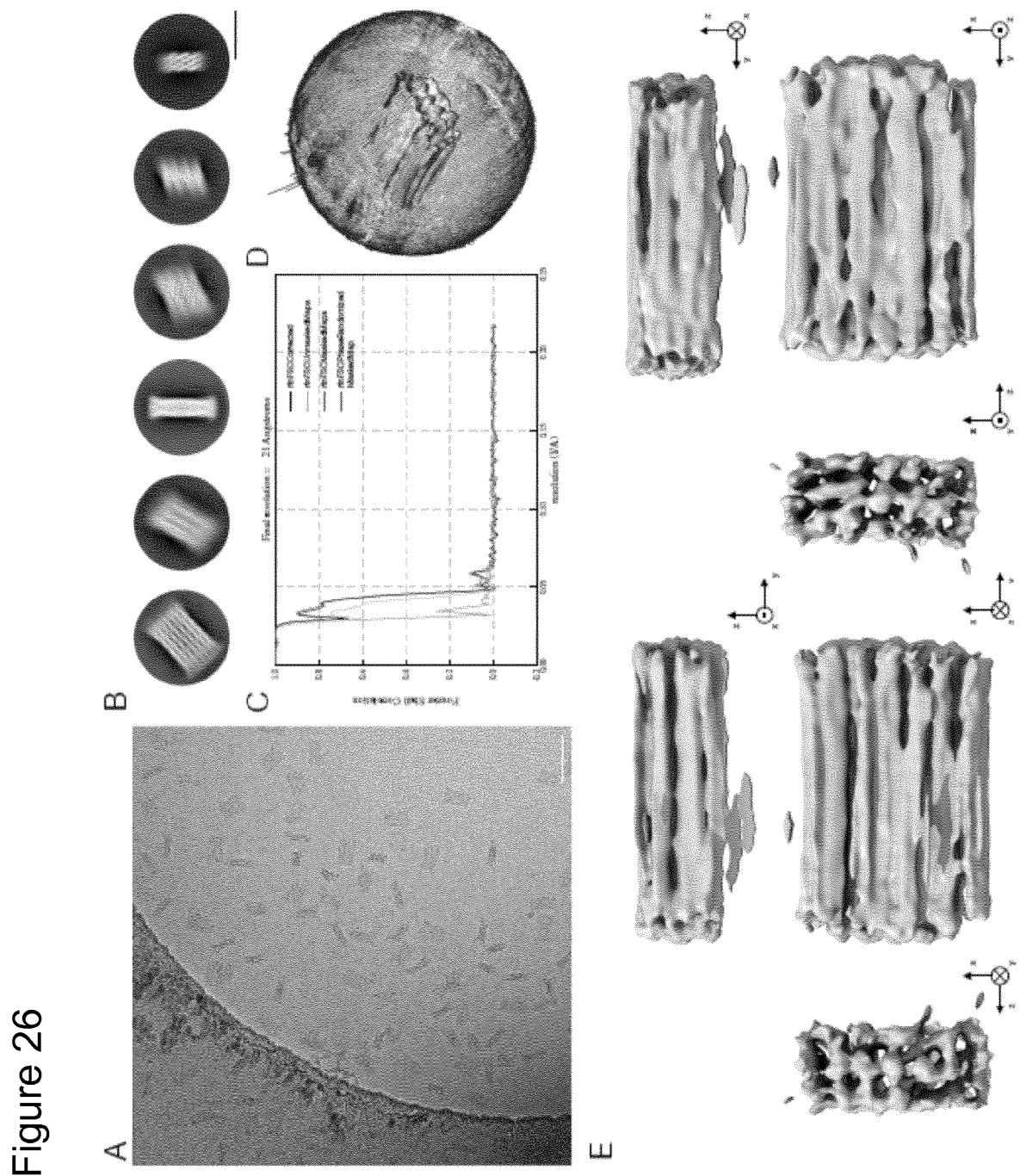
FIG. 26 shows cryo-EM data of the brick-like object with TT motifs 1 to 4 after crosslinking in folding buffer. (A) Motion corrected and dose weighted cryo-EM micrograph of the dataset with the brick-like object with TT motifs 1 to 4 after crosslinking in folding buffer with 5 mM $MgCl_2$. Scale bar represents 100 nm. Dose fractionated movies with 15 frames were acquired on a FEI Titan Krios G2 operated at 300 kV at a magnified pixel size of 2.3 Å and a total dose of 60 e-/Å2. (B) Representative two dimensional class averages showing different orientations. Scale bar represents 40 nm. (C) Graph of different FSC curves showing the resolution after sharpening. (D) Three dimensional histogram representing the orientational distribution of the particles. (E) Six different views of the sharpened final map reconstructed from 75 k individual particles. A B factor of −1,000 was used for sharpening.

To elucidate the effects of UV irradiation and CPD bond formation on the structure of a DNA object, we exemplarily determined five electron density maps using single-particle cryo-EM (FIG. 4, A to C). First, we collected single-particle cryo-EM data on a non-irradiated control multi-layer brick sample containing additional Ts at all strand termini and all strand crossover positions (FIG. 21). The reconstructed 3D-EM density map revealed the expected global rectangular brick-like shape (FIG. 4A). However, the object showed also a global twist deformation (FIG. 4D), whose extent was more pronounced than what was expected based on a previous analysis of a similar brick-like object lacking the additional Ts[17]. Presumably, the added Ts increase the flexibility of crossover sites, which may affect the packing geometry of helices. We determined the chirality of the twist deformation to be right-handed using a tomographic tilt-series. Second, we collected single-particle cryo-EM data of the brick-like object after exposure to UV irradiation (FIG. 22). The reconstructed 3D-EM density map again revealed the global rectangular brick-like shape (FIG. 4B). After irradiation, the right-handed global twist was significantly diminished (FIG. 4D). We attribute the twist reduction to the creation of the additional covalent bonds at the crossover sites which reduces the junction flexibility and aligns the helices again in a geometry closer to the default honeycomb-packing design. Previously, Chen and coworkers UV irradiated single-layer DNA origami rectangles to investigate radiation damages and observed a twist-reducing flattening effect[61]. However, since the samples of Chen and coworkers were not specifically designed to contain thymidine-thymidine crosslinking sites, the mechanism leading to twist removal may be different from our samples. Third, we collected single-particle cryo-EM data of the irradiated brick-like object once it had been dissolved in physiological ionic strength PBS buffer (FIG. 23). The resulting 3D-EM density map again revealed a global rectangular brick-like shape (FIG. 4C). A slice-by-slice comparison of the three cryo-EM maps indicates that the internal network of crossovers has been preserved after irradiation and exposure to low ionic strength conditions (FIG. 4E, FIG. 24). The overall aspect ratio of the cryo-EM density map determined for the crosslinked sample at low (physiological) ionic strength was different compared to the cryo-EM density maps which were determined at higher ionic strength in the presence of magnesium (FIGS. 4, A to C and F). The object's cross-section expanded in physiological conditions by approximately 15% and shrank in the helical direction by approximately 8%. The deformation presumably is a consequence of the strong electrostatic repulsion in PBS buffer, which pushes the helices away from each other. Without UV irradiation, these forces would normally lead to disassembly of the object. However, the additional covalent CPD bonds after UV light exposure prevent the double-helical DNA domains from unwinding and dissociating. Finally, we also collected single-particle cryo-EM data of the brick-like variant designed with additional T loops for inter-helical bonds before and after exposure to UV irradiation, respectively. The resulting 3D-EM density maps again revealed the expected global rectangular brick-like shape (FIG. 25 and FIG. 26, respectively). However, the internal crossover lattice was less well resolved than in the design variants that lacked the additional T loops, which we attribute to the more pronounced molecular heterogeneity in these samples that is caused by the presence of additional flexible T loops.

Figure 5:
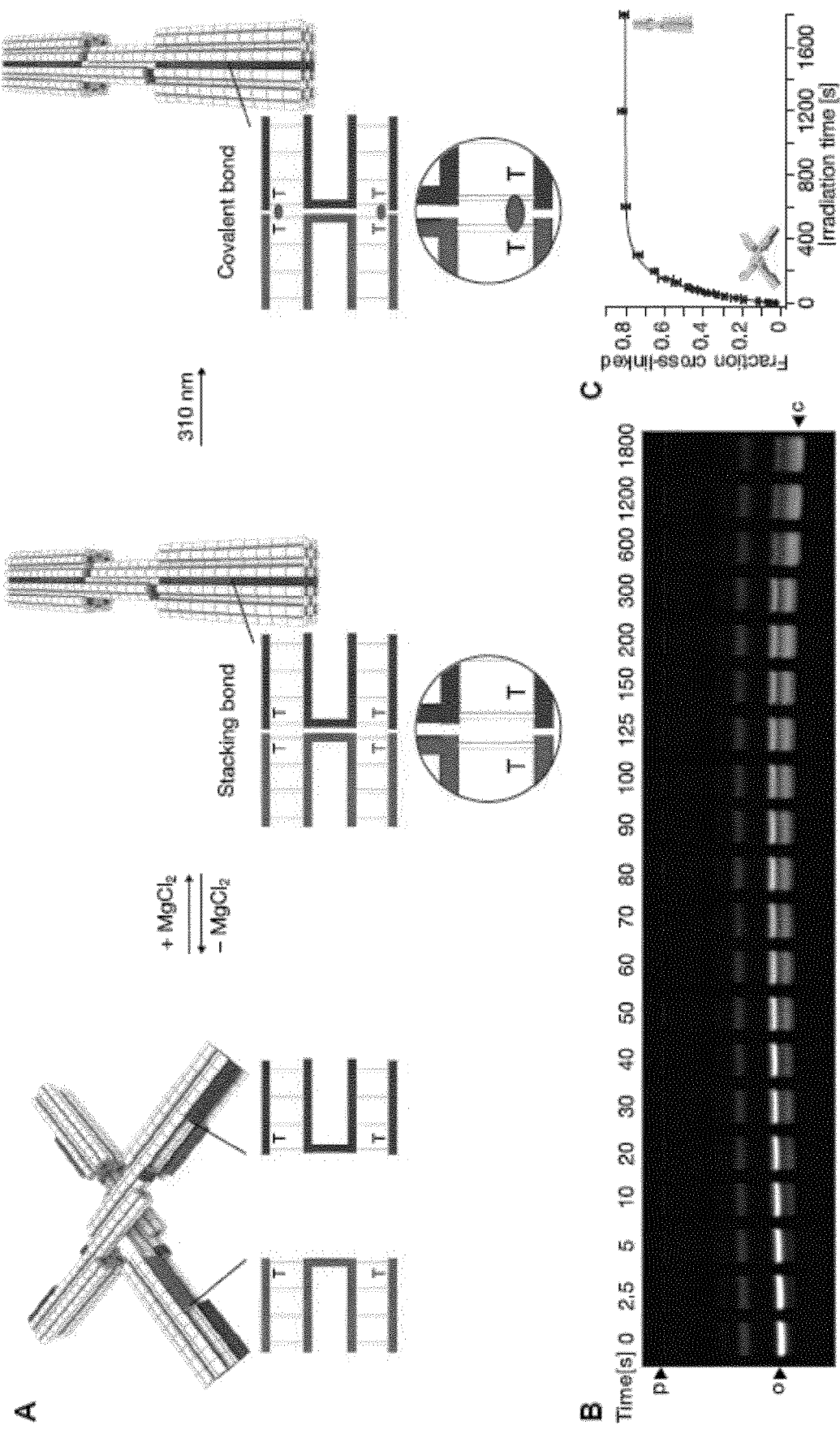
FIG. 5 shows the covalent bonding of conformational states and higher-order assemblies. (A) Schematics of the two-state switch that consists of two rigid beams flexibly connected in the middle by an immobile Holliday junction. Cylinders in the models represent double-helical DNA domains, and shape-complementary surface features are highlighted in lighter and darker grey. Insets show blow-ups of the blunt-ended interfaces of protruding (lighter grey) and recessive (darker grey) surface features. Thymidines directly located at the blunt-end site can be crosslinked upon UV light irradiation. The resulting CPD bond is indicated as a lighter grey ellipsoid. (B) Laser-scanned fluorescent image of 2.0% agarose gel stained with ethidium bromide. Switch samples were irradiated at 310 nm for different periods of time and loaded on the gel; o and c: species of particles populating open and closed state, respectively. (C) Plot of the fraction of crosslinked switch particles as a function of time obtained from the gel in (B). The experiment was performed in triplicate; data points represent the mean and error bars represent the standard deviation. (D) Exemplary TEM micrographs; top: non-irradiated sample with particles populating the open state; bottom: irradiated (20 min at 310 nm) sample with particles locked in the closed conformational state. Scale bar: 100 nm. Inset: average 2D particle micrograph of crosslinked particles. Scale bar: 20 nm. (E) Top left: model of the multi-layer DNA origami brick that polymerizes into linear filaments. Field of views of TEM micrographs recorded at the indicated conditions. Scale bar: 100 nm.
Figure 5:
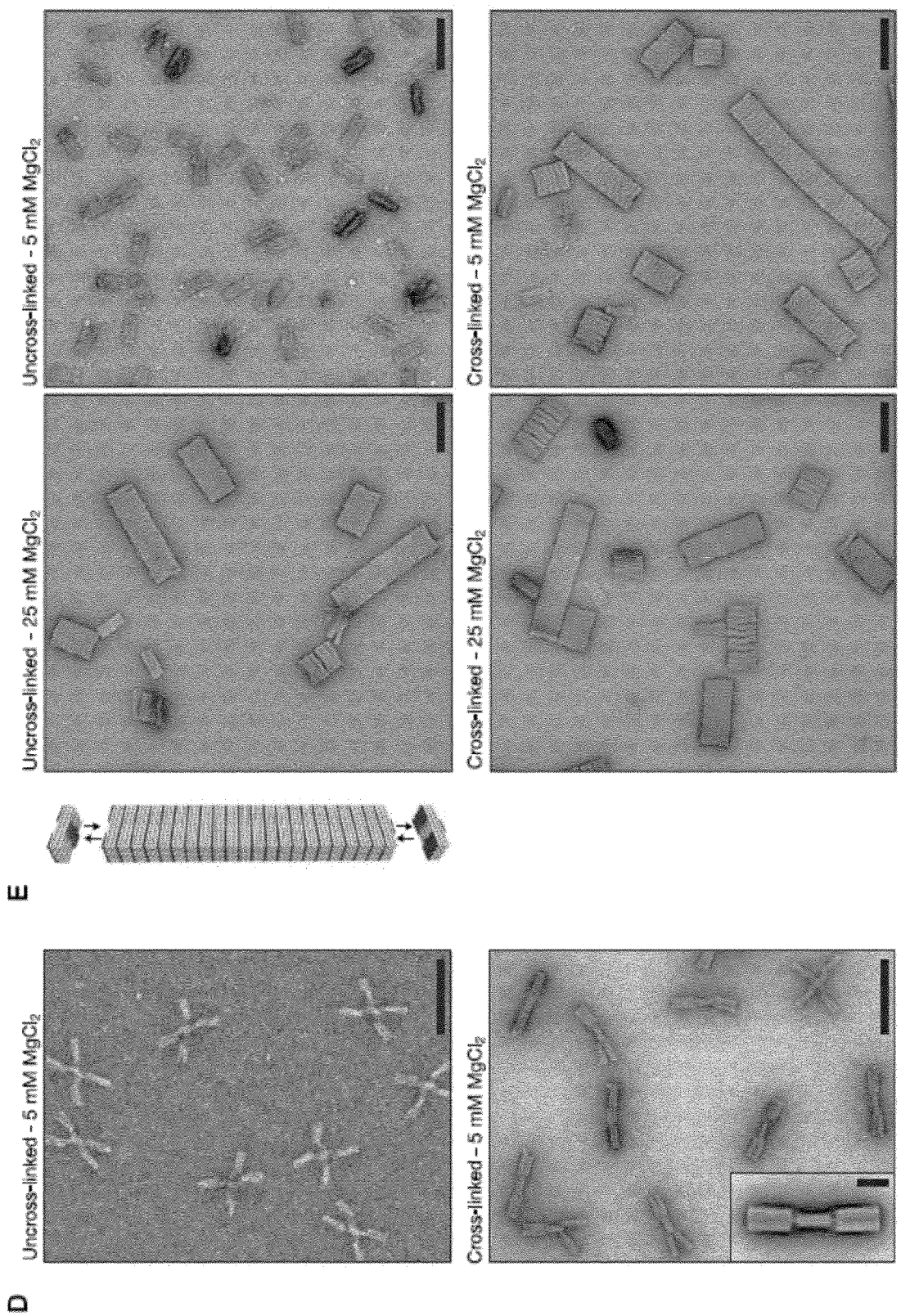
Figure 27:
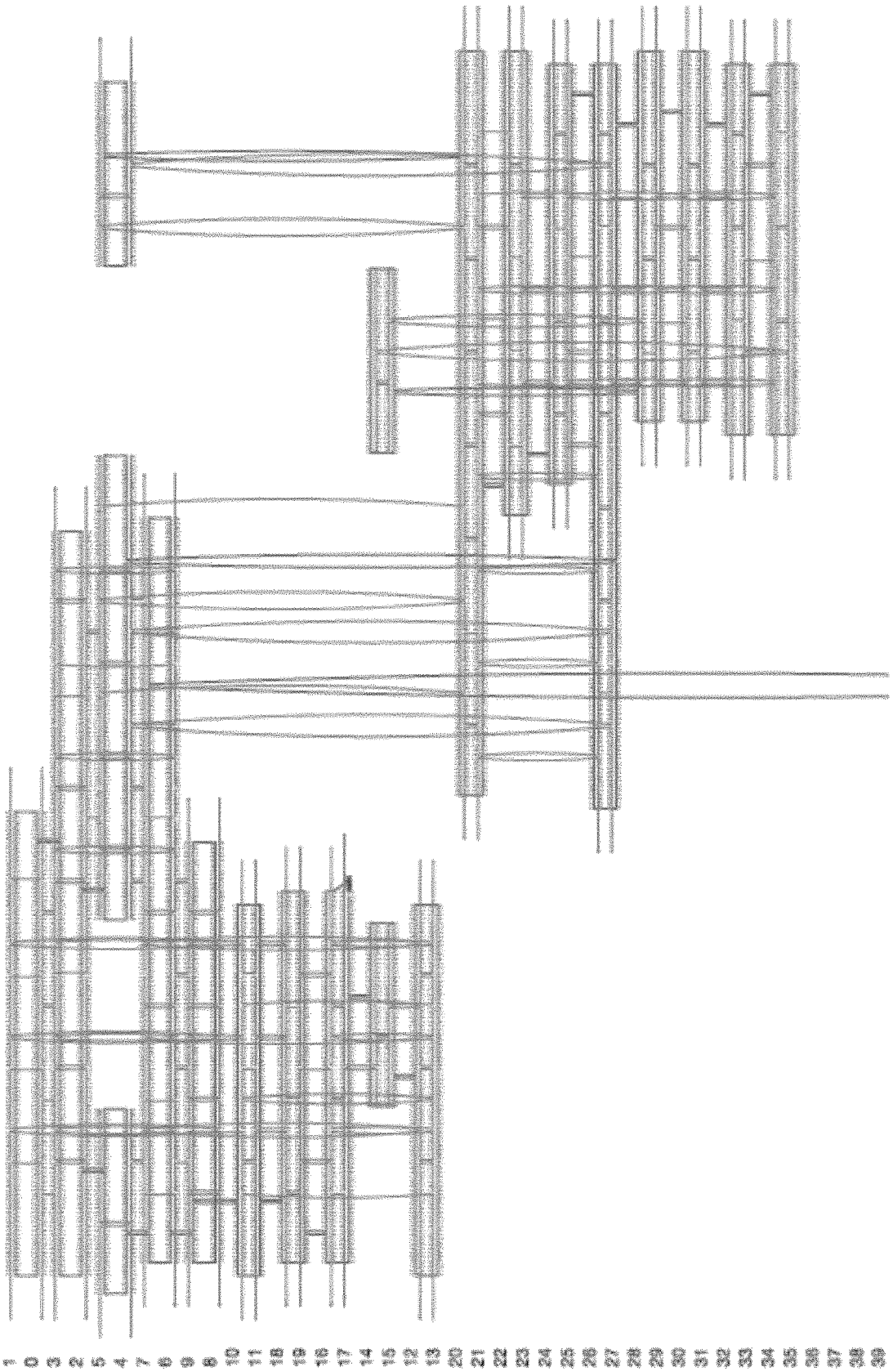
FIG. 27 shows the design diagram of the switch object prepared using caDNAno[66]. Interfaces are passivated with poly-thymine overhangs. Inset lower right: Cross-section of the object designed in honeycomb lattice.
Figure 28:
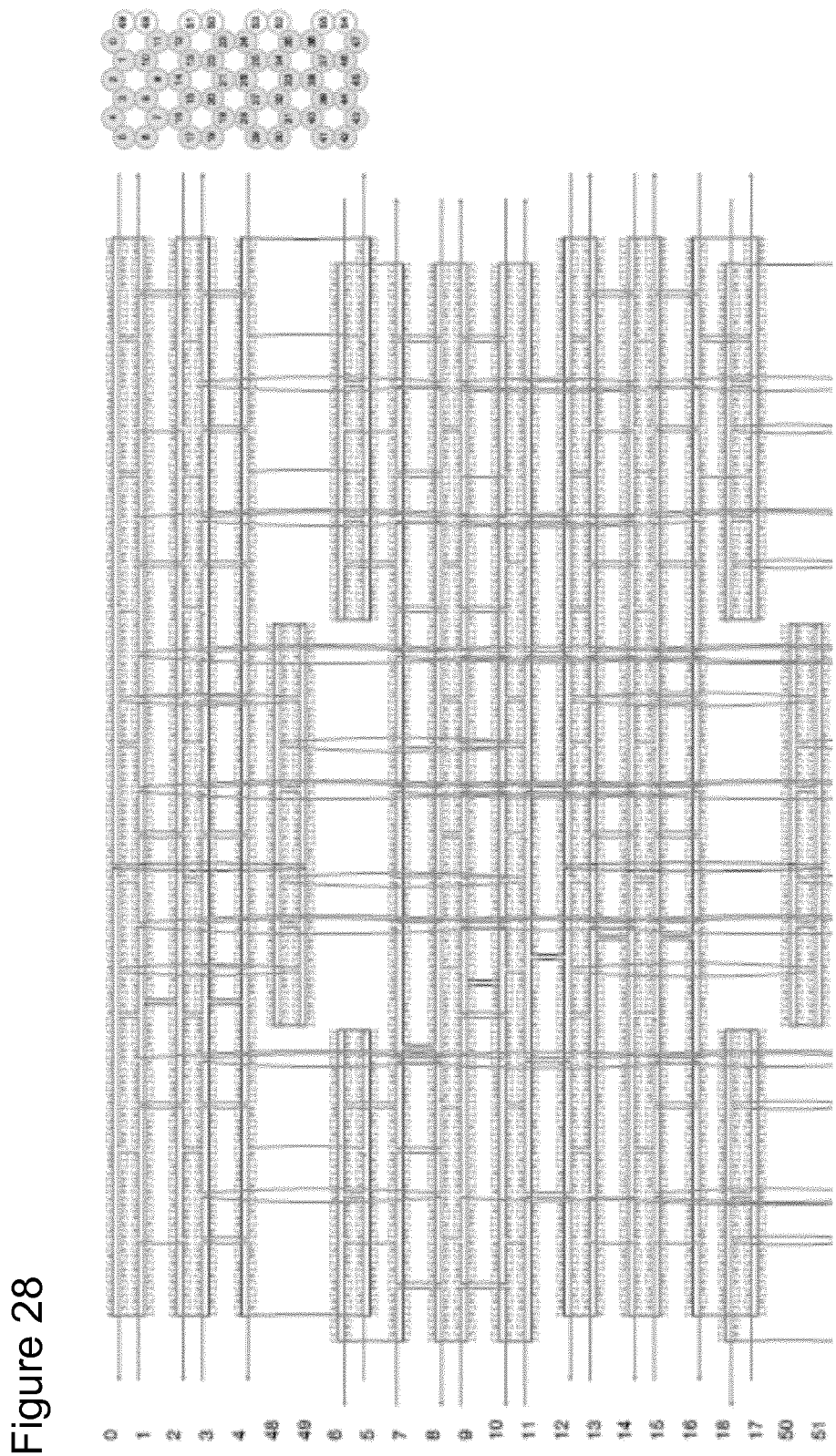
FIG. 28 shows the design diagram of the polymerization brick object prepared using caDNAno[66]. Interfaces are passivated with poly-thymine overhangs. Inset upper right: Cross-section of the object designed in honeycomb lattice.
Figure 29:
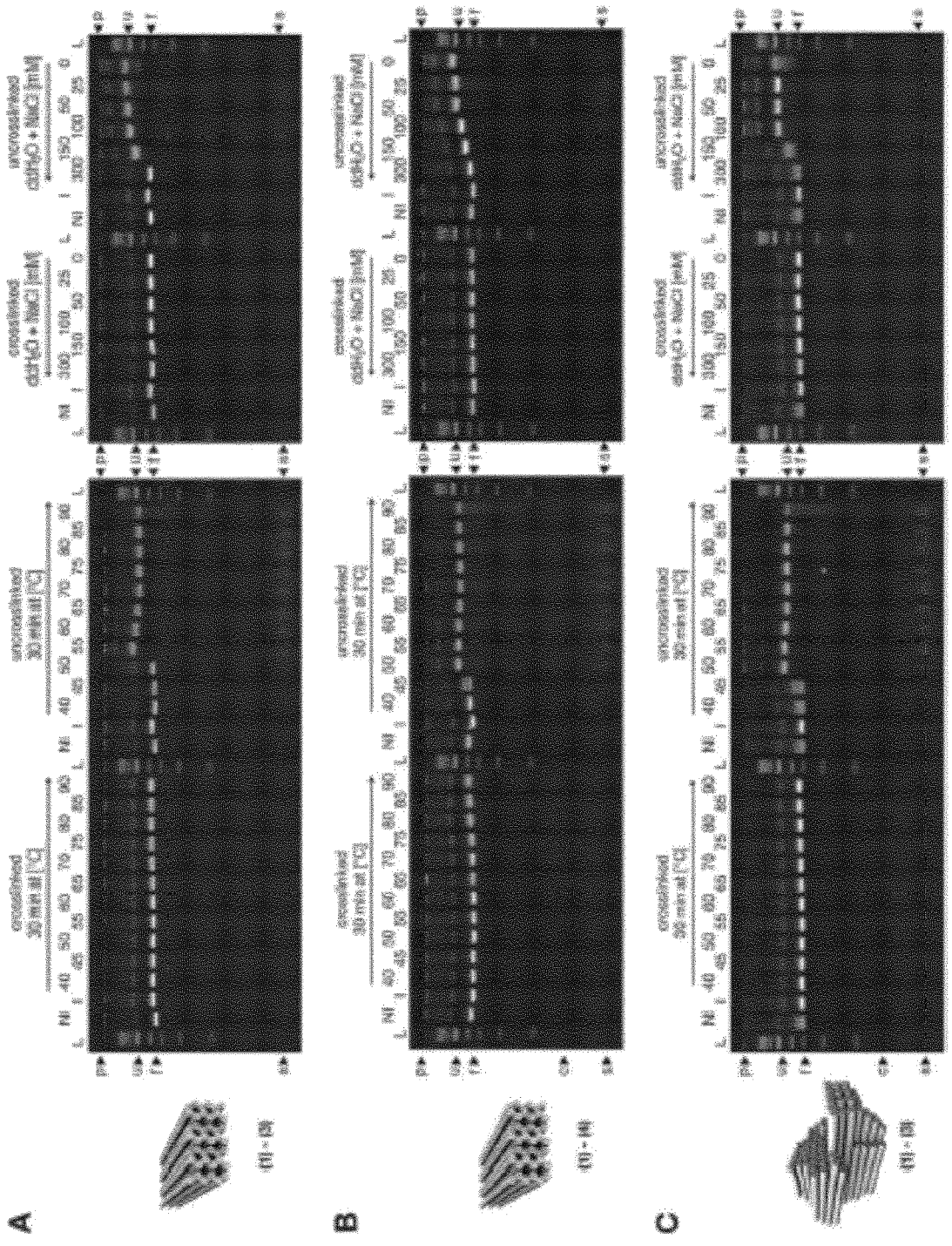
FIG. 29 shows the laser-scanned fluorescent image of a 2.0% agarose gel placed in a water bath. (A) From left to right: model of the brick-like DNA origami object featuring additional thymidines at all strand termini and at all strand crossover positions; laser-scanned fluorescent images of 2.0% agarose gels stained with ethidium bromide. Irradiated (135 min at 310 nm) and non-irradiated samples were either incubated for 30 min at different temperatures or incubated for 3 h at room temperature in double-distilled water containing successively lower concentrations of monovalent sodium chloride, respectively. p: pocket; u: unfolded species; f: folded species; c: crosslinked staple strands; s: un-crosslinked staple strands; L: 1 KB ladder; NI and I: non-irradiated and irradiated reference samples in folding buffer with 5 mM $MgCl_2$, respectively. The images of the gels were globally auto-leveled. (B) and (C) as in (A) but with the brick-like DNA origami object featuring additional thymidines at all strand termini, at all strand crossover positions, and 5-T loops and the pointer object featuring additional thymidines at all strand termini and at all strand crossover positions, respectively.

Covalently Bonding Conformational States and Higher-Order Assemblies Across Interfaces The targeted introduction of base-paired thymidines also enables us to covalently crosslink DNA-based mechanisms and higher-order assemblies across binding interfaces. We demonstrate here the possibility of locking conformational states with a previously described two-state switch[11] (FIG. 27). The closed state of the switch is stabilized by base-pair-stacking contacts when the shape-complementary surfaces of its two beams come in direct contact (FIG. 5A). The object may be switched between the two states by raising and lowering the temperature, or through addition of cations such as magnesium chloride. We hypothesized that in the closed state, terminal thymidines positioned directly at the blunt-ended base-pair-stacking contacts may be in sufficient proximity to allow the formation of CPD dimer bonds upon UV irradiation. The switch design already contained several such TT-stacking contacts. A time-resolved analysis of the effects of UV irradiation on the switch in the presence of 30 mM $MgCl_2$ (which stabilizes the closed state) reveals that after 30 min exposure, about 80% of the particles were irreversibly trapped in the closed state. We conclude this from the band pattern in gel electrophoresis under the low ionic strength conditions, which normally lead to opening of the switch at 5 mM $MgCl_2$ (FIGS. 5, B and C). Hence, the CPD bonds may also be formed between fully separate double-helical DNA domains that are held in proximity. In addition, we demonstrate the possibility of stabilizing higher-order assemblies with a previously described multi-layer DNA origami brick (FIG. 28) that oligomerizes at high-ionic strength via shape-complementary base-pair-stacking contacts into linear filaments[11]. The filaments, by default, dissolve when the ionic strength of the solution is lowered again (FIG. 5E). By placing TT motifs at the base-pair-stacking contacts, the higher-order filaments may also be covalently stabilized by simple UV irradiation. As a result, the filaments no longer dissociate when exposed again to low ionic strength conditions, as seen by TEM imaging (FIG. 5E). The possibility of stabilizing particular conformational states or higher-order assemblies may be especially useful to prepare containers or mechanisms built from many subunits for applications in physiological or low ionic strength conditions. Interior design, as shown in FIG. 1, and interfacial bonding schemes, as illustrated in FIG. 5, could be combined to yield subunits and higher order assemblies that withstand a wide range of conditions.

DISCUSSION

Users of our method can simply define sites of covalent bonding in DNA assemblies by creating TT sequence motifs, where the two Ts need not be positioned within double-helical domains. The objects studied herein featured, by default, several sites for CPD bond formation because the bacteriophage-derived scaffold strand itself already contained multiple TT and AA motifs. To suppress the formation of undesired CPD dimers upon irradiation and to avoid the extra T insertions if so desired, new custom scaffold sequences may be developed in the future. By design, these sequences could lack TT motifs and feature AA motifs in the regular intervals that correspond to the internal junction spacing rules in honeycomb- or square lattice-packing geometries. Scaffold-free DNA objects such as tile-brick structures[15] may also be specifically designed with sequences that selectively place TT motifs at crossovers and at strand termini to enable covalent bonding by UV irradiation. Our results show that the mere proximity of thymidines is sufficient to template the formation of covalent linkages through UV irradiation. Moreover, the thymidines do not necessarily need to be placed within a double-helical context to form these linkages. The cryo-EM maps presented here show that the DNA objects preserve their global shape after UV treatment. Our maps also add to the body of structural data in DNA nanotechnology and help understand the connection between design details and resulting shape. For example, we presented a multilayer DNA origami cryo-EM map at physiological ionic strength. Formerly, it was not possible to analyze these structures because the objects would "explode" under these conditions. Our cryo-EM map at physiological conditions reveals a substantial swelling behavior, which helps appreciate the contribution of electrostatics to global shape. Future designs for physiological conditions will need to consider the swelling behavior to produce shapes according to specifications. Our method supports a broader applicability of DNA-based nanotechnology, in particular for the more structurally complex multilayer 3D DNA objects, which arguably offer attractive degrees of freedom to designers but tend to be more sensitive to environmental conditions. Because of the simplicity, sequence programmability, and scalability, covalent bonding by UV irradiation will help pave the way for applications of DNA nanostructures in a wide variety of conditions for a range of fields.

Example 2: Materials and Methods 2.1. Folding of DNA Origami Objects

The reaction mixtures contained scaffold DNA at a concentration of 20 nM and oligonucleotide strands at 200 nM each. The folding buffer included 5 mM TRIS, 1 mM EDTA, 5 mM NaCl (pH 8) and 20 mM $MgCl_2$. The reaction mixtures were subjected to a thermal annealing ramp using TETRAD (MJ Research, now Bio-Rad) thermal cycling devices. Oligonucleotides were purchased from Eurofins MWG (Ebersberg, Germany).

- The 213 oligos used for generating the "brick-like object with TT-motifs 1 to 3" are shown in the Sequence Listing with SEQ ID NOs: 1 to 213.
- The 176 oligos used for generating the "brick-like object with TT-motifs 1 to 4" are shown in the Sequence Listing with SEQ ID NOs: 214 to 389.
- The 159 oligos used for generating the "pointer" object are shown in the Sequence Listing with SEQ ID NOs: 390 to 548.
- The 206 oligos used for generating the "switch" object are shown in the Sequence Listing with SEQ ID NOs: 549 to 754.
- The 211 oligos used for generating the "polymerization brick" object are shown in the Sequence Listing with SEQ ID NOs: 755 to 965.

The table below shows the folding ramps used to assemble the objects described in this study.

| Object name | Denaturation temperature for 15 min [° C.] | Folding ramp | Storage temperature [° C.] | Scaffold |
| --- | --- | --- | --- | --- |
| Brick-like, TT-motifs (1)-(3) | 65 | [60-20° C.]; 60 min/1° C. | 20 | p7560 |
| Brick-like, TT-motifs (1)-(4) | 65 | [60-20° C.]; 60 min/1° C. | 20 | p7560 |
| Pointer | 65 | [60-20° C.]; 60 min/1° C. | 20 | p7249 |
| Switch | 65 | [58-55° C.]: 90 min/1° C. | 25 | p8064 |
| Polymerization Brick | 65 | [60-44° C.]: 60 min/1° C. | 25 | p8064 |

2.2. Purification and Enrichment of DNA Origami Objects

After the folding reaction, all reaction products were purified using one round of PEG-precipitation[63]. The resulting pellet was dissolved in folding buffer (5 mM TRIS, 1 mM EDTA, 5 mM NaCl) including 5 mM $MgCl_2$. The final volume was chosen to get a monomer concentration of 100 nM. The samples were equilibrated at 30° C. and 450 rpm overnight in a shaker incubator (Thermomix comfort from Eppendorf). All procedures were performed as previously described[64].

2.3. UV-Irradiation

For UV-irradiation, we used a 300 W xenon light source (MAX-303 from Asahi Spectra) with a high transmission bandpass filter centered around 310 nm (XAQA310 from Asahi Spectra). We used a light guide (Asahi Spectra) to couple the light into the sample by placing it directly on top of a 0.65 ml reaction tube. Unless otherwise indicated, the brick-like samples were irradiated for 135 min, the pointer samples for 120 min, and the polymerizing brick samples for 30 min. Samples were irradiated in folding buffer (5 mM TRIS, 1 mM EDTA, 5 mM NaCl) including 30 mM $MgCl_2$, unless otherwise stated.

2.4. Ultrafiltration for Enrichment and Buffer Exchange

All samples (crosslinked and un-crosslinked) were subjected to three rounds of ultrafiltration (Amicon Ultra 500 µl with 100 k cutoff). Ultrafiltration was carried out at 20° C. and 7 k relative centrifugal force (Eppendorf 5424R). The buffer was replaced by folding buffer (5 mM TRIS, 1 mM EDTA, 5 mM NaCl; including 5 mM $MgCl_2$), PBS, or double distilled water supplemented with 300, 150, 100, 50, 25, or 0 mM NaCl. Samples used for cryo electron microscopy were concentrated to 1,000 nM.

2.5. Gel Electrophoresis of DNA Origami Objects

Samples were electrophoresed on 2.0% agarose gels containing 0.5× tris-borate-EDTA and 5 mM $MgCl_2$ for around 2 h at 90 V bias voltage in a gel box immersed in a water or ice bath, unless otherwise stated. Samples were loaded on the gel at a monomer concentration of approximately 5 nM. The electrophoresed agarose gels were scanned using a Typhoon FLA 9500 laser scanner (GE Healthcare) at a resolution of 25 µm/pixel. The resulting 16-bit tif images were analyzed using ImageJ 1.440.

2.6. Negative-Stain Transmission Electron Microscopy (TEM): Preparation, Acquisition and Data Processing Samples were adsorbed on glow-discharged, collodion-supported, carbon-coated (10 nm) Cu400 TEM grids (in-house production) and stained using a 2% aqueous uranyl formate solution containing 25 mM sodium hydroxide. Samples were incubated for 15-300 s depending on the buffer/solvent used. For samples dissolved in solvents including low concentrations of positively charged ions, we used higher monomer concentrations (50 nM) and longer incubation times. We used magnifications between 10,000× to 30,000× to aquire the data. Imaging was performed on different microscopes; see table below.

| Microscope | Operating voltage (kV) | Camera | Objects |
|---|---|---|---|
| Philips CM 100 | 100 | AMT 4 megapixels CCD camera | Switch; Polymerization Brick |
| FEI Tecnai 120 | 120 | Tietz TemCam-F416 (4k × 4k) | Brick-like, TT-motifs (1)-(3) Brick-like, TT-motifs (1)-(4) Pointer |

TEM micrographs used in the figures were high-pass filtered to remove long-range staining gradients, and the contrast was auto-leveled (Adobe Photoshop CS6). For 2D image processing, libraries of individual particle micrographs were created by particle picking using the RELION-2 picking routine[65]. Generation of average 2D particle micrographs was performed using RELION-2[65]. Typically, around 2,000 individual particles were averaged.

2.7. Cryo-Electron Microscopy: Preparation, Acquisition and Processing of Data

For the brick-like object with TT motifs 1 to 3, concentrations between 700 nM and 850 nM were used. The samples were applied to C-Flat 1.2/1.3, 1.2/1.3 thick, 2/1 or 2/2 thick grids (Protochips). Plunge freezing was performed with an FEI Vitrobot Mark V instrument with a blot time of 3 s, a blot force of −1, and a drain time of 0 s under 95% humidity and at 22° C. For the brick-like object with TT motifs 1 to 4, concentrations between 560 nM to 800 nM were used. The samples were applied to C-Flat 1.2/1.3, 2/1 or 2/2 thick grids. Plunge freezing was performed with an FEI Vitrobot Mark V with a blot time of 3 s, a blot force of −1, and a drain time of 0 s under 95% humidity and at 22° C. Automated data collection was performed on a Titan Krios G2 electron microscope (FEI) operated at 300 kV and equipped first with a Falcon III direct detector (FEI). We used EPU for single particle and FEI Tomography for tilt series acquisition. For all brick-like objects under different conditions, movies comprising 15 frames, 1.5 s to 2 s exposure time and a total dose of 60 $e^-/Å^2$ were recorded on a Falcon III (FEI) direct electron detection camera in fractioning mode, at a calibrated magnification of 29,000× with a magnified pixel size of 2.3 Å. Defocus values ranging from −1 to −3 µm were used. The recorded movies were subjected to motion correction with MotionCor2[67] and subsequently contrast transfer function parameters were estimated with CTFFIND4.1[68], all subsequent processing steps were performed in RELION-2.1[65,69]. For each dataset, references for automated picking were calculated from about 5,000 manually selected particles. With the picked particles, multiple rounds of reference-free 2D classification were performed. The best 2D class averages, as judged by visual inspection, were selected. An initial model was produced from a bild file, generated by CanDo. After multiple rounds of 3D classification, the classes showing the most features were selected for 3D auto-refinement, and subsequently, post-processing for sharpening of the refined map was performed with different manually selected B factors. A cryo-tomogram for validation of the twist direction was acquired with FEI tomography, with a defocus of −3 µm at a calibrated magnification of 29,000× corresponding to a magnified pixel size of 2.3 Å. The session was set up as bidirectional tilting in increments of 2° up to 50°, and the dose per image was set to ~2 $e^-/Å^2$. The resulting tilt series was processed with the IMOD 4.9 routine[70].

2.8. Additional Experiments 2.8.1 Experiment Leading to Results Shown in FIG. 2:

Samples were folded and PEG-purified, and the $MgCl_2$ concentration was adjusted to 30 mM. After UV-irradiation, the buffer was exchanged to the target buffer/solvent by using ultracentrifugation. Before gel electrophoresis, the samples were incubated for around 2 to 3 h at room temperature. Samples for the temperature screen were incubated for 30 min at the indicated temperatures. The samples for negative-stain TEM were prepared at a monomer concentration of 50 nM, with incubation on the grid for 3 to 5 min.

Figure 3:
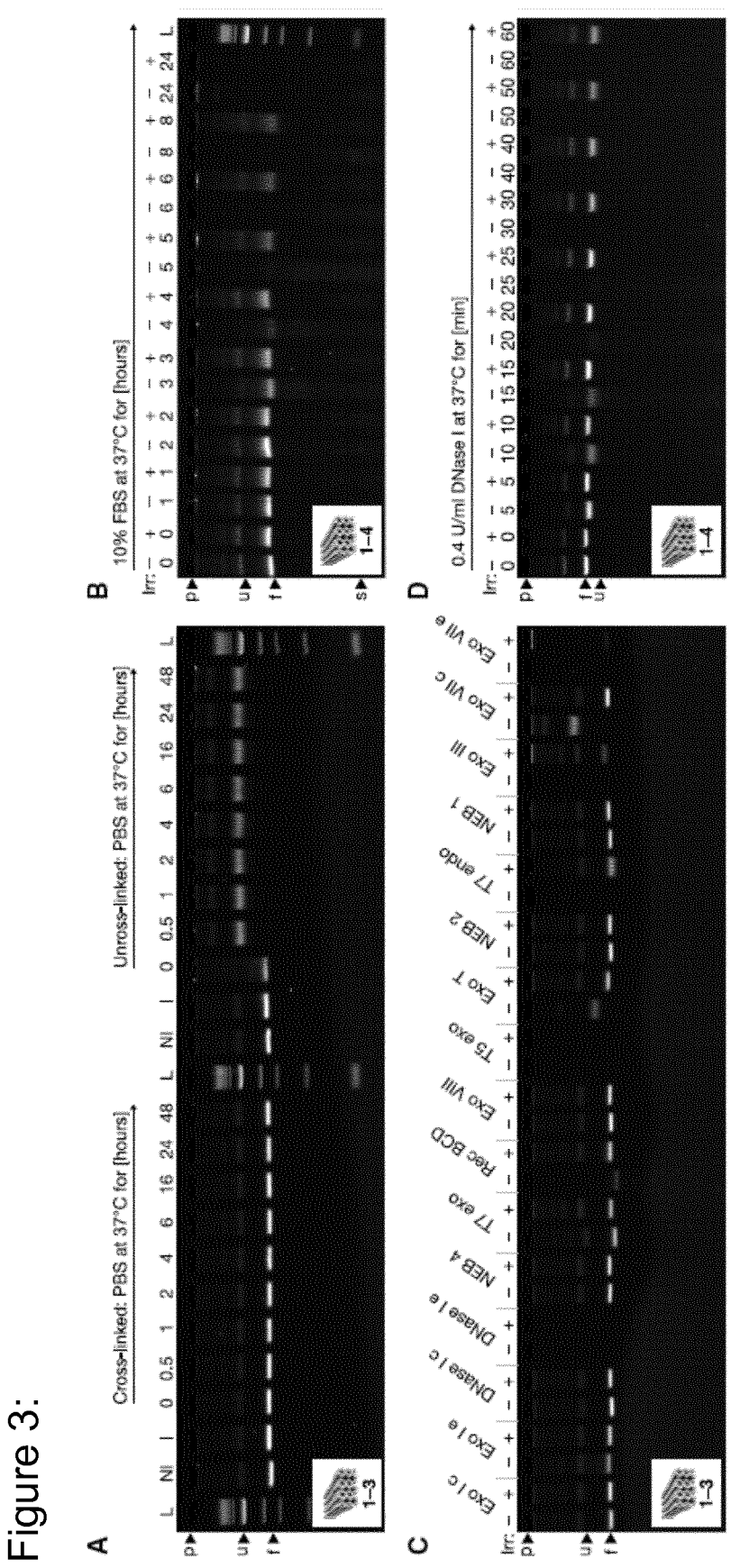
FIG. 3 shows assays demonstrating the stability under physiological conditions. Laser-scanned fluorescent images of 2.0% agarose gels stained with ethidium bromide. Cross-linked samples were irradiated for 135 min at 310 nm. (A) The brick-like DNA origami object featuring additional thymidines at all strand termini and at all strand crossover positions was incubated for different periods of time in physiological phosphate buffered saline (PBS) solution at 37° C. (B) The brick-like DNA origami object featuring additional thymidines at all strand termini, at all strand crossover positions, and 5T-loops was incubated for different periods of time in 10% fetal bovine serum (FBS) at 37° C. (C) The brick-like DNA origami object from (A) was exposed to a set of different nucleases (100 U/ml) for 24 h at 37° C. Lanes labeled with a "c" indicate controls, in which the sample was dissolved in the corresponding buffers in the absence of nuclease. (D) The brick-like DNA origami object from (B) was exposed to DNase I (0.4 U/ml) for different periods of time at 37° C. (B) to (D) non-irradiated and irradiated samples were loaded on the gel alternatingly. All images of the gels were globally auto-leveled.

2.8.2 Experiment Leading to Results Shown in FIG. 3:

In FIG. 3B, the stability screen in folding buffer (5 mM $MgCl_2$) supplemented with 10% Fetal Bovine Serum (not heat-inactivated, Gibco™, A3160801, Thermo Fisher Scientific) was performed at a monomer concentration of 20 nM at 37° C. for the indicated time. The samples were frozen in liquid nitrogen and analyzed using agarose gel electrophoreses.

In FIG. 3C, all nucleases were purchased from NewEngland Biolabs and used at a concentration of 100 U/mL in the supplied manufacture's buffer. The samples (10 nM) were incubated at 37° C. for 24 h.

In FIG. 3D, the time course of the stability against DNase I nuclease digestion was performed at a monomer concentration of 10 nM in the supplied DNase I buffer at 37° C.

2.8.3 Experiment Leading to Results Shown in FIG. 5:

In FIG. 5, the irradiation time screen for the switch was performed in triplicate. The irradiated volume was 25 µl at a monomer concentration of 5 nM. For the analysis of the gel shown in FIG. 5B, we calculated the ratio between the band including closed particles and the bands including open and closed particles. The greyscale values for each band were obtained by integration. The data points in FIG. 5C represent the average, and the error bars represent the standard deviation of the three independent experiments. For the assembly of the filaments, monomers were folded and PEG-purified. The pellet was dissolved in folding buffer (5 mM $MgCl_2$) to obtain a monomer concentration of 100 nM. After equilibration, the $MgCl_2$ concentration was adjusted to 20 mM, and the sample was incubated at 40° C. for 3 days in the TETRAD to obtain filaments. One part of the sample was irradiated at 310 nm for 30 min. The $MgCl_2$ concentration was decreased to 5 mM by the addition of EDTA.

REFERENCES

1 Jones, M. R., Seeman, N. C. & Mirkin, C. A. Nanomaterials. Programmable materials and the nature of the DNA bond. *Science* 347, 1260901, doi: 10.1126/science.1260901 (2015).

2 Seeman, N. C. Nanomaterials based on DNA. *Annual review of biochemistry* 79, 65-87, doi: 10.1146/annurev-biochem-060308-102244 (2010).

3 Rothemund, P. W. Folding DNA to create nanoscale shapes and patterns. *Nature* 440, 297-302, doi: 10.1038/nature04586 (2006).

4 Douglas, S. M. et al. Self-assembly of DNA into nanoscale three-dimensional shapes. *Nature* 459, 414-418, doi: 10.1038/nature08016 (2009).

5 Hong, F., Zhang, F., Liu, Y. & Yan, H. DNA Origami: Scaffolds for Creating Higher Order Structures. *Chemical reviews*, doi: 10.1021/acs.chemrev.6b00825 (2017).

6 Dietz, H., Douglas, S. M. & Shih, W. M. Folding DNA into twisted and curved nanoscale shapes. *Science* 325, 725-730, doi: 10.1126/science. 1174251 (2009).

7 Han, D. et al. DNA origami with complex curvatures in three-dimensional space. *Science* 332, 342-346, doi: 10.1126/science. 1202998 (2011).

8 Veneziano, R. et al. Designer nanoscale DNA assemblies programmed from the top down. *Science* 352, 1534, doi: 10.1126/science.aaf4388 (2016).

9 Benson, E. et al. DNA rendering of polyhedral meshes at the nanoscale. *Nature* 523, 441-444, doi: 10.1038/nature14586 (2015).

10 Han, D. et al. DNA gridiron nanostructures based on four-arm junctions. *Science* 339, 1412-1415, doi: 10.1126/science. 1232252 (2013).

11 Gerling, T., Wagenbauer, K. F., Neuner, A. M. & Dietz, H. Dynamic DNA devices and assemblies formed by shape-complementary, non-base pairing 3D components. *Science* 347, 1446-1452, doi: 10.1126/science.aaa5372 (2015).

12 Funke, J. J. & Dietz, H. Placing molecules with Bohr radius resolution using DNA origami. *Nature nanotechnology* 11, 47-52, doi: 10.1038/nnano.2015.240 (2016).

13 Bai, X. C., Martin, T. G., Scheres, S. H. & Dietz, H. Cryo-EM structure of a 3D DNA-origami object. *Proceedings of the National Academy of Sciences of the United States of America* 109, 20012-20017, doi: 10.1073/pnas.1215713109 (2012).

14 Zhang, F. et al. Complex wireframe DNA origami nanostructures with multi-arm junction vertices. *Nature nanotechnology* 10, 779-784, doi: 10.1038/nnano.2015.162 (2015).

15 Wei, B., Dai, M. & Yin, P. Complex shapes self-assembled from single-stranded DNA tiles. *Nature* 485, 623-626, doi: 10.1038/nature11075 (2012).

16 Ke, Y., Ong, L. L., Shih, W. M. & Yin, P. Three-dimensional structures self-assembled from DNA bricks. *Science* 338, 1177-1183, doi: 10.1126/science. 1227268 (2012).

17 Wagenbauer, K. F., Sigl, C. & Dietz, H. Gigadalton-scale shape-programmable DNA assemblies. *Nature* 552, 78-83, doi: 10.1038/nature24651 (2017).

18 Ong, L. L. et al. Programmable self-assembly of three-dimensional nanostructures from 10,000 unique components. *Nature* 552, 72-77, doi: 10.1038/nature24648 (2017).

19 Knudsen, J. B. et al. Routing of individual polymers in designed patterns. *Nature nanotechnology* (2015).

20 Jahn, K. et al. Functional patterning of DNA origami by parallel enzymatic modification. *Bioconjug Chem* 22, 819-823, doi: 10.1021/bc2000098 (2011).

21 Praetorius, F. & Dietz, H. Self-assembly of genetically encoded DNA-protein hybrid nanoscale shapes. *Science* 355, doi: 10.1126/science.aam5488 (2017).

22 Ketterer, P., Willner, E. M. & Dietz, H. Nanoscale rotary apparatus formed from tight-fitting 3D DNA components. *Science Advances* 2, e1501209, doi: 10.1126/sciadv.1501209 (2016).

23 Marras, A. E., Zhou, L., Su, H. J. & Castro, C. E. Programmable motion of DNA origami mechanisms. *Proceedings of the National Academy of Sciences of the United States of America* 112, 713-718, doi: 10.1073/pnas.1408869112 (2015).

24 Douglas, S. M., Bachelet, I. & Church, G. M. A logic-gated nanorobot for targeted transport of molecular payloads. *Science* 335, 831-834, doi: 10.1126/science.1214081 (2012).

25 Douglas, S. M., Chou, J. J. & Shih, W. M. DNA-nanotube-induced alignment of membrane proteins for NMR structure determination. *Proceedings of the National Academy of Sciences of the United States of America* 104, 6644-6648, doi: 10.1073/pnas.0700930104 (2007).

26 Berardi, M. J., Shih, W. M., Harrison, S. C. & Chou, J. J. Mitochondrial uncoupling protein 2 structure determined by NMR molecular fragment searching. *Nature* 476, 109-113, doi: 10.1038/nature10257 (2011).

27 Martin, T. G. et al. Design of a molecular support for cryo-EM structure determination. *Proceedings of the National Academy of Sciences of the United States of America* 113, E7456-E7463, doi: 10.1073/pnas.1612720113 (2016).

28 Derr, N. D. et al. Tug-of-war in motor protein ensembles revealed with a programmable DNA origami scaffold. *Science* 338, 662-665, doi: 10.1126/science.1226734 (2012).

29 Wei, R., Martin, T. G., Rant, U. & Dietz, H. DNA origami gatekeepers for solid-state nanopores. *Angewandte Chemie* 51, 4864-4867, doi: 10.1002/anie.201200688 (2012).

30 Langecker, M. et al. Synthetic lipid membrane channels formed by designed DNA nanostructures. *Science* 338, 932-936, doi: 10.1126/science. 1225624 (2012).

31 Funke, J. J. et al. Uncovering the forces between nucleosomes using DNA origami. *Sci Adv* 2, e1600974, doi: 10.1126/sciadv.1600974 (2016).

32 Kilchherr, F. et al. Single-molecule dissection of stacking forces in DNA. *Science* 353, doi: 10.1126/science.aaf5508 (2016).

33 Nickels, P. C. et al. Molecular force spectroscopy with a DNA origami-based nanoscopic force clamp. *Science* 354, 305-307, doi: 10.1126/science.aah5974 (2016).

34 Gopinath, A., Miyazono, E., Faraon, A. & Rothemund, P. W. Engineering and mapping nanocavity emission via precision placement of DNA origami. *Nature* 535, 401-405, doi: 10.1038/nature18287 (2016).

35 Steinhauer, C., Jungmann, R., Sobey, T. L., Simmel, F. C. & Tinnefeld, P. DNA origami as a nanoscopic ruler for super-resolution microscopy. *Angewandte Chemie* 48, 8870-8873, doi: 10.1002/anie.200903308 (2009).

36 Bui, H. et al. Programmable periodicity of quantum dot arrays with DNA origami nanotubes. *Nano letters* 10, 3367-3372, doi: 10.1021/nl101079u (2010).

37 Acuna, G. P. et al. Fluorescence enhancement at docking sites of DNA-directed selfassembled nanoantennas. *Science* 338, 506-510, doi: 10.1126/science.1228638 (2012).

38 Kuzyk, A. et al. DNA-based self-assembly of chiral plasmonic nanostructures with tailored optical response. *Nature* 483, 311-314, doi: 10.1038/nature10889 (2012).

39 Roller, E. M., Argyropoulos, C., Hoegele, A., Liedl, T. & Pilo-Pais, M. Plasmon-Exciton Coupling Using DNA Templates. *Nano letters*, doi: 10.1021/acs.nanolett.6b03015 (2016).

40 Roller, E. M. et al. DNA-assembled nanoparticle rings exhibit electric and magnetic resonances at visible frequencies. *Nano letters* 15, 1368-1373, doi: 10.1021/nl5046473 (2015).

41 Kuhler, P. et al. Plasmonic DNA-origami nanoantennas for surface-enhanced Raman spectroscopy. *Nano letters* 14, 2914-2919, doi: 10.1021/nl5009635 (2014).

42 Schreiber, R. et al. Chiral plasmonic DNA nanostructures with switchable circular dichroism. *Nature communications* 4, 2948, doi: 10.1038/ncomms3948 (2013).

43 Kershner, R. J. et al. Placement and orientation of individual DNA shapes on lithographically patterned surfaces. *Nature nanotechnology* 4, 557-561, doi: 10.1038/nnano.2009.220 (2009).

44 Maune, H. T. et al. Self-assembly of carbon nanotubes into two-dimensional geometries using DNA origami templates. *Nature nanotechnology* 5, 61-66, doi: 10.1038/nnano.2009.311 (2010).

45 Hung, A. M. et al. Large-area spatially ordered arrays of gold nanoparticles directed by lithographically confined DNA origami. *Nature nanotechnology* 5, 121-126, doi: 10.1038/nnano.2009.450 (2010).

46 Li, S. et al. A DNA nanorobot functions as a cancer therapeutic in response to a molecular trigger in vivo. *Nat Biotechnol* 36, 258-264, doi: 10.1038/nbt.4071 (2018).

47 Praetorius, F., Kick, B., Behler, K. L., Honemann, M. N., Weuster-Botz, D., Dietz, H. Biotechnological mass-production of DNA origami. *Nature*, in revision (2017).

48 Cassinelli, V. et al. One-Step Formation of "Chain-Armor"-Stabilized DNA Nanostructures. *Angewandte Chemie* 54, 7795-7798, doi: 10.1002/anie.201500561 (2015).

49 De Stefano, M., Gothelf, K. V. Dynamic Chemistry of Disulfide Terminated Oligonucleotides in Duplexes and Double-Crossover Tiles. *Chembiochem: a European journal of chemical biology* 17, doi: 10.1002/cbic.201600076 (2016).

50 O'Neill, P., Rothemund, P. W., Kumar, A. & Fygenson, D. K. Sturdier DNA nanotubes via ligation. *Nano letters* 6, 1379-1383, doi: 10.1021/nl0603505 (2006).

51 Ponnuswamy, N. et al. Oligolysine-based coating protects DNA nanostructures from low-salt denaturation and nuclease degradation. *Nature communications* 8, 15654, doi: 10.1038/ncomms15654 (2017).

52 Agarwal, N. P., Matthies, M., Gur, F. N., Osada, K. & Schmidt, T. L. Block Copolymer Micellization as a Protection Strategy for DNA Origami. *Angewandte Chemie* 56, 5460-5464, doi: 10.1002/anie.201608873 (2017).

53 Taylor, J. S. Unraveling the Molecular Pathway from Sunlight to Skin-Cancer. *Accounts of chemical research* 27, 76-82, doi: DOI 10.1021/ar00039a003 (1994).

54 Lima-Bessa, K. M. & Menck, C. F. M. Skin cancer: Lights on genome lesions. *Current Biology* 15, R58-R61, doi: 10.1016/j.cub.2004.12.056 (2005).

55 Lewis, R. J. & Hanawalt, P. C. Ligation of oligonucleotides by pyrimidine dimers—a missing 'link' in the origin of life? *Nature* 298, 393-396 (1982).

56 Castro, C. E. et al. A primer to scaffolded DNA origami. *Nature methods* 8, 221-229, doi: 10.1038/nmeth.1570 (2011).

57 Sobczak, J. P., Martin, T. G., Gerling, T. & Dietz, H. Rapid folding of DNA into nanoscale shapes at constant temperature. *Science* 338, 1458-1461, doi: 10.1126/science.1229919 (2012).

58 Wagenbauer, K. F., Wachauf, C. H. & Dietz, H. Quantifying quality in DNA self-assembly. *ature communications* 5, 3691, doi: 10.1038/ncomms4691 (2014).

59 Jiang, Y. et al. UVA generates pyrimidine dimers in DNA directly. *Biophysical journal* 96, 1151-1158, doi: 10.1016/j.bpj.2008.10.030 (2009).

60 Cherepanova, A. et al. Immunochemical assay for deoxyribonuclease activity in body fluids. *J Immunol Methods* 325, 96-103, doi: 10.1016/j.jim.2007.06.004 (2007).

61 Chen, H., Li, R., Li, S., Andreasson, J. & Choi, J. H. Conformational Effects of UV Light on DNA rigami. *Journal of the American Chemical Society* 139, 1380-1383, doi: 10.1021/jacs.6b10821 (2017).

62 A. Rajendran, M. Endo, Y. Katsuda, K. Hidaka, H. Sugiyama, Photo-cross-linking-assisted thermal stability of DNA origami structures and its application for higher-temperature self-assembly. J. Am. Chem. Soc. 133, 14488-14491 (2011).

63 E. Stahl, T. G. Martin, F. Praetorius, H. Dietz, Facile and scalable preparation of pure and dense DNA origami solutions. Angewandte Chemie 53, 12735-12740 (2014).

64 K. F. Wagenbauer et al., How we make DNA origami. Chembiochem: a European journal of chemical biology, (2017).

65 D. Kimanius, B. O. Forsberg, S. H. Scheres, E. Lindahl, Accelerated cryo-EM structure determination with parallelisation using GPUs in RELION-2. Elife 5, (2016).

66 S. M. Douglas et al., Rapid prototyping of 3D DNA-origami shapes with caDNAno. Nucleic acids esearch 37, 5001-5006 (2009).

67 Zheng, S. Q., Palovcak, E., Armache, J.-P., Verba, K. A., Cheng, Y., & Agard, D. A. MotionCor2: anisotropic correction of beam-induced motion for improved cryo-electron microscopy. Nature Methods, 14 (4) (2017).

68 Rohou, A., & Grigorieff, N. CTFFIND4: Fast and accurate defocus estimation from electron micrographs. Journal of Structural Biology, 192 (2), 216-221 (2015).

69 S. H. Scheres, Bayesian View on Cryo-EM Structure Determination. Journal of Molecular Biology, 415 (2), 406-418 (2012).

70 Kremer, J. R., Mastronarde, D. N., & McIntosh, J. R. Computer Visualization of Three-Dimensional Image Data Using IMOD. Journal of Structural Biology, 116 (1), 71-76 (1996).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The invention claimed is:

1. A method for increasing the stability of a non-naturally occurring nucleic acid nanostructure, wherein said nanostructure comprises at least one double-helical substructure comprising a first single-stranded polynucleotide having a sequence binding via the formation of hydrogen bonds to at least two non-contiguous sequence stretches present on one or more complementary second single-stranded polynucleotides, the method comprising: exposing said nucleic acid nanostructure to UV irradiation, wherein said step of exposing said nucleic acid nanostructure to UV irradiation results in the formation of at least one chemical bond between two pyrimidine nucleotides, wherein each of the two pyrimidine nucleotides is independently selected from thymidine and cytosine.

2. The method of claim 1, wherein said non-naturally occurring nucleic acid nanostructure comprises either a two- or a three-dimensional arrangement of a plurality of said double-helical substructures.

3. The method of claim 2, wherein said double-helical substructures each consist of between 10 and 5,000 complementary nucleotide pairs, wherein exposure of the nucleic acid nanostructure to UV irradiation results in the formation of chemical bonds between said double-helical substructures at intervals of every seven, eight or nine bases.

4. The method of claim 3, wherein said connections between said double helical substructures results in a honeycomb-, square-, or hexagonal-packing geometry or any combination therein.

5. The method of claim 2, wherein at least 85% of the first and second single stranded polynucleotides are part of at least two different double-helical substructures.

6. The method of claim 1, wherein said double-helical substructure comprises:
the first single-stranded polynucleotide, and a set of the second single-stranded polynucleotides, wherein the first single-stranded polynucleotide is a backbone molecule to which each of the second single-stranded polynucleotides is hybridized,
wherein each of the second single-stranded polynucleotides consists of an n specific sequence consisting of n core sequences, with n being an integer independently selected from the range of 1 to 40, wherein each of said n core sequences consists of (i) a sequence that is complementary to a region on said first single-stranded polynucleotide, wherein the region on said first single-stranded polynucleotide complementary to the $n^{th}$ core sequence is not contiguous with the regions on said first single-stranded polynucleotide complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and/or (iv) one or more insertions of a pyrimidine nucleotide stretch $P_m$,
wherein each m is an integer independently selected from the range of 0 to 40,
wherein each P is independently selected from a thymidine and a cytosine residue, and
wherein at least one pyrimidine nucleotide stretch $P_m$ comprised by at least one polynucleotide of the set of second single-stranded polynucleotides comprises at least one pyrimidine residue.

7. The method of claim 6, wherein the first single-stranded polynucleotide comprises at least 100 nucleotides.

8. The method of claim 7, wherein the first single-stranded polynucleotide has at least 70% sequence identity to the DNA of a filamentous bacteriophage.

9. The method of claim 8, wherein said filamentous bacteriophage is M13.

10. The method of claim 1, wherein said double-helical substructure comprises a set consisting of the first single-stranded polynucleotide and the one or more second single-stranded polynucleotides, wherein each of the first single-stranded polynucleotides and the second single-stranded polynucleotides in the set consists of an n-specific sequence consisting of n core sequences, with n being an integer independently selected from the range of 1 to 40, wherein each of said n core sequences consists of (i) a sequence that is complementary to the sequence of another member of said set, wherein the region on said another member complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and/or (iv) one or more insertions of a pyrimidine nucleotide stretch $P_m$,
wherein each m is an integer independently selected from the range of 0 to 40,
wherein at least one pyrimidine nucleotide stretch $P_m$ comprised by at least one polynucleotide of the comprises at least one pyrimidine residue,
and
wherein each P is independently selected from a thymidine and a cytosine residue.

11. The method of claim 6, wherein for each of said pyrimidine nucleotide stretches $P_m$ at the 3' ends and at the 5' ends, m is either 0 or 1, and P is a thymidine residue.

12. The method of claim 6, wherein each of said core sequences consists of x nucleotides, with x being independently selected from an integer that is a multiple of 7, 8 or 16.

13. The method of claim 1, wherein said UV irradiation is performed with UV light at a wavelength of 250 nm to 350 nm.

14. The method of claim 1, wherein said UV irradiation is performed:
a) on a sample with a volume of 5 to 2,000 µl;
b) on a concentration of the nucleic acid nanostructure in the sample that is between 1 and 500 nM;
c) at a temperature of 0 to 25° C.;
d) in a TRIS-buffered solution;
e) with a Xenon light source using a light guide to couple the light beam into the sample with a distance of less than 5 cm between the solution surface of the sample and the terminus of the light guide; and
f) by exposing the sample to UV-irradiation for between 1 and 6 hours with an intensity of the UV-light of between about 1 and 10 mW/cm².

15. The method of claim 1, wherein said step of exposing said nucleic acid nanostructure to UV irradiation is performed for 30, 120, or 135 minutes.

16. A nucleic acid nanostructure comprising at least one double-helical substructure comprising:
(a) a first single-stranded polynucleotide, and a set of second single-stranded polynucleotides, wherein the first single-stranded polynucleotide is a backbone molecule to which each of the second single-stranded polynucleotides is hybridized, wherein each of the second single-stranded polynucleotides consists of an n-specific sequence consisting of n core sequences, with n being an integer selected from the range of 1 to 40, wherein each of said n core sequences consists of (i) a sequence that is complementary to a region on said first single-stranded polynucleotide, wherein the region complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and/or (iv) one or more insertions of a pyrimidine nucleotide stretch $P_m$, wherein each m is an integer independently selected from the range of 0 to 40, wherein each P is independently selected from a thymidine and a cytosine residue, and wherein at least one pyrimidine nucleotide stretch $P_m$ comprised by at least one polynucleotide of the set of second single-stranded polynucleotides comprises at least one pyrimidine residue; or (b) a set of single stranded polynucleotides, wherein each of the single-stranded polynucleotides consists of an n-specific sequence consisting of n core sequences, with n being independently selected from the range of 1 to 40, wherein each of said n core sequences consists of (i) a sequence that is complementary to the sequence of another member of said set of single-stranded polynucleotides, wherein the region on said another member complementary to the $n^{th}$ core sequence is not contiguous with the regions complementary to the $(n-1)^{th}$ and $(n+1)^{th}$ core sequence, (ii) a pyrimidine nucleotide stretch $P_m$, at the 3' end, (iii) a pyrimidine nucleotide stretch $P_m$ at the 5' end, and/or (iv) one or more insertions of a pyrimidine nucleotide stretch $P_m$, wherein each m is an integer independently selected from the range of 0 to 40, and wherein each P is independently selected from a thymidine and a cytosine residue, and wherein at least one pyrimidine nucleotide stretch $P_m$ comprised by at least one polynucleotide of the set of single-stranded polynucleotides comprises at least one pyrimidine residue;

and wherein the nanostructure comprises one or more UV-induced bridges between spatially adjacent thymine and/or cytosine residues.

17. The nucleic acid nanostructure of claim 16, wherein for each of said pyrimidine nucleotide stretches $P_m$ at the 3' ends and at the 5' ends m is either 0 or 1 and P is a thymidine residue.

18. The nucleic acid nanostructure of claim 16, wherein said one or more bridges comprise a pyrimidine dimer selected from a cyclobutane pyrimidine dimer and a (6,4) pyrimidine-pyrimidone.

19. The nucleic acid nanostructure of claim 16, wherein one or more of said bridges are intrahelical bridges between the thymidine or cytosine residues at the 3' and 5' ends of two adjacent single-stranded polynucleotides or core sequences being part of the same double-helical substructure of said nucleic acid nanostructure.

20. The nucleic acid nanostructure of claim 16, wherein one or more of said bridges are interhelical bridges between thymidine or cytosine residues comprised in single-stranded polynucleotides or parts of such single-stranded polynucleotides that are part of two different double-helical substructures of said nucleic acid nanostructure, particularly between two thymidine residues comprised in two of said insertions.

21. A complex nucleic acid nanostructure resulting from assembly of two or more nucleic acid nanostructures according to claim 16.

22. The complex nucleic acid nanostructure of claim 21, wherein said assembly comprises one or more UV-induced bridges between two or more of said nucleic acid nanostructures.

* * * * *